United States Patent
Zhang et al.

(10) Patent No.: US 11,186,570 B2
(45) Date of Patent: Nov. 30, 2021

(54) INTERMEDIATE OF ERIBULIN AND PREPARATION METHOD THEREFOR

(71) Applicant: SELECTION BIOSCIENCE LLC, Shanghai (CN)

(72) Inventors: Fuyao Zhang, Shanghai (CN); Huoming Li, Shanghai (CN); Xinning Zhang, Shanghai (CN)

(73) Assignee: SELECTION BIOSCIENCE LLC, Shanghai (CN)

(*) Notice: Subject to any disclaimer, the term of this patent is extended or adjusted under 35 U.S.C. 154(b) by 0 days.

(21) Appl. No.: 16/613,329

(22) PCT Filed: May 17, 2018

(86) PCT No.: PCT/CN2018/087247
§ 371 (c)(1),
(2) Date: Nov. 13, 2019

(87) PCT Pub. No.: WO2018/210297
PCT Pub. Date: Nov. 22, 2018

(65) Prior Publication Data
US 2020/0095235 A1    Mar. 26, 2020

(30) Foreign Application Priority Data

May 17, 2017   (CN) .......................... 201710350260.5

(51) Int. Cl.
*C07D 307/30* (2006.01)
*C07D 407/14* (2006.01)
(Continued)

(52) U.S. Cl.
CPC .......... *C07D 407/14* (2013.01); *C07D 307/28* (2013.01); *C07D 407/06* (2013.01); *C07D 493/04* (2013.01)

(58) Field of Classification Search
CPC ................................................... C07D 307/30
See application file for complete search history.

(56) References Cited

FOREIGN PATENT DOCUMENTS

| CA | 2822994 A1 | 12/2005 |
|---|---|---|
| CA | 2787919 A1 | 8/2011 |

(Continued)

OTHER PUBLICATIONS

First Office Action of counterpart European application EP18801562.2 dated Jul. 28, 2020, 4 pages.
First Office Action of counterpart Chinese application CN201710350260.5 dated Jul. 20, 2020, 28 pages.
Cheng-Guo Dong et al., "New syntheses of E7389 C14-C35 and halichondrin C14-C38 building blocks: Reductive cyclization and oxy-Michael cyclization approaches", J. Am. Chem. Soc., vol. 131, No. 43, 2009, pp. 15642-15646.

Cheng-Guo Dong et al., "Supporting information new syntheses of E7389 C14-C35 and halichondrin C14-C38 building blocks: Reductive cyclization and oxy-Michael cyclization approaches", J. Am. Chem. Soc., vol. 131, No. 43, 2009, pp. 15642-15646.
Dae-Shik Kim et al., "New Syntheses of E7389 C14-C35 and Halichondrin C14-C38 Building Blocks: Double-Inversion Approach", J. Am Chem. Soc., 2009, vol. 131, No. 43, pp. 15636-15641.
Katrina L. Jackson et al., "A Total Synthesis of Norhalichondrin B", Angew. Chem. Int. Ed. Engl, 2009, vol. 48, No. 13, pp. 2346-2350.
Charles E. Chase et al., "Process Development of Halaven (R): Synthesis of the C1-C13 Fragment from D-(-)-Gulono 1,4-lactone", Synlett, 2013, vol. 24, pp. 323 326.

(Continued)

*Primary Examiner* — John S Kenyon
(74) *Attorney, Agent, or Firm* — MH2 Technology Law Group LLP

(57) ABSTRACT

Disclosed are an intermediate of Eribulin and a preparation method therefor. In particular, disclosed are compounds as represented by formula II, formula III and formula V and a preparation method therefor. Ar is $C_{1-10}$ alkyl substituted, alkyloxy substituted or unsubstituted aryl; $R^1$ and $R^2$ is an acetal protecting group or a thioacetal protecting group; $R^3$ is hydrogen or a hydroxyl protecting group; and X is halogen or a leaving group. The preparation method therefor has the advantages of mild reaction conditions, high selectivity, easy purification, low synthesis cost and the like, being suitable for large scale production.

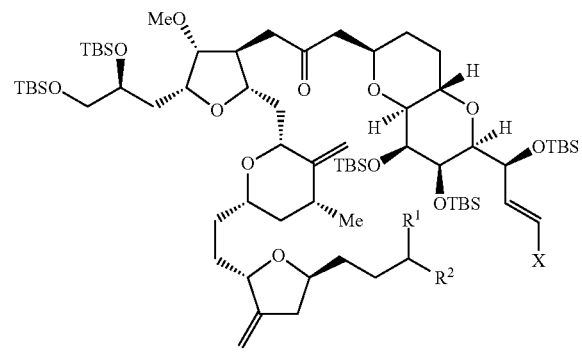

II

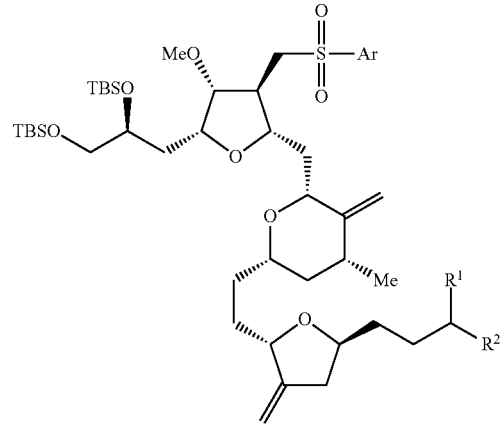

III (Continued)

-continued

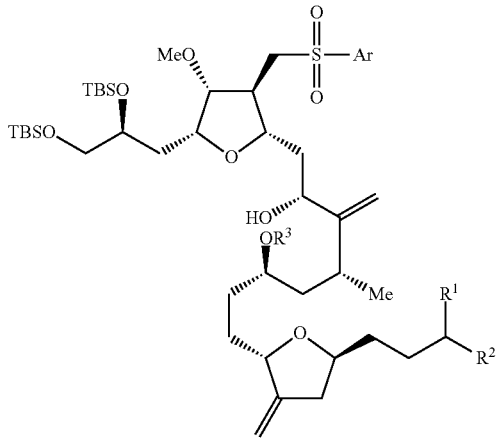

V

25 Claims, No Drawings

(51) Int. Cl.
*C07D 307/28* (2006.01)
*C07D 407/06* (2006.01)
*C07D 493/04* (2006.01)

(56) References Cited

FOREIGN PATENT DOCUMENTS

| CN | 1993342 A | 7/2007 | |
|---|---|---|---|
| CN | 102803254 A | 11/2012 | |
| CN | 104334562 A | 2/2015 | |
| CN | 105431438 A | 3/2016 | |
| CN | 105713031 A | 6/2016 | |
| CN | 108658956 | 10/2018 | |
| WO | 2005118565 A1 | 12/2005 | |
| WO | WO-2011094339 A1 * | 8/2011 | ........... C07D 407/06 |
| WO | 2013142999 A1 | 10/2013 | |
| WO | 2015000070 A1 | 1/2015 | |

OTHER PUBLICATIONS

Brian C. Austad et al., "Process Development of Halaven (R): Synthesis of the C14-C35 Fragment via Iterative Nozaki-Hiyama-Kishi Reaction-Williamson Ether Cyclization", Synlett, 2013, vol. 24, pp. 327-332.
Brian C. Austad et al., "Commercial Manufacture of Halaven (R): Chemoselective Transformations En Route to Structurally Complex Macrocyclic Ketones", Synlett, 2013, vol. 24, pp. 333-337.
International Search Report and Written Opinion of PCT/CN2018/087247 dated Jul. 18, 2018, 17 pages.
Extended European Search Report issued in the counterpart European application No. 18801562.2 dated Feb. 7, 2020, 8 pages.

* cited by examiner

INTERMEDIATE OF ERIBULIN AND PREPARATION METHOD THEREFOR

CROSS-REFERENCE TO RELATED APPLICATIONS

This application is a national stage entry from International Application No. PCT/CN2018/087247, filed on May 17, 2018, published as International Publication No. WO 2018/210297 A1 on Nov. 22, 2018, and claims priority under 35 U.S.C. § 119 from Chinese patent application No. 201710350260.5, filed on May 17, 2017, the entire contents of all of which are incorporated herein by reference.

The application claims the benefit of the Chinese Application No. 201710350260.5 filed on May 17, 2017, which is incorporated herein by reference in its entirety.

FIELD OF THE INVENTION

The present disclosure relates to an intermediate of eribulin and a preparation method thereof.

BACKGROUND OF THE INVENTION

Eribulin (represented by formula I) is a structurally optimized derivative of halichondrin B, which is a macrolide isolated from the marine sponge *Halichondria okadai*. It functions as a microtubule kinetic inhibitor. Eribulin mesylate injection (Halaven) was approved by FDA on Nov. 15, 2010, for the treatment of metastatic breast cancer patients who have previously received at least two chemotherapeutic regimens. Since then, Eisai has been actively devoted to exploring more indications for eribulin. On Jan. 28, 2016, Halaven was approved by FDA for the treatment of patients with unresectable or metastatic liposarcoma who have received a prior regimen. It thus becomes the first single agent to distinctly improve an overall survival in patients with advanced soft tissue sarcoma. Currently, Halaven has been approved for the treatment of metastatic breast cancer in more than 60 countries all over the world, and for the treatment of unresectable or metastatic soft tissue sarcoma in US, Japan and EU. In addition, Eisai also submitted new drug application for Halaven to Chinese Food & Drug Administration for the treatment of locally advanced or metastatic breast cancer in August, 2016. It is indicated from recent preclinical and translational researches that, besides anti-mitotic effects, Halaven also induces tumor vascular remodeling in advanced breast cancer tumor tissue, improves vascular perfusion and permeability of tumor core region, and reduces hypoxia of tumor microenvironment. Furthermore, Halaven could improve the epithelial state and decrease the migration capacity of breast cancer cells.

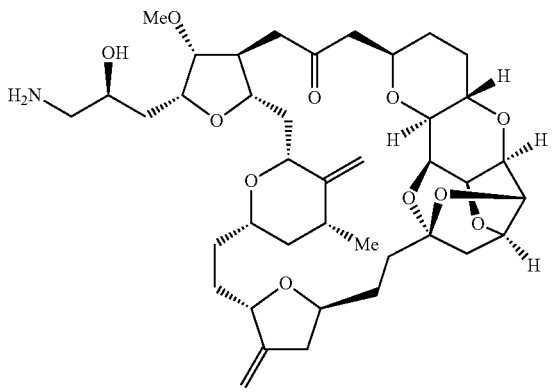

I

As a structurally complex molecule, eribulin contains 40 carbon atoms, 19 of which are chiral carbons. Up to date, the commercial supply of eribulin could only rely on total synthesis, and the synthetic route is extremely complicated. Hence, it is very challenging for the design of the synthetic route and the development of the synthetic process, wherein the precise control of the diastereoselectivity for every chiral center is particularly of great importance.

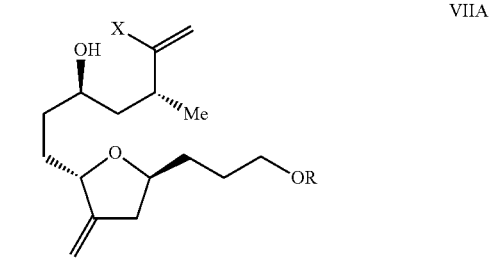

VIIA

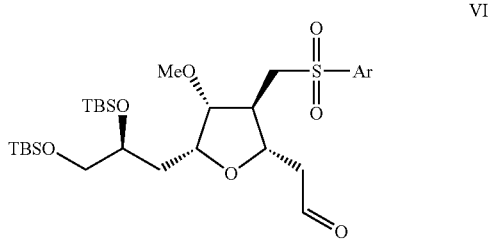

VI

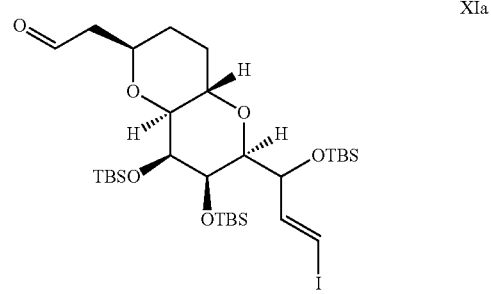

XIa

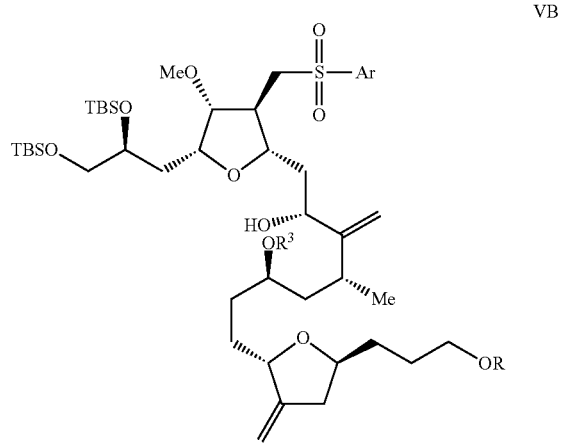

VB

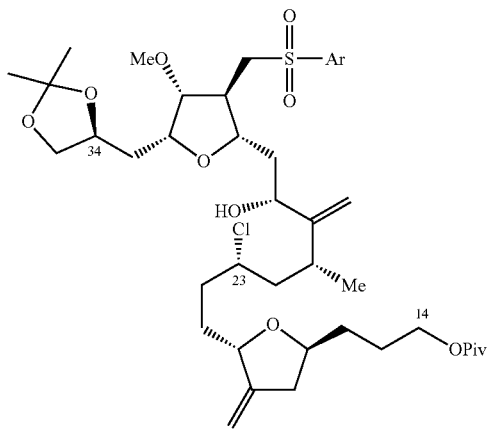

VD

Currently, the synthesis of eribulin is mainly realized by the convergent assembly of three intermediates with similar complexity, whose basic structures are shown as formula VIIIA, formula VI and formula XIa. Specifically, coupling reaction between derivatives of compound of formula VIII and derivatives of compound of formula VI generates derivatives of compound of formula VB. After a few steps' transformation, the resulting product is condensed with derivatives of compound of formula XIa. And the condensation product is pushed forwards to eribulin, ultimately. During the process of fragments assembly, there exist a huge amount of functional group manipulation steps. Therefore, more and more chemists focus on the development of fast and efficient strategy for fragment assembly.

Eisai disclosed an intermediate of formula VC after the first fragment assembly in WO2005118565A1. The functional group at C14 is a protected alcohol. In order to be prepared for the second fragment assembly, the alcohol should undergo an oxidation reaction to be transformed into an aldehyde.

ChiaTai TianQing disclosed an intermediate of formula VE in CN105713031A.

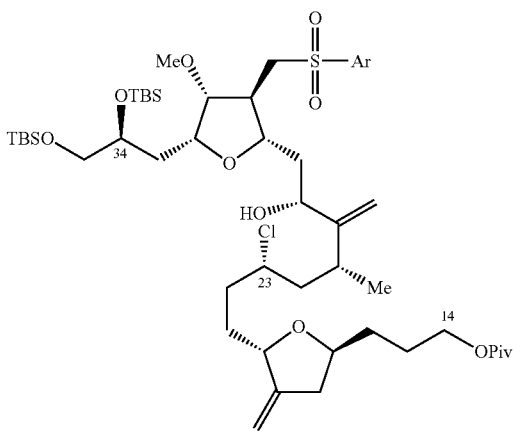

VE

Alphora Research Inc. from Canada synthesized an intermediate of formula VF. In this intermediate, they introduced the amino functional group from eribulin at C35 in advance. However, the oxidation state at C14 is still alcohol.

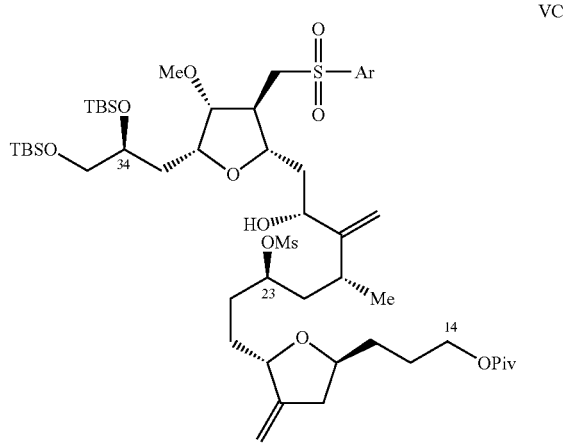

VC

Kishi's lab from Harvard University reported an intermediate of formula VD. Compared with compound of formula VC, the mesylate group at C23 is replaced with a configuration inverted chlorine, by which means the ring closure step is also modified.

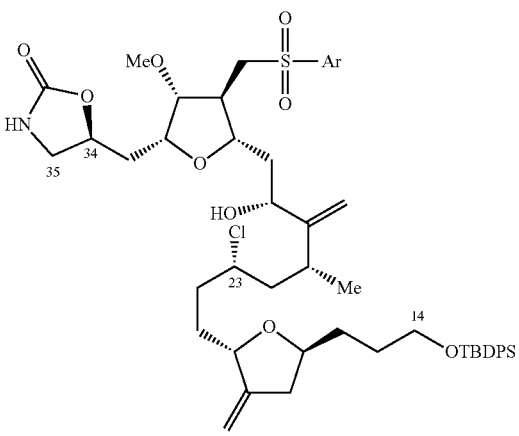

VF

In conclusion, there is notable commonality for the reported synthetic strategies, of which the oxidation state at C14 is basically alcohol. The oxidation state should be adjusted by oxidant to be ready for the subsequent transformation. Hence, there is a need in the art for more synthetic strategies to enrich and optimize the total synthesis of eribulin.

CONTENT OF THE INVENTION

The object of the disclosure is to provide an intermediate of eribulin and a preparation method thereof.

To solve the defects of current synthetic methods of the eribulin intermediate of formula V that diversification is lack and adjustment of the oxidation state of C14 is needed, the present disclosure provides a C14 acetal protected intermediate of formula V, which is obtained through a first fragment assembly starting from C14 acetal protected intermediate of formula VIII. In the following transformations, C14 functional group could be released to aldehyde functional group just by hydrolysis, thus avoiding the oxidation state adjustment at this carbon atom, reducing the step of oxidation reaction, and making the synthetic route greener and more efficient. The synthesis of intermediate of formula V, III and II involves mild reaction conditions, high synthetic yield and easy purification, thus is suitable for industrial production of eribulin intermediate of formula IV.

The present disclosure provides a compound of formula III,

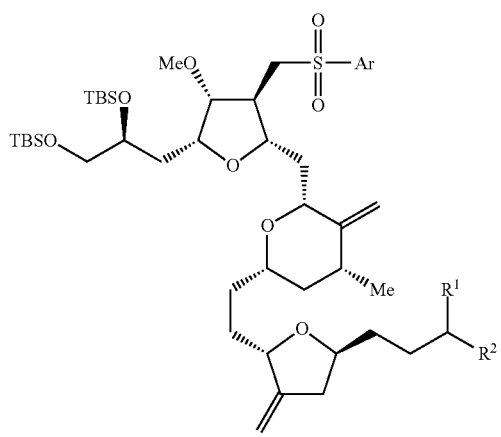

III wherein Ar is an aryl substituted by $C_{1-10}$ alkyl or alkoxy, or an unsubstituted aryl, preferably a phenyl substituted by $C_{1-10}$ alkyl at the para-position, or an unsubstituted phenyl; $R^1$ and $R^2$ are acetal or thioacetal protecting group, and $R^1$ and $R^2$ are each independently $C_{1-10}$ alkoxy or $C_{1-10}$ alkyl-thio, or $R^1$ and $R^2$ together with the carbon atom to which they are attached form cyclic acetal or cyclic thioacetal; preferably $R^1$ and $R^2$ together with the carbon atom to which they are attached form cyclic acetal or cyclic thioacetal, more preferably $R^1$ and $R^2$ together with the carbon atom to which they are attached form substituted or unsubstituted ethylene glycol acetal, or substituted or unsubstituted propanediol acetal.

In the compound of formula III, Ar can be a phenyl or a phenyl substituted by $C_{1-4}$ alkyl (e.g. methyl, ethyl, n-propyl or isopropyl) at the para-position, for example Ar can be phenyl, para-methylphenyl or para-ethylphenyl.

In the compound of formula III, $R^1$ and $R^2$ can be each independently $C_{1-5}$ alkoxy (e.g. $C_{1-3}$ alkoxy, e.g. methoxy, ethoxy, n-propoxy or isopropoxy), or $R^1$ and $R^2$ together with the carbon to which they are attached can form 5-7 membered cyclic acetal (5-membered cyclic acetal such as

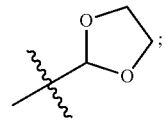 [SMILES: *C1OCCO1];

6-membered cyclic acetal such as

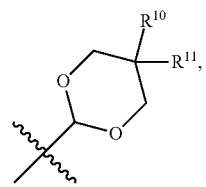, wherein $R^{10}$ and $R^{11}$ are each independently hydrogen or $C_{1-3}$ alkyl (e.g. methyl), provided that $R^{10}$ and $R^{11}$ are not both hydrogen) or 5-7 membered cyclic thioacetal (e.g.

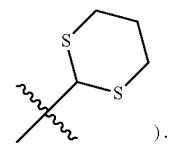 [SMILES: *C1SCCCS1]).

Preferably, $R^1$ and $R^2$ together with the carbon atom to which they are attached form ethylene glycol acetal or propanediol acetal.

The compound of formula III can be selected from the group consisting of:

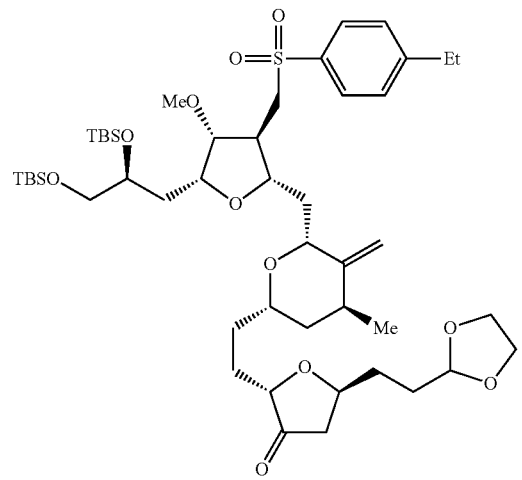

7
-continued
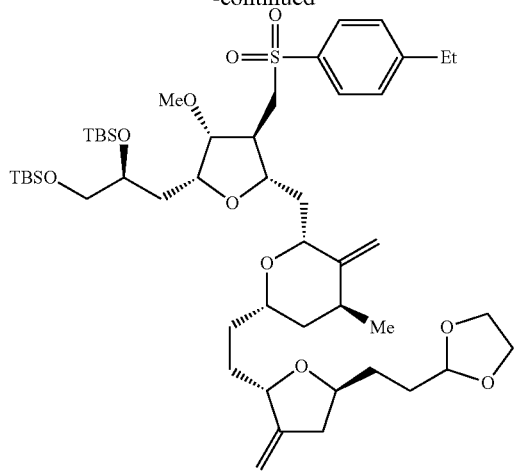
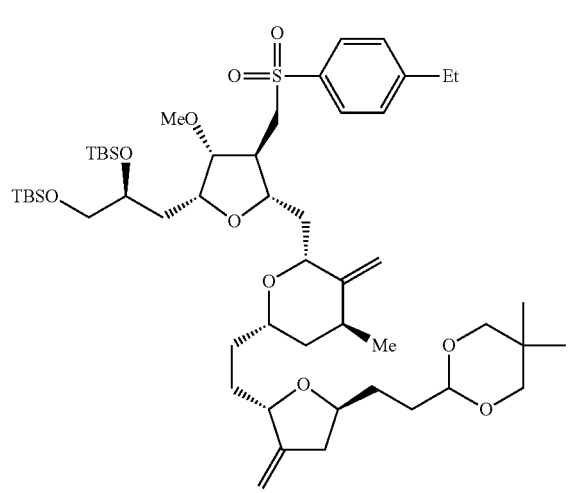
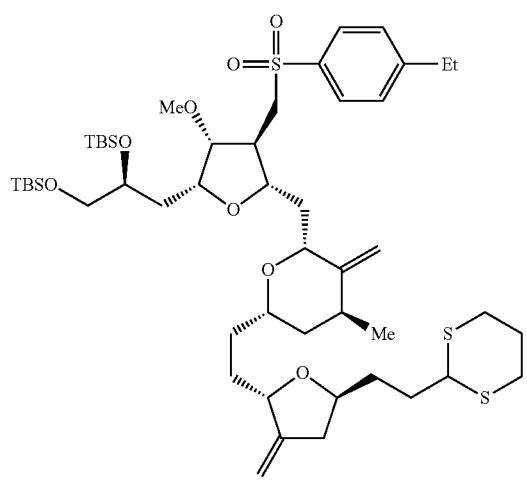
8
-continued
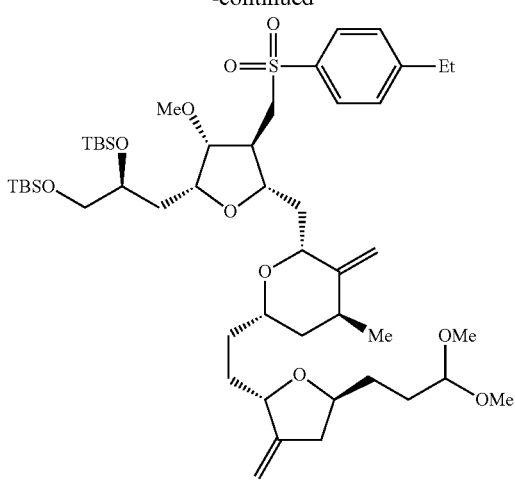
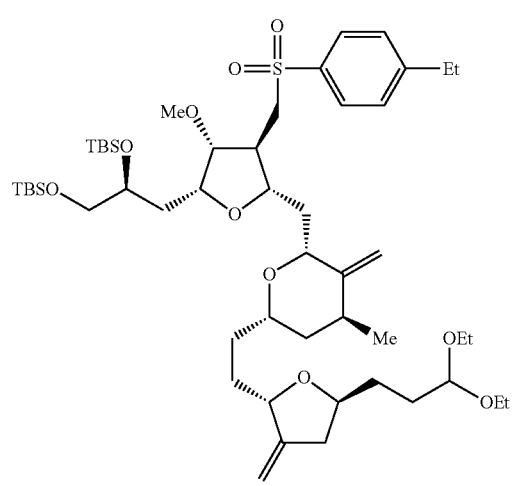
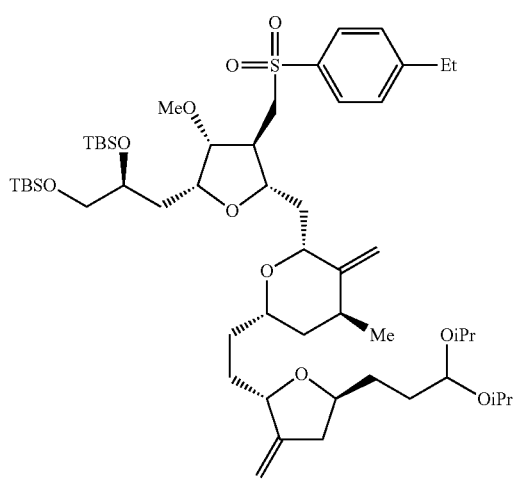

-continued

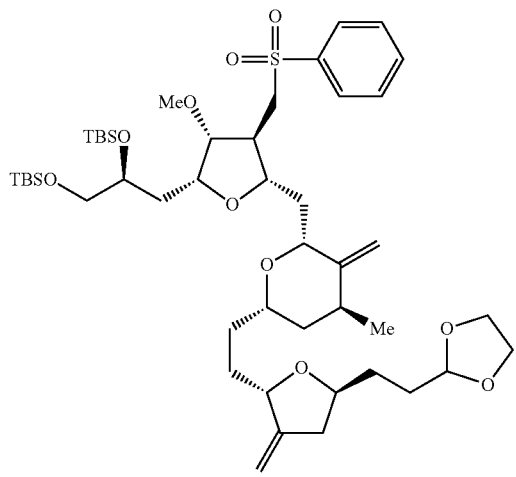

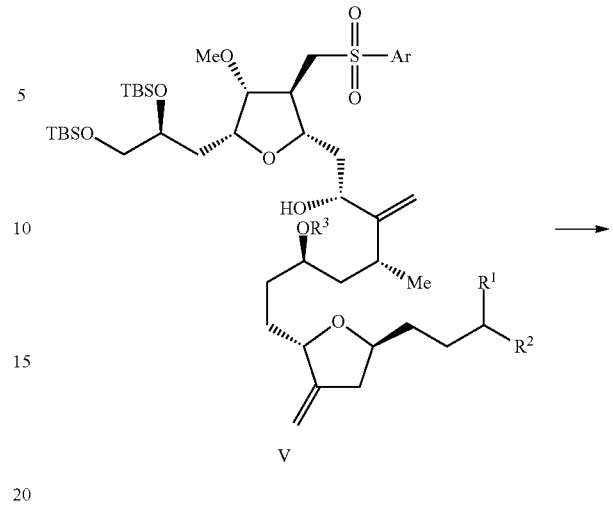

V

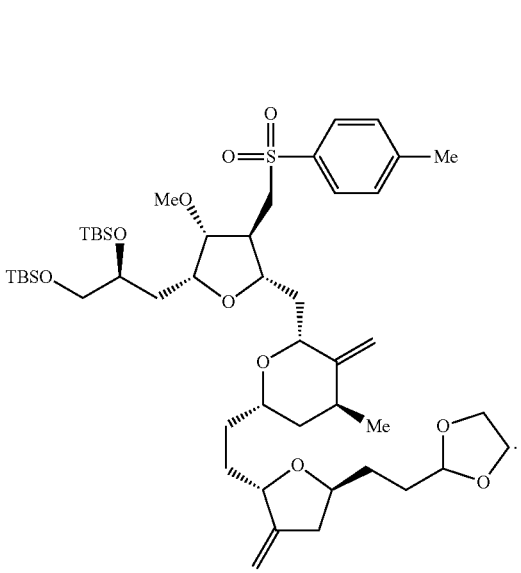

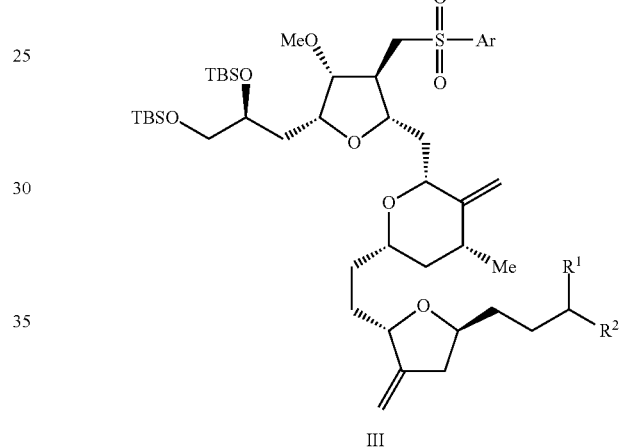

III wherein Ar, $R^1$ and $R^2$ are as defined in the compound of formula III;

$R^3$ is hydrogen or hydroxyl protecting group, preferably methylsulfonyl, p-toluenesulfonyl or trifluoromethanesulfonyl.

In the preparation method (method A) of the compound of formula III, $R^3$ can be methylsulfonyl.

In the preparation method (method A) of the compound of formula III, the intramolecular cyclization reaction can be conducted in an organic solvent. The organic solvent can be conventional solvent(s) for such reactions in the art, for example the organic solvent can be one or more solvents selected from the group consisting of $C_6$-$C_{10}$ alkane solvent (e.g. hexane, heptane), arene solvent (e.g. toluene), ether solvent (e.g. THF (i.e. tetrahydrofuran), 2-methyltetrahydrofuran, MTBE (i.e. methyl t-butyl ether)) and ester solvent (e.g. t-butyl acetate, isopropyl acetate). The amount of the organic solvent can be a conventional amount for such reactions in the art. For example, the molar concentration of the compound of formula V in the organic solvent can be 0.001-5 mol/L.

In the preparation method (method A) of the compound of formula III, the base in the basic condition can be one or more bases selected from the group consisting of NaH, In a preferred embodiment of the disclosure, in the compound of formula III, Ar is preferably phenyl, para-methylphenyl or para-ethylphenyl; $R^1$ and $R^2$ together with the carbon atom to which they are attached form ethylene glycol acetal or propanediol acetal.

The present disclosure also provides a preparation method (method A) of the compound of formula III, comprising conducting an intramolecular cyclization reaction of the compound of formula V to give the compound of formula III; wherein the intramolecular cyclization reaction is preferably conducted under a basic condition;

t-BuOK, t-BuONa, BuLi, LDA, LiHMDS, KHMDS and NaHMDS. The amount of the base can be a conventional amount for such reactions in the art. For example, the molar ratio of the base to the compound of formula V can be 1-10:1.

In the preparation method (method A) of the compound of formula III, the progress of the intramolecular cyclization reaction can be monitored by ordinary analysis methods in the art (e.g. TLC, HPLC, GC or NMR, preferably TLC). Generally, it is deemed as the completion of the reaction when there is no longer any transformation of the compound of formula V.

In the preparation method (method A) of the compound of formula III, the temperature of the intramolecular cyclization reaction can be a conventional reaction temperature for such reactions in the art, for example, −30-30° C.

In a preferred embodiment of the disclosure, the preparation method (method A) of the compound of formula III can comprise the following steps:

adding a base to a solution of the compound of formula V in an organic solvent at −30-30° C., and stirring at this condition for 10 min to 6 h; after completion of the reaction is indicated by TLC, quenching the reaction with saturated NH₄Cl aqueous solution; extracting the mixture with ethyl acetate, concentrating, and isolating the compound of formula III.

In the preferred embodiment of the preparation method (method A) of the compound of formula III, the organic solvent is preferably one or more solvents selected from the group consisting of toluene, hexane, heptane, THF, 2-methyltetrahydrofuran, MTBE, t-butyl acetate and isopropyl acetate.

In the preferred embodiment of the preparation method (method A) of the compound of formula III, the base is one or more bases selected from the group consisting of NaH, t-BuOK, t-BuONa, BuLi, LDA, LiHMDS, KHMDS and NaHMDS.

The present disclosure also provides a preparation method (method B) of the compound of formula III, comprising conducting an intramolecular cyclization reaction of the compound of formula VA; wherein the intramolecular cyclization reaction is preferably conducted in the presence of a Lewis acid and a Lewis base:

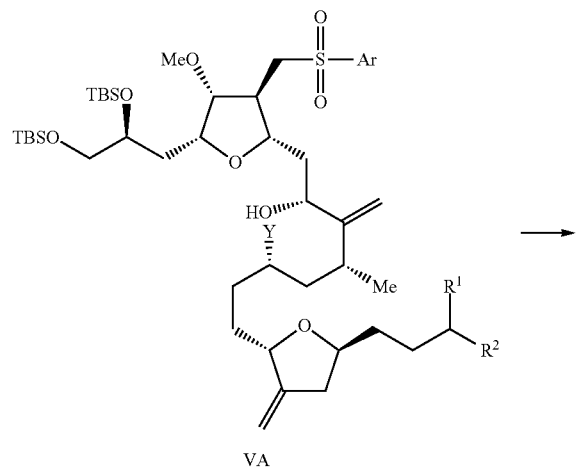

VA

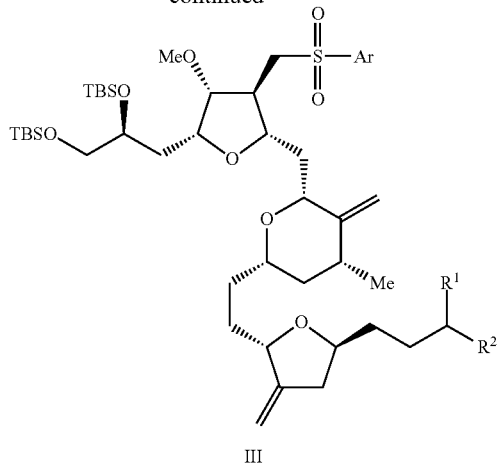

III wherein Ar, $R^1$ and $R^2$ are as defined in the compound of formula III;

Y is halogen, preferably chloride, bromide or iodide.

In the preparation method (method B) of the compound of formula III, Y can be chloride.

In the preparation method (method B) of the compound of formula III, the intramolecular cyclization reaction can be conducted in an organic solvent. The organic solvent can be conventional solvent(s) for such reactions in the art, for example the organic solvent can be one or more solvents selected from the group consisting of arene solvent (e.g. toluene), nitrile solvent (e.g. acetonitrile), ether solvent (e.g. THF) and ester solvent (e.g. ethyl acetate, t-butyl acetate, isopropyl acetate). The amount of the organic solvent can be a conventional amount for such reactions in the art. For example, the molar concentration of the compound of formula VA in the organic solvent can be 0.001-5 mol/L.

In the preparation method (method B) of the compound of formula III, the Lewis acid can be Ag₂O and/or silver salts, for example the Lewis acid can be one or more Lewis acids selected from the group consisting of Ag₂O, AgClO₄, AgOTf (i.e. silver trifluormethanesulfonate), AgBF₄ and AgPF₆ (e.g. Ag₂O, AgOTf, AgBF₄ or AgPF₆). The amount of the Lewis acid can be a conventional amount for such reactions in the art. For example, the molar ratio of the Lewis acid to the compound of formula VA can be 0.1-10:1.

In the preparation method (method B) of the compound of formula III, the Lewis base can be one or more Lewis bases selected from the group consisting of 2,6-di-tert-butyl-4-methylpyridine, 2,6-lutidine, 2,4,6-collidine and pyridine. The amount of the Lewis base can be a conventional amount for such reactions in the art. For example, the molar ratio of the Lewis base to the compound of formula VA can be 0.1-10:1.

In the preparation method (method B) of the compound of formula III, the progress of the intramolecular cyclization reaction can be monitored by ordinary analysis methods in the art (e.g. TLC, HPLC, GC or NMR, preferably TLC). Generally, it is deemed as the completion of the reaction when there is no longer any transformation of the compound of formula VA.

In the preparation method (method B) of the compound of formula III, the temperature of the intramolecular cyclization reaction can be a conventional reaction temperature for such reactions in the art, for example, 0-60° C.

In a preferred embodiment of the disclosure, the preparation method (method B) of the compound of formula III can comprise the following steps:

adding a Lewis acid and a Lewis base to an organic solution of the compound of formula VA at 0-60° C., and stirring at this condition for 6-48 h; after completion of the reaction is indicated by TLC, quenching the reaction with saturated NH$_4$Cl aqueous solution; extracting the mixture with ethyl acetate; concentrating and isolating the compound of formula III.

In the preferred embodiment of the preparation method (method B) of the compound of formula III, the organic solvent is preferably one or more solvents selected from the group consisting of toluene, THF, acetonitrile, ethyl acetate, isopropyl acetate and t-butyl acetate.

In the preferred embodiment of the preparation method (method B) of the compound of formula III, the Lewis acid is preferably one or more Lewis acids selected from the group consisting of Ag$_2$O, AgClO$_4$, AgOTf, AgBF$_4$ and AgPF$_6$ (e.g. Ag$_2$O, AgOTf, AgBF$_4$ or AgPF$_6$).

In the preferred embodiment of the preparation method (method B) of the compound of formula III, the Lewis base is preferably one or more Lewis bases selected from the group consisting of 2,6-di-tert-butyl-4-methylpyridine, 2,6-lutidine, 2,4,6-collidine and pyridine.

The present disclosure also provides a compound of formula V,

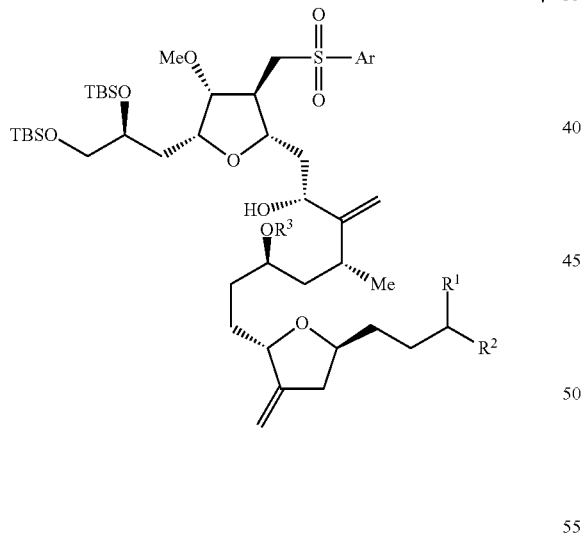

V wherein Ar, R$^1$ and R$^2$ are as defined in the compound of formula III;

R$^3$ is hydrogen or hydroxyl protecting group, preferably methylsulfonyl, p-toluenesulfonyl or trifluoromethanesulfonyl.

In the compound of formula V, R$^3$ can be methylsulfonyl.

In a preferred embodiment of the disclosure, in the compound of formula V, R$^1$ and R$^2$ together with the carbon atom to which they are attached form ethylene glycol acetal or propanediol acetal; Ar is phenyl, para-methylphenyl or para-ethylphenyl; R$^3$ is methylsulfonyl.

The compound of formula V can be selected from the group consisting of:

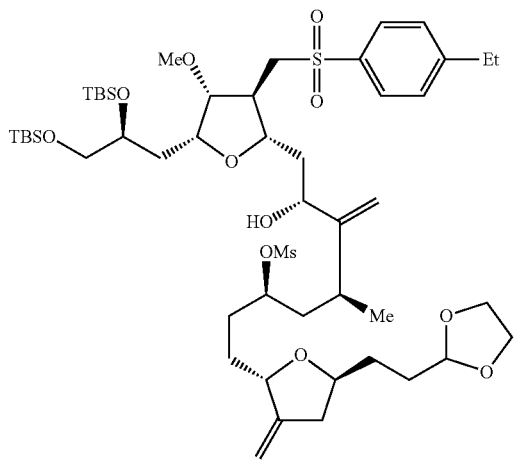

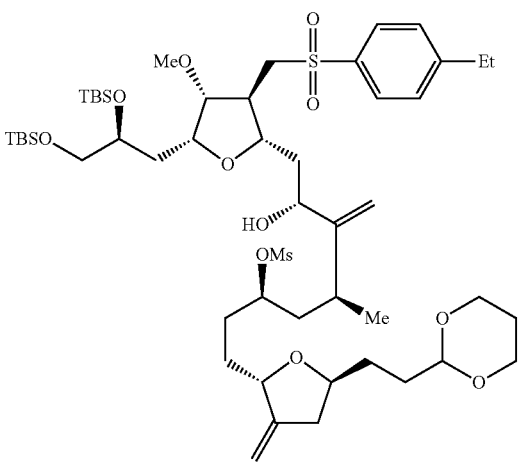

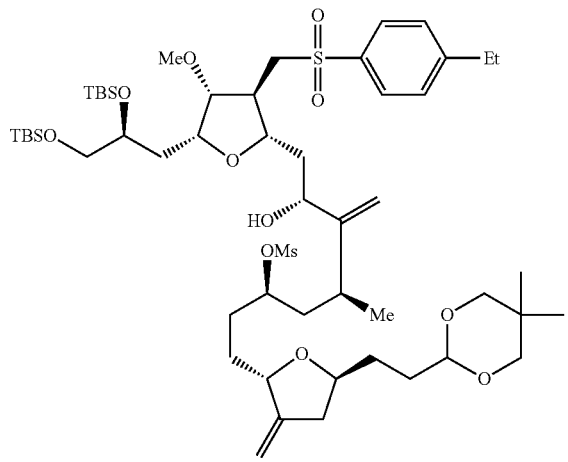

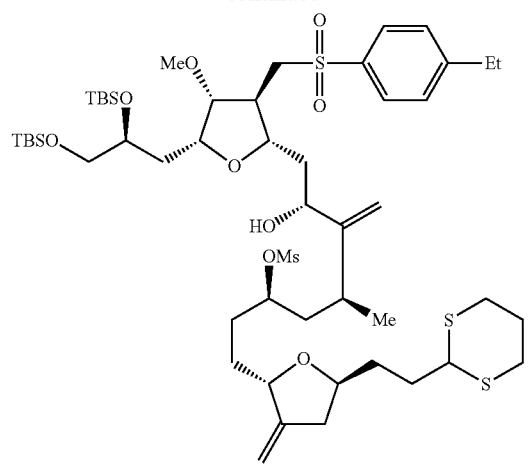
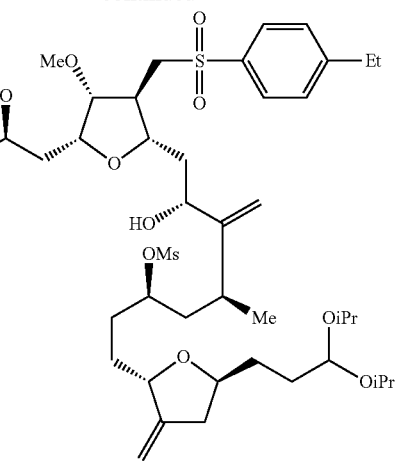
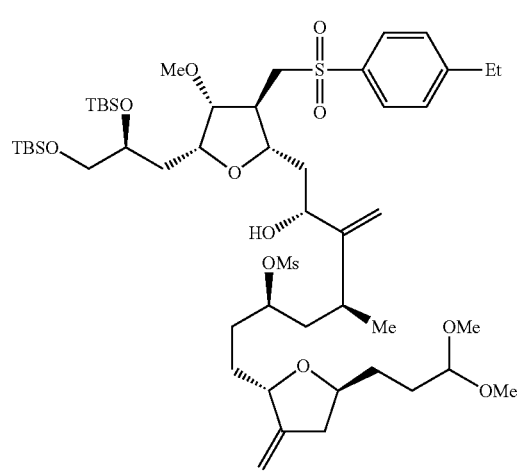
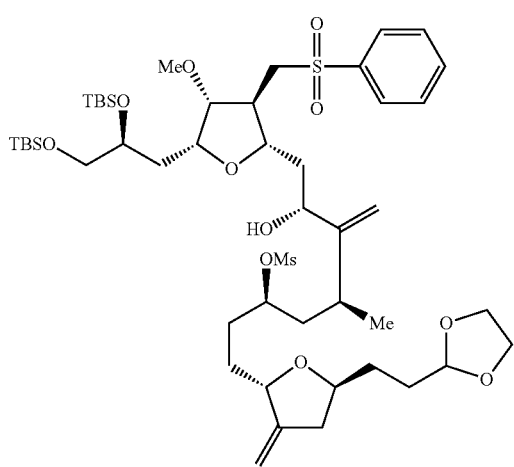
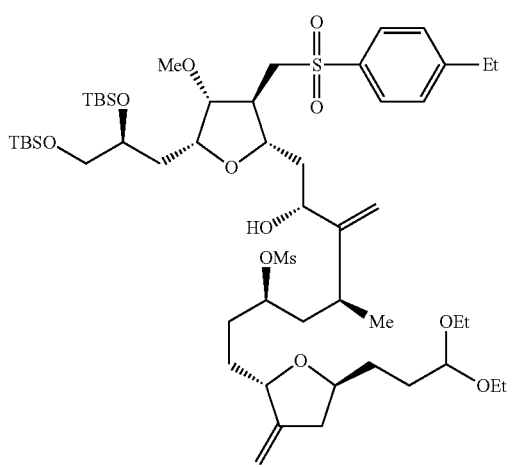
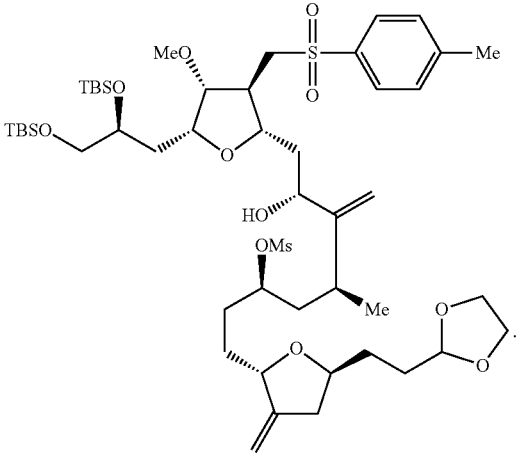

The present disclosure also provides a preparation method of the compound of formula V, comprising conducting a NHK reaction of the compound of formula VI and the compound of formula VII to give the compound of formula V:

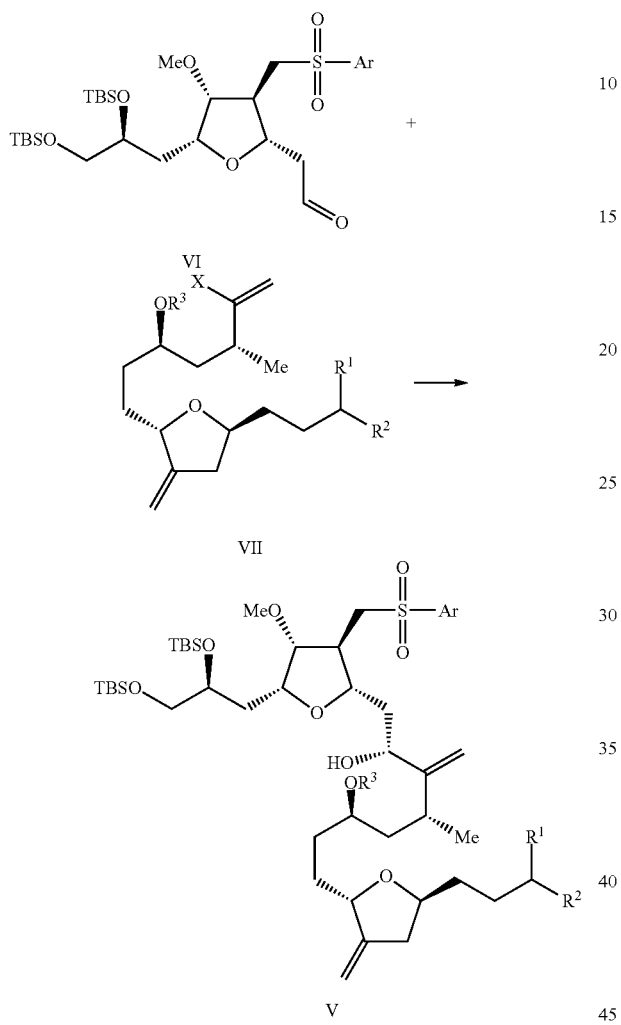

wherein Ar, $R^1$, $R^2$ and $R^3$ are as defined in the compound of formula V;

X is halogen or a leaving group, preferably chloride, bromide, iodide or trifluoromethanesulfonyloxy.

In the preparation method of the compound of formula V, X can be chloride, bromide or iodide. X can also be iodide.

In the preparation method of the compound of formula V, the NHK reaction can be conducted in an organic solvent. The organic solvent can be a conventional solvent for such reactions in the art, for example the organic solvent can be one or more solvents selected from the group consisting of ester solvent (e.g. ethyl acetate), nitrile solvent (e.g. acetonitrile), ether solvent (e.g. MTBE, THF, 2-methyltetrahydrofuran), sulfoxide solvent (e.g. DMSO) and haloalkane solvent (e.g. chloroalkane solvent, for example, DCM). The amount of the organic solvent can be a conventional amount for such reactions in the art. For example, the molar concentration of the compound of formula VII in the organic solvent can be 0.01-5 mol/L.

In the preparation method of the compound of formula V, the NHK reaction can be conducted in the presence of a halogenated chromium salt and/or a halogenated nickel salt. The halogenated chromium salt can be a chlorinated chromium salt (e.g. $CrCl_2$, $CrCl_3$). The halogenated nickel salt can be a chlorinated nickel salt (e.g. $NiCl_2$). The amount of the halogenated chromium salt and the halogenated nickel salt can be a conventional amount for such reactions in the art. For example, the molar ratio of the halogenated chromium salt to the compound of formula VII can be 0.01-10:1. The molar ratio of the halogenated nickel salt to the compound of formula VII can be 0.0001-10:1

In the preparation method of the compound of formula V, the NHK reaction can be conducted in the presence of a base. The base can be one or more bases selected from the group consisting of $Et_3N$, pyridine, 2,6-lutidine, 2,4,6-collidine, proton sponge and DIPEA (i.e. N,N-diisopropylethylamine). The amount of the base can be a conventional amount for such reactions in the art. For example, the molar ratio of the base to the compound of formula VII can be 1-20:1.

In the preparation method of the compound of formula V, the molar ratio of the compound of formula VII to the compound of formula VI can be 0.1-10:1.

In the preparation method of the compound of formula V, the NHK reaction can be conducted in the presence of a ligand. The ligand can be a conventional ligand for such reactions in the art, for example, the ligand can be

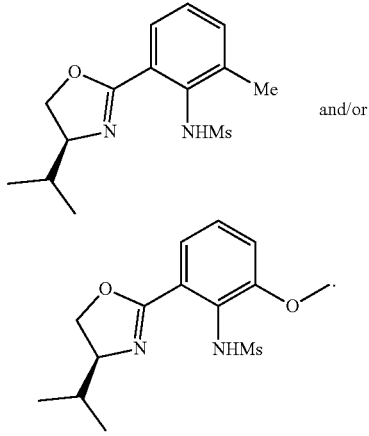

The amount of the ligand can be a conventional amount for such reactions in the art. For example, the molar ratio of the ligand to the compound of formula VII can be 0.1-10:1.

In the preparation method of the compound of formula V, the progress of the NHK reaction can be monitored by ordinary analysis methods in the art (e.g. TLC, HPLC, GC or NMR, preferably TLC). Generally, it is deemed as the completion of the reaction when there is no longer any transformation of the compound of formula VII.

In the preparation method of the compound of formula V, the temperature of the NHK reaction can be a conventional reaction temperature for such reactions in the art, for example, 0-60° C.

In a preferred embodiment of the disclosure, the preparation method of the compound of formula V can comprise the following steps:

adding the compound of formula VI, the compound of formula VII, a ligand, $CrCl_2$ (or $CrCl_3$) and $NiCl_2$ to a reaction flask, dissolving with an organic solvent and a base; stirring the reaction system at 0-60° C. under an oil bath for 2-48 h; after completion of the reaction is indicated by TLC, quenching the reaction with saturated NaHCO₃ aqueous solution, extracting with ethyl acetate, concentrating, and isolating the compound of formula V, or using the compound of formula V directly for the next step without purification.

In the preferred embodiment of the preparation method of the compound of formula V, the organic solvent is preferably one or more solvents selected from the group consisting of ethyl acetate, acetonitrile, MTBE, THF, DMSO, 2-methyltetrahydrofuran and DCM.

In the preferred embodiment of the preparation method of the compound of formula V, the base is preferably one or more bases selected from the group consisting of Et₃N, pyridine, 2,6-lutidine, 2,4,6-collidine, proton sponge and DIPEA.

In the preferred embodiment of the preparation method of the compound of formula V, the ligand can be

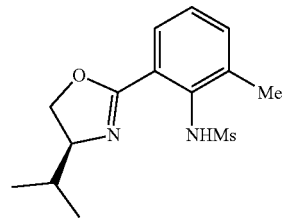

and/or

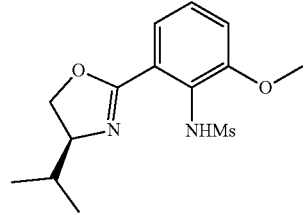

The present disclosure also provides a compound of formula VA,

VA

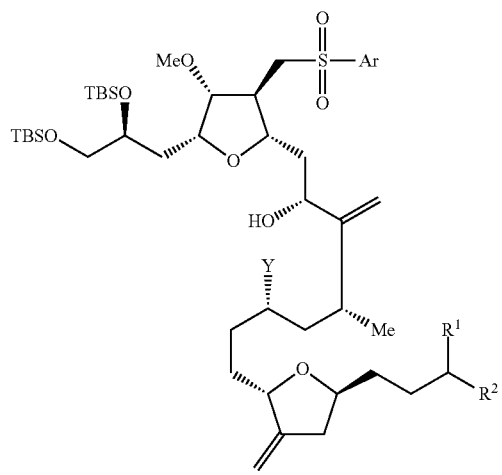

wherein Ar, R¹ and R² are as defined in the compound of formula III;
Y is halogen, preferably chloride, bromide or iodide.
In the compound of formula VA, Y can be chloride.
In a preferred embodiment of the disclosure, in the compound of formula VA, R¹ and R² together with the carbon atom to which they are attached form ethylene glycol acetal or propanediol acetal; Ar is phenyl, para-methylphenyl or para-ethylphenyl; Y is chloride.

The compound of formula VA can be selected from the group consisting of:

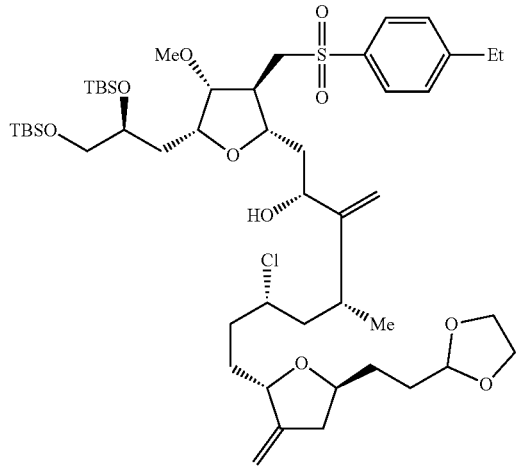

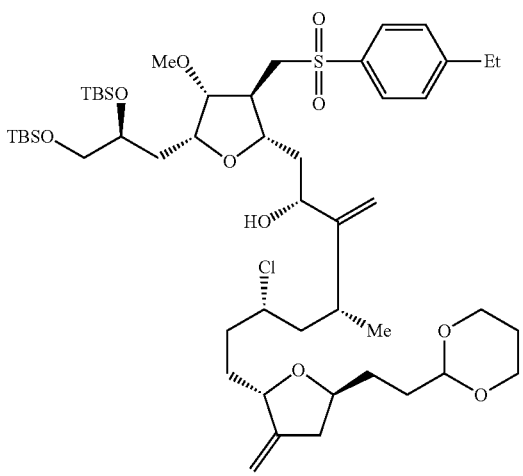 [SMILES: C=C([C@H](C)C[C@@H](Cl)CC[C@@H]1O[C@@H](CCC2OCCO2)CC1=C)[C@H](O)C[C@@H]1O[C@H](C[C@@H](CO[Si](C)(C)C(C)(C)C)O[Si](C)(C)C(C)(C)C)[C@H](OC)[C@H]1CS(=O)(=O)c1ccc(C)cc1]

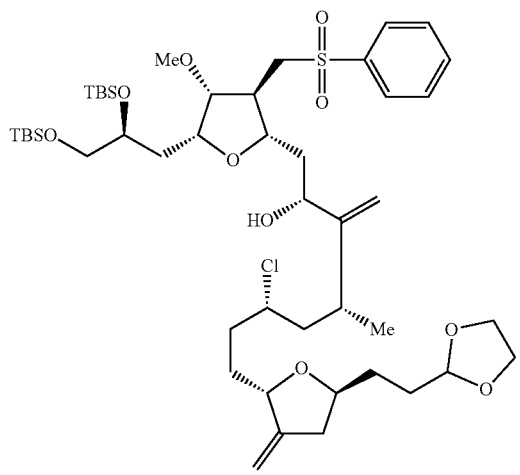

-continued

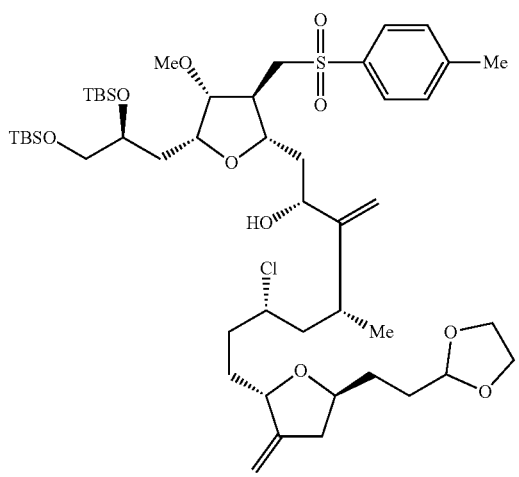

The present disclosure also provides a preparation method of the compound of formula VA, comprising conducting a NHK reaction of the compound of formula VI and the compound of formula VIIA to give the compound of formula VA:

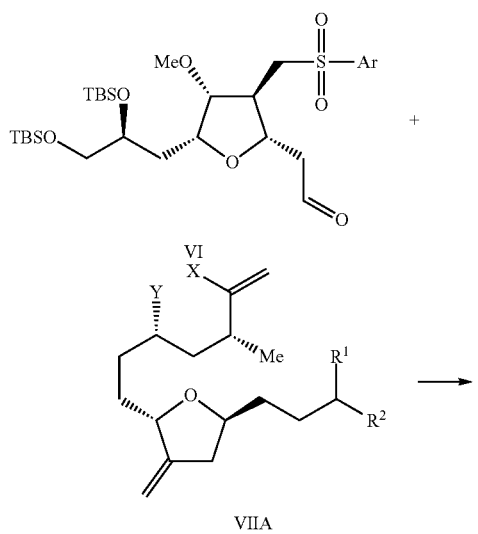

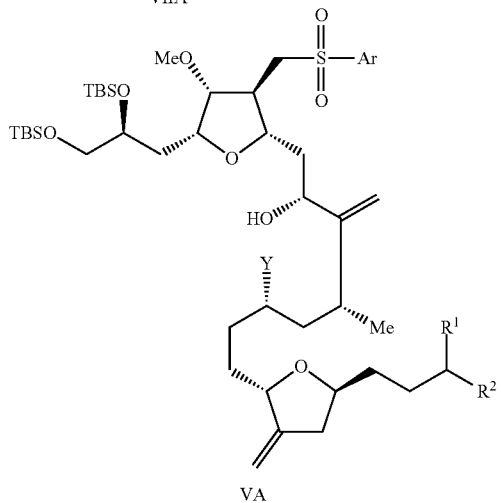

wherein Ar, $R^1$, $R^2$ and Y are as defined in the compound of formula VA;

X is halogen or a leaving group, preferably chloride, bromide, iodide or trifluoromethanesulfonyloxy.

In the preparation method of the compound of formula VA, X can be chloride, bromide or iodide. X can also be iodide.

In the preparation method of the compound of formula VA, the NHK reaction can be conducted in an organic solvent. The organic solvent can be a conventional solvent for such reactions in the art, for example the organic solvent can be one or more solvents selected from the group consisting of ester solvent (e.g. ethyl acetate), nitrile solvent (e.g. acetonitrile), ether solvent (e.g. MTBE, THF, 2-methyltetrahydrofuran), sulfoxide solvent (e.g. DMSO) and haloalkane solvent (e.g. chloroalkane solvent, for example, DCM). The amount of the organic solvent can be a conventional amount for such reactions in the art. For example, the molar concentration of the compound of formula VIIA in the organic solvent can be 0.01-5 mol/L.

In the preparation method of the compound of formula VA, the NHK reaction can be conducted in the presence of a halogenated chromium salt and/or a halogenated nickel salt. The halogenated chromium salt can be a chlorinated chromium salt (e.g. $CrCl_2$, $CrCl_3$). The halogenated nickel salt can be a chlorinated nickel salt (e.g. $NiCl_2$). The amount of the halogenated chromium salt and the halogenated nickel salt can be a conventional amount for such reactions in the art. For example, the molar ratio of the halogenated chromium salt to the compound of formula VIIA can be 0.01-10:1. The molar ratio of the halogenated nickel salt to the compound of formula VIIA can be 0.0001-10:1

In the preparation method of the compound of formula VA, the molar ratio of the compound of formula VIIA to the compound of formula VI can be 0.1-10:1

In the preparation method of the compound of formula VA, the NHK reaction can be conducted in the presence of a base. The base can be one or more bases selected from the group consisting of $Et_3N$, pyridine, 2,6-lutidine, 2,4,6-collidine, proton sponge and DIPEA. The amount of the base can be a conventional amount for such reactions in the art. For example, the molar ratio of the base to the compound of formula VIIA can be 1-20:1.

In the preparation method of the compound of formula VA, the NHK reaction can be conducted in the presence of a ligand. The ligand can be the a conventional ligand for such reactions in the art, for example the ligand can be

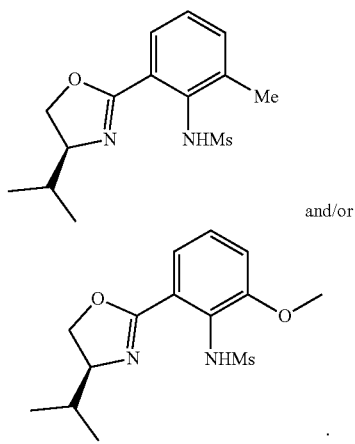

and/or

The amount of the ligand can be a conventional amount for such reactions in the art. For example, the molar ratio of the ligand to the compound of formula VIIA can be 0.1-10:1.

In the preparation method of the compound of formula VA, the progress of the NHK reaction can be monitored by ordinary analysis methods in the art (e.g. TLC, HPLC, GC or NMR, preferably TLC). Generally, it is deemed as the completion of the reaction when there is no longer any transformation of compound of formula VIIA.

In the preparation method of the compound of formula VA, the temperature of the NHK reaction can be a conventional reaction temperature for such reactions in the art, for example, 0-60° C.

In a preferred embodiment of the disclosure, the preparation method of the compound of formula VA can comprise the following steps:

adding the compound of formula VI, the compound of formula VIIA, a ligand, $CrCl_2$ (or $CrCl_3$) and $NiCl_2$ to a reaction flask, dissolving with an organic solvent and a base, stirring the reaction system at 0-60° C. under an oil bath for 2-48 h; after completion of the reaction is indicated by TLC, quenching the reaction with saturated $NaHCO_3$ aqueous solution; extracting with ethyl acetate, concentrating, and isolating the compound of formula VA, or using the compound of formula VA directly for the next step without purification.

In the preferred embodiment of the preparation method of the compound of formula VA, the organic solvent is preferably one or more solvents selected from the group consisting of ethyl acetate, acetonitrile, MTBE, THF, DMSO, 2-methyltetrahydrofuran and DCM.

In the preferred embodiment of the preparation method of the compound of formula VA, the base is preferably one or more bases selected from the group consisting of $Et_3N$, pyridine, 2,6-lutidine, 2,4,6-collidine, proton sponge and DIPEA.

In the preferred embodiment of the preparation method of the compound of formula VA, the ligand can be

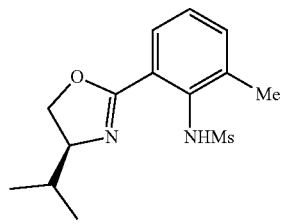

and/or

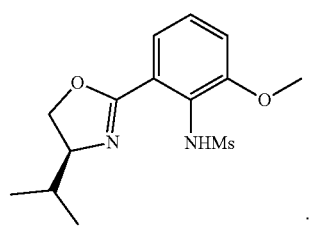

The present disclosure also provides a compound of formula VII,

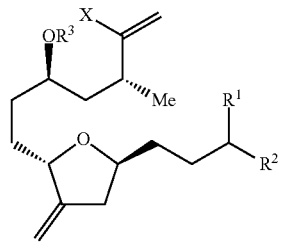

wherein $R^1$, $R^2$ and $R^3$ are as defined in the compound of formula V;

X is halogen or a leaving group, preferably chloride, bromide, iodide or trifluoromethanesulfonyloxy.

In the preparation method of the compound of formula VII, X can be chloride, bromide or iodide, for example X can be iodide.

In a preferred embodiment of the disclosure, in the compound of formula VII, $R^1$ and $R^2$ together with the carbon atom to which they are attached form ethylene glycol acetal or propanediol acetal; $R^3$ is methanesulfonyl; X is iodide.

The compound of formula VII can be selected from the group consisting of:

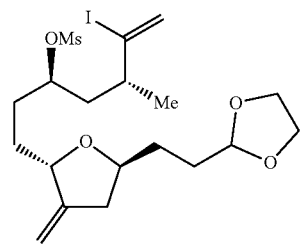

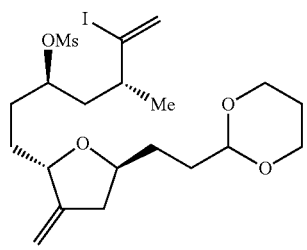

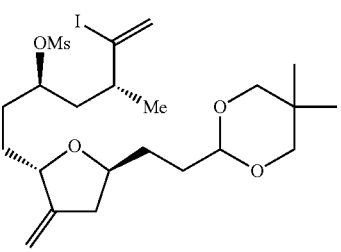

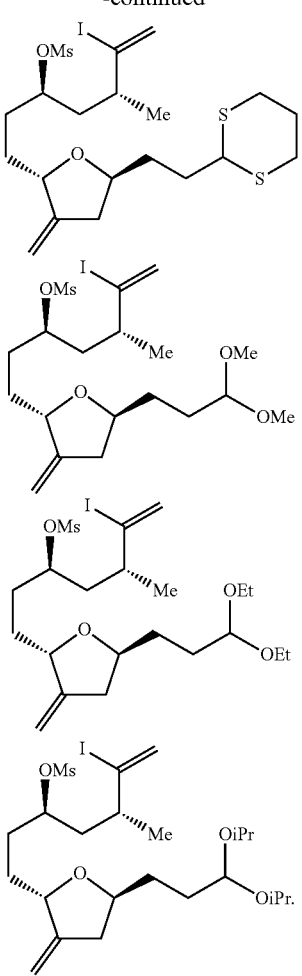

The present disclosure also provides a preparation method of the compound of formula VII, comprising conducting a hydroxyl protecting reaction of the compound of formula VIII to give the compound of formula VII:

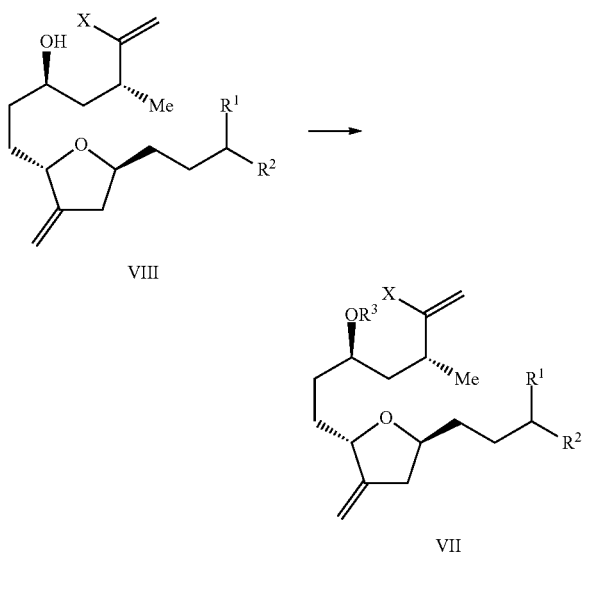

wherein $R^1$, $R^2$, $R^3$ and X are as defined in the compound of formula VII, and $R^3$ is not hydrogen.

In the preparation method of the compound of formula VII, the hydroxyl protecting reaction can be conducted in an organic solvent. The organic solvent can be a conventional solvent for such reactions in the art, for example the organic solvent can be one or more solvents selected from the group consisting of ester solvent (e.g. ethyl acetate), nitrile solvent (e.g. acetonitrile), arene solvent (e.g. toluene), ether solvent (e.g. THF, 2-methyltetrahydrofuran), amide solvent (e.g. DMF) and haloalkane solvent (e.g. chloroalkane solvent, for example, DCM). The amount of the organic solvent can be a conventional amount for such reactions in the art. For example, the molar concentration of the compound of formula VIII in the organic solvent can be 0.01-5 mol/L.

In the preparation method of the compound of formula VII, the hydroxyl protecting reaction can be conducted in the presence of a base. The base can be one or more bases selected from the group consisting of $Et_3N$, pyridine, 2,6-lutidine, 2,4,6-collidine and DIPEA. The amount of the base can be a conventional amount for such reactions in the art. For example, the molar ratio of the base to the compound of formula VIII can be 1-20:1.

In the preparation method of the compound of formula VII, the hydroxyl protecting reaction can be conducted in the presence of a sulfonylation reagent. The sulfonylation reagent can be selected from the group consisting of MsCl, $Ms_2O$, TsCl (i.e. p-toluenesulfonyl chloride), $Ts_2O$ (i.e. p-toluenesulfonic anhydride) or $Tf_2O$ (i.e. trifluoromethanesulfonic anhydride), for example the sulfonylation reagent can be MsCl or $Ms_2O$. The amount of the sulfonylation reagent can be a conventional amount for such reactions in the art. For example, the molar ratio of the sulfonylation reagent to the compound of formula VIII can be 1-10:1.

In the preparation method of the compound of formula VII, the progress of the hydroxyl protecting reaction can be monitored by ordinary analysis methods in the art (e.g. TLC, HPLC, GC or NMR, preferably TLC). Generally, it is deemed as the completion of the reaction when there is no longer any transformation of compound of formula VIII.

In the preparation method of the compound of formula VII, the temperature of the hydroxyl protecting reaction can be a conventional reaction temperature for such reactions in the art, for example, −40-50° C., for example −10-20° C.

In a preferred embodiment of the disclosure, the preparation method of the compound of formula VII can comprise the following steps:

adding a base to an organic solution of the compound of formula VIII at −30-40° C., then adding a sulfonylation reagent slowly; after completion of the addition, stirring the reaction system at such condition for 15 min-6 h; after completion of the reaction is indicated by TLC, quenching the reaction with saturated $NaHCO_3$ aqueous solution, extracting with ethyl acetate, concentrating, and isolating the compound of formula VII.

In the preferred embodiment of the preparation method of the compound of formula VII, the organic solvent is preferably one or more solvent(s) selected from the group consisting of ethyl acetate, acetonitrile, toluene, THF, 2-methyltetrahydrofuran, DMF and DCM.

In the preferred embodiment of the preparation method of the compound of formula VII, the base is preferably one or more bases selected from the group consisting of $Et_3N$, pyridine, 2,6-lutidine, 2,4,6-collidine and DIPEA.

In the preferred embodiment of the preparation method of the compound of formula VII, the sulfonylation reagent is preferably selected from the group consisting of MsCl, Ms$_2$O, TsCl, Ts$_2$O or Tf$_2$O.

The present disclosure also provides a compound of formula VIIA,

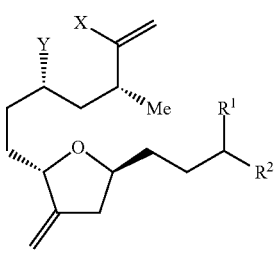

VIIA wherein R$^1$, R$^2$ and X are as defined in the compound of formula VII;

Y is halogen, preferably chloride, bromide or iodide.

In the compound of formula VIIA, Y can be chloride.

In a preferred embodiment of the disclosure, in the compound of formula VIIA, R$^1$ and R$^2$ together with the carbon atom to which they are attached form ethylene glycol acetal or propanediol acetal; X is iodide; Y is chloride.

The compound of formula VIIA can be selected from the group consisting of:

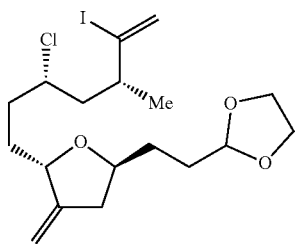

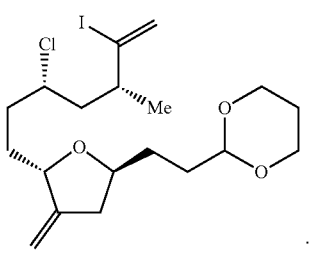

The present disclosure also provides a preparation method of the compound of formula VIIA, comprising conducting a substitution reaction of the compound of formula VII to give the compound of formula VIIA:

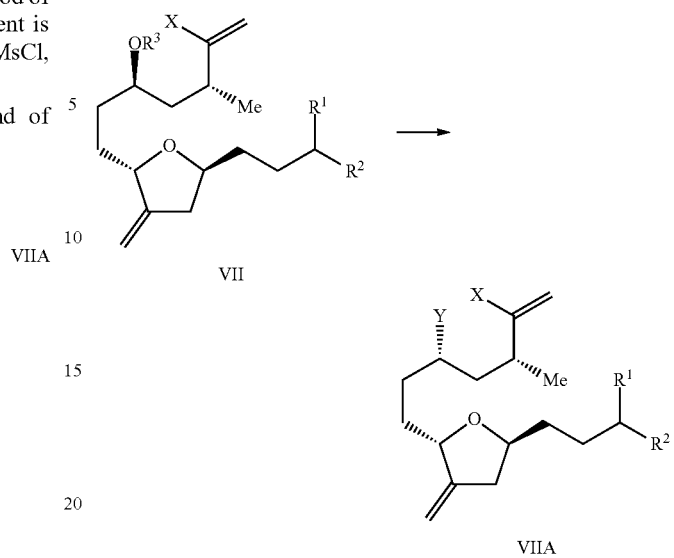

wherein R$^1$, R$^2$, X and Y are as defined in the compound of formula VIIA;

R$^3$ is hydrogen or a hydroxyl protecting group, preferably methanesulfonyl, p-toluenesulfonyl or trifluoromethanesulfonyl.

In the compound of formula VIIA, R$^3$ can be methanesulfonyl.

In the preparation method of the compound of formula VIIA, the substitution reaction can be conducted in an organic solvent. The organic solvent can be a conventional solvent for such reactions in the art, for example the organic solvent can be one or more solvents selected from the group consisting of ester solvent (e.g. ethyl acetate), nitrile solvent (e.g. acetonitrile), arene solvent (e.g. toluene), ether solvent (e.g. THF), amide solvent (e.g. DMF, DMPU (i.e. 1,3-dimethyl-3,4,5,6-tetrahydro-2(1H)-pyrimidinone)) and haloalkane solvent (e.g. chloroalkane solvent, for example, DCM). For example, the organic solvent can be DMF or DMPU. The amount of the organic solvent can be a conventional amount for such reactions in the art. For example, the molar concentration of the compound of formula VII in the organic solvent can be 0.01-5 mol/L.

In the preparation method of the compound of formula VIIA, the substitution reaction can be conducted in the presence of a halogenation reagent, wherein a chlorination reagent such as the group consisting of LiCl, NaCl, Bu$_3$NBnCl (i.e. tributylbenzylammonium chloride), NH$_4$Cl and Bu$_4$NCl (i.e. tetrabutylammonium chloride); a bromination reagent such as LiBr, NaBr, Bu$_3$NBnBr (i.e. tributylbenzylammonium bromide), NH$_4$Br and Bu$_4$NBr (i.e. tetrabutylammonium bromide); an iodination reagent such as LiI, NaI, Bu$_3$NBnI (i.e. tributylbenzylammonium iodide), NH$_4$I and Bu$_4$NI (i.e. tetrabutylammonium iodide). For example, the halogenation reagent can be Bu$_3$NBnCl or Bu$_4$NCl. The amount of the halogenation reagent can be a conventional amount for such reactions in the art. For example, the molar ratio of the halogenation reagent to the compound of formula VII can be (1-50):1.

In the preparation method of the compound of formula VIIA, the progress of the substitution reaction can be monitored by ordinary analysis methods in the art (e.g. TLC, HPLC, GC or NMR, preferably TLC). Generally, it is deemed as the completion of the reaction when there is no longer any transformation of compound of formula VII.

In the preparation method of the compound of formula VIIA, the temperature of the substitution reaction can be a conventional reaction temperature for such reactions in the art, for example, −40-80° C., for example −20-60° C.

In a preferred embodiment of the disclosure, the preparation method of the compound of formula VIIA can comprise the following steps:

adding a halogenation reagent to the an organic solution of the compound of formula VII at −20-60° C., stirring at such condition for 1-48 h. After completion of the reaction is indicated by TLC, quenching the reaction with water, extracting with ethyl acetate, concentrating and isolating the compound of formula VIIA.

In the preferred embodiment of the preparation method of the compound of formula VIIA, the organic solvent is preferably one or more solvents selected from the group consisting of ethyl acetate, acetonitrile, toluene, DCM, DMF, DMPU and THF (e.g. DMPU or DMF).

In the preferred embodiment of the preparation method of the compound of formula VIIA, the halogenation reagent is preferably selected from the group consisting of LiCl, NaCl, $Bu_3NBnCl$, $NH_4Cl$, $Bu_4NCl$, LiBr, NaBr, $Bu_3NBnBr$, $NH_4Br$, $Bu_4NBr$, LiI, NaI, $Bu_3NBnI$, $NH_4I$ or $Bu_4NI$ (e.g. $Bu_3NBnCl$ or $Bu_4NCl$).

The present disclosure also provides a compound of formula II,

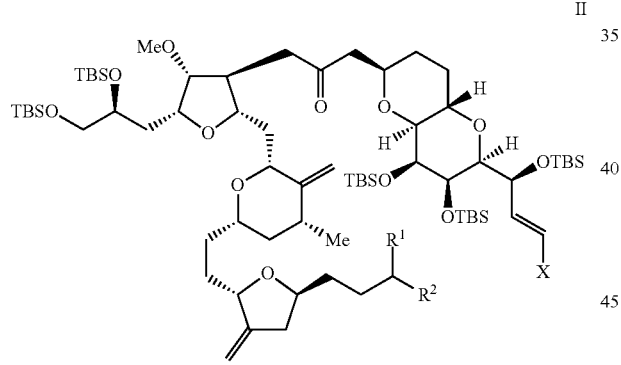

II wherein $R^1$ and $R^2$ are acetal or thioacetal protecting group, and $R^1$ and $R^2$ are each independently $C_{1-10}$ alkoxy or $C_{1-10}$ alkylthio, or $R^1$ and $R^2$ together with the carbon atom to which they are attached form cyclic acetal or cyclic thioacetal; preferably $R^1$ and $R^2$ together with the carbon atom to which they are attached form cyclic acetal or cyclic thioacetal, more preferably substituted or unsubstituted ethylene glycol acetal, or substituted or unsubstituted propanediol acetal;

X is halogen or a leaving group, preferably chloride, bromide, iodide or trifluoromethanesulfonyloxy.

In the compound of formula II, $R^1$ and $R^2$ can be each independently $C_{1-5}$ alkoxy (e.g. $C_{1-3}$ alkoxy, more preferably methoxy, ethoxy, n-propoxy or isopropoxy), or $R^1$ and $R^2$ can together with the carbon atom to which they are attached form 5-7 membered cyclic acetal (5-membered cyclic acetal such as

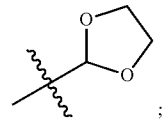 [SMILES: *C1OCCO1]

6-membered cyclic acetal such as

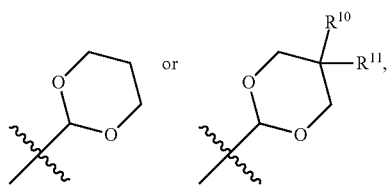

wherein $R^{10}$ and $R^{11}$ are each independently hydrogen or C1-3 alkyl (e.g. methyl), provided that $R^{10}$ and $R^{11}$ are not both hydrogen) or 5-7 membered cyclic thioacetal (e.g.

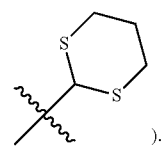

).

Preferably, $R^1$ and $R^2$ together with the carbon atom to which they are attached form substituted or unsubstituted ethylene glycol acetal, or substituted or unsubstituted propanediol acetal.

In the compound of formula II, X can be iodide.

In a preferred embodiment of the disclosure, in the compound of formula II, X is iodide; $R^1$ and $R^2$ together with the carbon atom to which they are attached form ethylene glycol acetal or propanediol acetal.

The compound of formula II can be selected from the group consisting of

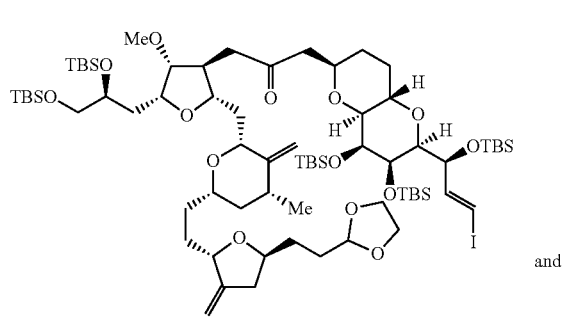

and

-continued

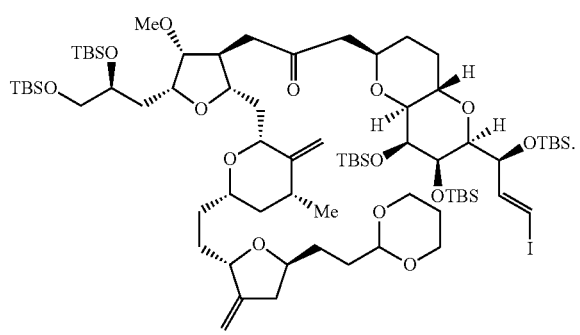

I

The present disclosure also provides a preparation method of the compound of formula II, comprising conducting a reductive elimination reaction of the compound of formula IX:

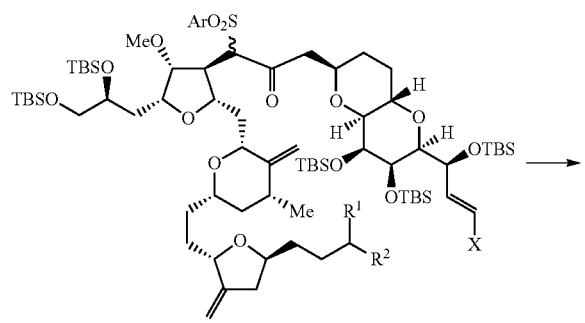

IX

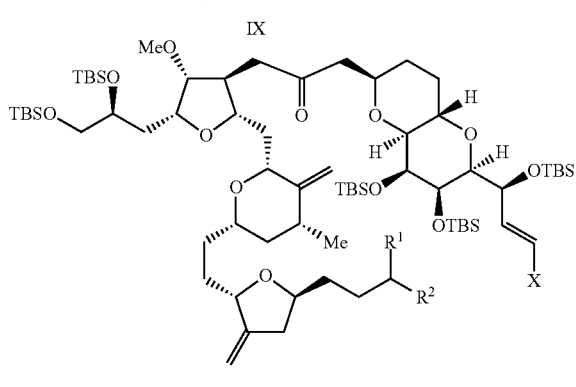

II wherein X, $R^1$ and $R^2$ are as defined in the compound of formula II;

Ar is an aryl substituted by $C_{1-10}$ alkyl or alkoxy, or an unsubstituted aryl, preferably a phenyl substituted by $C_{1-10}$ alkyl at para-position, or an unsubstituted phenyl.

In the preparation method of the compound of formula II, Ar can be a phenyl or a phenyl substituted by $C_{1-4}$ alkyl (e.g. methyl, ethyl, n-propyl or isopropyl) at para-position. Preferably, Ar is phenyl, para-methylphenyl or para-ethylphenyl.

In the preparation method of the compound of formula II, the reductive elimination reaction can be conducted in an organic solvent. The organic solvent can be a conventional solvent for such reactions in the art, for example, ether solvent (e.g. THF). The amount of the organic solvent can be a conventional amount for such reactions in the art. For example, the molar concentration of the compound of formula IX in the organic solvent can be 0.001-5 mol/L.

In the preparation method of the compound of formula II, the reductive elimination reaction can be conducted in the presence of a reductant. The reductant can be one or more reductants selected from the group consisting of $SmI_2$, $CrCl_2$, $CrCl_3$, Mn powder and Zn powder (e.g. $SmI_2$, $CrCl_2$—Mn powder or $CrCl_2$—Zn powder). The amount of the reductant can be a conventional amount for such reactions in the art. For example, the molar ratio of the reductant to the compound of formula IX can be 1-20:1.

In the preparation method of the compound of formula II, the progress of the reductive elimination reaction can be monitored by ordinary analysis methods in the art (e.g. TLC, HPLC, GC or NMR, preferably TLC). Generally, it is deemed as the completion of the reaction when there is no longer any transformation of compound of formula IX.

In the preparation method of the compound of formula II, the temperature of the reductive elimination reaction can be a conventional reaction temperature for such reactions in the art, for example, −78-30° C.

In a preferred embodiment of the disclosure, the preparation method of compound of formula II can comprise the following steps:

adding a reductant to a solution of the compound of formula IX in THF at −78-30° C., stirring at −78-30° C. for 10 min-12 h. After completion of the reaction is indicated by TLC, quenching the reaction with $K_2CO_3$ aqueous solution, extracting with ethyl acetate, concentrating, and isolating the compound of formula II.

In the preferred embodiment of the preparation method of the compound of formula II, the reductant is preferably one or more reductants selected from the group consisting of $SmI_2$, $CrCl_2$, $CrCl_3$, Mn powder and Zn powder (e.g. $SmI_2$, $CrCl_2$—Mn powder or $CrCl_2$—Zn powder).

The present disclosure also provides a preparation method (method M) of the compound of formula IV, comprising conducting a hydrolysis reaction of the compound of formula II to give the compound of formula IV:

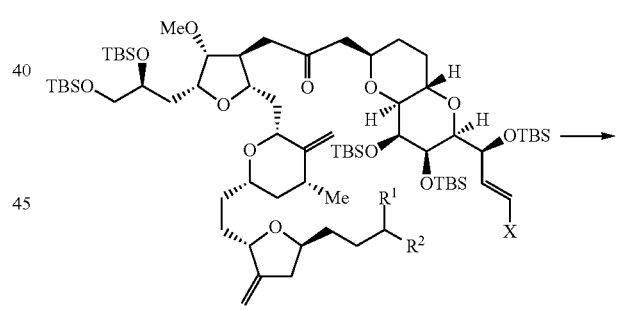

II

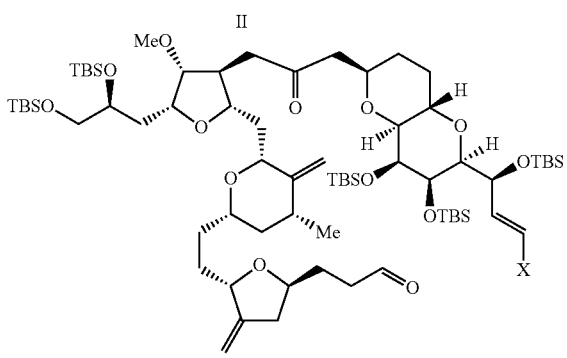

IV wherein X, $R^1$ and $R^2$ are as defined in the compound of formula II.

In the preparation method (method M) of eribulin intermediate of compound of formula IV, the hydrolysis reaction can be conducted in an organic solvent. The organic solvent can be a conventional solvent for such reactions in the art, for example, haloalkane solvent (e.g. chloroalkane solvent, for example, DCM). The amount of the organic solvent can be a conventional amount for such reactions in the art. For example, the molar concentration of the compound of formula II to the organic solvent can be 0.001-5 mol/L.

In the preparation method (method M) of eribulin intermediate of compound of formula IV, the hydrolysis reaction can be conducted in the presence of a hydrolysis reagent. The hydrolysis reagent can be one or more reagents selected from the group consisting of HCl, p-TsOH (i.e. p-toluenesulfonic acid), PPTS (i.e. pyridinium p-toluenesulfonate), $BF_3 \cdot OEt_2$ (i.e. boron trifluoride etherate), TMS OTf, $Ti(OiPr)_4$ (i.e. titanium tetraisopropanolate), $TiCl_4$, pyridine, 2,6-lutidine and 2,4,6-collidine (e.g. one or more reagents selected from the group consisting of 2,6-lutidine, pyridine and TMSOTf, for example 2,6-lutidine and TMSOTf, for example pyridine and TMSOTf). The amount of the hydrolysis reagent can be a conventional amount for such reactions in the art. For example, the molar ratio of the hydrolysis reagent to the compound of formula II can be 0.1-20:1.

In the preparation method (method M) of eribulin intermediate of compound of formula IV, the progress of the hydrolysis reaction can be monitored by ordinary analysis methods in the art (e.g. TLC, HPLC, GC or NMR, preferably TLC). Generally, it is deemed as the completion of the reaction when there is no longer any transformation of compound of formula II.

In the preparation method (method M) of eribulin intermediate of compound of formula IV, the temperature of the hydrolysis reaction can be a conventional reaction temperature for such reactions in the art, for example, −30-40° C.

In a preferred embodiment of the disclosure, the preparation method (method M) of eribulin intermediate of compound of formula IV can comprise the following steps:

adding a hydrolysis reagent to a solution of the compound of formula II in DCM at −30-40° C., stirring for 1-24 h. After completion of the reaction is indicated by TLC, quenching the reaction with 1 N HCl aqueous solution, extracting with ethyl acetate, concentrating, and isolating the compound of formula IV.

In the preferred embodiment of the preparation method (method M) of eribulin intermediate of the compound of formula IV, the hydrolysis reagent is preferably one or more reagents selected from the group consisting of HCl, p-TsOH, PPTS, $BF_3 \cdot OEt_2$, TMSOTf, $Ti(OiPr)_4$, $TiCl_4$, pyridine, 2,6-lutidine and 2,4,6-collidine (e.g. one or more reagents selected from the group consisting of 2,6-lutidine, pyridine and TMSOTf; for example 2,6-lutidine and TMSOTf; for example pyridine and TMSOTf).

The present disclosure also provides a compound of formula IX,

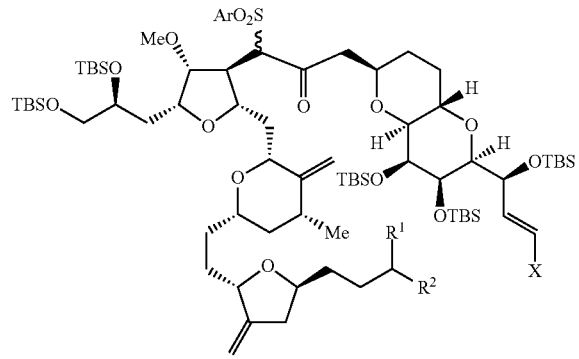

IX wherein X, $R^1$ and $R^2$ are as defined in the compound of formula II;

Ar is an aryl substituted by $C_{1-10}$ alkyl or alkoxy, or an unsubstituted aryl, preferably a phenyl substituted by $C_{1-10}$ alkyl at para-position or an unsubstituted phenyl.

In the compound of formula IX, Ar can be a phenyl or a phenyl substituted by $C_{1-4}$ alkyl (e.g. methyl, ethyl, n-propyl or isopropyl) at para-position; preferably phenyl, para-methylphenyl or para-ethylphenyl.

In a preferred embodiment of the disclosure, in the compound of formula IX, Ar is preferably phenyl, para-methylphenyl or para-ethylphenyl; $R^1$ and $R^2$ together with the carbon atom to which they are attached form ethylene glycol acetal or propanediol acetal; X is iodide.

The compound of formula IX can be selected from the group consisting of:

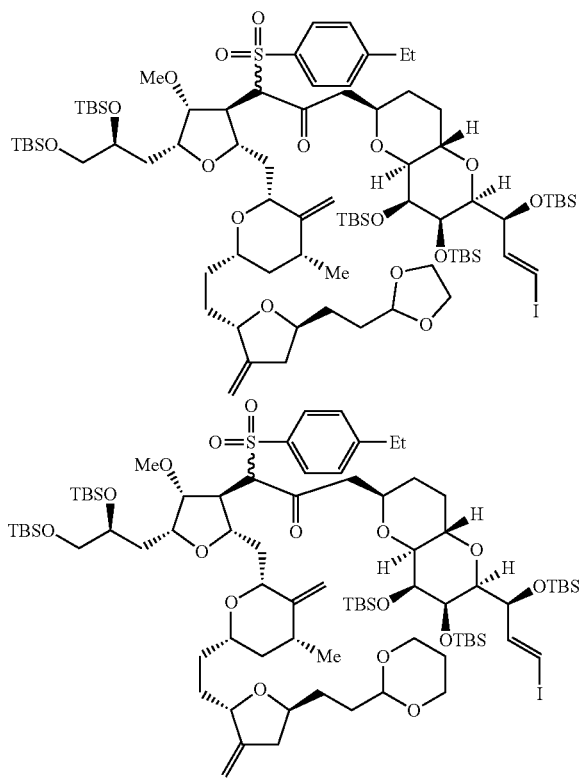

-continued

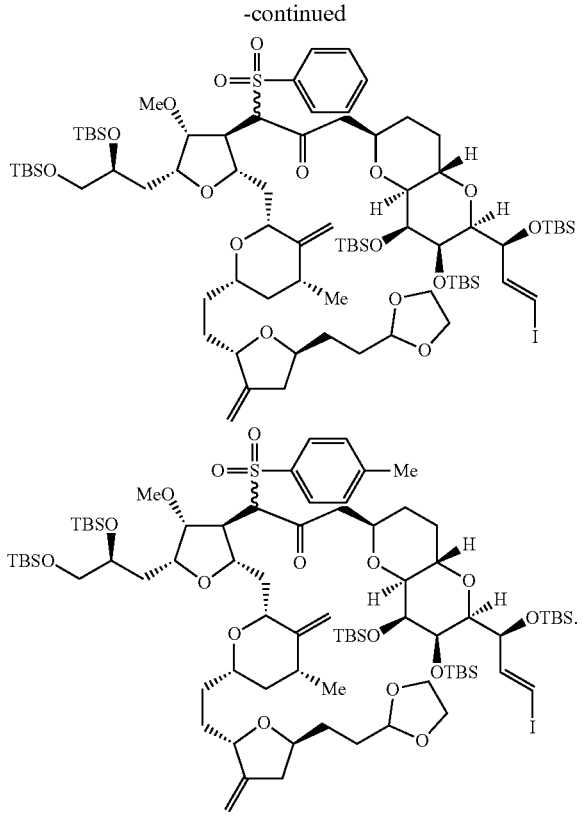

The present disclosure also provides a preparation method of the compound of formula IX, comprising conducting an oxidation reaction of the compound of formula X to give the compound of formula IX:

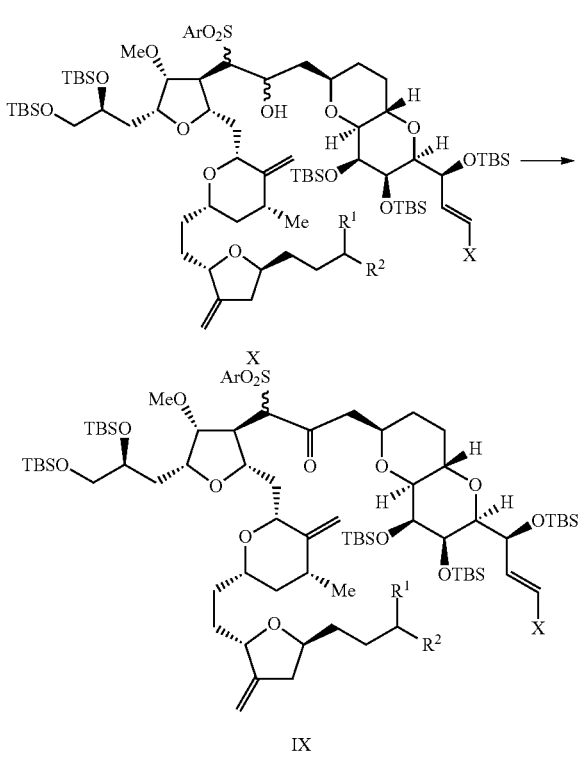

wherein Ar, X, R$^1$ and R$^2$ are as defined in the compound of formula IX.

In the preparation method of the compound of formula IX, the oxidation reaction can be conducted in an organic solvent. The organic solvent can be a conventional solvent for such reactions in the art, for example, chloroalkane solvent (e.g. chloroalkane solvent, for example, DCM) and or sulfoxide solvent (e.g. DMSO). The amount of the organic solvent can be a conventional amount for such reactions in the art. For example, the molar concentration of the compound of formula X in the organic solvent can be 0.001-5 mol/L.

In the preparation of the compound of formula IX, the oxidant in the oxidation reaction can be a conventional oxidant for such reactions in the art, for example, the oxidant can be one or more oxidants selected from the group consisting of Dess-Martin oxidant, Swern oxidant, IBX oxidant, TEMPO-NaClO and TEMPO-PhI(OAc)$_2$ (e.g. Dess-Martin oxidant, IBX oxidant, TEMPO-NaClO and TEMPO-PhI(OAc)$_2$). The amount of the oxidant can be a conventional amount for such reactions in the art. For example, the molar ratio of the oxidant to the compound of formula X can be 1-20:1.

In the preparation method of the compound of formula IX, the progress of the oxidation reaction can be monitored by ordinary analysis methods in the art (e.g. TLC, HPLC, GC or NMR, preferably TLC). Generally, it is deemed as the completion of the reaction when there is no longer any transformation of compound of formula X.

In the preparation method of the compound of formula IX, the temperature of the oxidation reaction can be a conventional reaction temperature for such reactions in the art, for example, −20-60° C.

In a preferred embodiment of the disclosure, the preparation method of the compound of formula IX can comprise the following steps:

adding an oxidant to a solution of the compound of formula X in an organic solvent at −20-60° C., stirring at this temperature for 1-6 h, after completion of the reaction is indicated by TLC, quenching the reaction with Na$_2$S$_2$O$_3$ and NaHCO$_3$ aqueous solution, extracting with ethyl acetate, concentrating, and isolating the compound of formula IX.

In the preferred embodiment of the preparation method of the compound of formula IX, the oxidant is preferably one or more oxidants selected from the group consisting of Dess-Martin oxidant, Swern oxidant, IBX oxidant, TEMPO-NaClO and TEMPO-PhI(OAc)$_2$ (e.g. Dess-Martin oxidant, IBX oxidant, TEMPO-NaClO and TEMPO-PhI(OAc)$_2$).

The present disclosure also provides a preparation method of the compound of formula XII, comprising conducting a of hydrolysis reaction the compound of formula IX to give the compound of formula XII:

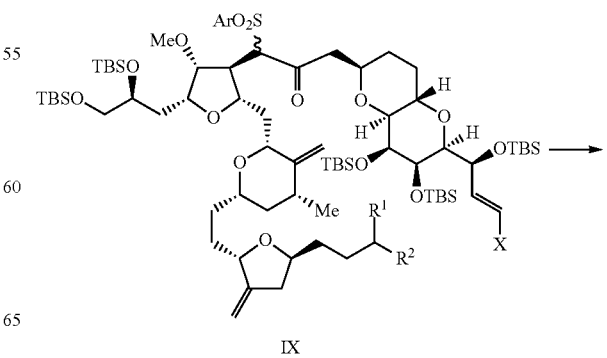

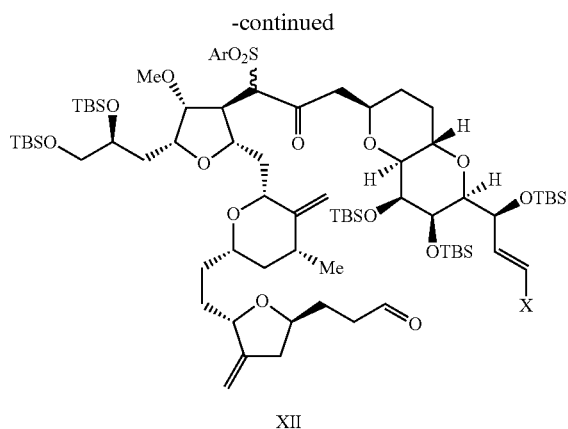

XII wherein Ar, X, R¹ and R² are as defined in the compound of formula IX.

In the preparation method of the compound of formula XII, the hydrolysis reaction can be conducted in an organic solvent. The organic solvent can be a conventional solvent for such reactions in the art, for example, the organic solvent can be one or more solvents selected from the group consisting of haloalkane solvent (e.g. chloroalkane solvent, for example, DCM), arene solvent (e.g. toluene), and nitrile solvent (e.g. acetonitrile). The amount of the organic solvent can be a conventional amount for such reactions in the art. For example, the molar concentration of the compound of formula IX in the organic solvent can be 0.001-5 mol/L.

In the preparation method of the compound of formula XII, the hydrolysis reaction can be conducted in the presence of a hydrolysis reagent. The hydrolysis reagent can be one or more reagents selected from the group consisting of HCl, p-TsOH, PPTS, BF₃·OEt₂, TMSOTf, Ti(OiPr)₄, TiCl₄, Ce(NH₄)₂(NO₃)₆, pyridine, 2,6-lutidine and 2,4,6-collidine (e.g. one or more reagents selected from the group consisting of 2,6-lutidine, TMSOTf, PPTS and Ce(NH₄)₂(NO₃)₆). The amount of the hydrolysis reagent can be a conventional amount for such reactions in the art. For example, the molar ratio of the hydrolysis reagent to the compound of formula IX can be 0.1-20:1.

In the preparation method of the compound of formula XII, the progress of the hydrolysis reaction can be monitored by ordinary analysis methods in the art (e.g. TLC, HPLC, GC or NMR, preferably TLC). Generally, it is deemed as the completion of the reaction when there is no longer any transformation of compound of formula IX.

In the preparation method of the compound of formula XII, the temperature of the hydrolysis reaction can be a conventional reaction temperature for such reactions in the art, for example, −20-40° C.

In a preferred embodiment of the disclosure, the preparation method of the compound of formula XII can comprise the following steps:

adding a hydrolysis reagent to a solution of the compound of formula IX in an organic solvent at −20-40° C., stirring for 1-12 h; after completion of the reaction is indicated by TLC, quenching the reaction with 1 N HCl aqueous solution, extracting with ethyl acetate, concentrating, and isolating the compound of formula XII.

In the preferred embodiment of the preparation method of the compound of formula XII, the organic solvent is preferably one or more solvents selected from the group consisting of DCM, toluene, and acetonitrile.

In the preferred embodiment of the preparation method of the compound of formula XII, the hydrolysis reagent is preferably one or more reagents selected from the group consisting of HCl, p-TsOH, PPTS, BF₃·OEt₂, TMSOTf, Ti(OiPr)₄, TiCl₄, Ce(NH₄)₂(NO₃)₆, pyridine, 2,6-lutidine and 2,4,6-collidine (e.g. one or more reagents selected from the group consisting of 2,6-lutidine, TMSOTf, PPTS and Ce(NH₄)₂(NO₃)₆).

The present disclosure also provides a compound of formula X,

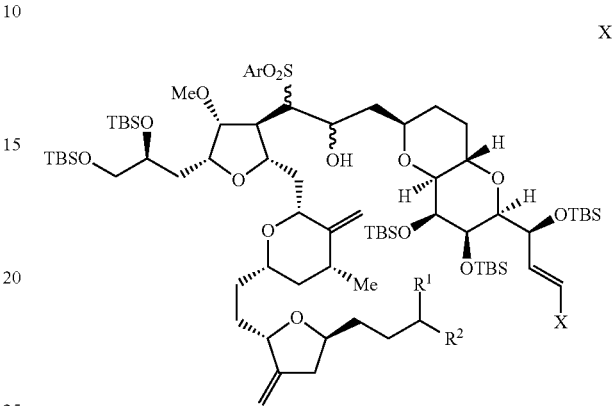

X where Ar, X, R¹ and R² are as defined in the compound of formula IX.

In a preferred embodiment of the disclosure, in the compound of formula X, Ar is preferably phenyl, para-methylphenyl or para-ethylphenyl; R¹ and R² together with the carbon atom to which they are attached form ethylene glycol acetal or propanediol acetal; X is iodide.

The compound of formula X can be selected from the group consisting of:

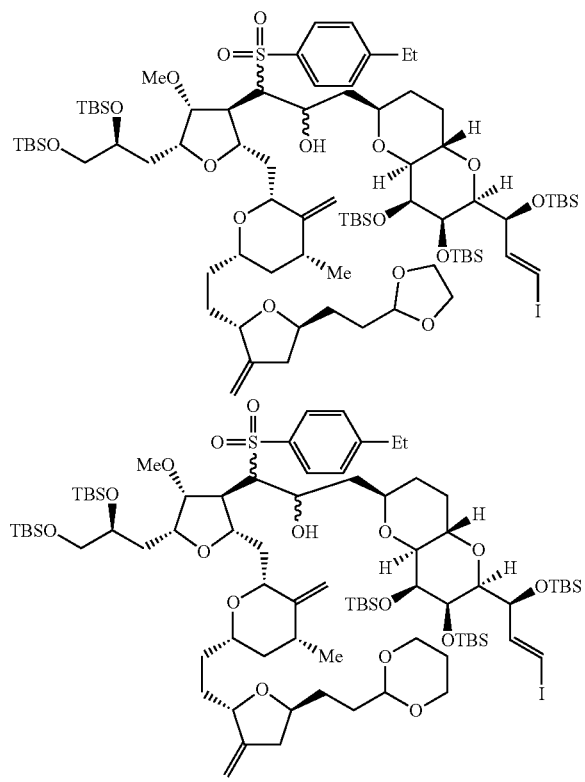

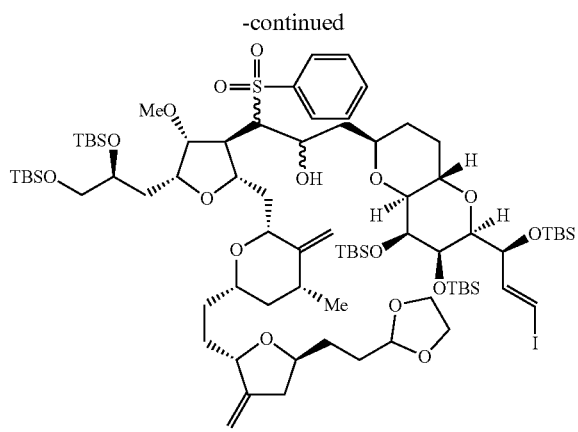

The present disclosure also provides a preparation method of the compound of formula X, comprising conducting a condensation reaction of the compound of formula XI and the compound of formula III under a basic condition to give the compound of formula X:

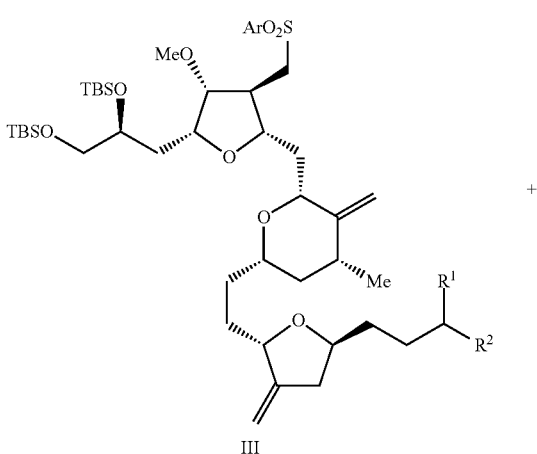

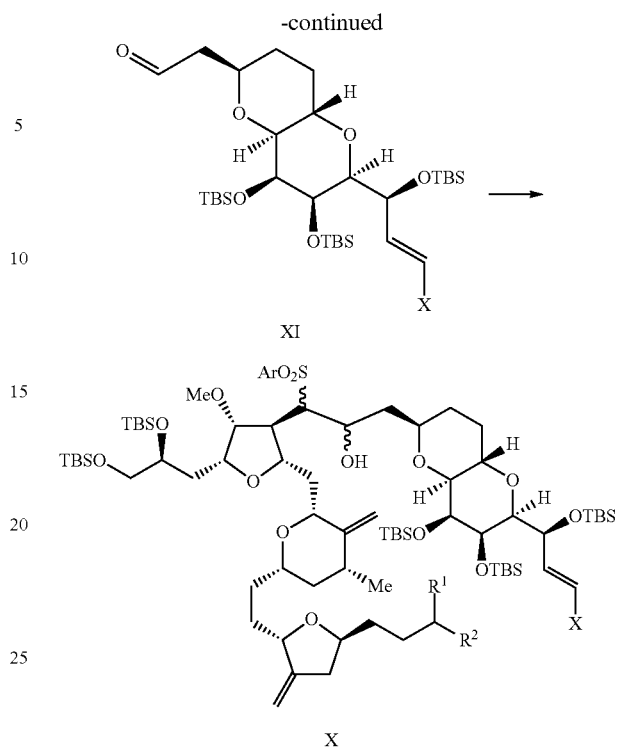

wherein Ar, X, $R^1$ and $R^2$ are as defined in the compound of formula X.

In the preparation method of the compound of formula X, the condensation reaction can be conducted in an organic solvent. The organic solvent can be a conventional solvent for such reactions in the art, for example, the organic solvent can be C6-C10 alkane solvent (e.g. heptane) and/or ether solvent (e.g. THF, 2-methyltetrahydrofuran). The amount of the organic solvent can be a conventional amount for such reactions in the art. For example, the molar concentration of the compound of formula III in the organic solvent can be 0.001-5 mol/L.

In the preparation method of the compound of formula X, the base in the basic condition can be a conventional base for such reactions in the art, for example the base can be one or more bases selected from the group consisting of NaH, BuLi (e.g. n-BuLi, s-BuLi or t-BuLi), DIPEA, LDA, KHMDS, LiHMDS and NaHMDS (e.g. n-BuLi, LDA or LiHMDS). The amount of the base can be a conventional amount for such reactions in the art. For example, the molar ratio of the base to the compound of formula III can be 0.5-5:1.

In the preparation method of the compound of formula X, the molar ratio of the compound of formula III to the compound of formula XI can be 0.1-10:1.

In the preparation method of the compound of formula X, the progress of the condensation reaction can be monitored by ordinary analysis methods in the art (e.g. TLC, HPLC, GC or NMR, preferably TLC). Generally, it is deemed as the completion of the reaction when there is no longer any transformation of compound of formula III.

In the preparation method of the compound of formula X, the temperature of the condensation reaction can be a conventional reaction temperature for such reactions in the art, for example, −78-0° C.

In a preferred embodiment of the disclosure, the preparation method of the compound of formula X can comprise the following steps:

adding a solution of a base to a solution of the compound of formula III in an organic solvent at −78-0° C., stirring at such condition for 15 min to 1 h; adding a solution of the compound of formula XI in THF, and stirring for 30 min to 4 h; after completion of the reaction is indicated by TLC, quenching the reaction with saturated NH$_4$Cl aqueous solution, extracting with ethyl acetate, concentrating, and isolating the compound of formula X.

In the preferred embodiment of the preparation method of the compound of formula X, the organic solvent is preferably one or more solvents selected from the group consisting of THF, 2-methyltetrahydrofuran and heptane.

In the preferred embodiment of the preparation method of the compound of formula X, the base is preferably one or more bases selected from the group consisting of NaH, BuLi, DIPEA, LDA, KHMDS, LiHMDS and NaHMDS (e.g. n-BuLi, LDA or LiHMDS).

The present disclosure also provides a method (method K) of the compound of formula IV, comprising conducting a reductive elimination reaction of the compound of formula XII to give the compound of formula IV:

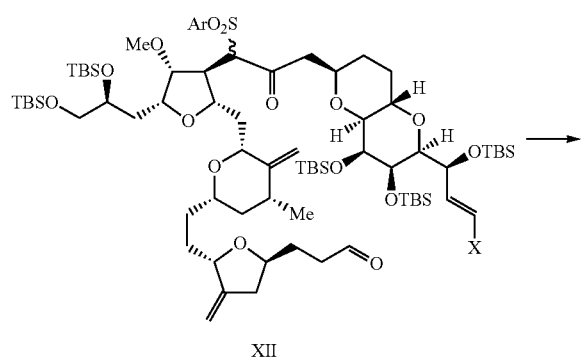

XII

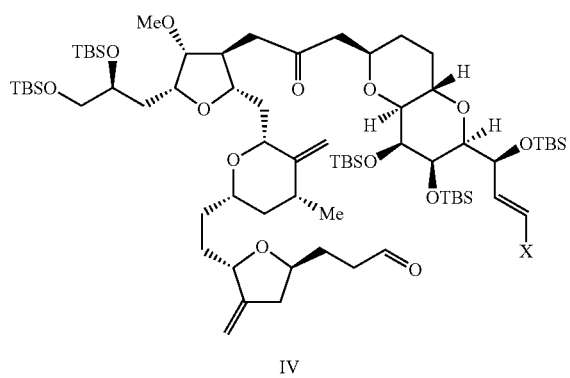

IV where Ar is an aryl substituted by $C_{1-10}$ alkyl or alkoxy, or an unsubstituted aryl, preferably a phenyl substituted by $C_{1-10}$ alkyl at para-position or a unsubstituted phenyl;

X is halogen or a leaving group, preferably chloride, bromide, iodide or trifluoromethanesulfonyloxy.

In the preparation method (method K) of the compound of formula IV, Ar can be a phenyl or a phenyl substituted by $C_{1-4}$ alkyl (e.g. methyl, ethyl, n-propyl or isopropyl) at para-position, preferably phenyl, para-methylphenyl or para-ethylphenyl.

In the preparation method (method K) of the compound of formula IV, X can be chloride, bromide and iodide, preferably iodide.

In the preparation method (method K) of the compound of formula IV, the reductive elimination reaction can be conducted in an organic solvent. The organic solvent can be a conventional solvent for such reactions in the art, for example, ether solvent (e.g. THF). The amount of the organic solvent can be a conventional amount for such reactions in the art. For example, the molar concentration of the compound of formula XII in the organic solvent can be 0.001-5 mol/L.

In the preparation method (method K) of the compound of formula IV, the reductive elimination reaction can be conducted in the presence of a reductant, for example, the reductant can be one or more reductants selected from the group consisting of SmI$_2$, CrCl$_2$, CrCl$_3$, Mn powder and Zn powder (e.g. SmI$_2$, CrCl$_2$—Mn powder or Zn powder). The amount of the reductant can be a conventional amount for such reactions in the art. For example, the molar ratio of the reductant to the compound of formula XII can be 0.1-20:1.

In the preparation method (method K) of the compound of formula IV, the progress of the reductive elimination reaction can be monitored by ordinary analysis methods in the art (e.g. TLC, HPLC, GC or NMR, preferably TLC). Generally, it is deemed as the completion of the reaction when there is no longer any transformation of compound of formula XII.

In the preparation method (method K) of the compound of formula IV, the temperature of the reductive elimination reaction can be a conventional reaction temperature for such reactions in the art, for example, −50-30° C.

In a preferred embodiment of the disclosure, the preparation method (method K) of the compound of formula IV can comprise the following steps:

adding a reductant to a solution of the compound of formula XII in THF at −50-30° C., stirring for 30 min-4 h. After completion of the reaction is indicated by TLC, quenching the reaction with K$_2$CO$_3$ aqueous solution, extracting with ethyl acetate, concentrating, and isolating the compound of formula IV.

In the preferred embodiment of the preparation method (method K) of the compound of formula IV, the reductant is preferably one or more reductants selected from the group consisting of SmI$_2$, CrCl$_2$, Mn powder, Zn powder and CrCl$_3$.

The present disclosure also provides a preparation method (method P) of eribulin intermediate of formula IV, comprising:

i) conducting a condensation reaction of the compound of formula III and the compound of formula XI to prepare the compound of formula X;

ii) conducting an oxidation reaction of the compound of formula X to prepare the compound of formula IX;

iii) conducting a reductive elimination reaction of the compound of formula IX to prepare the compound of formula II;

iv) conducting a hydrolysis reaction of the compound of formula II to give the compound of formula IV;

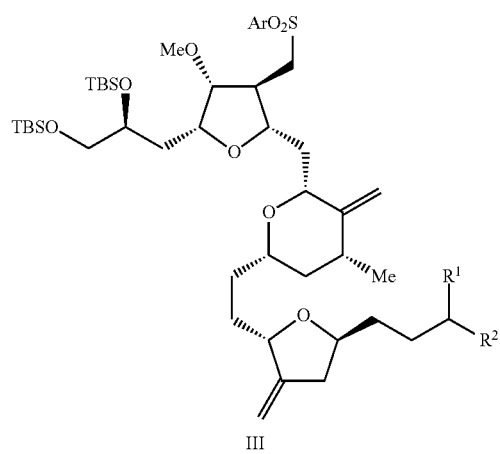

III

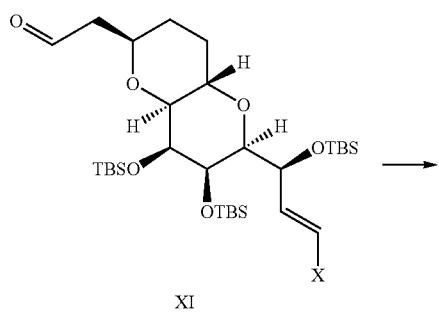

XI

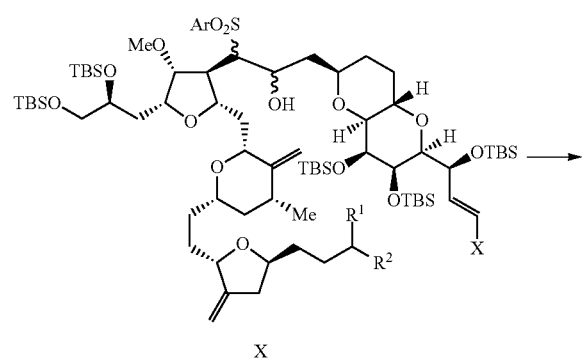

X

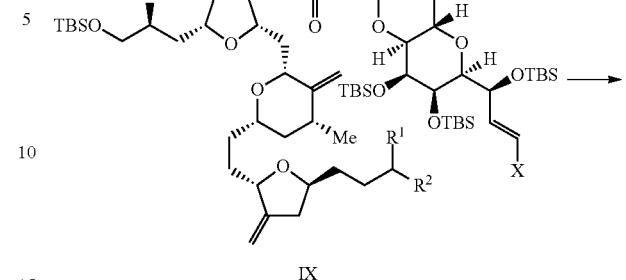

IX

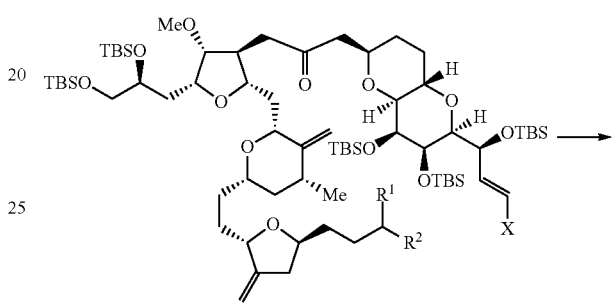

II

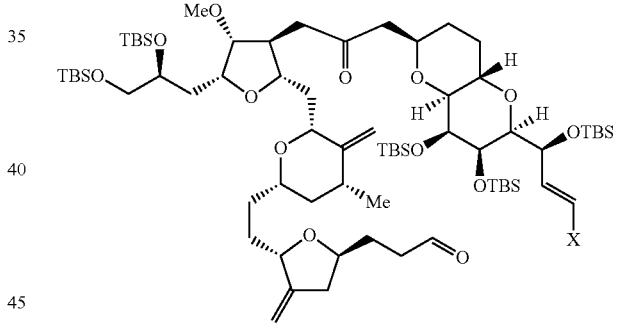

IV wherein Ar, X, $R^1$ and $R^2$ are as defined in above.

In the preparation method (method P) of eribulin intermediate of formula IV, the reaction condition of each step can be described as above.

The present disclosure also provides a preparation method (method Q) of the compound of formula IV, comprising:

i) conducting a condensation reaction of the compound of formula III and the compound of formula XI to prepare the compound of formula X;

ii) conducting an oxidation reaction of the compound of formula X to prepare the compound of formula IX;

iii) conducting a hydrolysis reaction of the compound of formula IX to prepare the compound of formula XII;

iv) conducting a reductive elimination reaction of the compound of formula XII to give the compound of formula IV;

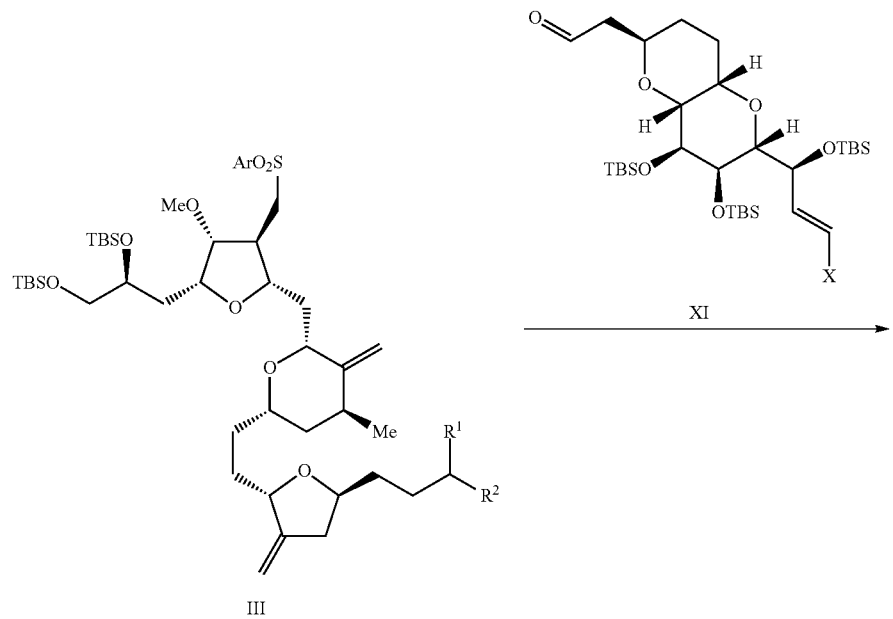
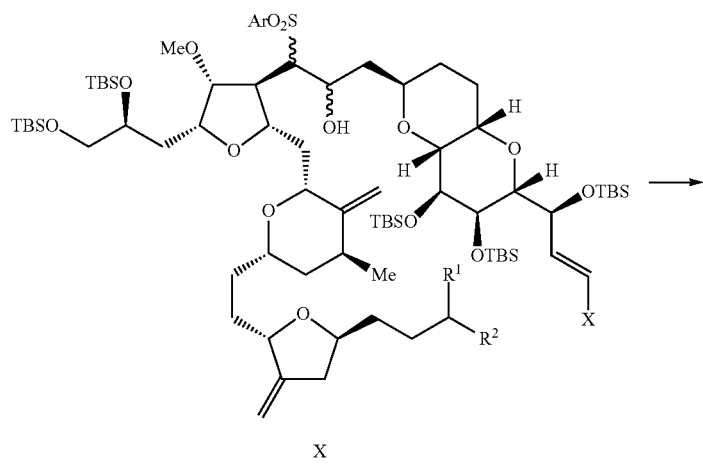
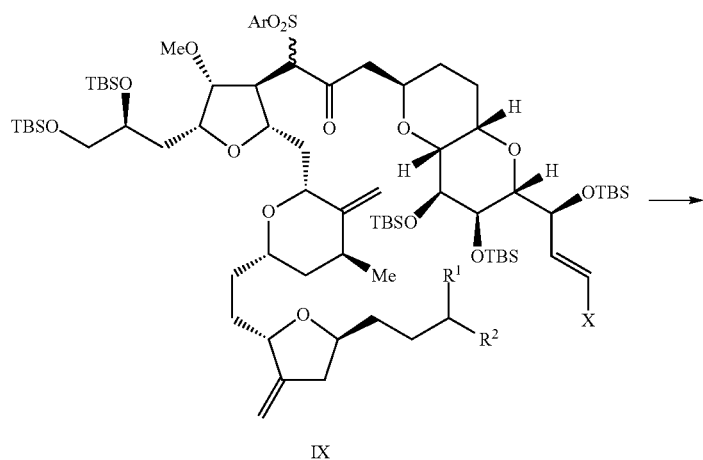

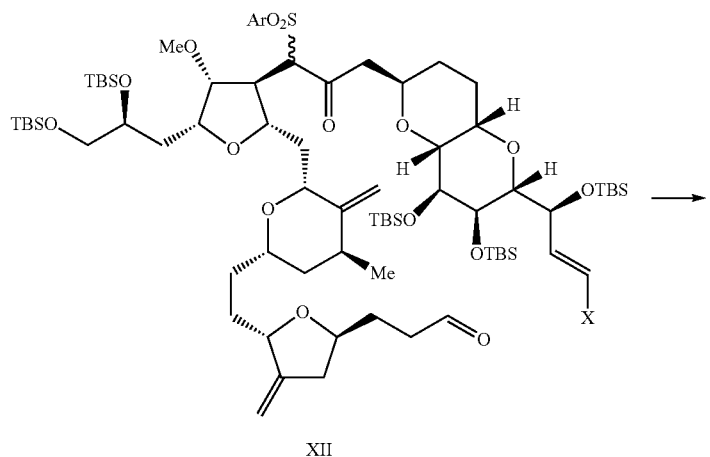
XII
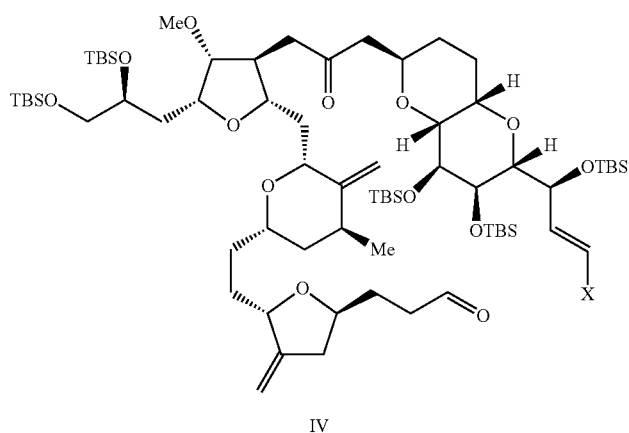
IV
wherein Ar, X, R¹ and R² are as defined in above.
In the preparation method (method Q) of eribulin intermediate of formula IV, the reaction condition of each step can be described as above.
The present disclosure also provides a preparation method (method A) of the compound of formula IV, comprising the following steps:
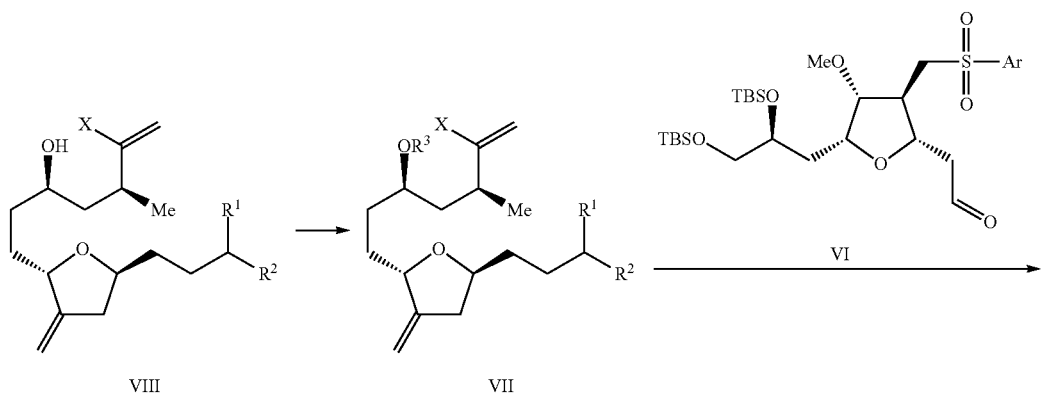

-continued
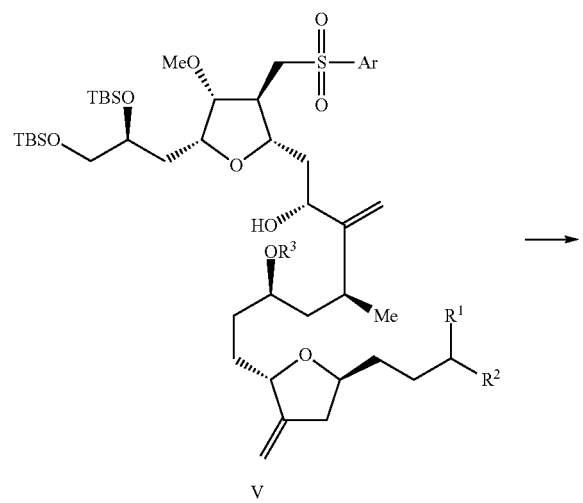
V
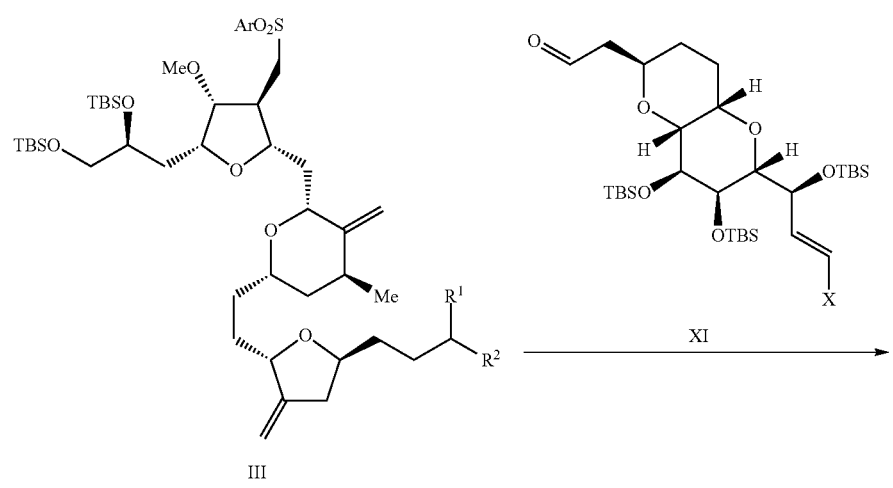
III
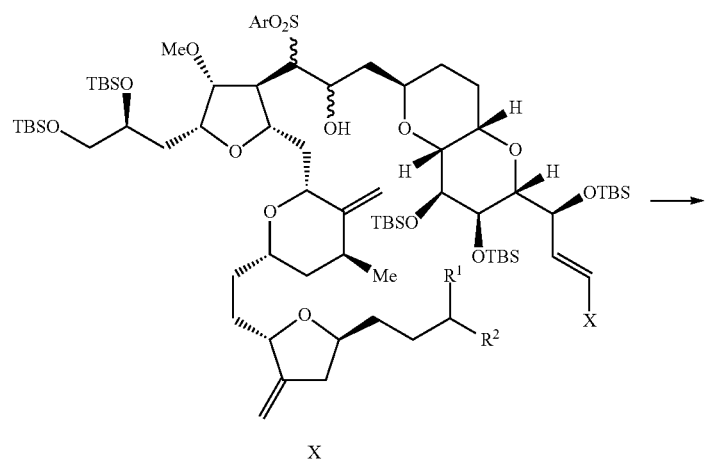
X

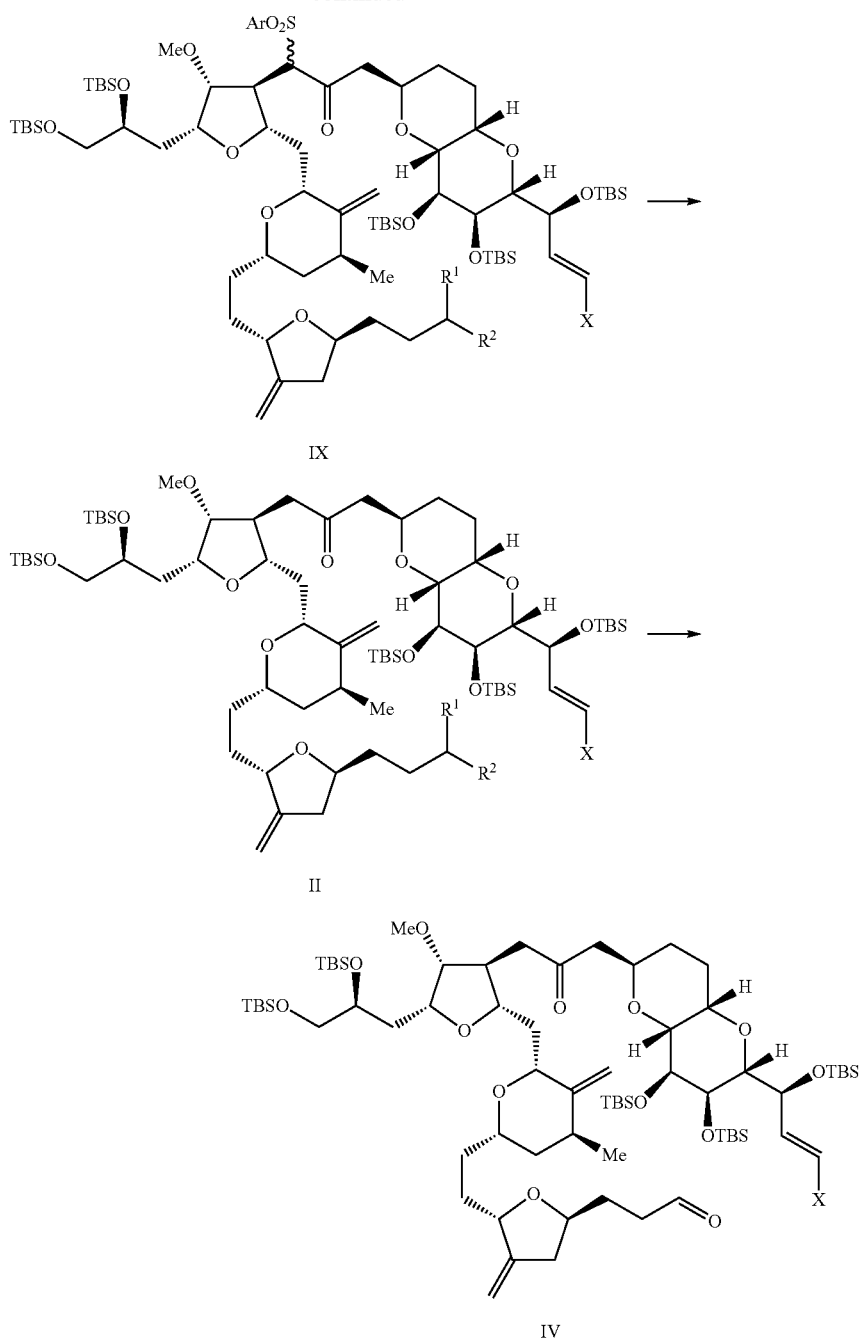

wherein Ar is an aryl substituted by $C_{1-10}$ alkyl or alkoxy, or an unsubstituted aryl, preferably a phenyl substituted by $C_{1-10}$ alkyl at para-position or an unsubstituted phenyl;

$R^1$ and $R^2$ are acetal or thioacetal protecting group, and $R^1$ and $R^2$ are each independently $C_{1-10}$ alkoxy or $C_{1-10}$ alkylthio, or $R^1$ and $R^2$ together with the carbon atom to which they are attached form cyclic acetal or cyclic thioacetal. Preferably, $R^1$ and $R^2$ together with the carbon atom to which they are attached form cyclic acetal or cyclic thioacetal, more preferably substituted or unsubstituted ethylene glycol acetal, or substituted or unsubstituted propanediol acetal; $R^3$ is hydroxyl protecting group, preferably methanesulfonyl, p-toluenesulfonyl or trifluoromethanesulfonyl; X is halogen or a leaving group, preferably chloride, bromide, iodide or trifluoromethanesulfonyloxy.

In the preparation method (method A) of eribulin intermediate of formula IV, Ar can be a phenyl or a phenyl substituted by C1-4 alkyl (e.g. methyl, ethyl, n-propyl or isopropyl) at para-position. Ar is preferably phenyl, para-methylphenyl or para-ethylphenyl.

In the preparation method (method A) of eribulin intermediate of formula IV, $R^1$ and $R^2$ are each independently C alkoxy (e.g. $C_{1-3}$ alkoxy, for example methoxy, ethoxy, n-propoxy or isopropoxy), or $R^1$ and $R^2$ can together with the carbon atom to which they are attached form 5-7 membered cyclic acetal (5-membered cyclic acetal such as

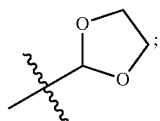 [SMILES: *C1OCCO1]

6-membered cyclic acetal such as

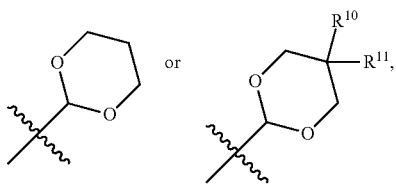

wherein $R^{10}$ and $R^{11}$ are each independently hydrogen or $C_{1-3}$ alkyl (e.g. methyl), provided that $R^{10}$ and $R^{11}$ are not both hydrogen) or 5-7 membered cyclic thioacetal (e.g.

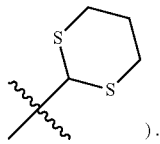

Preferably, $R^1$ and $R^2$ together with the carbon atom to which they are attached form ethylene glycol acetal or propanediol acetal.

In the preparation method (method A) of eribulin intermediate of formula IV, $R^3$ can be methanesulfonyl.

In the preparation method (method A) of eribulin intermediate of formula IV, X can be chloride, bromide or iodide, for example X can be iodide.

In the preparation method (method A) of eribulin intermediate of formula IV, the reaction condition of each step can be described as above.

The preparation method (method A) of eribulin intermediate of formula IV can comprise the following steps:

i) conducting a hydroxyl protecting reaction of the compound of formula VIII to prepare the compound of formula VII; wherein the hydroxyl protecting reaction is preferably conducted under a basic condition; the hydroxyl protecting reaction is preferably conducted in the presence of one or more reagents selected from the group consisting of $Et_3N$, pyridine, NaH, $K_2CO_3$, 2,4,6-collidine, 2,6-lutidine, BuLi, DIPEA, LDA, KHMDS, LiHMDS and NaHMDS;

ii) conducting a NHK reaction of the compound of formula VI and the compound of formula VII to prepare the compound of formula V; wherein the NHK reaction is preferably conducted in the presence of one or more reagents selected from the group consisting of $CrCl_2$, $CrCl_3$ and $CrBr_3$;

iii) conducting an intramolecular cyclization reaction of the compound of formula V to prepare the compound of formula III; wherein the intramolecular cyclization reaction is preferably conducted under a basic condition; the intramolecular cyclization reaction is preferably conducted in the presence of one or more reagents selected from the group consisting of $Et_3N$, pyridine, NaH, $K_2CO_3$, 2,4,6-collidine, 2,6-lutidine, BuLi, DIPEA, LDA, KHMDS, LiHMDS and NaHMDS;

iv) conducting a condensation reaction of the compound of formula III and the compound of formula XI to prepare the compound of formula X; wherein the condensation reaction is preferably conducted under a basic condition the condensation reaction is preferably conducted in the presence of one or more reagents selected from the group consisting of NaH, BuLi, DIPEA, LDA, KHMDS, LiHMDS and NaHMDS;

v) conducting an oxidation reaction of the compound of formula X to prepare the compound of formula IX; wherein the oxidant is preferably one or more oxidants selected from the group consisting of Dess-Martin oxidant, Swern oxidant, IBX oxidant, TEMPO-NaClO and TEMPO-PhI(OAc)$_2$;

vi) conducting a reductive elimination reaction of the compound of formula IX to prepare the compound of formula II; wherein the reductive elimination reagent is preferably conducted in the presence of one or more reagents selected from the group consisting of $SmI_2$, $CrCl_2$, Mn powder, Zn powder and $CrCl_3$;

vii) conducting a hydrolysis reaction of the compound of formula II to give the compound of formula IV; wherein the hydrolysis reaction is preferably conducted under an acidic or a neutral condition; the hydrolysis reaction is preferably conducted in the presence of one or more reagents selected from the group consisting of HCl, p-TsOH, PPTS, $BF_3 \cdot OEt_2$, TMSOTf, Ti(OiPr)$_4$, TiCl$_4$, pyridine, 2,6-lutidine and 2,4,6-collidine.

In a preferred embodiment of the disclosure, in the preparation method of eribulin intermediate of formula IV, Ar is preferably phenyl, para-methylphenyl or para-ethylphenyl; X is iodide; $R^1$ and $R^2$ together with the carbon atom to which they are attached form ethylene glycol acetal or propanediol acetal.

The present disclosure also provides a preparation method (method A) of the compound of formula IVa, comprising the following steps:

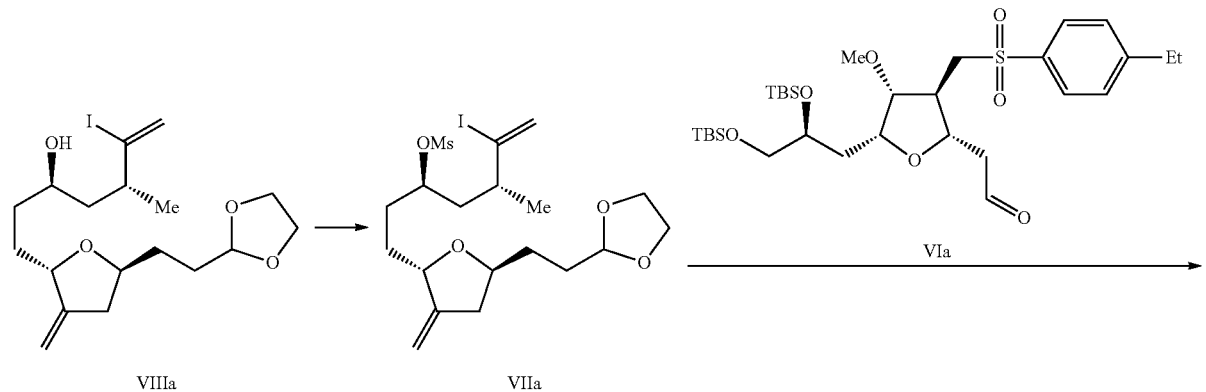

-continued
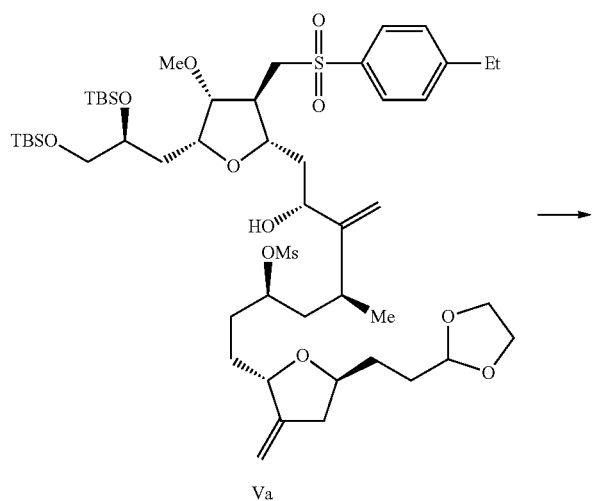
Va
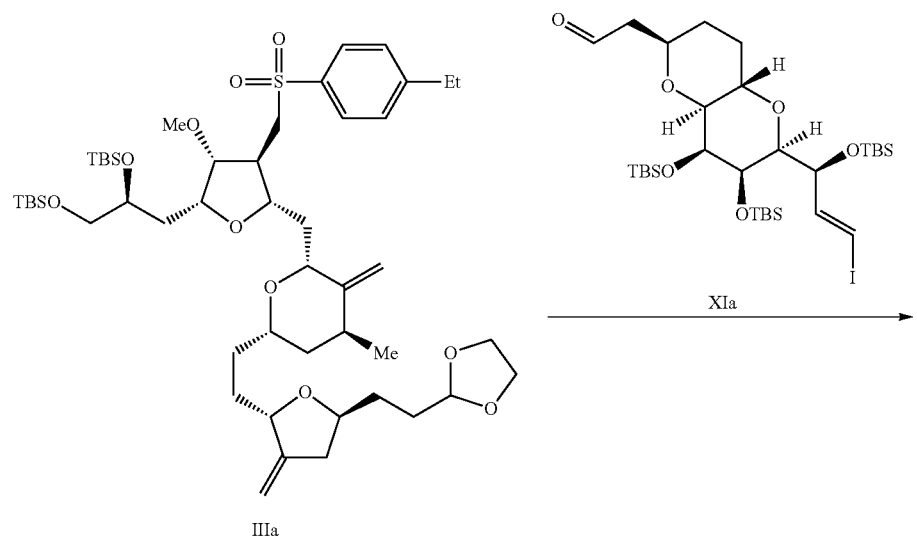
IIIa
XIa
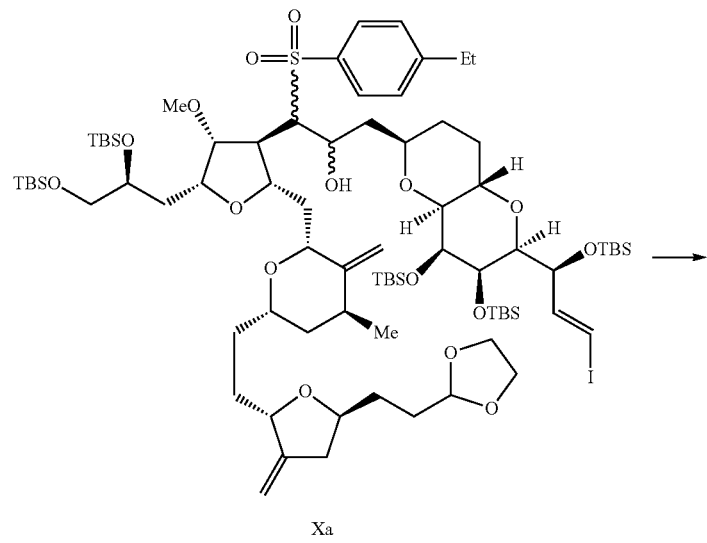
Xa

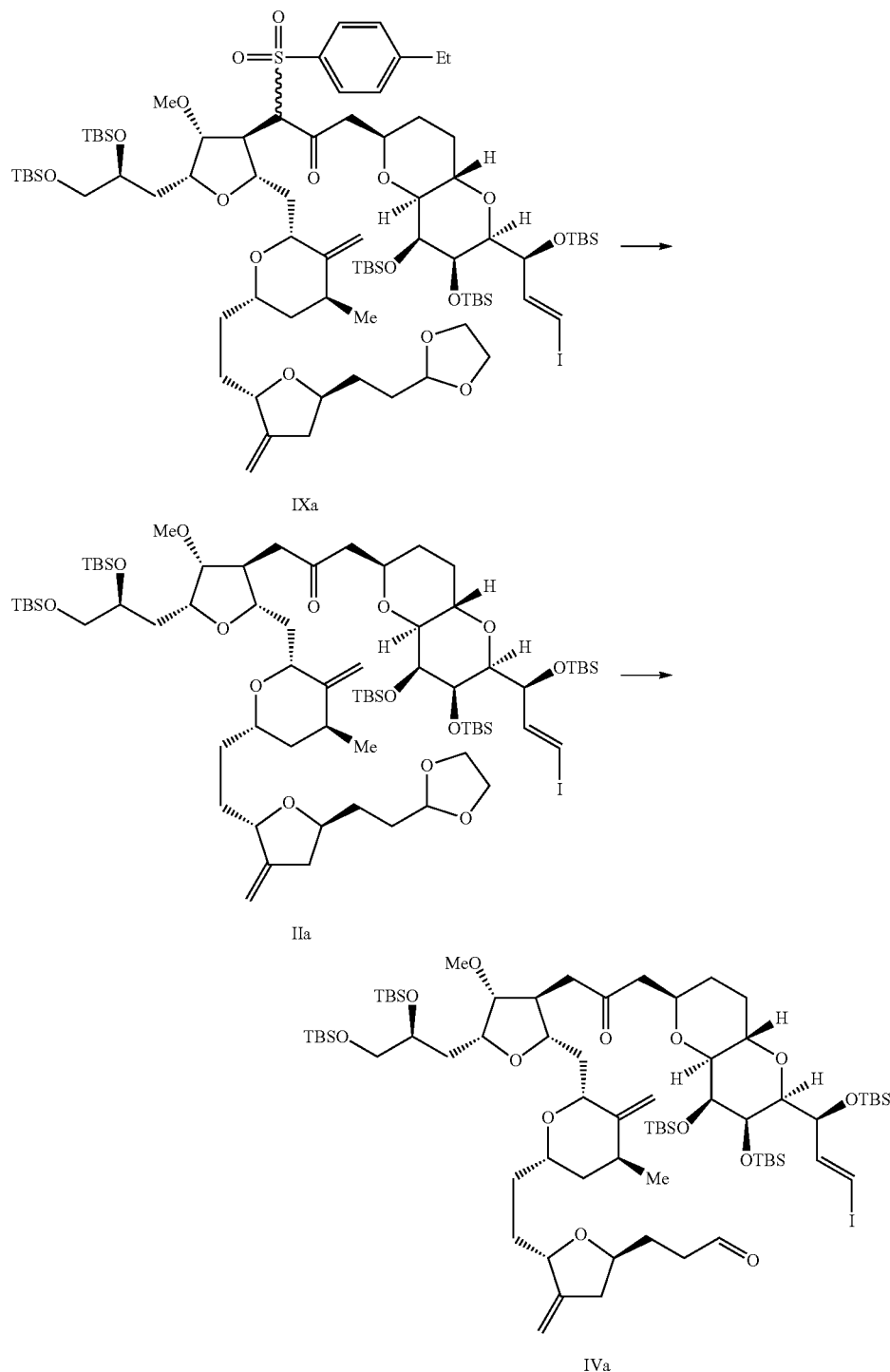

i) conducting a reaction of the compound of formula VIIIa and MsCl under a basic condition to prepare the compound of formula VIIa;

ii) conducting a NHK reaction of the compound of formula VIIa and the compound of formula VIa in the presence of CrCl₂ to prepare the compound of formula Va;

iii) conducting an intramolecular cyclization reaction of the compound of formula Va in the presence of KHMDS to prepare the compound of formula IIIa;

iv) conducting a condensation reaction of the compound of formula IIIa and the compound of formula XIa in the presence of BuLi or LDA to prepare the compound of formula Xa;

v) conducting an oxidation reaction of the compound of formula Xa in the presence of Dess-Martin oxidant to prepare the compound of formula IXa;

vi) conducting a reductive elimination reaction of the compound of formula IXa in the presence of SmI₂ to prepare the compound of formula IIa;

vii) conducting a hydrolysis reaction of the compound of formula IIa in the presence of TMSOTf and 2,6-lutidine to give the compound of formula IVa.

In the preparation method (method A) of the compound of formula IVa, the reaction condition of each step can be described as above.

The present disclosure also provides a preparation method (method B) of the compound of formula IVa, comprising the following steps:

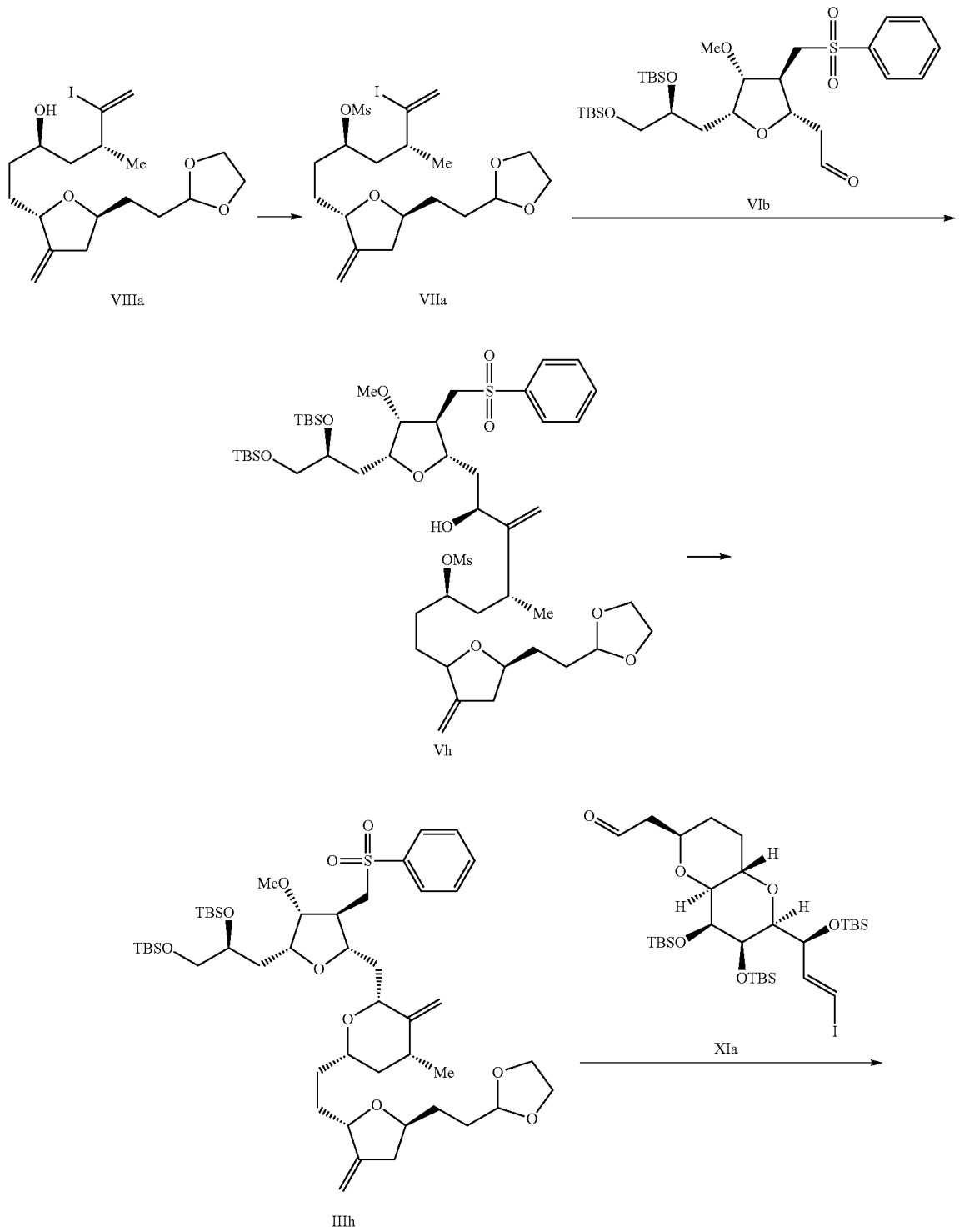

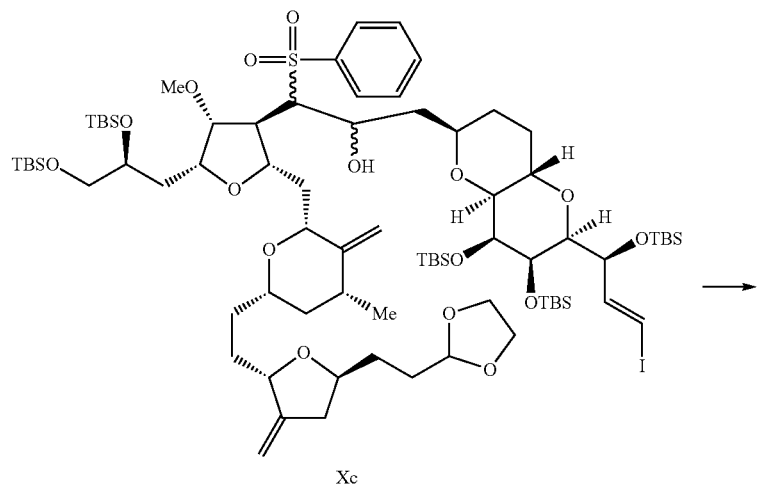
Xc
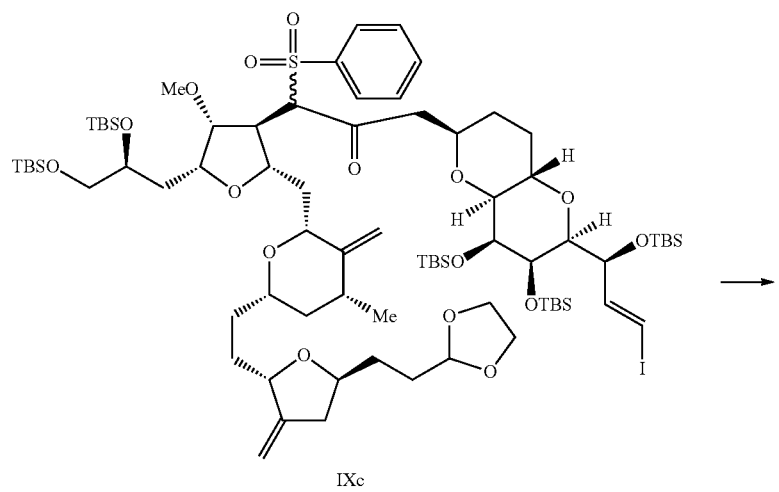
IXc
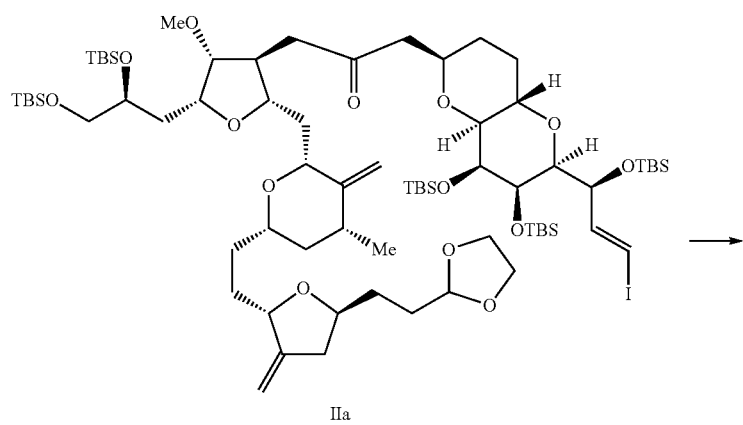
IIa

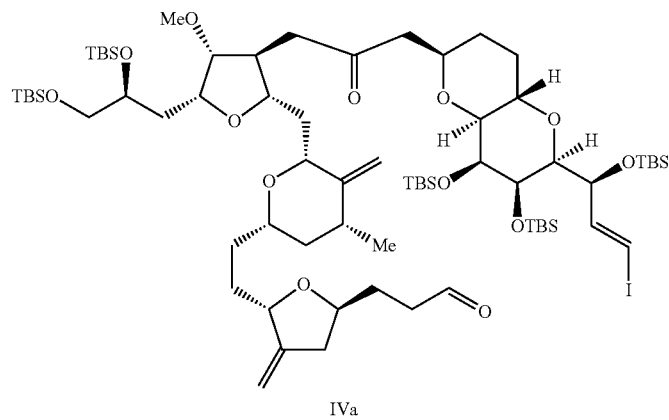

IVa i) conducting a reaction of the compound of formula VIIIa and MsCl under a basic condition to prepare the compound of formula VIIa;

ii) conducting a NHK reaction of the compound of formula VIIa and the compound of formula VIb in the presence of $CrCl_2$ to prepare the compound of formula Vh;

iii) conducting an intramolecular cyclization reaction of the compound of formula Vh in the presence of KHMDS to prepare the compound of formula IIIh;

iv) conducting a condensation reaction of the compound of formula IIIh and the compound of formula XIa in the presence of BuLi or LDA to prepare the compound of formula Xc;

v) conducting an oxidation reaction of the compound of formula Xc in the presence of TEMPO oxidant to prepare the compound of formula IXc;

vi) conducting a reductive elimination reaction of the compound of formula IXc in the presence of $CrCl_2$ and Mn powder to prepare the compound of formula IIa;

vii) conducting a hydrolysis reaction of the compound of formula IIa in the presence of $Ce(NH_4)_2(NO_3)_6$ to give the compound of formula IVa.

In the preparation method (method B) of eribulin intermediate of compound of formula IVa, the reaction condition of each step is described as above.

The present disclosure also provides a preparation method (method B) of the compound of formula IV, comprising the following steps:

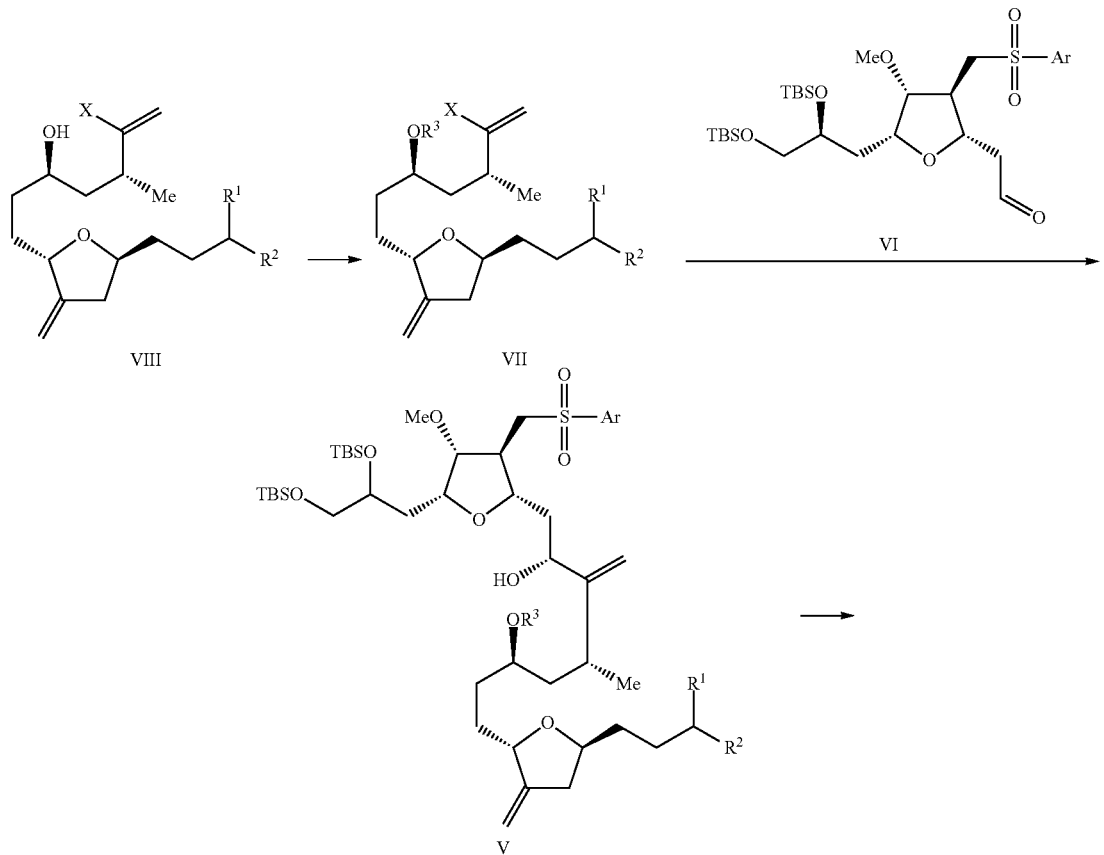

-continued
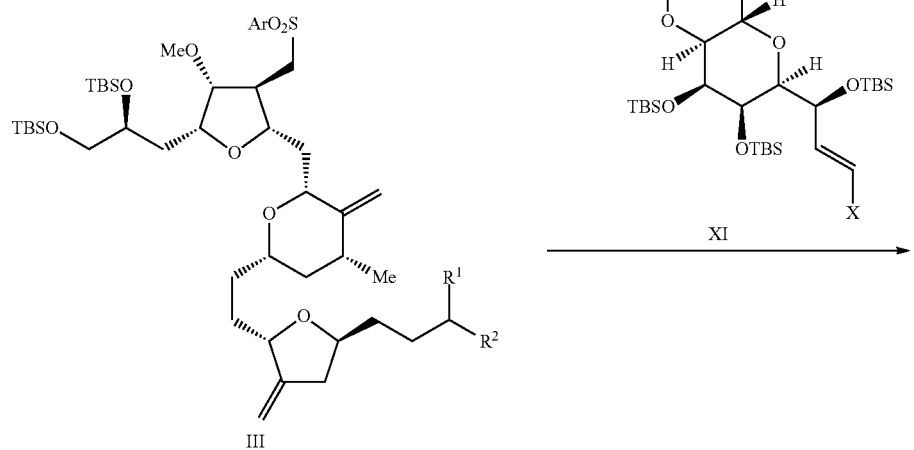
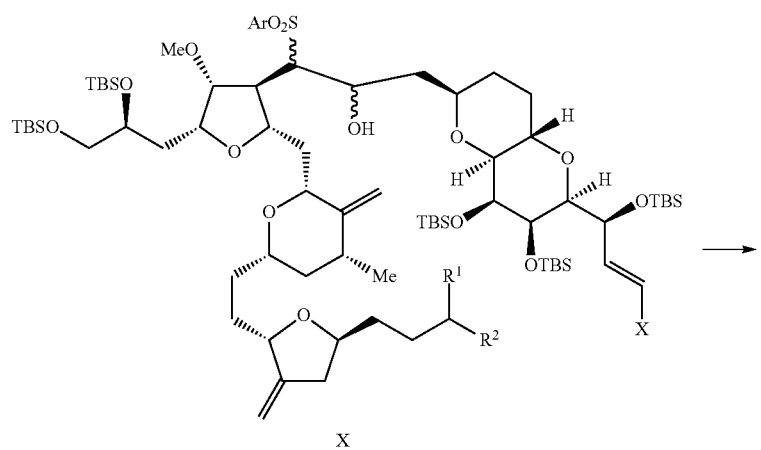
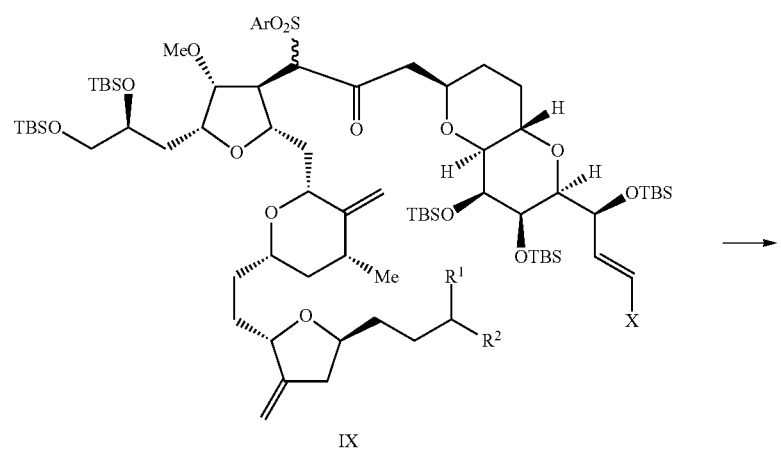

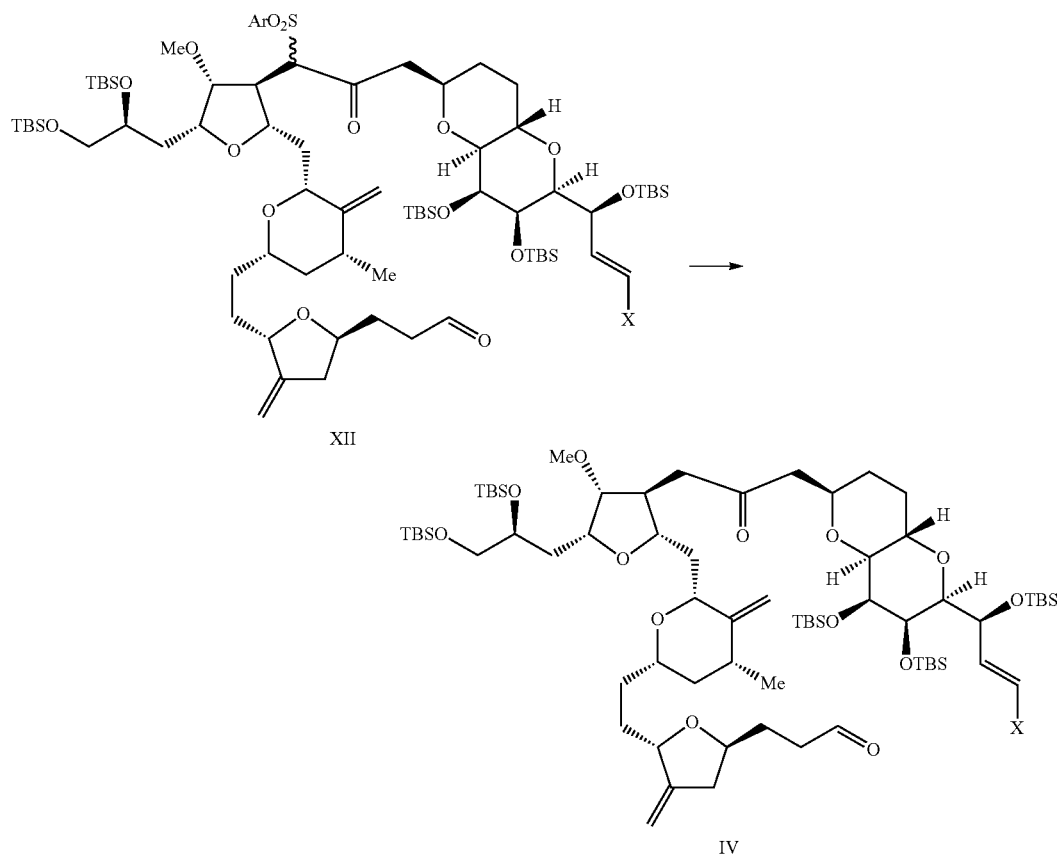

wherein Ar is an aryl substituted by $C_{1-10}$ alkyl or alkoxy or an unsubstituted aryl, preferably a phenyl substituted by $C_{1-10}$ alkyl at para-position or an unsubstituted phenyl;

$R^1$ and $R^2$ are acetal or thioacetal protecting group, and $R^1$ and $R^2$ are each independently $C_{1-10}$ alkoxy or $C_{1-10}$ alkyl-thio, or $R^1$ and $R^2$ together with the carbon atom to which they are attached form cyclic acetal or cyclic thioacetal; preferably $R^1$ and $R^2$ together with the carbon atom to which they are attached form cyclic acetal or cyclic thioacetal, more preferably substituted or unsubstituted ethylene glycol acetal, or substituted or unsubstituted propanediol acetal; $R^3$ is hydroxyl protecting group, preferably methanesulfonyl, p-toluenesulfonyl or trifluoromethanesulfonyl; X is halogen or a leaving group, preferably chloride, bromide, iodide or trifluoromethanesulfonyloxy.

In the preparation method (method B) of eribulin intermediate of formula IV, Ar, $R^1$, $R^2$, $R^3$ and X can be as defined in the preparation method (method B) of eribulin intermediate of the compound of formula IV.

The preparation method (method B) of eribulin intermediate of formula IV can comprise the following steps:

i) conducting a hydroxyl protecting reaction of the compound of formula VIII to prepare the compound of formula VII; wherein the hydroxyl protecting reaction is preferably conducted under a basic condition; the hydroxyl protecting reaction is preferably conducted in the presence of one or more reagents selected from the group consisting of $Et_3N$, pyridine, NaH, $K_2CO_3$, 2,4,6-collidine, 2,6-lutidine, BuLi, DIPEA, LDA, KHMDS, LiHMDS and NaHMDS;

ii) conducting a NHK reaction of the compound of formula VI and the compound of formula VII to prepare the compound of formula V; wherein the NHK reaction is preferably conducted in the presence of one or more reagents selected from the group consisting of $CrCl_2$, $CrCl_3$ and $CrBr_3$;

iii) conducting an intramolecular cyclization reaction of the compound of formula V to prepare the compound of formula III; wherein the intramolecular cyclization reaction is preferably conducted under a basic condition; the intramolecular cyclization reaction is preferably conducted in the presence of one or more reagents selected from the group consisting of NaH, BuLi, DIPEA, LDA, KHMDS, LiHMDS and NaHMDS;

iv) conducting a condensation reaction of the compound of formula III and the compound of formula XI to prepare the compound of formula X; wherein the condensation reaction is preferably conducted under a basic condition; the condensation reaction is preferably conducted in the presence of one or more reagents selected from the group consisting of $Et_3N$, pyridine, NaH, $K_2CO_3$, 2,4,6-collidine, 2,6-lutidine, BuLi, LDA, KHMDS, LiHMDS and NaHMDS;

v) conducting an oxidation reaction of the compound of formula X to prepare the compound of formula IX; the oxidation reaction is preferably conducted in the presence of one or more reagents selected from the group consisting of Dess-Martin oxidant, Swern oxidant, IBX oxidant, TEMPO-NaClO and TEMPO-PhI(OAc)$_2$;

vi) conducting a hydrolysis reaction of the compound of formula IX to prepare the compound of formula XII; the hydrolysis reaction is preferably conducted under an acidic or a neutral condition; the hydrolysis reaction is preferably conducted in the presence of one or more reagents selected from the group consisting of HCl, p-TsOH, PPTS, BF$_3$·OEt$_2$, TMSOTf, Ti(OiPr)$_4$, TiCl$_4$, pyridine, 2,6-lutidine and 2,4,6-collidine;

vii) conducting a reductive elimination reaction of the compound of formula XII to give the compound of formula IV; the reductive elimination reaction is preferably conducted in the presence of one or more reagents selected from the group consisting of SmI$_2$, CrCl$_2$, Mn powder, Zn powder and CrCl$_3$.

In the preparation method (method B) of eribulin intermediate of formula IV, the reaction condition of each step can be described as above.

In a preferred embodiment of the disclosure, in the preparation method (method B) of eribulin intermediate of formula IV, Ar is preferably phenyl, para-methylphenyl or para-ethylphenyl; X is iodide; R$^1$ and R$^2$ together with the carbon atom to which they are attached form ethylene glycol acetal or propanediol acetal.

The present disclosure also provides a preparation method (method C) of the compound of formula IVa, comprising the following steps:

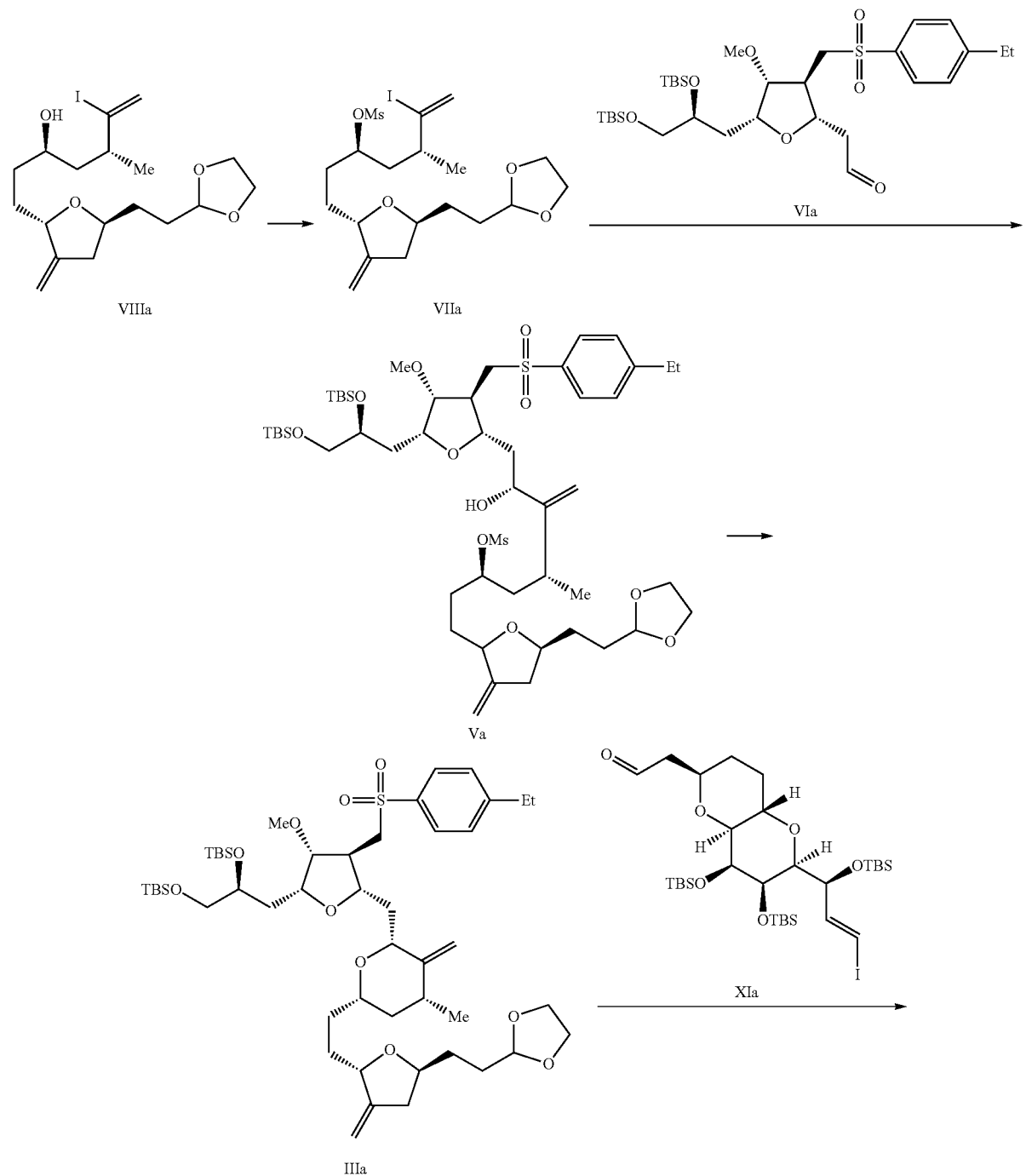

-continued
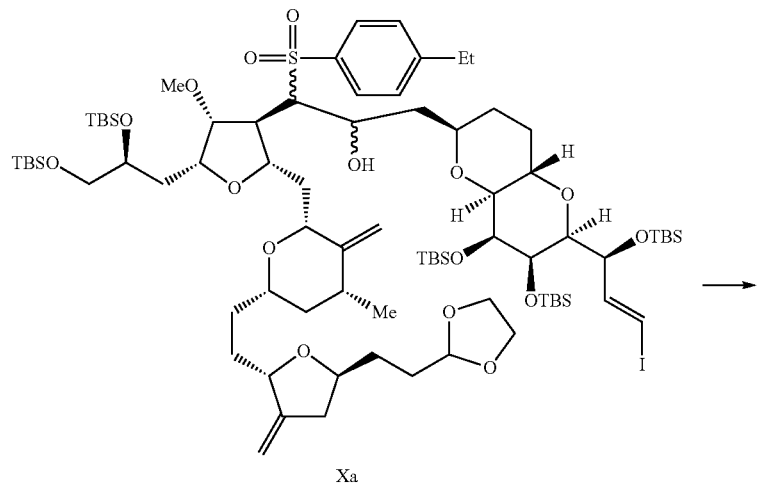
Xa
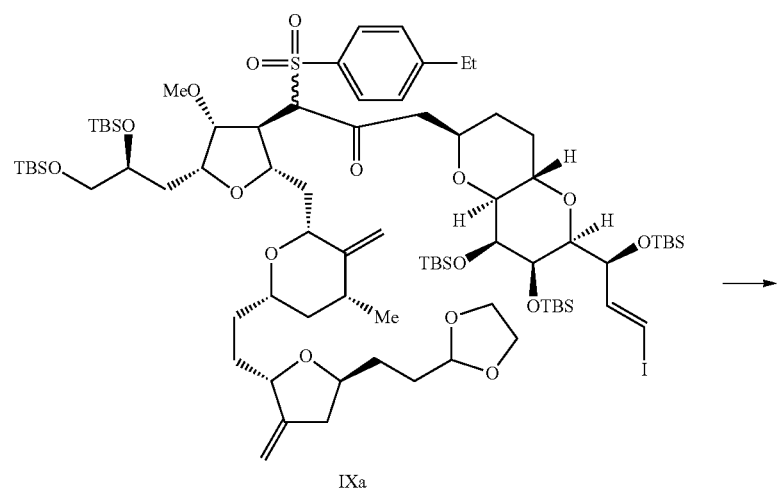
IXa
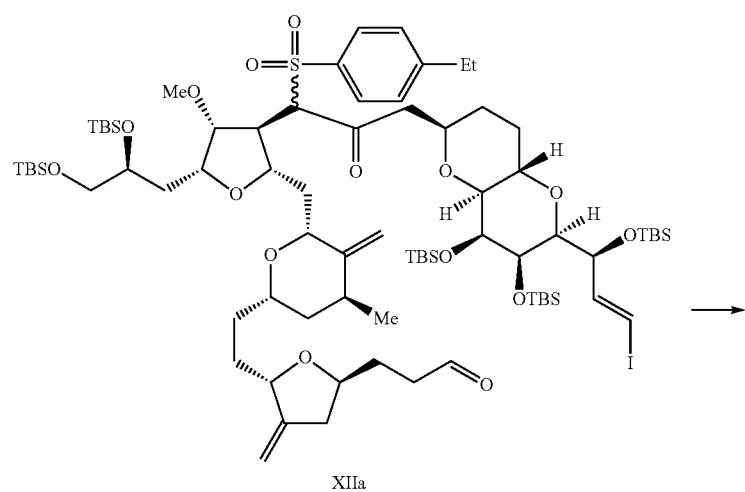
XIIa

-continued

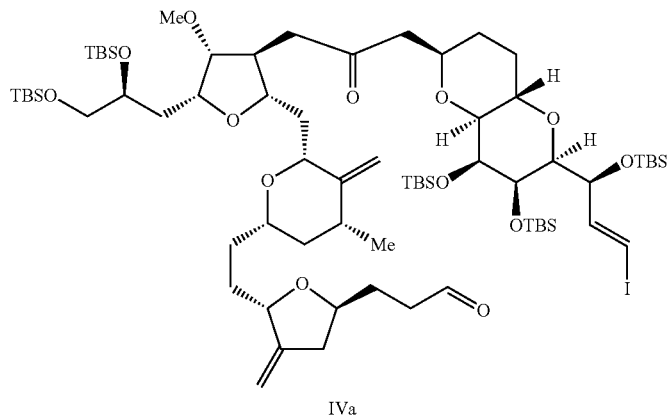

IVa i) conducting a reaction of the compound of formula VIIIa and $Ms_2O$ under a basic condition to prepare the compound of formula VIIa;

ii) conducting a NHK reaction of the compound of formula VIIa and the compound of formula VIa in the presence of $CrCl_2$ to prepare the compound of formula Va;

iii) conducting an intramolecular cyclization reaction of the compound of formula Va in the presence of KHMDS to prepare the compound of formula IIIa;

iv) conducting a condensation reaction of the compound of formula IIIa and the compound of formula XIa in the presence of BuLi or LDA to prepare the compound of formula Xa;

v) conducting an oxidation reaction of the compound of formula Xa in the presence of TEMPO oxidant to prepare the compound of formula IXa;

vi) conducting a hydrolysis reaction of the compound of formula IXa in the presence of TMSOTf and 2,6-lutidine to prepare the compound of formula XIIa;

vii) conducting a reductive elimination reaction of the compound of formula XIIa in the presence of $SmI_2$ to give the compound of formula IVa.

In the preparation method (method C) of eribulin intermediate of formula IVa, the reaction condition of each step can be described as above.

The present disclosure also provides a preparation method (method D) of the compound of formula IVa, comprising the following steps:

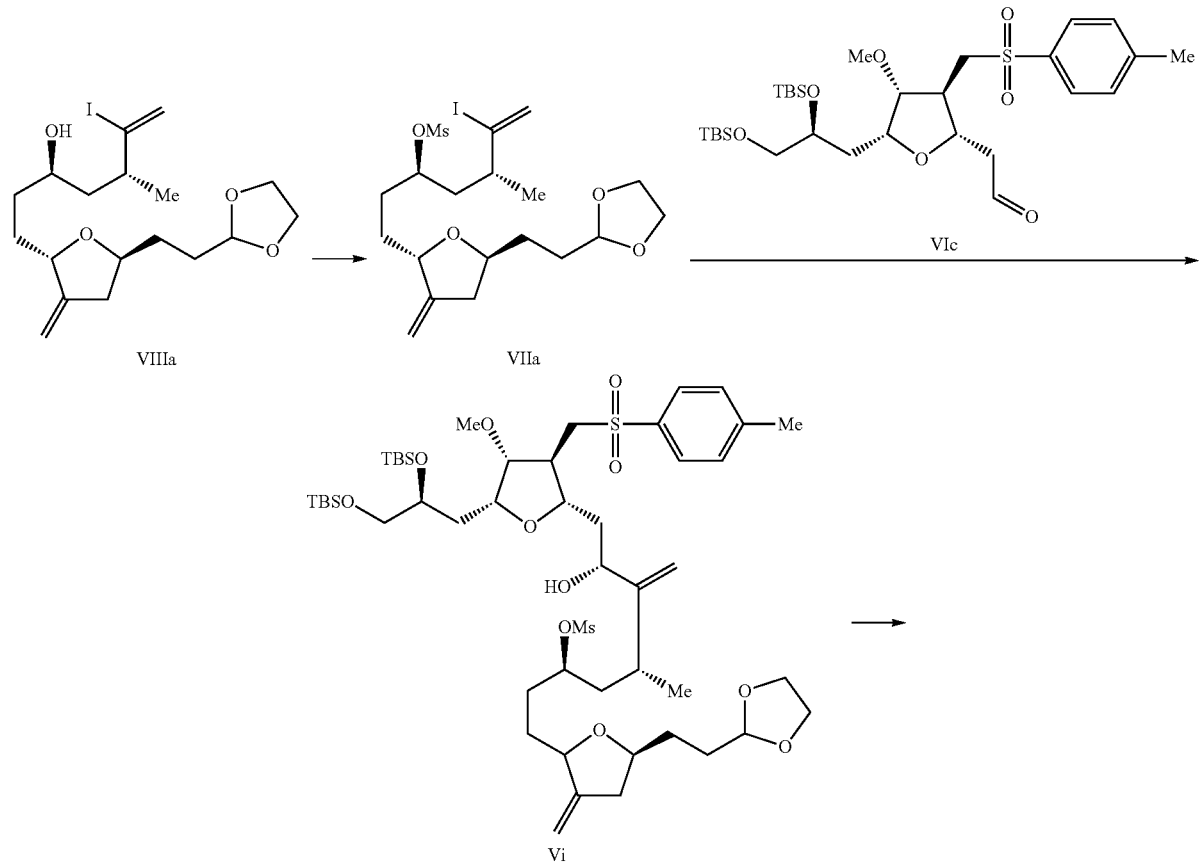

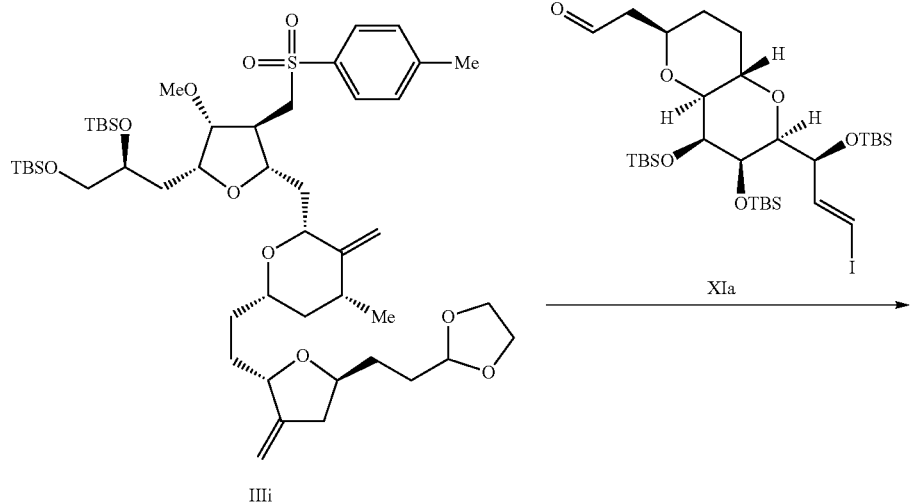
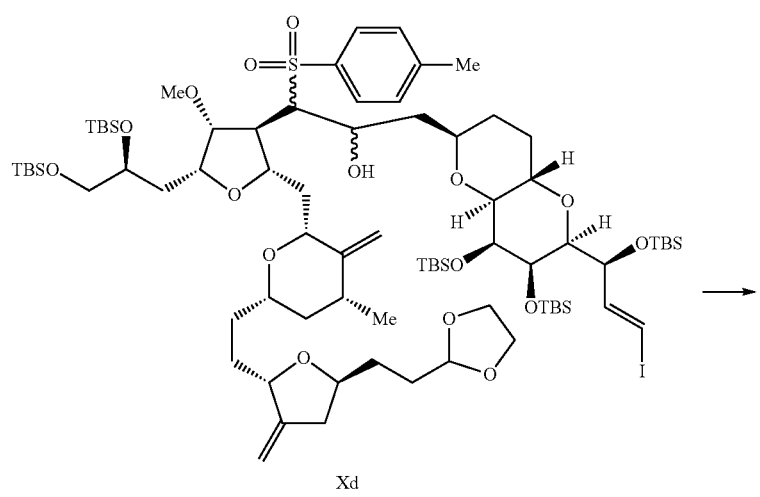
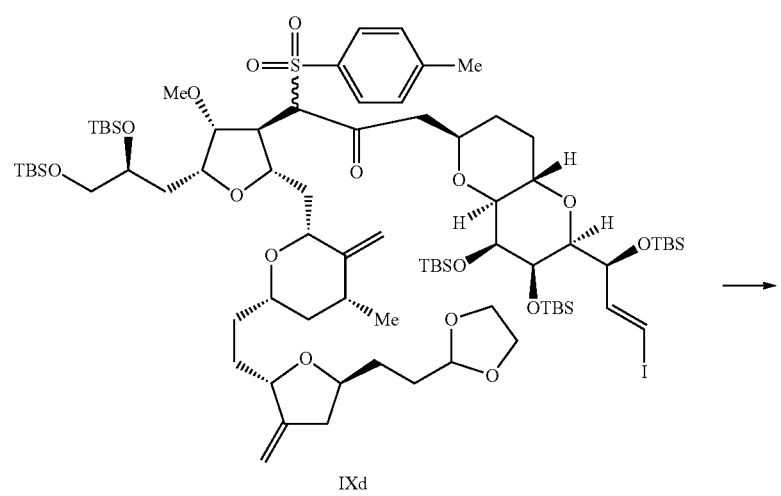

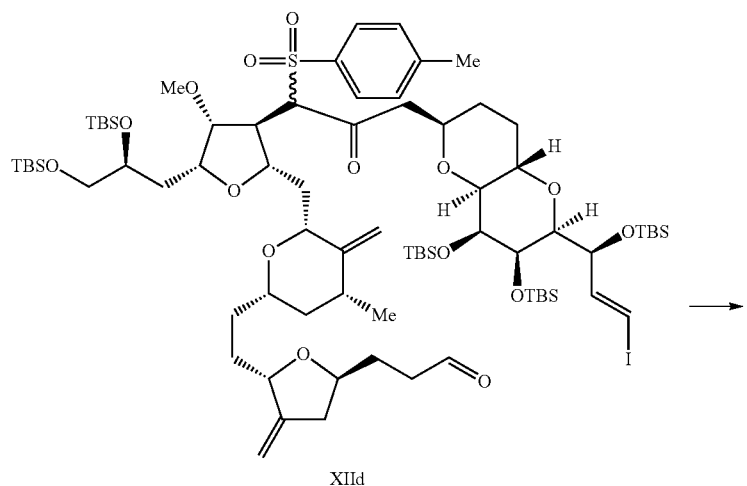

XIId

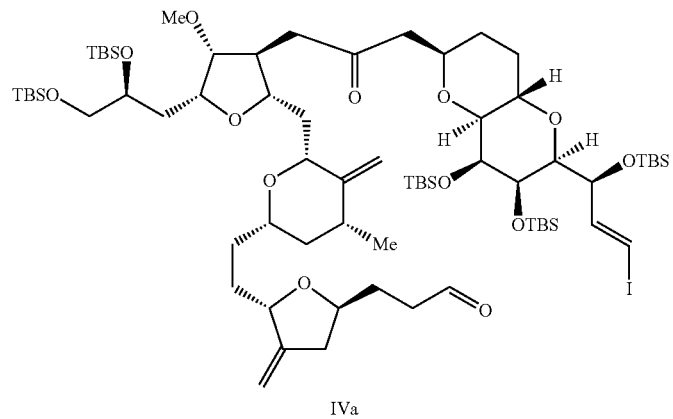

IVa i) conducting a reaction of the compound of formula VIIIa and MsCl under a basic condition to prepare the compound of formula VIIa;

ii) conducting a NHK reaction of the compound of formula VIIa and the compound of formula VIc in the presence of $CrCl_2$ to prepare the compound of formula Vi;

iii) conducting an intramolecular cyclization reaction of the compound of formula Vi in the presence of KHMDS to prepare the compound of formula IIIi.

iv) conducting a condensation reaction of the compound of formula IIIi and the compound of formula XIa in the presence of BuLi or LDA to prepare the compound of formula Xd;

v) conducting an oxidation reaction of the compound of formula Xd in the presence of Dess-Martin oxidant to prepare the compound of formula IXd;

vi) conducting a hydrolysis reaction of the compound of formula IXd in the presence of TMSOTf and 2,6-lutidine to prepare the compound of formula XIId;

vii) conducting a reductive elimination reaction of the compound of formula XIId in the presence of $SmI_2$ to give the compound of formula IVa.

In the preparation method (method D) of the compound of formula IVa, the reaction condition of each step can be described as above.

The present disclosure also provides a preparation method (method C) of the compound of formula IV, comprising the following steps:

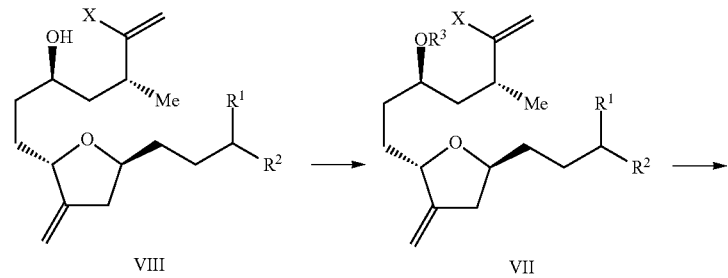

VIII → VII

-continued
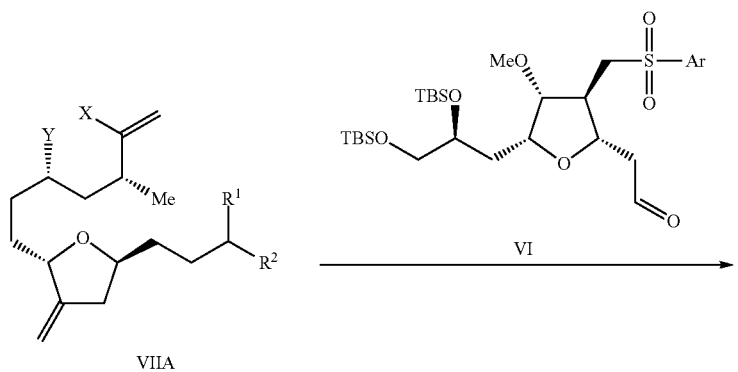
VIIA + VI →
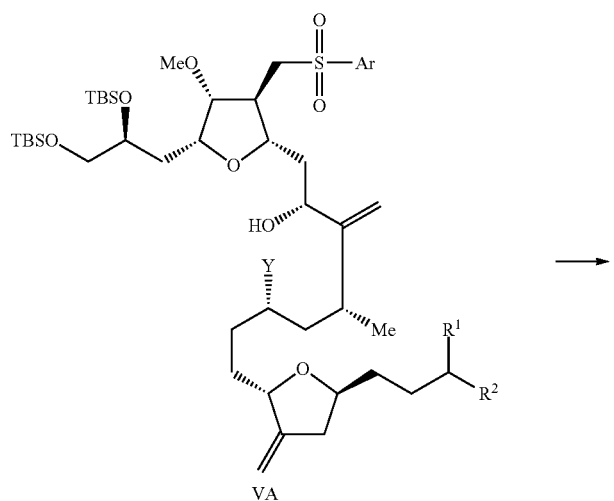
VA →
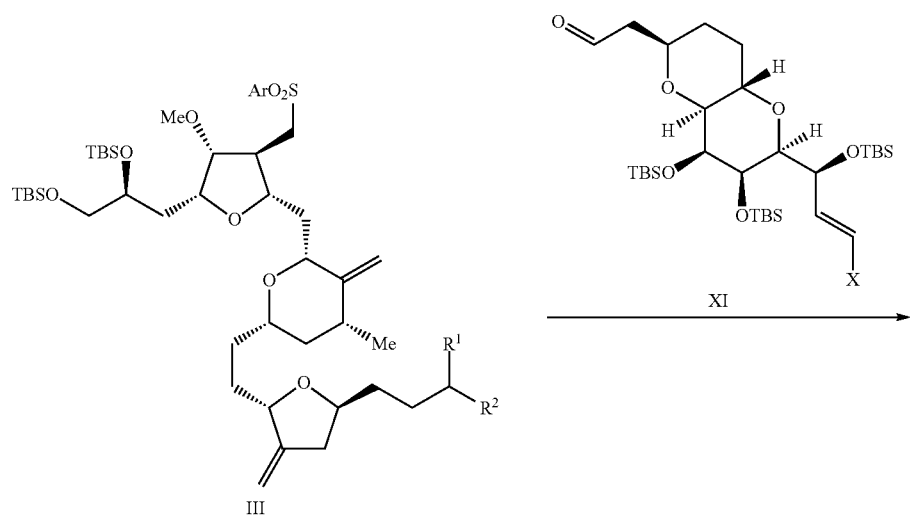
III + XI →

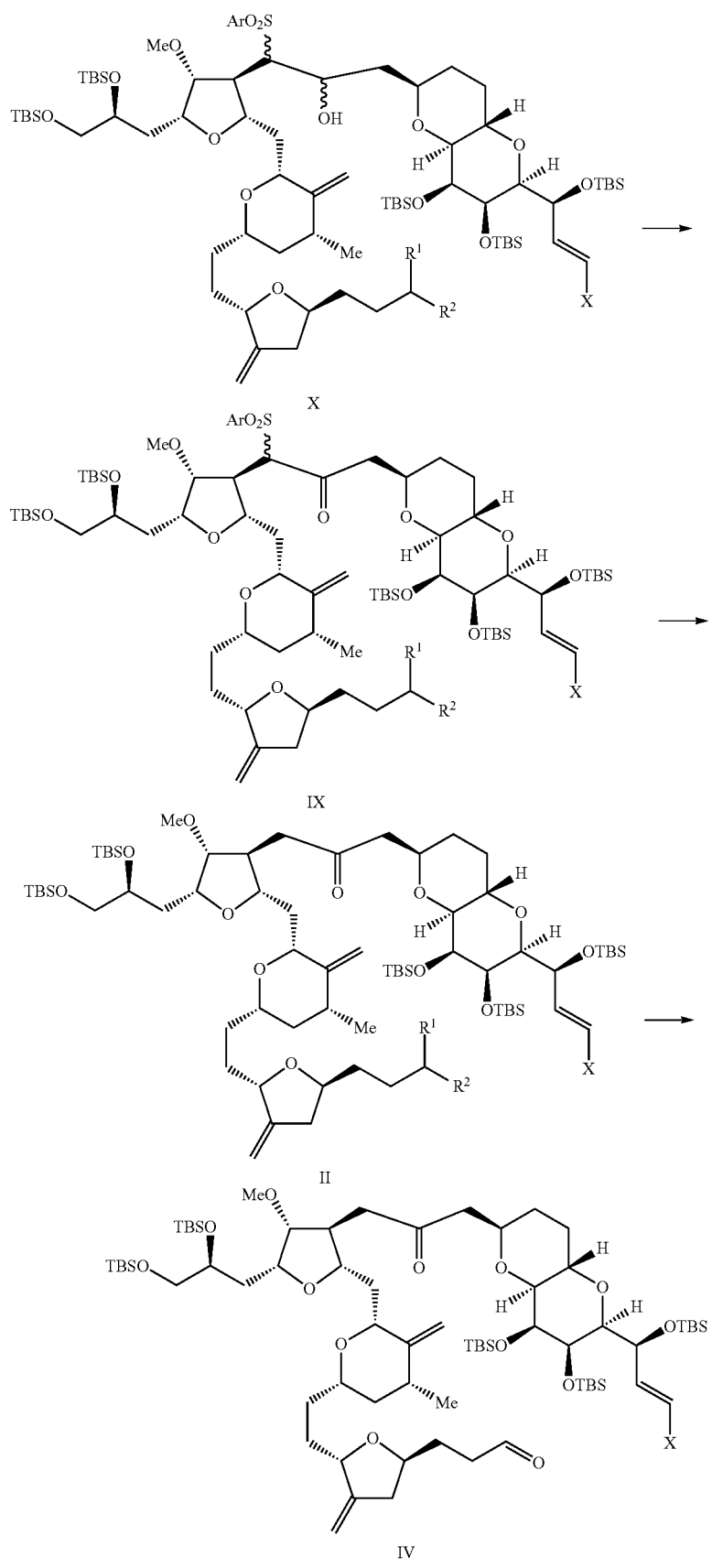

wherein Ar is an aryl substituted by $C_{1-10}$ alkyl or alkoxy or an unsubstituted aryl, preferably a phenyl substituted by $C_{1-10}$ alkyl at para-position or an unsubstituted phenyl;

$R^1$ and $R^2$ are acetal or thioacetal protecting group, and $R^1$ and $R^2$ are each independently $C_{1-10}$ alkoxy or $C_{1-10}$ alkylthio, or $R^1$ and $R^2$ together with the carbon atom to which they are attached form cyclic acetal or cyclic thioacetal; preferably $R^1$ and $R^2$ together with the carbon atom to which they are attached form cyclic acetal or cyclic thioacetal, more preferably substituted or unsubstituted ethylene glycol acetal, or substituted or unsubstituted propanediol acetal; $R^3$ is hydroxyl protecting group, preferably methanesulfonyl, p-toluenesulfonyl or trifluoromethanesulfonyl; X is halogen or a leaving group, preferably chloride, bromide, iodide or trifluoromethanesulfonyloxy;

Y is halogen, preferably chloride, bromide or iodide.

In the preparation method (method C) of eribulin intermediate of formula IV, Ar, $R^1$, $R^2$, $R^3$ and X can be as defined in the preparation method (method B) of eribulin intermediate of formula IV.

In the preparation method (method C) of eribulin intermediate of formula IV, Y can be chloride.

The preparation method (method C) of eribulin intermediate of formula IV can comprise the following step:

i) conducting a hydroxyl protecting reaction of the compound of formula VIII to prepare the compound of formula VII; wherein the hydroxyl protecting reaction is preferably conducted under a basic condition; the hydroxyl protecting reaction is preferably conducted in the presence of one or more reagents selected from the group consisting of $Et_3N$, pyridine, NaH, $K_2CO_3$, 2,4,6-collidine, 2,6-lutidine, BuLi, DIPEA, LDA, KHMDS, LiHMDS and NaHMDS;

ii) conducting a substitution reaction of the compound of formula VII to prepare the compound of formula VIIA; wherein the substitution reaction is preferably conducted in the presence of one or more reagents selected from the group consisting of LiCl, NaCl, $Bu_3NBnCl$, $NH_4Cl$, $Bu_4NCl$, LiBr, NaBr, $Bu_3NBnBr$, $NH_4Br$, $Bu_4NBr$, LiI, NaI, $Bu_3NBnI$, $NH_4I$ or $Bu_4NI$;

iii) conducting a NHK reaction of the compound of formula VI and the compound of formula VIIA to prepare the compound of formula VA; wherein the NHK reaction is preferably conducted in the presence of one or more reagents selected from the group consisting of $CrCl_2$, $CrCl_3$ and $CrBr_3$;

iv) conducting an intramolecular cyclization of the compound of formula VA to prepare the compound of formula III; wherein the intramolecular cyclization reaction is preferably conducted in the presence of a Lewis acid, and the Lewis acid is preferably one or more Lewis acids selected from the group consisting of $Ag_2O$, $AgClO_4$, AgOTf, $AgBF_4$ and $AgPF_6$;

v) conducting a condensation reaction of the compound of formula III and the compound of formula XI to prepare the compound of formula X; wherein the condensation reaction is preferably conducted under a basic condition; the condensation reaction is preferably conducted in the presence of one or more reagents selected from the group consisting of $Et_3N$, pyridine, NaH, $K_2CO_3$, 2,4,6-collidine, 2,6-lutidine, BuLi, LDA, KHMDS, LiHMDS and NaHMDS;

vi) conducting an oxidation reaction of the compound of formula X to prepare the compound of formula IX; wherein the oxidation reaction is preferably conducted in the presence of one or more oxidants selected from the group consisting of Des s-Martin oxidant, Swern oxidant, IBX oxidant, TEMPO-NaClO and TEMPO-PhI(OAc)$_2$;

vii) conducting a reductive elimination reaction of the compound of formula IX to prepare the compound of formula II; wherein the reductive elimination reaction is preferably conducted in the presence of one or more reagents selected from the group consisting of $SmI_2$, $CrCl_2$, Mn powder, Zn powder and $CrCl_3$ and the like;

viii) conducting a hydrolysis reaction of the compound of formula II to give the compound of formula IV; wherein the hydrolysis reaction is preferably conducted under an acidic or a neutral condition; the hydrolysis reaction is preferably conducted in the presence of one or more reagents selected from the group consisting of HCl, p-TsOH, PPTS, $BF_3$·$OEt_2$, TMSOTf, $Ti(OiPr)_4$, $TiCl_4$, pyridine, 2,6-lutidine and 2,4,6-collidine.

In the preparation method (method C) of eribulin intermediate of formula IV, the reaction condition of each step can be described as above.

In a preferred embodiment of the disclosure, in the preparation method (method C) of eribulin intermediate of formula IV, Ar is preferably phenyl, para-methylphenyl or para-ethylphenyl; X is iodide; Y is chloride; $R^1$ and $R^2$ together with the carbon atom to which they are attached form ethylene glycol acetal or propanediol acetal.

The present disclosure also provides a preparation method (method E) of the compound of formula IVa, comprising the following steps:

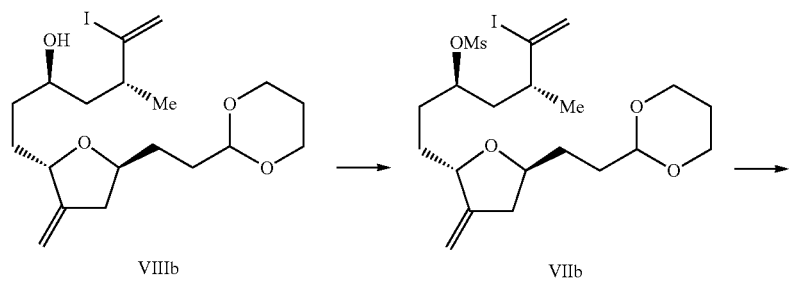

-continued
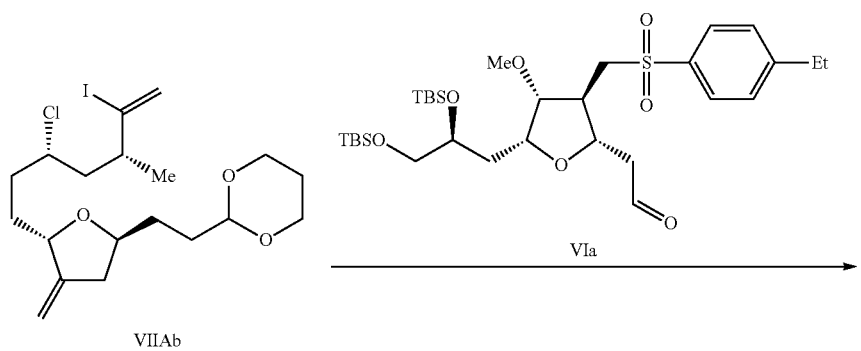
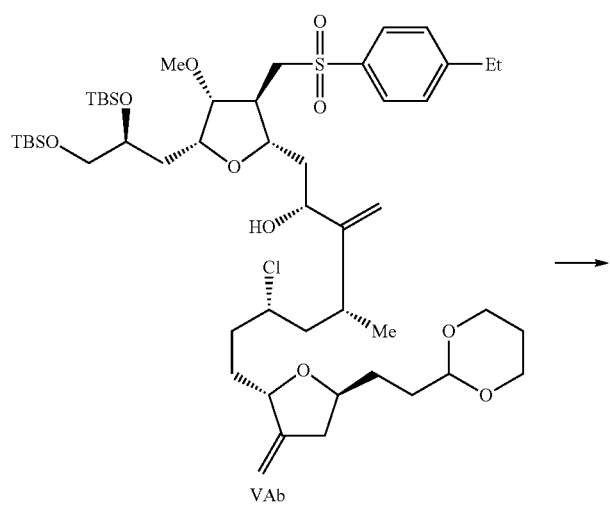
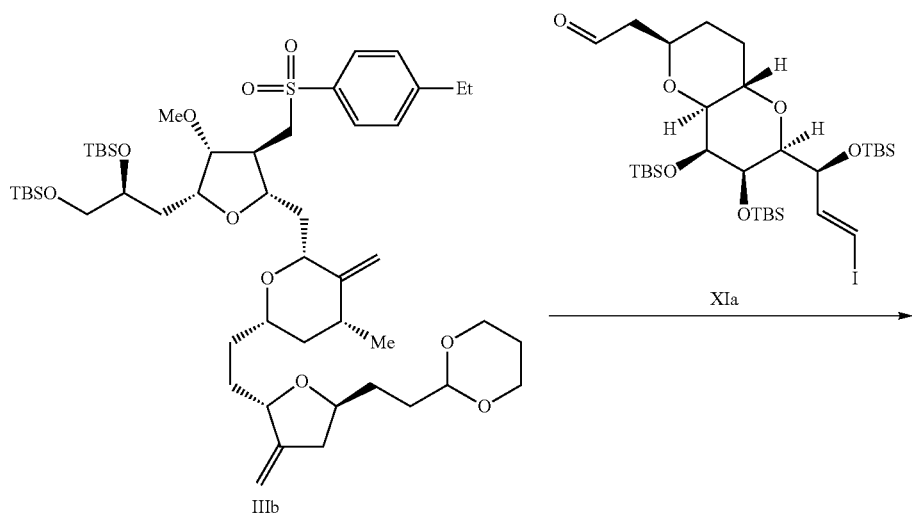

-continued
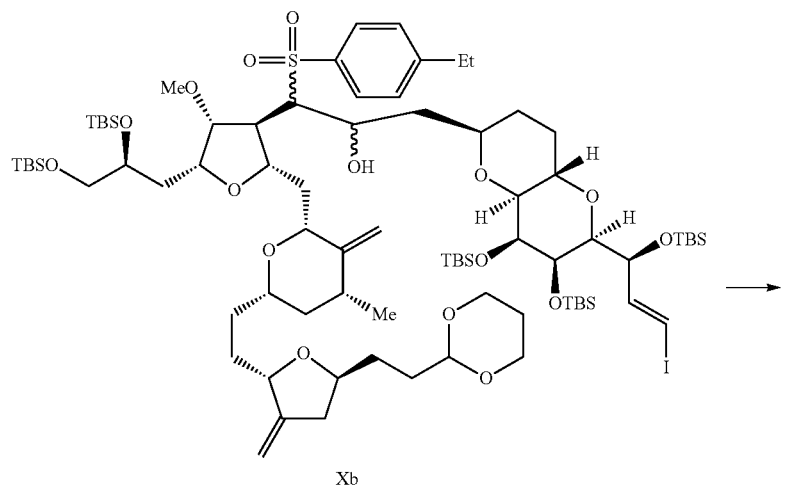
Xb
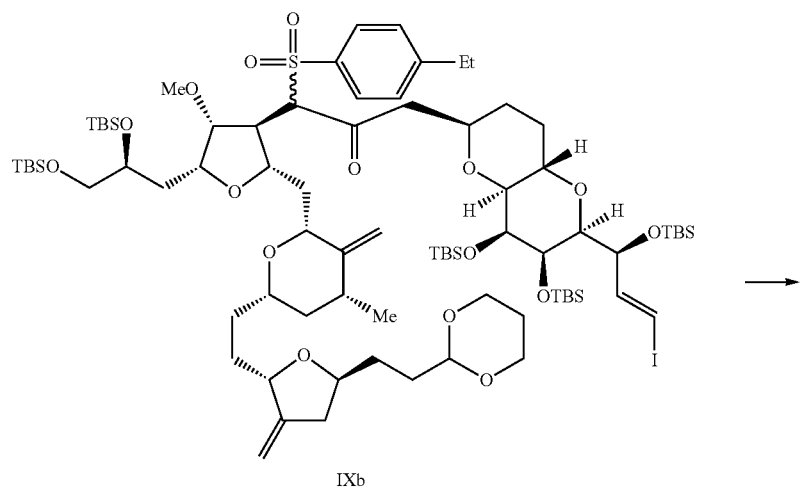
IXb
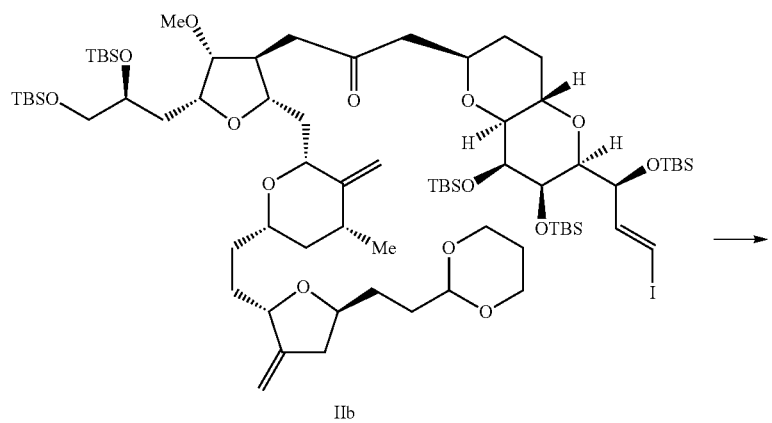
IIb

-continued

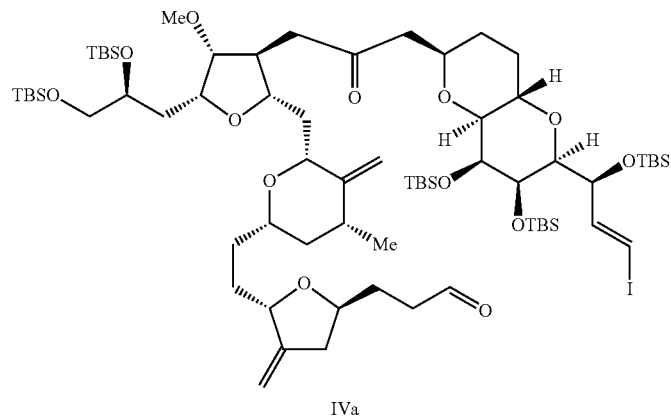

IVa i) conducting a reaction of the compound of formula VIIIb and MsCl under a basic condition to prepare the compound of formula VIIb;

ii) conducting a chlorination reaction of the compound of formula VIIb in the presence of $Bu_3NBnCl$ to prepare the compound of formula VIIAb;

iii) conducting a NHK reaction of the compound of formula VIIAb and the compound of formula VIa in the present of $CrCl_2$ to prepare the compound of formula VAb;

iv) conducting an intramolecular cyclization reaction of the compound of formula VAb in the presence of $AgBF_4$ to prepare the compound of formula IIb.

v) conducting a condensation reaction of the compound of formula IIb and the compound of formula XIa in the presence of BuLi or LDA to prepare the compound of formula Xb;

vi) conducting an oxidation reaction of the compound of formula Xb in the presence of Dess-Martin oxidant to prepare the compound of formula IXb;

vii) conducting a reductive elimination reaction of the compound of formula IXb in the presence of $SmI_2$ to prepare the compound of formula IIb;

viii) conducting a hydrolysis reaction of the compound of formula IIb in the presence of TMSOTf and 2,6-lutidine to give the compound of formula IVa.

In the preparation method (method E) of the compound of formula IVa, the reaction condition of each step can be described as above.

The present disclosure also provides a preparation method (method F) of the compound of formula IVa, comprising the following steps:

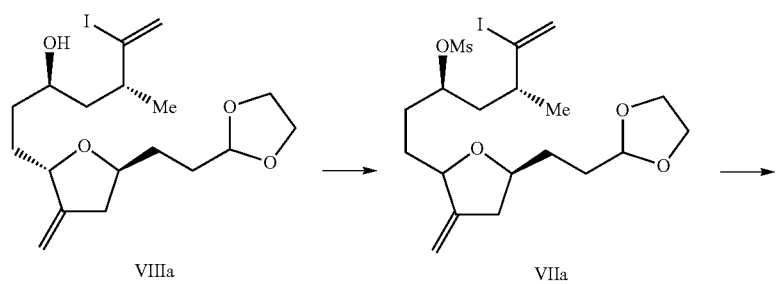

VIIIa → VIIa →

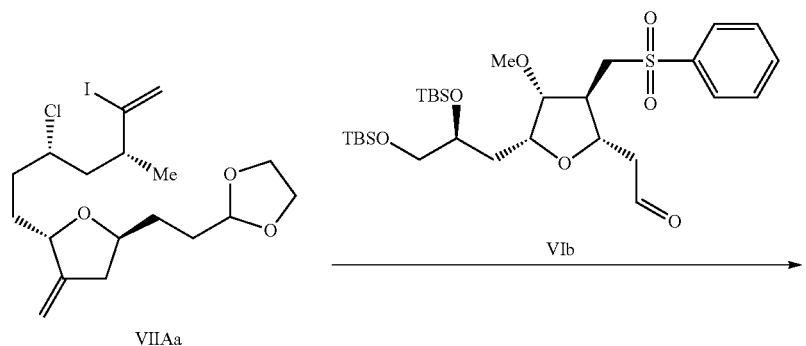

VIIAa VIb

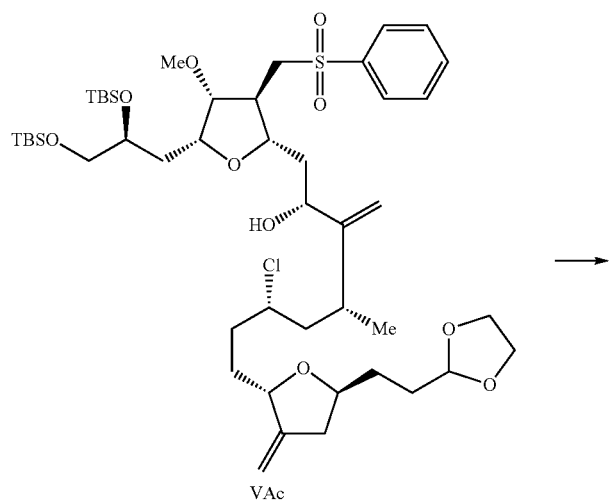
VAc
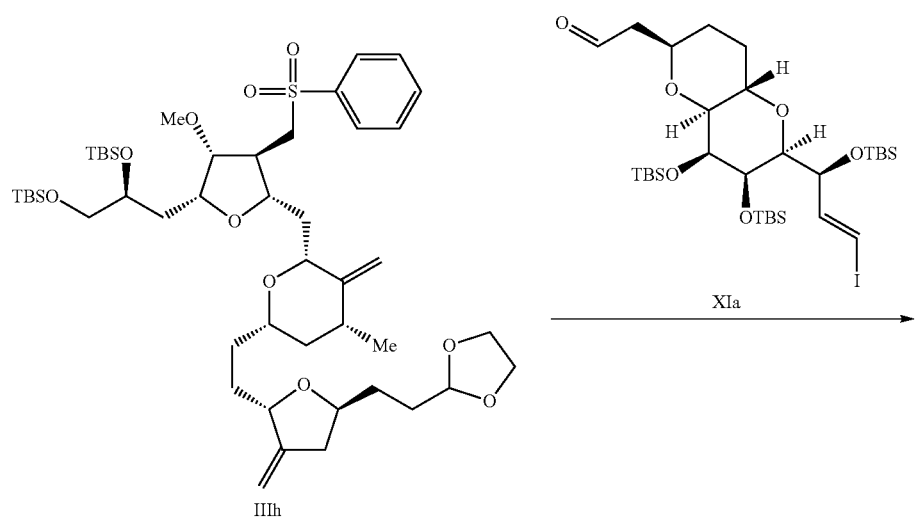
IIIh
XIa
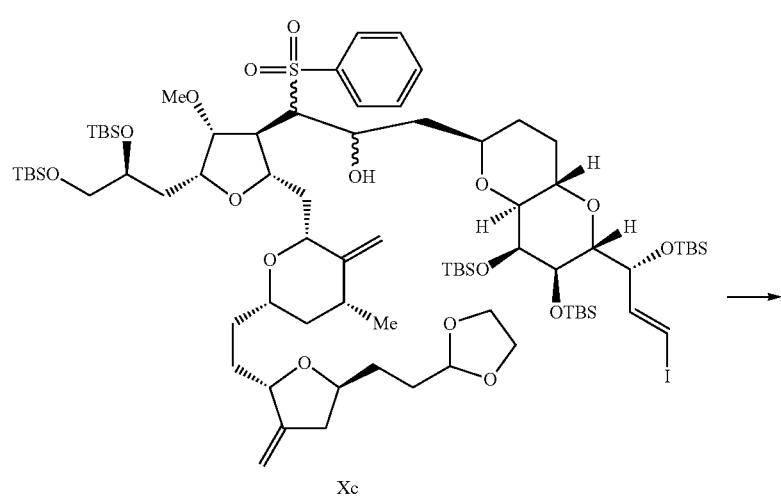
Xc

-continued

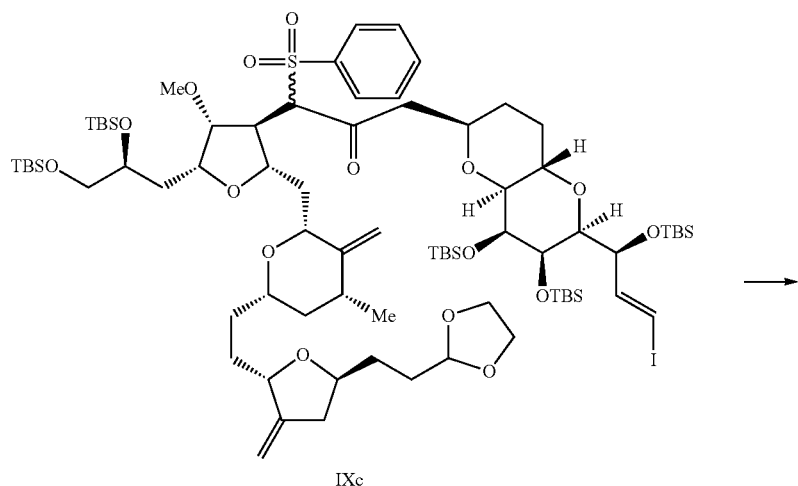

IXc

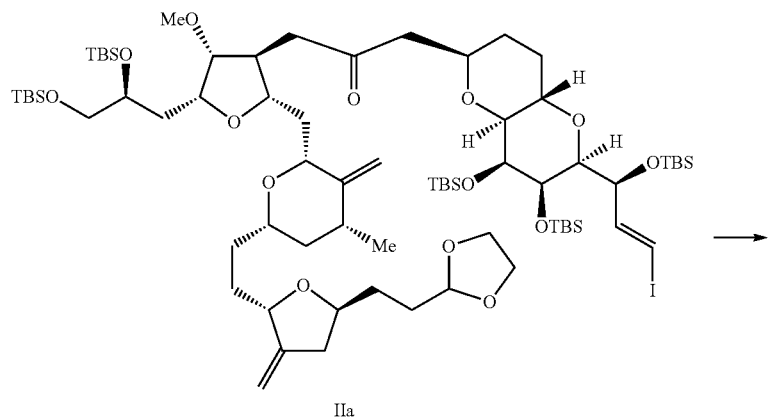

IIa

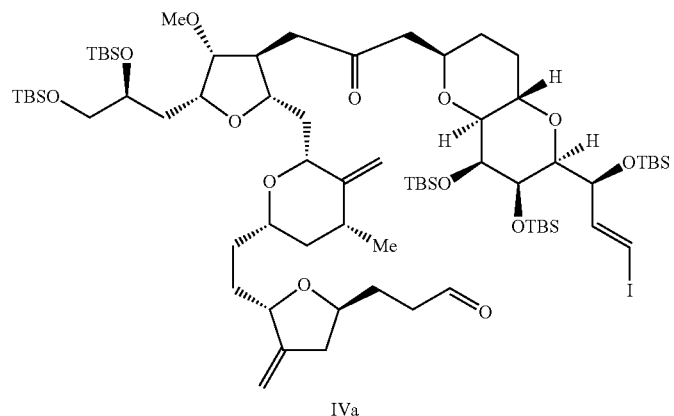

IVa i) conducting a reaction of the compound of formula VIIIa and MsCl under a basic condition to prepare the compound of formula VIIa;

ii) conducting a chlorination reaction of the compound of formula VIIa in the presence of $Bu_3NBnCl$ to prepare the compound of formula VIIAa;

iii) conducting a NHK reaction of the compound of formula VIIAa and the compound of formula VIb in the present of $CrCl_2$ to prepare the compound of formula VAc;

iv) conducting an intramolecular cyclization reaction of the compound of formula VAc in the presence of $AgBF_4$ to prepare the compound of formula IIIh.

v) conducting a condensation reaction of the compound of formula IIIh and the compound of formula XIa in the presence of BuLi or LDA to prepare the compound of formula Xc;

vi) conducting an oxidation reaction of the compound of formula Xc in the presence of Dess-Martin oxidant to prepare the compound of formula IXc;

vii) conducting a reductive elimination reaction of the compound of formula IXc in the presence of SmI$_2$ to prepare the compound of formula IIa;

viii) conducting a hydrolysis reaction of the compound of formula IIa in the presence of TMSOTf and 2,6-lutidine to give the compound of formula IVa.

In the preparation method (method F) of the compound of formula IVa, the reaction condition of each step can be described as above.

The present disclosure also provides a preparation method (method D) of the compound of formula IV, comprising the following steps:

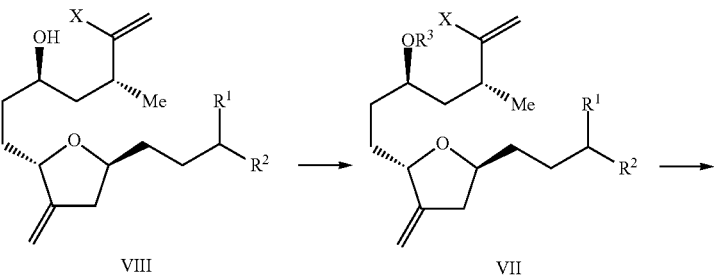

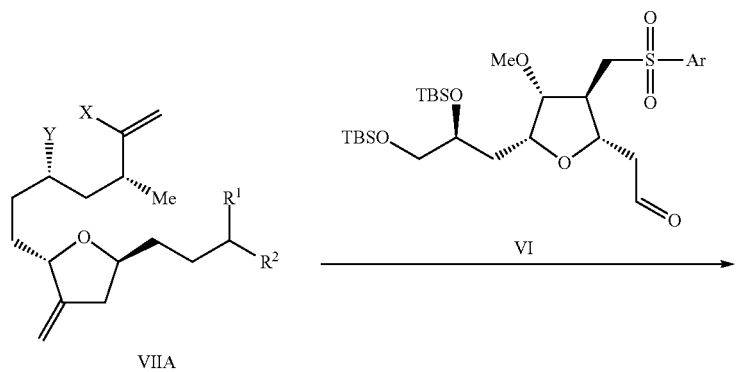

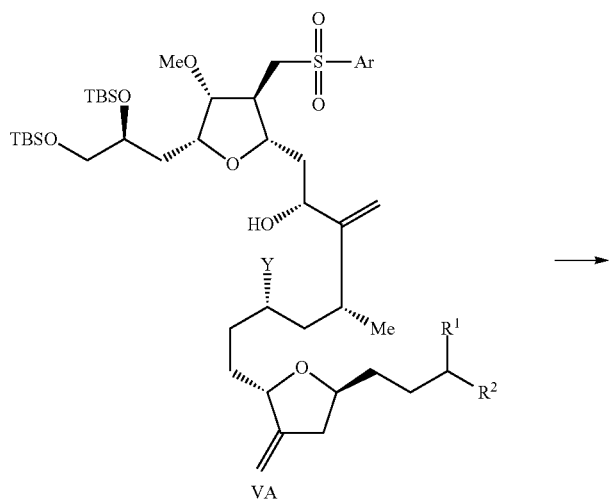

-continued
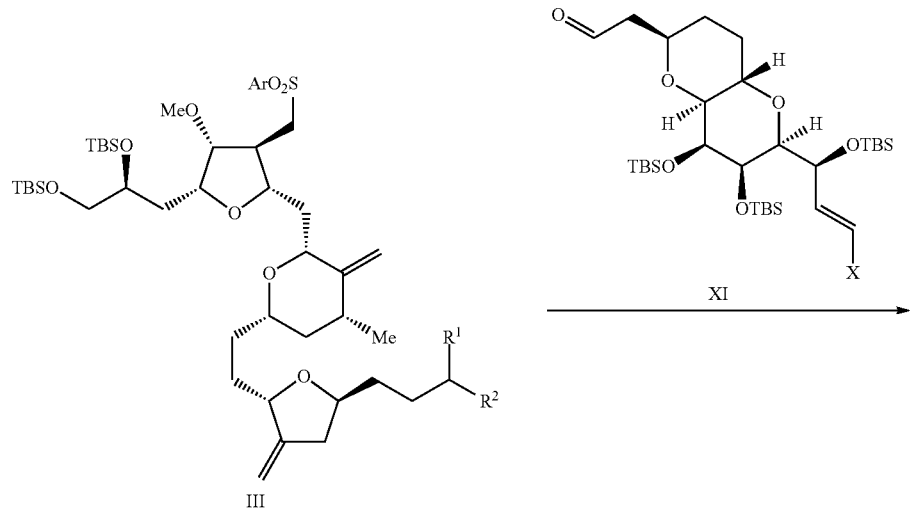
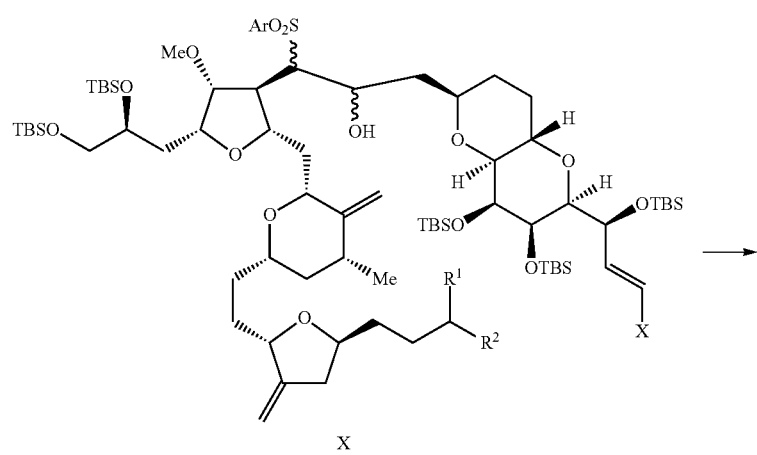
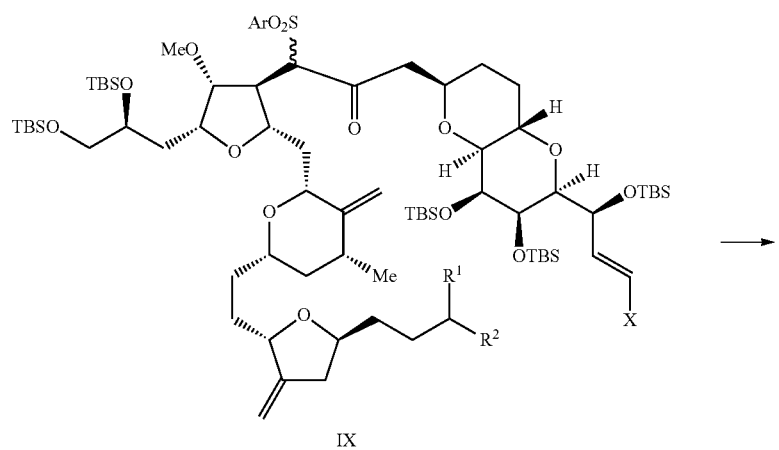

-continued

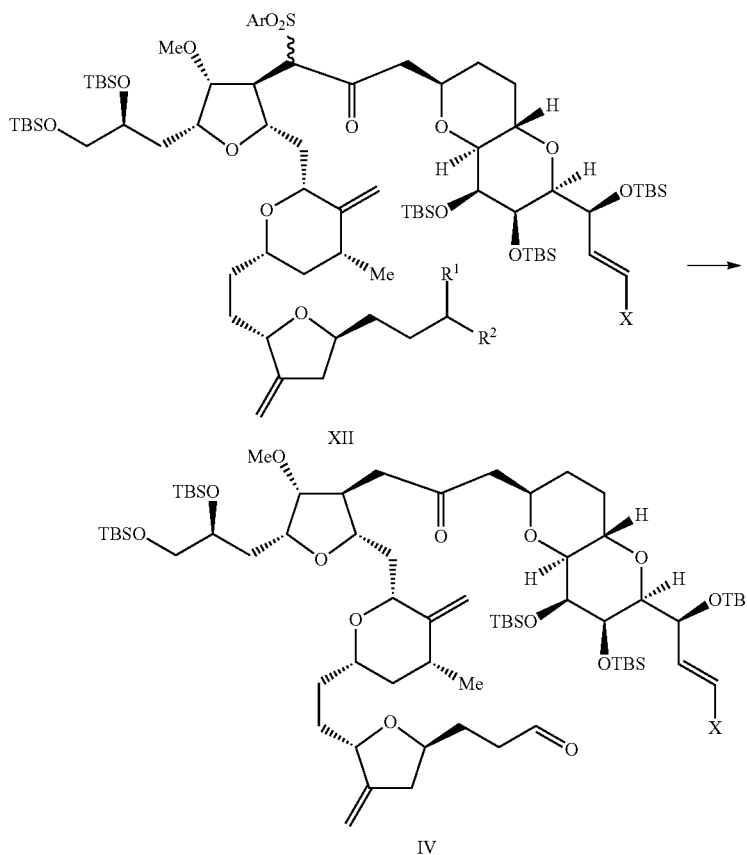

wherein Ar is an aryl substituted by $C_{1-10}$ alkyl or alkoxy or an unsubstituted aryl, preferably a phenyl substituted by $C_{1-10}$ alkyl at para-position or a unsubstituted phenyl;

$R^1$ and $R^2$ are acetal or thioacetal protecting group, and $R^1$ and $R^2$ are each independently $C_{1-10}$ alkoxy or $C_{1-10}$ alkylthio, or $R^1$ and $R^2$ together with the carbon atom to which they are attached form cyclic acetal or cyclic thioacetal; preferably $R^1$ and $R^2$ together with the carbon atom to which they are attached form cyclic acetal or cyclic thioacetal, more preferably substituted or unsubstituted ethylene glycol acetal, or substituted or unsubstituted propanediol acetal; $R^3$ is hydroxyl protecting group, preferably methanesulfonyl, p-toluenesulfonyl or trifluoromethanesulfonyl; X is halogen or a leaving group, preferably chloride, bromide, iodide or trifluoromethanesulfonyloxy;

Y is halogen, preferably chloride, bromide or iodide.

In the preparation method (method D) of eribulin intermediate of formula IV, Ar, $R^1$, $R^2$, $R^3$ and X can be as defined in the preparation method (method B) of eribulin intermediate of formula IV.

In the preparation method (method D) of eribulin intermediate of formula IV, the reaction condition of each step can be described as above.

In the preparation method (method D) of eribulin intermediate of formula IV, Y can be chloride.

The preparation method (method D) of eribulin intermediate of formula IV can comprise the following steps:

i) conducting a hydroxyl protecting reaction of the compound of formula VIII to prepare the compound of formula VII; wherein the hydroxyl protecting reaction is preferably conducted under a basic condition; and the hydroxyl protecting reaction is preferably conducted in the presence of one or more reagents selected from the group consisting of $Et_3N$, pyridine, NaH, $K_2CO_3$, 2,4,6-collidine, 2,6-lutidine, BuLi, DIPEA, LDA, KHMDS, LiHMDS and NaHMDS;

ii) conducting a substitution reaction of the compound of formula VII to prepare the compound of formula VIIA; wherein the substitution reaction is preferably conducted in the presence of one or more reagents selected from the group consisting of LiCl, NaCl, $Bu_3NBnCl$, $NH_4Cl$, $Bu_4NCl$, LiBr, NaBr, $Bu_3NBnBr$, $NH_4Br$, $Bu_4NBr$, LiI, NaI, $Bu_3NBnI$, $NH_4I$ and $Bu_4NI$;

iii) conducting a NHK reaction of the compound of formula VI and the compound of formula VIIA to prepare the compound of formula VA; wherein the NHK reaction is preferably conducted in the presence of one or more reagents selected from the group consisting of $CrCl_2$, $CrCl_3$ and $CrBr_3$;

iv) conducting an intramolecular cyclization reaction of the compound of formula VA to prepare the compound of formula III; wherein the intramolecular cyclization reaction is preferably conducted in the presence of a Lewis acid, and the Lewis acid is preferably one or more Lewis acids selected from the group consisting of $Ag_2O$, $AgClO_4$, AgOTf, $AgBF_4$ and $AgPF_6$;

v) conducting a condensation reaction of the compound of formula III and the compound of formula XI to prepare the compound of formula X; wherein the condensation reaction is preferably conducted under a basic condition; the condensation reaction is preferably conducted in the presence of one or more reagents selected from the group consisting of NaH, BuLi, DIPEA, LDA, KHMDS, LiHMDS and NaHMDS;

vi) conducting an oxidation reaction of the compound of formula X to prepare the compound of formula IX; wherein the oxidation reaction is preferably conducted in the presence of one or more oxidants selected from the group consisting of Des s-Martin oxidant, Swern oxidant, IBX oxidant, TEMPO-NaClO and TEMPO-PhI(OAc)$_2$;

vii) conducting a hydrolysis reaction of the compound of formula IX to prepare the compound of formula XII; wherein the hydrolysis reaction is preferably conducted under an acidic or a neutral condition; the hydrolysis reaction is preferably conducted in the presence of one or more reagents selected from the group consisting of HCl, p-TsOH, PPTS, BF$_3$. OEt$_2$, TMSOTf, Ti(OiPr)$_4$, TiCl$_4$, pyridine, 2,6-lutidine and 2,4,6-collidine;

viii) conducting a reductive elimination reaction of the compound of formula XII to give the compound of formula IV; wherein the reductive elimination reaction is preferably conducted in the presence of one or more reagents selected from the group consisting of SmI$_2$, CrCl$_2$, Mn powder, Zn powder and CrCl$_3$;

In a preferred embodiment of the disclosure, in the preparation method (method D) of eribulin intermediate of formula IV, Ar is preferably phenyl, para-methylphenyl or para-ethylphenyl; X is iodide; Y is chloride; R$^1$ and R$^2$ together with the carbon atom to which they are attached form ethylene glycol acetal or propanediol acetal.

The present disclosure also provides a preparation method (method G) of the compound of formula IVa, comprising the following steps:

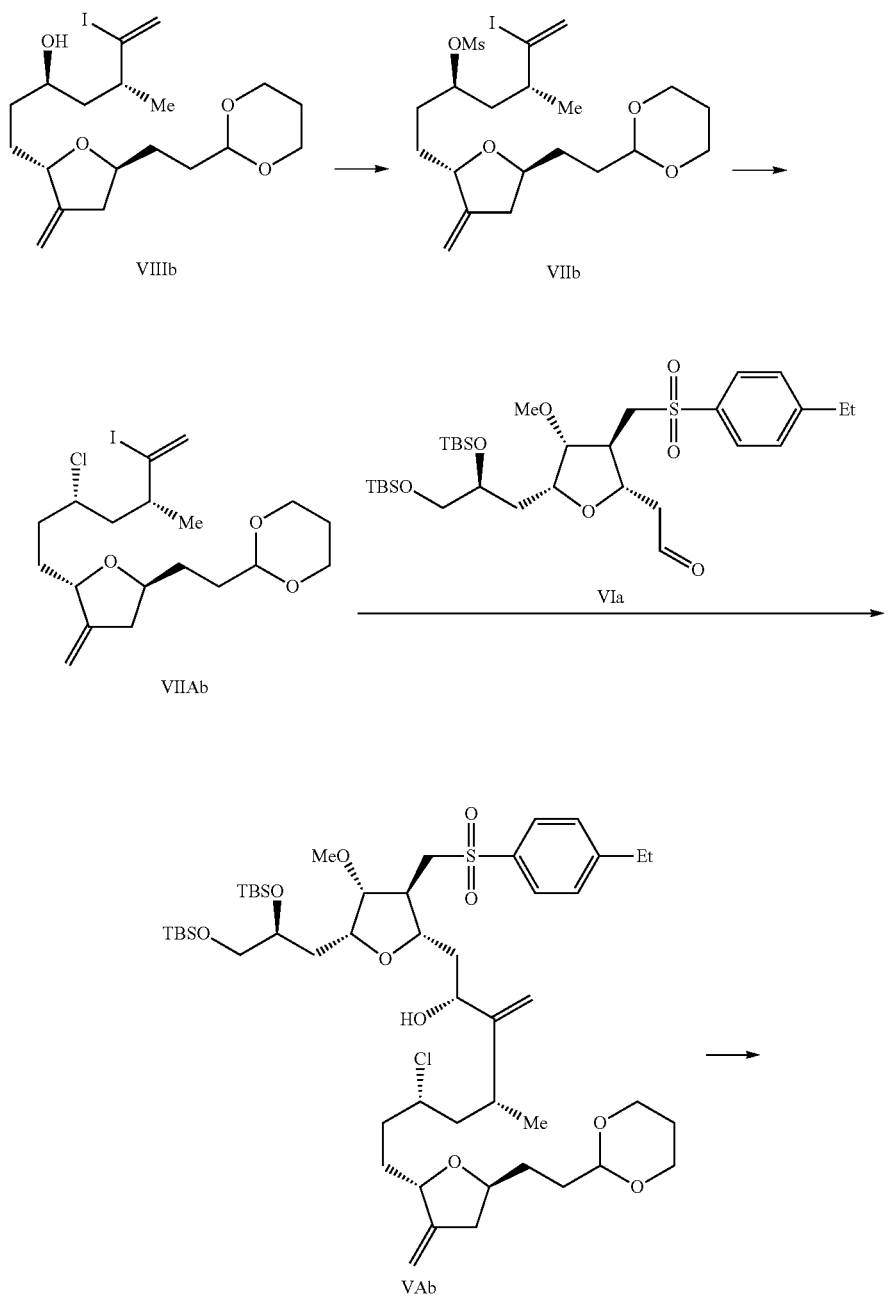

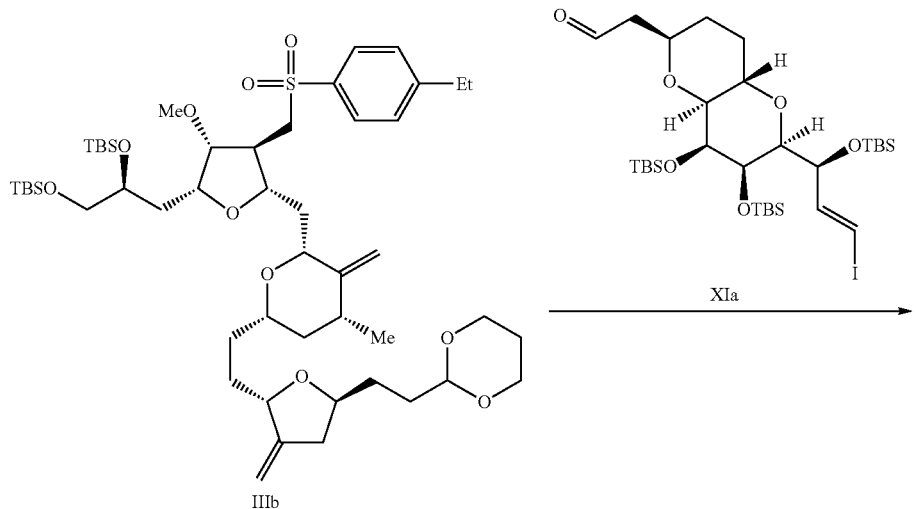
IIIb
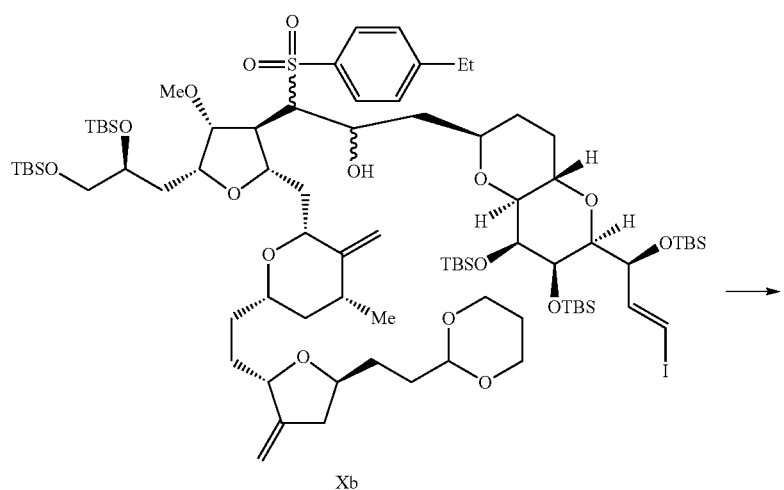
Xb
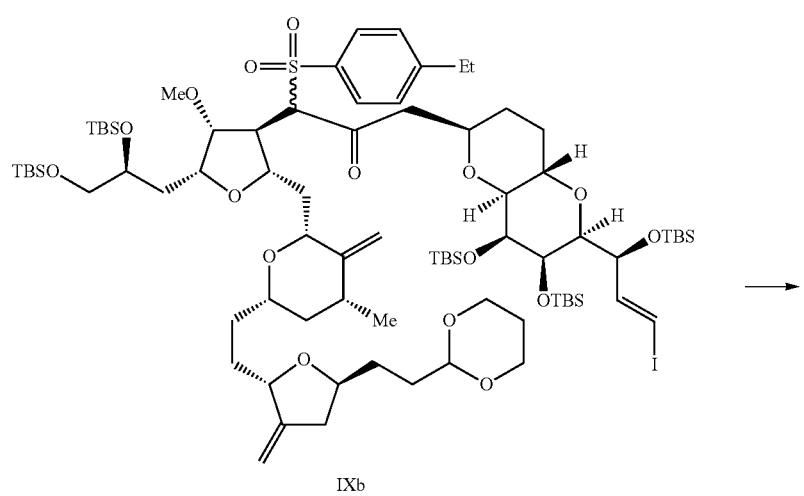
IXb

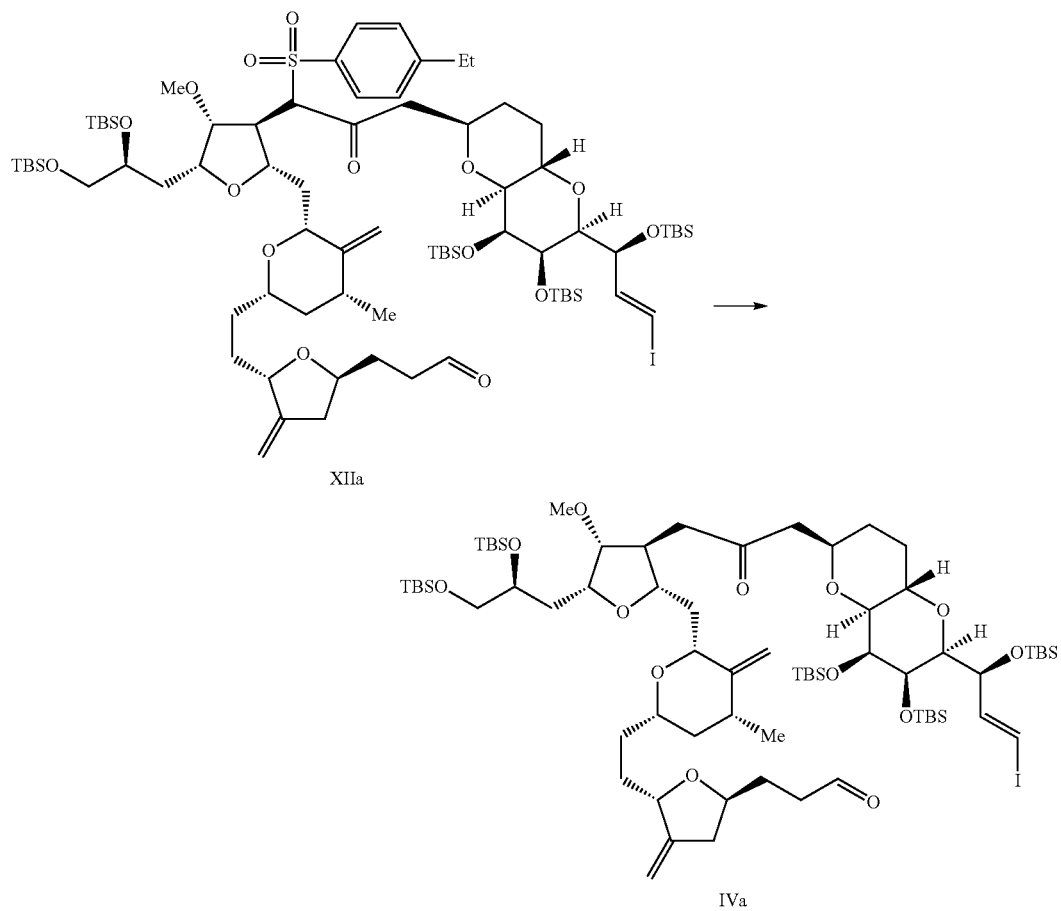

XIIa

IVa i) conducting a reaction of the compound of formula VIIIb and MsCl under a basic condition to prepare the compound of formula VIIb;

ii) conducting a chlorination reaction of the compound of formula VIIb in the presence of $Bu_4NCl$ to prepare the compound of formula VIIAb;

iii) conducting a NHK reaction of the compound of formula VIIAb with the compound of formula VIa in the present of $CrCl_2$ to prepare the compound of formula VAb;

iv) conducting an intramolecular cyclization reaction of the compound of formula VAb in the presence of $AgPF_6$ to prepare the compound of formula IIIb;

v) conducting a condensation reaction of the compound of formula IIIb and the compound of formula XIa in the presence of BuLi or LDA to prepare the compound of formula Xb;

vi) conducting an oxidation reaction of the compound of formula Xb in the presence of Dess-Martin oxidant to prepare the compound of formula IXb;

vii) conducting a hydrolysis reaction of the compound of formula IXb in the presence of TMSOTf and 2,6-lutidine to prepare the compound of formula XIIa;

viii) conducting a reductive elimination reaction of the compound of formula XIIa in the presence of $SmI_2$ to give the compound of formula IVa.

In the preparation method (method G) of the compound of formula IVa, the reaction condition of each step can be described as above.

The present disclosure also provides a preparation method (method H) of the compound of formula IVa, comprising the following steps:

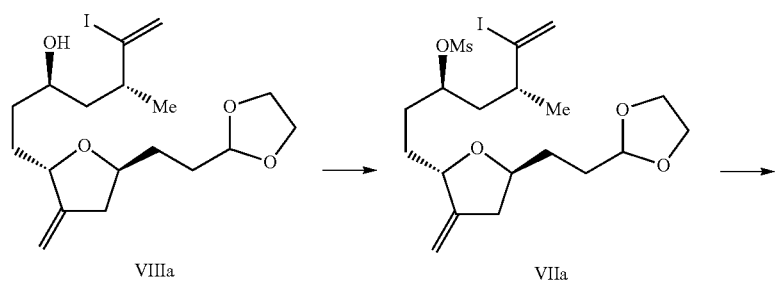

VIIIa      VIIa

-continued
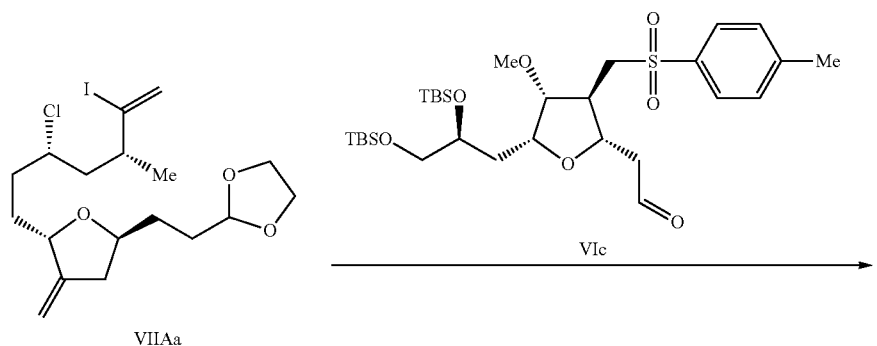
VIIAa
VIc
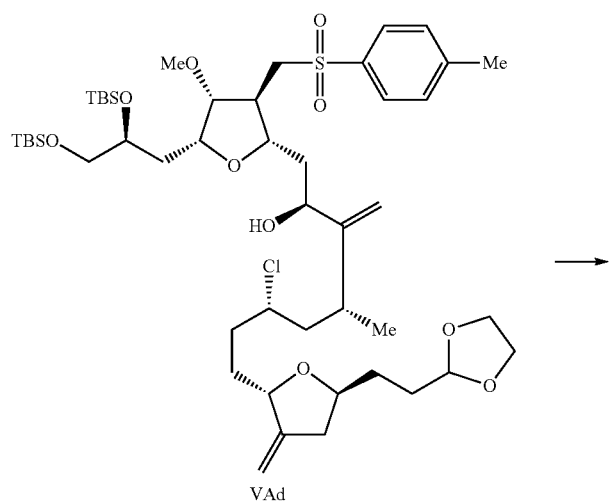
VAd
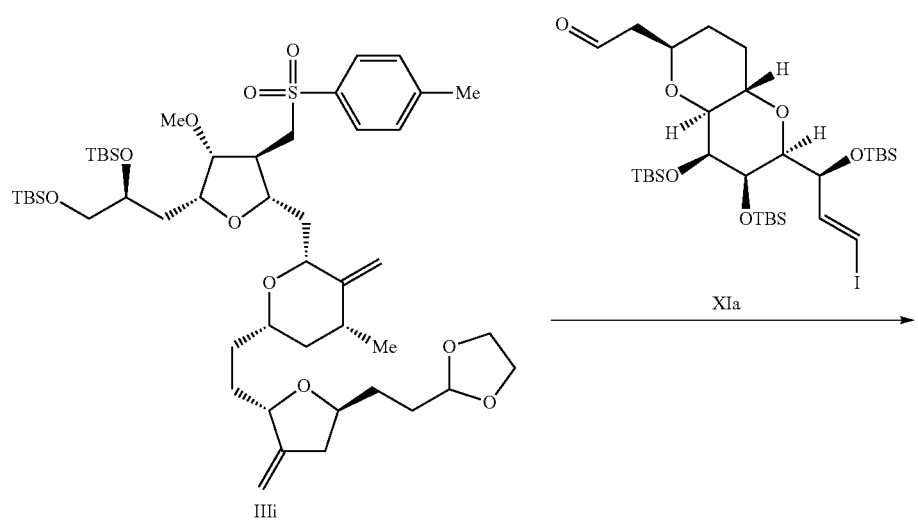
IIIi
XIa

-continued
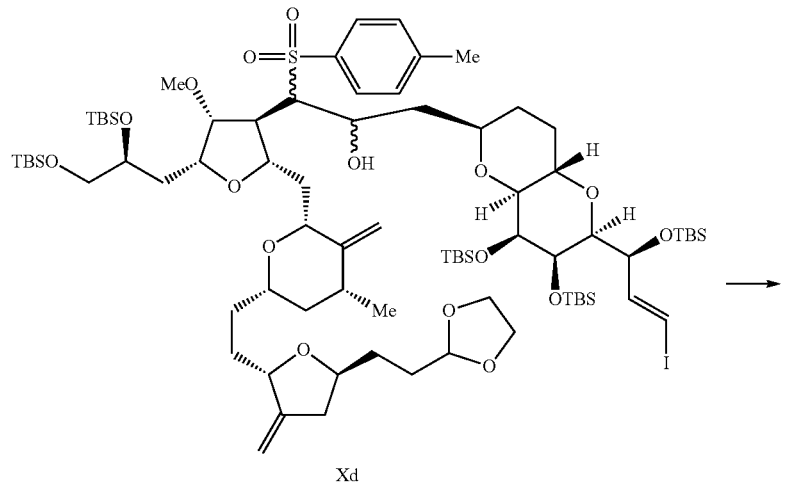
Xd
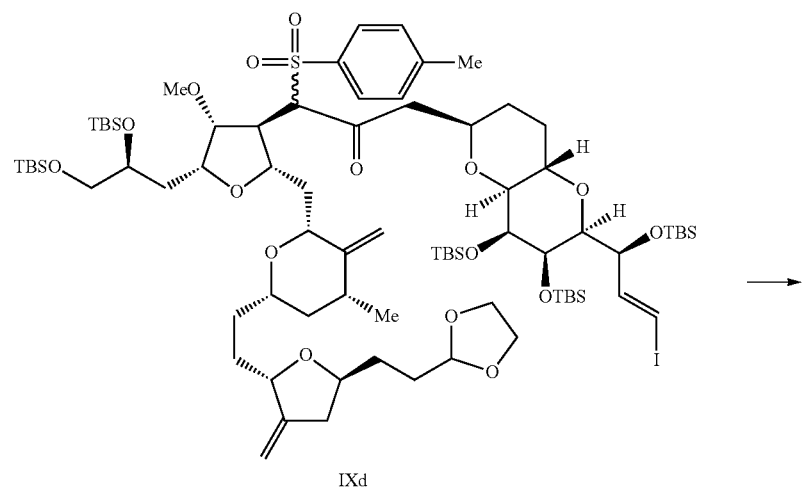
IXd
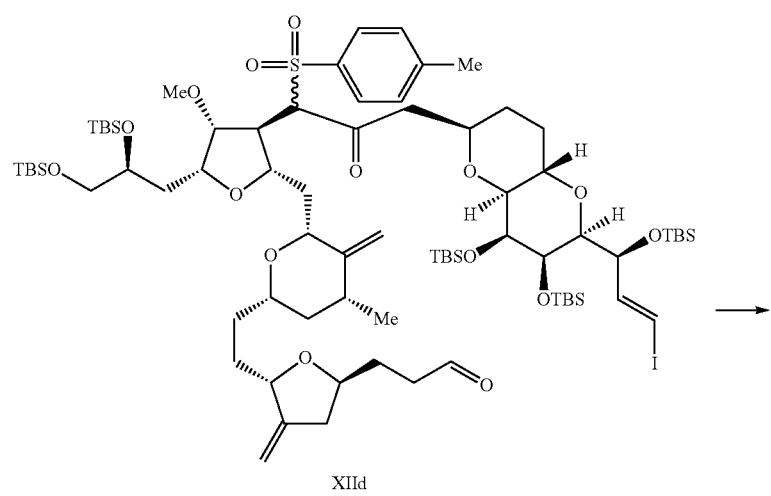
XIId

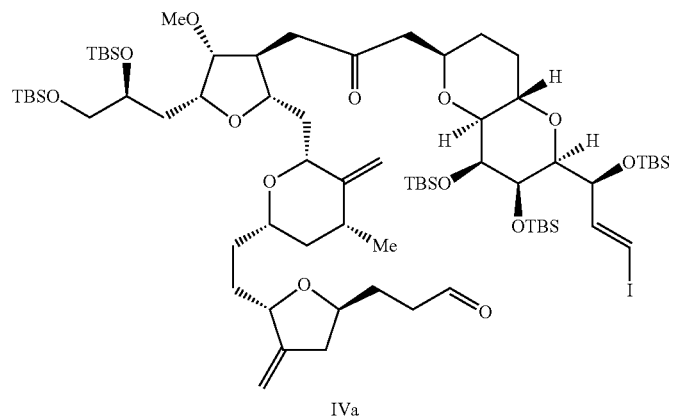

IVa i) conducting a reaction of the compound of formula VIIIa and MsCl under a basic condition to prepare the compound of formula VIIa;

ii) conducting a chlorination reaction of the compound of formula VIIa in the presence of $Bu_4NCl$ to prepare the compound of formula VIIAa;

iii) conducting a NHK reaction of the compound of formula VIIAa and the compound of formula VIc in the present of $CrCl_2$ to prepare the compound of formula VAd;

iv) conducting an intramolecular cyclization reaction of the compound of formula VAd in the presence of $AgPF_6$ to prepare the compound of formula IIIi.

v) conducting a condensation reaction of the compound of formula IIIi and the compound of formula XIa in the presence of BuLi or LDA to prepare the compound of formula Xd;

vi) conducting an oxidation reaction of the compound of formula Xd in the presence of Dess-Martin oxidant to prepare the compound of formula IXd;

vii) conducting a hydrolysis reaction of the compound of formula IXd in the presence of TMSOTf and 2,6-lutidine to prepare the compound of formula XIId;

viii) conducting a reductive elimination reaction of the compound of formula XIId in the presence of $SmI_2$ to give the compound of formula IVa.

In the preparation method (method H) of the compound of formula IVa, the reaction condition of each step can be described as above.

If some intermediates of the above steps are commercially available, the compound of formula IV can be prepared via shorter routes. For example, the intermediate of formula III can be purchased, and then the compound of formula IV can be prepared from this intermediate according to the above methods.

Furthermore, the present disclosure also provides a preparation method of eribulin, comprising preparing the compound of formula II, III or V according to the previously mentioned methods of the present disclosure, and then preparing eribulin from the compound of formula II, III or V according to known methods, which can refer to the following literatures: *J. Am. Chem. Soc.* 2009, 131, 15636; *Angew. Chem. Intl. Ed.* 2009, 48, 2346; *Synlett.* 2013, 24, 323; *Synlett.* 2013, 24, 327; *Synlett.* 2013, 24, 333.

Unless otherwise indicated, the terms used herein have the following meanings:

In the present disclosure, ethylene glycol acetal is

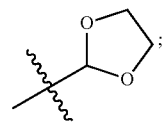

propanediol acetal is

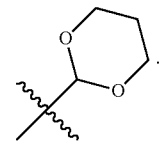 [SMILES: *C1OCCCO1]

"Alkyl" refers to saturated aliphatic hydrocarbon groups, including linear and branched chains containing from 1 to 10 carbon atom(s), and preferably from 1 to 6 carbon atom(s). Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When the alkyl group is substituted, the substituent(s) can be located at any available connection point, and preferably the substituent(s) is one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, and oxo.

"alkoxy" refers to "RO—", wherein R is saturated aliphatic hydrocarbon groups, including linear and branched chains containing from 1 to 10 carbon atom(s), and preferably from 1 to 6 carbon atom(s). Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When the alkyl group is substituted, the substituent(s) can be located at any available connection point, and preferably the substituent(s) is one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, and oxo.

"alkylthio" refers to "RS—", wherein R is saturated aliphatic hydrocarbon groups, including linear and branched chains containing from 1 to 10 carbon atom(s), and preferably from 1 to 6 carbon atom(s). Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When the alkyl group is substituted, the substituent(s) can be located at any available connection point, and preferably the substituent(s) is one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio, heterocycloalkylthio, and oxo group.

"Aryl" refers to a 6- to 14-membered all-carbon monocyclic ring or polycyclic fused ring (a fused ring system means that each ring in the system shares an adjacent pair of carbon atoms with another ring in the system) with a conjugated π-electron system, preferably 6- to 10-membered, more preferably phenyl group and naphthyl group, most preferably phenyl group. The aryl group could be substituted or unsubstituted. When the aryl group is substituted, the substituent(s) is preferably one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyoxy, heterocycloalkoxy, cycloalkylthio, and heterocycloalkylthio.

The hydroxyl protecting groups used in the present disclosure are appropriate hydroxyl protecting groups known in the art. See the hydroxyl protecting groups described in "Protective Groups in Organic Synthesis", 5$^{Th}$ Ed. T. W. Greene & P. G. M. Wuts. For example, the hydroxyl protecting groups are preferably $(C_{1-10}$ alkyl or aryl)$_3$ silyl group, e.g. triethylsilyl, triisopropylsilyl, tert-butyldimethylsilyl, tert-butyldiphenylsilyl, etc. The hydroxyl protecting groups can also be $C_{1-10}$ alkyl or substituted alkyl groups, e.g. methyl, tert-butyl, allyl, benzyl, methoxymethyl, ethoxyethyl, 2-tetrahydropyranyl (THP), etc. The hydroxyl protecting groups can also be $(C_{1-10}$ alkyl or aryl)acyl groups, e.g. formyl, acetyl, benzoyl, etc. The hydroxyl protecting groups can also be $(C_{1-6}$ alkyl or $C_{6-10}$ aryl) sulfonyl groups or $(C_{1-6}$ alkoxy or $C_{6-10}$ aryloxy)carbonyl groups.

The acetal protecting groups used in the present disclosure are appropriate acetal protecting groups known in the art. See the acetal protecting groups described in "Protective Groups in Organic Synthesis", 5$^{Th}$ Ed. T. W. Greene & P. G. M. Wuts. For example, the acetal protecting groups are preferably $C_{1-10}$ alkoxy groups, e.g. dimethylacetal, diethylacetal, diisopropylacetal, ethylene glycol acetal, propanediol acetal, etc.

The thioacetal protecting groups used in the present disclosure are appropriate thioacetal protecting groups known in the art. See the thioacetal protecting groups described in "Protective Groups in Organic Synthesis", 5$^{Th}$ Ed. T. W. Greene & P. G. M. Wuts. For example, the thioacetal protecting groups are preferably $C_{1-10}$ alkylthio groups, e.g. dimethylthioacetal, diethylthioacetal, ethanedithioacetal, propanedithioacetal, etc.

The leaving groups used in the present disclosure are appropriate functional groups known in the art, which are suitable for leaving during the reaction. For example, the leaving groups are preferably methanesulfonyloxy, p-toluenesulfonyloxy, trifluoromethanesulfonyloxy, etc.

| List of abbreviations: | |
|---|---|
| Abbreviation | Full name |
| DMP | Dess-Martin oxidant |
| OMs | Methanesulfonyloxy |
| Et | Ethyl |
| Me | Methyl |
| iPr | Isopropyl |
| TBS | Tert-butyldimethylsilyl |
| DIBAL-H | Diisobutylaluminium hydride |
| KHMDS | Potassium bis(trimethylsilyl)amide |
| LiHMDS | Lithium bis(trimethylsilyl)amide |
| NaHMDS | Sodium bis(trimethylsilyl)amide |
| LDA | Lithium diisopropylamide |
| NaH | Sodium hydride |
| MsCl | Methanesulfonyl chloride |
| Ms$_2$O | Methanesulfonyl anhydride |
| TMSOTf | Trimethylsilyl trifluoromethanesulfonate |
| SmI$_2$ | Samarium diiodide |
| TEMPO | 2,2,6,6-tetramethylpiperidinooxy |
| PhI(OAc)$_2$ | Iodosobenzene diacetate |

DETAILED DESCRIPTION OF THE PREFERRED EMBODIMENTS

The present disclosure is described in detail with reference to the following specific examples so that those skilled in the art will understand the present disclosure in a more comprehensive manner. The specific examples are used only to illustrate the technical solution of the present disclosure, but are not intended to limit the scope of the present disclosure in any way.

Structural formulas of some compounds in the Examples are shown in the following table

| No. | Formula |
|---|---|
| IIa | 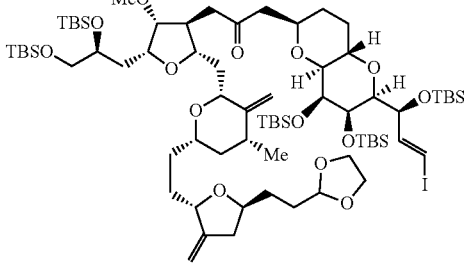 |

| No. | Formula |
|---|---|
| IIb | 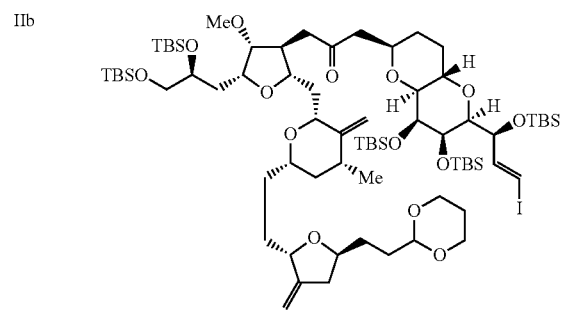 |
| IIIa | 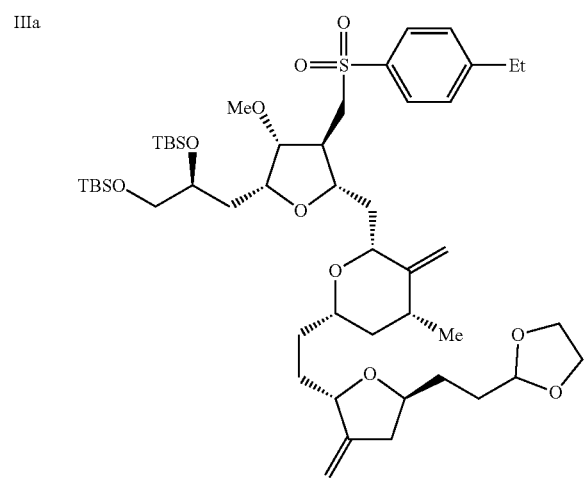 |
| IIIb | 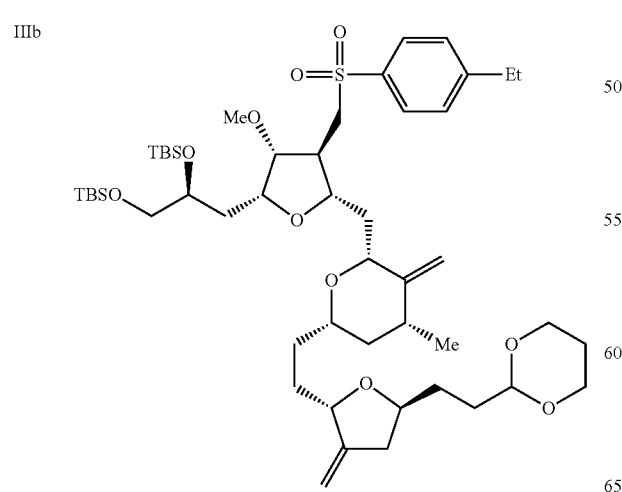 |
| No. | Formula |
|---|---|
| IIIc | 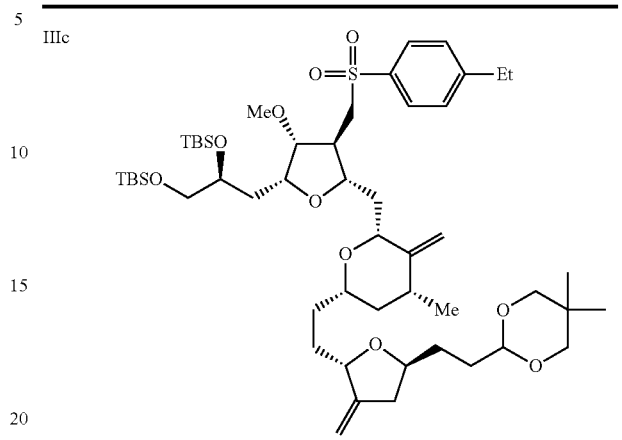 |
| IIId | 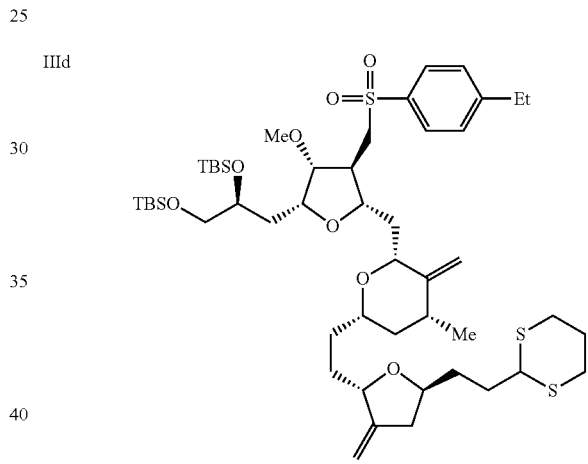 |
| IIIe | 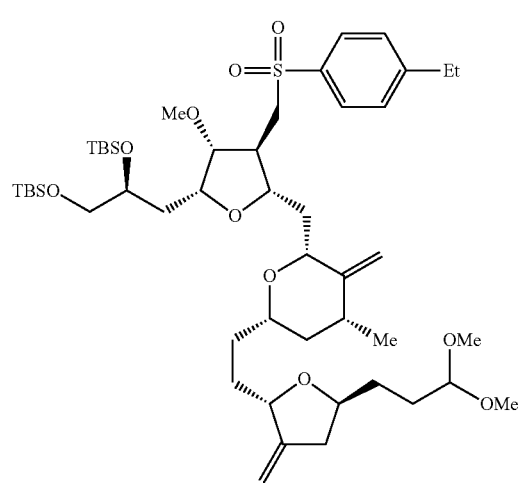 [SMILES: C=C1C[C@H](CCC(OC)OC)O[C@H]1CC[C@H]1C[C@@H](C)C(=C)[C@@H](C[C@@H]2O[C@H](C[C@@H](CO[Si](C)(C)C(C)(C)C)O[Si](C)(C)C(C)(C)C)[C@H](OC)[C@H]2CS(=O)(=O)c2ccc(CC)cc2)O1] |

| No. | Formula |
|---|---|
| IIIf | 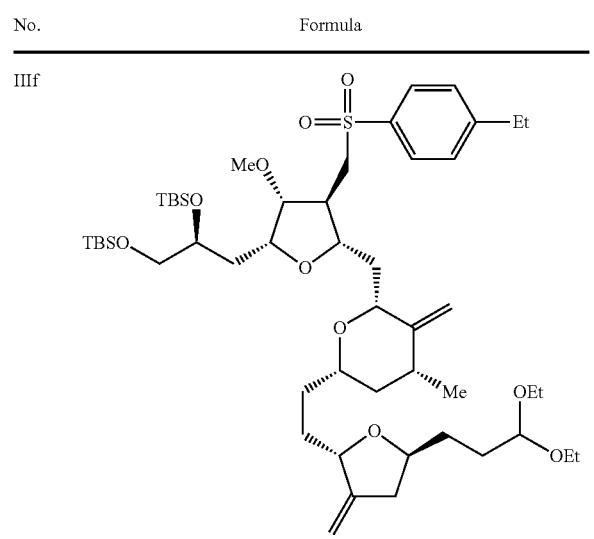 |
| IIIg | 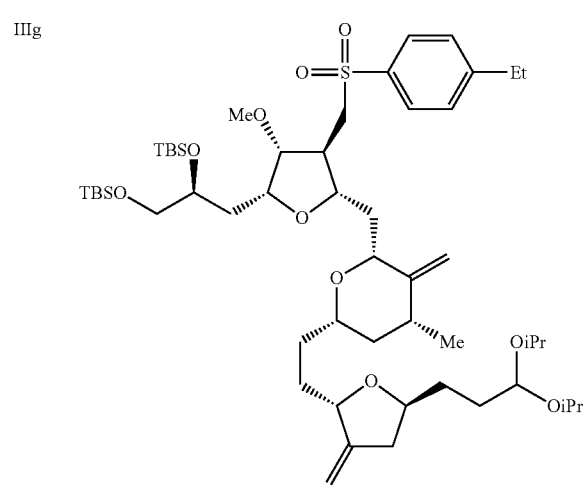 |
| IIIh | 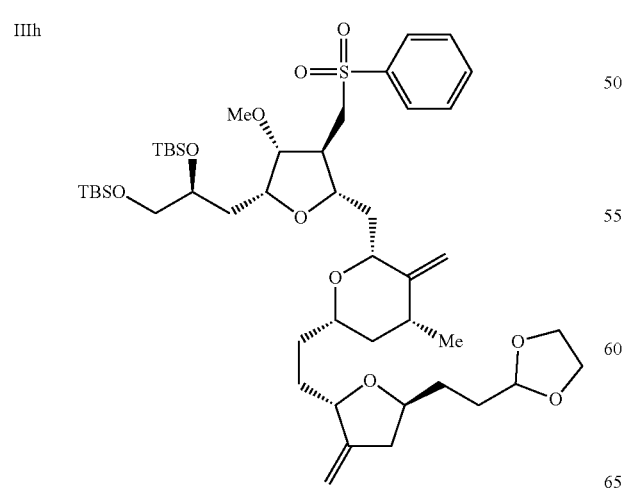 |
| No. | Formula |
|---|---|
| IIIi | 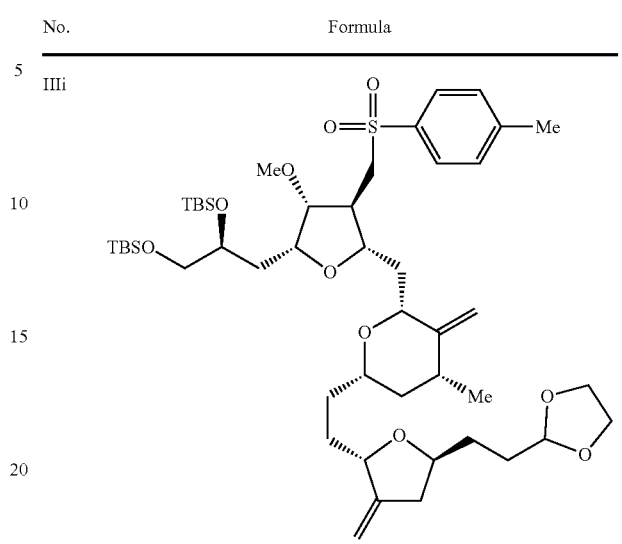 |
| IVa | 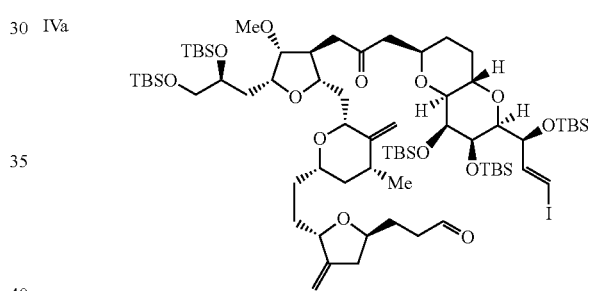 |
| Va | 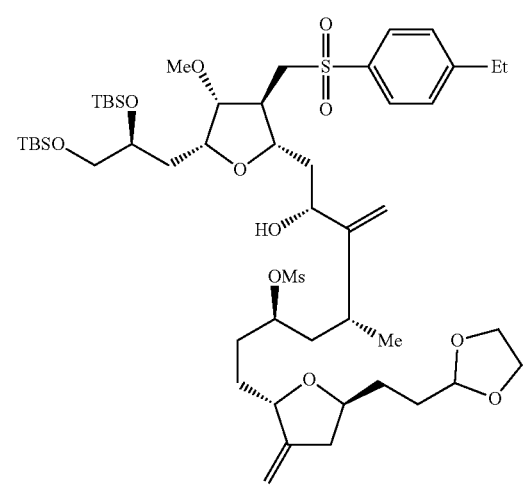 [SMILES: C=C([C@H](C)C[C@@H](CC[C@@H]1O[C@@H](CCC2OCCO2)CC1=C)OS(C)(=O)=O)[C@H](O)C[C@@H]1O[C@H](C[C@@H](CO[Si](C)(C)C(C)(C)C)O[Si](C)(C)C(C)(C)C)[C@H](OC)[C@H]1CS(=O)(=O)c1ccc(CC)cc1] |

| No. | Formula | No. | Formula |
|---|---|---|---|
| Vb | 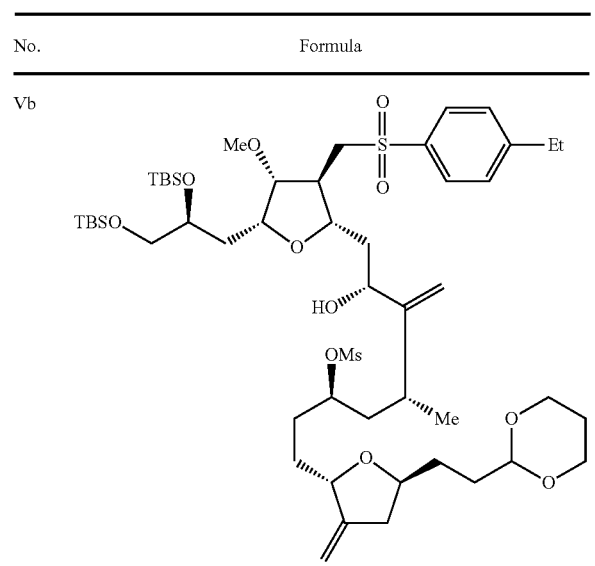 | Ve | 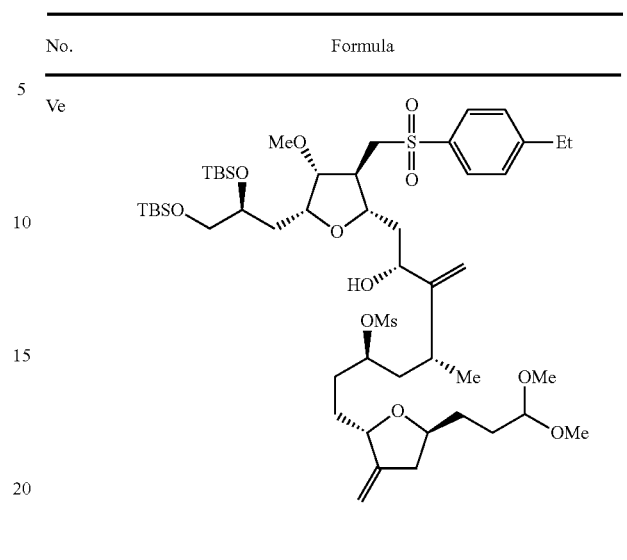 |
| Vc | 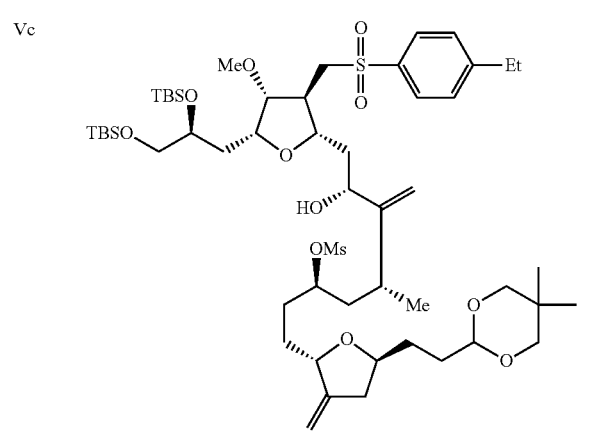 | Vf | 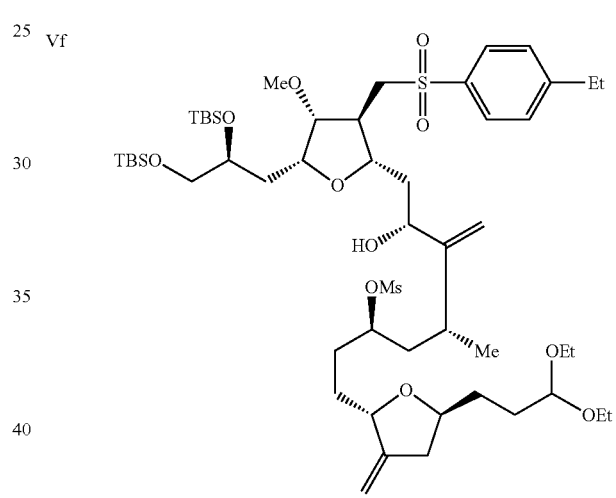 |
| Vd | 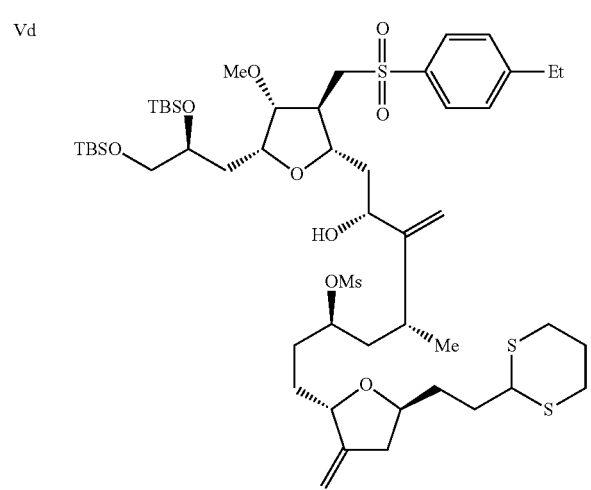 | Vg | 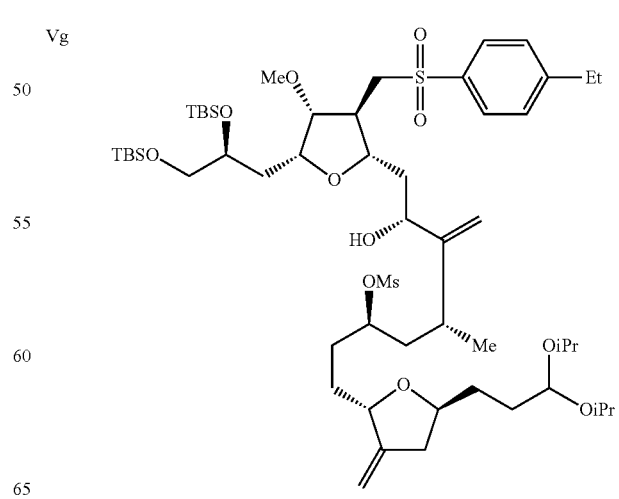 |

-continued
| No. | Formula |
|---|---|
| Vh | 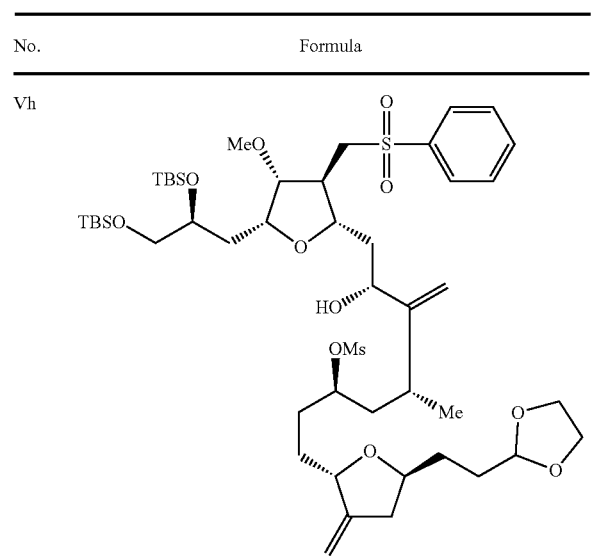 |
| Vi | |
| VAa | |
-continued
| No. | Formula |
|---|---|
| VAb | 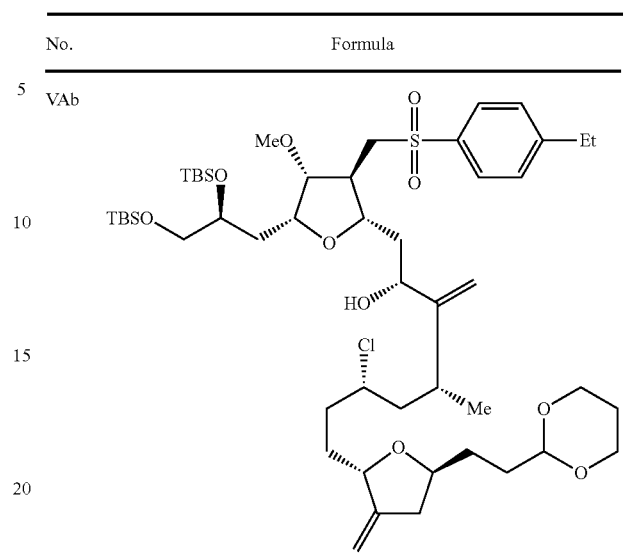 |
| VAc | |
| VAd | |

| No. | Formula |
|---|---|
| VIa | |
| VIb | |
| VIc | |
| VIIa | |
| VIIb | |
| VIIc | |
| VIId | |
| VIIe | |
| VIIf | |
| VIIg | |
| VIIAa | |
| VIIAb | |

| No. | Formula |
|---|---|
| VIIIa | |
| VIIIb | |
| VIIIc | |
| VIIId | |
| VIIIe | |
| VIIIf | |

| No. | Formula |
|---|---|
| VIIIg | |
| IXa | |
| IXb | |
| IXc | |

-continued

| No. | Formula |
|---|---|
| IXd | |
| Xa | |
| Xb | |
| Xc | |

-continued

| No. | Formula |
|---|---|
| Xd | |
| XIa | |
| XIIa | |
| XIIc | |

| No. | Formula |
|---|---|
| XIId | (structure: complex macrocyclic compound with TBSO, MeO, OTBS, Me, tosyl and aldehyde groups) |
| Ligand 1 | (structure: oxazoline with isopropyl group, attached to phenyl ring bearing Me and NHMs substituents) |
| Ligand 2 | (structure: oxazoline with isopropyl group, attached to phenyl ring bearing OMe and NHMs substituents) |

Examples 1-7 disclosed the synthesis of the compound of formula VII

Example 1: Preparation of the Compound of Formula VIIa

To the solution of compound of formula VIIIa (8.17 g, 18 mmol) in THF (150 mL) was added $Et_3N$ (16.2 g) at room temperature, then MsCl (12.1 g) was added slowly. The reaction was stirred at the same temperature for 1 h. After completion of the reaction was indicated by TLC, the reaction was quenched by saturated $NaHCO_3$ aqueous solution. The resultant was extracted with ethyl acetate. The organic phase was separated and concentrated, and then purified by column chromatography to obtain the compound of formula VIIa (8.76 g).

MS (ESI) m/z: 515 (M+H$^+$).
$^1$HNMR (400 MHz, CDCl$_3$): δ 6.36 (d, J=1.2 Hz, 1H), 5.84 (d, J=1.6 Hz, 1H), 5.01-4.99 (m, 1H), 4.90-4.85 (m, 2H), 4.72-4.65 (m, 1H), 4.41-4.35 (m, 1H), 4.08-4.01 (m, 1H), 3.98-3.94 (m, 2H), 3.87-3.83 (m, 2H), 3.02 (s, 3H), 2.71-2.64 (m, 1H), 2.31-2.25 (m, 1H), 2.10-2.02 (m, 1H), 1.94-1.75 (m, 4H), 1.73-1.51 (m, 6H), 1.00 (d, J=6.4 Hz, 3H).

Example 2: Preparation of the Compound of Formula VIIb

A solution of the compound of formula VIIIb (1.02 g, 2.1 mmol) in dichloromethane (15 mL) was cooled to −30° C., and then pyridine (2.3 g) and $Ms_2O$ (1.59 g) were added sequentially. The reaction solution was stirred at the same temperature for 3 h. After completion of the reaction was indicated by TLC, the reaction was quenched by saturated $NaHCO_3$ aqueous solution. The resultant was extracted with ethyl acetate. The organic phase was separated and concentrated, and then purified by column chromatography to obtain the compound of formula VIIb (1.06 g).

MS (ESI) m/z: 529 (M+H$^+$).
$^1$HNMR (400 MHz, CDCl$_3$): δ 6.36 (s, 1H), 5.85 (d, J=1.3 Hz, 1H), 5.00-4.98 (m, 1H), 4.90-4.86 (m, 1H), 4.72-4.65 (m, 1H), 4.60-4.50 (m, 1H), 4.42-4.38 (m, 1H), 4.15-4.02 (m, 2H), 3.87-3.73 (m, 2H), 3.02 (s, 3H), 2.72-2.66 (m, 1H), 2.54 (d, J=5.0 Hz, 1H), 2.40-2.26 (m, 1H), 2.19-2.06 (m, 2H), 1.79-1.28 (m, 11H), 1.01 (d, J=6.6 Hz, 3H).

Example 3: Preparation of the Compound of Formula VIII

A solution of the compound of formula VIIIc (0.68 g, 1.3 mmol) in ethyl acetate (15 mL) was cooled to −10° C., and then 2,6-lutidine (2.1 g) and $Ms_2O$ (1.06 g) were added sequentially. After completion of the addition, the reaction solution was stirred at the same temperature for 30 min. After completion of the reaction was indicated by TLC, the reaction was quenched by saturated $NaHCO_3$ aqueous solution. The resultant was extracted with ethyl acetate. The organic phase was separated and concentrated, and then purified by column chromatography to obtain the compound of formula VIII (0.72 g).

MS (ESI) m/z: 557 (M+H$^+$).
$^1$HNMR (400 MHz, CDCl$_3$): δ 6.36 (s, 1H), 5.85 (d, J=1.2 Hz, 1H), 5.00-4.96 (m, 1H), 4.90-4.85 (m, 1H), 4.73-4.65 (m, 1H), 4.52-4.42 (m, 1H), 4.42-4.37 (m, 1H), 3.87-3.73 (m, 2H), 3.38-3.30 (m, 2H), 3.02 (s, 3H), 2.72-2.65 (m, 1H), 2.55 (d, J=5.0 Hz, 1H), 2.40-2.25 (m, 1H), 1.80-1.28 (m, 11H), 1.18 (s, 3H), 1.01 (d, J=6.6 Hz, 3H), 0.71 (s, 3H).

Example 4: Preparation of the Compound of Formula VIId 2,4,6-Collidine (4.2 g) was added to a solution of the compound of formula VIIId (2.6 g, 4.8 mmol) in 2-methyltetrahydrofuran (30 mL) at 40° C. MsCl (3.9 g) was slowly added to the solution. After completion of the addition, the mixture was stirred at the same temperature for 15 min. After completion of the reaction was indicated by TLC, the reaction was quenched by saturated $NaHCO_3$ aqueous solution. The resultant was extracted with ethyl acetate. The organic phase was separated and concentrated, and then purified by column chromatography to obtain the compound of formula VIId (2.73 g).

MS (ESI) m/z: 561 (M+H$^+$).
$^1$H NMR (400 MHz, Chloroform-d) δ 6.36 (s, 1H), 5.86 (d, J=1.3 Hz, 1H), 5.04-5.00 (m, 1H), 4.90-4.86 (m, 1H), 4.73-4.65 (m, 1H), 4.50-4.40 (m, 1H), 4.19-4.00 (m, 1H), 3.02 (s, 3H), 2.99-2.78 (m, 4H), 2.74-2.70 (m, 1H), 2.45 (d, J=5.0 Hz, 1H), 2.37-2.23 (m, 1H), 2.20-2.05 (m, 2H), 2.05-1.28 (m, 11H), 1.01 (d, J=6.6 Hz, 3H).

Example 5: Preparation of the Compound of Formula VIIe

A solution of the compound of formula VIIIe (3.2 g, 6.4 mmol) in acetonitrile (30 mL) was cooled to 0° C., and then diisopropylethylamine (1.25 g) and MsCl (1.05 g) were added slowly and sequentially. After completion of the addition, the reaction was stirred at the same temperature for 2 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula VIIe (3.26 g).

MS (ESI) m/z: 517 (M+H$^+$).

$^1$H NMR (400 MHz, Chloroform-d) δ 6.37 (s, 1H), 5.76 (d, J=1.2 Hz, 1H), 5.05-5.00 (m, 1H), 4.90-4.85 (m, 1H), 4.75-4.65 (m, 1H), 4.40 (dd, J=7.0, 3.9 Hz, 2H), 3.34 (d, J=1.7 Hz, 6H), 3.03 (s, 3H), 2.38-2.25 (m, 1H), 2.15-2.10 (m, 1H), 1.83-1.28 (m, 11H), 1.01 (d, J=6.6 Hz, 3H).

Example 6: Preparation of the Compound of Formula VIIf

A solution of the compound of formula VIIIf (2.8 g, 5.4 mmol) in toluene (30 mL) was cooled to 10° C., and then triethylamine (2.6 g) and MsCl (2.3 g) were added slowly and sequentially. The reaction solution was stirred at the same temperature for 1 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula VIIf (2.9 g).

MS (ESI) m/z: 545 (M+H$^+$).

$^1$HNMR (400 MHz, Chloroform-d) δ 6.36 (s, 1H), 5.78 (d, J=1.2 Hz, 1H), 5.04-5.00 (m, 1H), 4.90-4.85 (m, 1H), 4.75-4.65 (m, 1H), 4.52 (t, J=5.5 Hz, 1H), 4.41 (brs, 1H), 3.72-3.47 (m, 4H), 3.03 (s, 3H), 2.75-2.68 (m, 1H), 2.52 (d, J=5.0 Hz, 1H), 2.41-2.26 (m, 1H), 1.85-1.28 (m, 11H), 1.23-1.18 (m, 6H), 1.01 (d, J=6.6 Hz, 3H).

Example 7: Preparation of the Compound of Formula VIIg

A solution of the compound of formula VIIIg (1.9 g, 3.5 mmol) in N,N-dimethylformamide (30 mL) was cooled to 10° C., and then triethylamine (2.3 g) and Ms$_2$O (1.7 g) were added slowly and sequentially. The reaction solution was stirred at the same temperature for 6 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula VIIg (2.02 g).

MS (ESI) m/z: 573 (M+H$^+$).

$^1$H NMR (400 MHz, Chloroform-d) δ 6.36 (s, 1H), 5.77 (d, J=1.3 Hz, 1H), 5.04-5.00 (m, 1H), 4.92-4.88 (m, 1H), 4.73-4.65 (m, 1H), 4.57 (t, J=5.1 Hz, 1H), 4.45-4.40 (m, 1H), 3.90-3.82 (m, 2H), 3.02 (s, 3H), 2.75-2.66 (m, 1H), 2.52 (d, J=5.0 Hz, 1H), 2.41-2.26 (m, 1H), 1.85-1.28 (m, 11H), 1.26-1.09 (m, 12H), 1.01 (d, J=6.6 Hz, 3H).

Examples 8-9 disclosed the synthesis of the compound of formula VIIA

Example 8: Preparation of the Compound of Formula VIIAa

The compound of formula VIIa (1.6 g, 3 mmol) was dissolved in 1,3-dimethyl-3,4,5,6-tetrahydro-2(1H)-pyrimidinone (DMPU) (20 mL) at −20° C. Tributylbenzylammonium chloride (12 g) was added to this solution. The reaction solution was stirred at room temperature for 48 h. The reaction was quenched by H$_2$O and the mixture was extracted with ethyl acetate. The organic phase was separated and concentrated, and then purified by column chromatography to obtain the compound of formula VIIAa (1.43 g).

MS (ESI) m/z: 455 (M+H$^+$).

$^1$H NMR (400 MHz, CDCl$_3$): δ 6.17 (d, J=1.2 Hz, 1H), 5.73 (d, J=1.2 Hz, 1H), 5.01-4.99 (m, 1H), 4.92-4.83 (m, 2H), 4.40-4.35 (m, 1H), 4.10-4.00 (m, 1H), 3.98-3.95 (m, 3H), 3.87-3.85 (m, 2H), 2.70-2.64 (m, 1H), 2.30-2.25 (m, 1H), 2.10-2.02 (m, 1H), 1.94-1.73 (m, 4H), 1.73-1.50 (m, 6H), 1.00 (d, J=6.4 Hz, 3H).

Example 9: Preparation of the Compound of Formula VIIAb

The compound of formula VIIb (1.6 g, 2.9 mmol) was dissolved in N,N-dimethylformamide (20 mL) at 60° C. Tetrabutylammonium chloride (10 g) was added to this solution. The reaction solution was stirred at the same temperature for 1 h. The reaction was quenched by H$_2$O and the mixture was extracted with ethyl acetate. The organic phase was separated and concentrated, and then purified by column chromatography to obtain the compound of formula VIIAb (1.25 g).

MS (ESI) m/z: 469 (M+H$^+$).

$^1$H NMR (400 MHz, CDCl$_3$): δ 6.18 (d, J=1.2 Hz, 1H), 5.72 (d, J=1.2 Hz, 1H), 5.00-4.98 (m, 1H), 4.92-4.86 (m, 1H), 4.58-4.50 (m, 1H), 4.43-4.38 (m, 1H), 4.15-4.00 (m, 2H), 3.97-3.91 (m, 1H), 3.86-3.70 (m, 2H), 2.70-2.65 (m, 1H), 2.52 (d, J=5.0 Hz, 1H), 2.40-2.25 (m, 1H), 2.20-2.05 (m, 2H), 1.80-1.29 (m, 11H), 1.02 (d, J=6.6 Hz, 3H).

Examples 10-18 disclosed the synthesis of the compound of formula V

Example 10: Preparation of the Compound of Formula Va

To a reaction flask were added the compound of formula VIIa (4.35 g, 8.5 mmol), the compound of formula VIa (5.7 g), ligand 1 (13.1 g), CrCl$_2$ (3.6 g) and NiCl$_2$ (1.05 g). The mixture was dissolved by addition of THF (60 mL) and triethylamine (2.2 g). The reaction solution was heated to 60° C. and stirred for 2 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula Va (7.35 g).

MS (ESI) m/z: 1017 (M+H$^+$).

$^1$H NMR (400 MHz, Chloroform-d) δ 7.83 (d, J=8.4 Hz, 2H), 7.41 (d, J=8.4 Hz, 2H), 5.21 (s, 1H), 4.99-4.86 (m, 1H), 4.89-4.84 (m, 3H), 4.79-4.76 (m, 1H), 4.36-4.35 (m, 1H), 4.19-4.16 (m, 1H), 4.05-3.68 (m, 10H), 3.57 (dd, J=10.4, 5.2 Hz, 1H), 3.47 (dd, J=10, 5.6 Hz, 1H), 3.38 (s, 3H), 3.17 (dd, J=14, 4.8 Hz, 1H), 3.04 (dd, J=14.4, 9.6 Hz, 1H), 3.01 (s, 3H), 2.75 (q, J=7.6 Hz, 2H), 2.69-2.63 (m, 1H), 2.59-2.55 (m, 1H), 2.33-1.38 (m, 16H), 1.27 (t, J=7.6 Hz, 3H), 1.07 (d, J=7.6 Hz, 3H), 0.88 (s, 9H), 0.87 (s, 9H), 0.07 (s, 6H), 0.05 (s, 3H), 0.04 (s, 3H), 0.00 (s, 6H).

Example 11: Preparation of the Compound of Formula Vb

To a reaction flask were added the compound of formula VIIb (0.87 g, 1.6 mmol), the compound of formula VIa (1.3 g), ligand 2 (3.1 g), CrCl$_2$ (0.86 g) and NiCl$_2$ (0.12 g). The mixture was dissolved by addition of 2-methyltetrahydrofuran (15 mL) and diisopropylethylamine (0.43 g). The reaction solution was heated to 30° C. and stirred for 4 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula Vb (1.32 g).

MS (ESI) m/z: 1031 (M+H$^+$).

$^1$H NMR (400 MHz, Chloroform-d) δ 7.81 (d, J=8.4 Hz, 2H), 7.43 (d, J=8.4 Hz, 2H), 5.21 (s, 1H), 5.00-4.86 (m, 1H), 4.88-4.85 (m, 3H), 4.80-4.72 (m, 1H), 4.60-4.52 (m, 1H), 4.45-4.40 (m, 1H), 4.16-3.69 (m, 9H), 3.58 (dd, J=10.4, 5.2 Hz, 1H), 3.45 (dd, J=10, 5.6 Hz, 1H), 3.38 (s, 3H), 3.17 (dd, J=14, 4.8 Hz, 1H), 3.05 (dd, J=14.4, 9.6 Hz, 1H), 3.01 (s, 3H), 2.74 (q, J=7.6 Hz, 2H), 2.69-2.60 (m, 1H), 2.60-2.55 (m, 1H), 2.30-1.35 (m, 18H), 1.27 (t, J=7.6 Hz, 3H), 1.08 (d, J=7.6 Hz, 3H), 0.88 (s, 9H), 0.86 (s, 9H), 0.07 (s, 6H), 0.05 (s, 3H), 0.04 (s, 3H), 0.00 (s, 6H).

Example 12: Preparation of the Compound of Formula Vc

To a reaction flask were added the compound of formula VIII (0.87 g, 1.6 mmol), the compound of formula VIa (1.3 g), ligand 1 (2.6 g), CrCl$_3$ (0.95 g), Mn powder (1.2 g) and NiCl$_2$ (0.22 g). The mixture was dissolved by addition of acetonitrile (10 mL) and pyridine (0.36 g). The reaction solution was stirred at 10° C. for 24 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula Vc (1.16 g).

MS (ESI) m/z: 1059 (M+H$^+$).

$^1$H NMR (400 MHz, Chloroform-d) δ 7.82 (d, J=8.4 Hz, 2H), 7.42 (d, J=8.4 Hz, 2H), 5.21 (s, 1H), 5.00-4.86 (m, 1H), 4.90-4.85 (m, 3H), 4.80-4.75 (m, 1H), 4.52-4.42 (m, 2H), 4.13-3.70 (m, 9H), 3.57 (dd, J=10.4, 5.2 Hz, 1H), 3.45 (dd, J=10, 5.6 Hz, 1H), 3.38 (s, 3H), 3.15 (dd, J=14, 4.8 Hz, 1H), 3.06 (dd, J=14.4, 9.6 Hz, 1H), 3.02 (s, 3H), 2.75 (q, J=7.6 Hz, 2H), 2.69-2.60 (m, 1H), 2.60-2.55 (m, 1H), 2.32-1.35 (m, 16H), 1.27 (t, J=7.6 Hz, 3H), 1.19 (s, 3H), 1.07 (d, J=7.6 Hz, 3H), 0.88 (s, 9H), 0.87 (s, 9H), 0.71 (s, 3H), 0.07 (s, 6H), 0.05 (s, 3H), 0.04 (s, 3H), 0.00 (s, 6H).

Example 13: Preparation of the Compound of Formula Vd

To a reaction flask were added the compound of formula VIId (0.87 g, 1.6 mmol), the compound of formula VIa (1.2 g), ligand 2 (2.4 g), CrCl$_2$ (1.2 g) and NiCl$_2$ (0.12 g). The mixture was dissolved by addition of DMSO (10 mL) and Et$_3$N (0.44 g). The reaction solution was stirred at 0° C. for 48 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula Vd (1.2 g).

MS (ESI) m/z: 1063 (M+H$^+$).

$^1$H NMR (400 MHz, Chloroform-d) δ 7.84 (d, J=8.4 Hz, 2H), 7.42 (d, J=8.4 Hz, 2H), 5.21 (s, 1H), 4.99-4.86 (m, 1H), 4.90-4.85 (m, 3H), 4.79-4.76 (m, 1H), 4.50-4.40 (m, 1H), 4.19-3.68 (m, 7H), 3.57 (dd, J=10.4, 5.2 Hz, 1H), 3.48 (dd, J=10, 5.6 Hz, 1H), 3.39 (s, 3H), 3.18 (dd, J=14, 4.8 Hz, 1H), 3.04 (dd, J=14.4, 9.6 Hz, 1H), 3.01 (s, 3H), 3.00-2.78 (m, 4H), 2.75 (q, J=7.6 Hz, 2H), 2.69-2.65 (m, 1H), 2.59-2.55 (m, 1H), 2.45 (d, J=5.0 Hz, 1H), 2.35-1.30 (m, 18H), 1.27 (t, J=7.6 Hz, 3H), 1.08 (d, J=7.6 Hz, 3H), 0.88 (s, 9H), 0.87 (s, 9H), 0.07 (s, 6H), 0.05 (s, 3H), 0.04 (s, 3H), 0.00 (s, 6H).

Example 14: Preparation of the Compound of Formula Ve

To a reaction flask were added the compound of formula VIIe (0.87 g, 1.7 mmol), the compound of formula VIa (1.2 g), ligand 1 (2.7 g), CrCl$_2$ (1.2 g) and NiCl$_2$ (0.12 g). The mixture was dissolved by addition of DCM (10 mL) and Et$_3$N (0.44 g). The reaction solution was stirred at 20° C. for 36 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula Ve (1.06 g).

MS (ESI) m/z: 1019 (M+H$^+$).

$^1$H NMR (400 MHz, Chloroform-d) δ 7.81 (d, J=8.4 Hz, 2H), 7.42 (d, J=8.4 Hz, 2H), 5.21 (s, 1H), 4.99-4.86 (m, 1H), 4.89-4.84 (m, 3H), 4.79-4.76 (m, 1H), 4.41 (dd, J=7.0, 4.0 Hz, 1H), 4.19-4.15 (m, 1H), 4.05-3.65 (m, 5H), 3.57 (dd, J=10.4, 5.2 Hz, 1H), 3.47 (dd, J=10, 5.6 Hz, 1H), 3.38 (s, 3H), 3.35 (s, 3H), 3.34 (s, 3H), 3.17 (dd, J=14, 4.8 Hz, 1H), 3.04 (dd, J=14.4, 9.6 Hz, 1H), 3.01 (s, 3H), 2.75 (q, J=7.6 Hz, 2H), 2.60-2.55 (m, 1H), 2.30-1.35 (m, 17H), 1.27 (t, J=7.6 Hz, 3H), 1.07 (d, J=7.6 Hz, 3H), 0.88 (s, 9H), 0.87 (s, 9H), 0.07 (s, 6H), 0.05 (s, 3H), 0.04 (s, 3H), 0.00 (s, 6H).

Example 15: Preparation of the Compound of Formula Vf

To a reaction flask were added the compound of formula VIIf (0.87 g, 1.7 mmol), the compound of formula VIa (1.5 g), ligand 1 (2.8 g), CrCl$_2$ (1.6 g) and NiCl$_2$ (0.21 g). The mixture was dissolved by addition of ethyl acetate (10 mL) and 2, 6-lutidine (0.44 g). The reaction solution was stirred at 20° C. for 18 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula Vf (1.12 g).

MS (ESI) m/z: 1047 (M+H$^+$).

$^1$H NMR (400 MHz, Chloroform-d) δ 7.83 (d, J=8.4 Hz, 2H), 7.41 (d, J=8.4 Hz, 2H), 5.21 (s, 1H), 4.99-4.86 (m, 1H), 4.90-4.85 (m, 3H), 4.80-4.75 (m, 1H), 4.53 (t, J=5.6 Hz, 1H), 4.41 (brs, 1H), 4.20-4.15 (m, 1H), 4.05-3.65 (m, 9H), 3.56 (dd, J=10.4, 5.2 Hz, 1H), 3.46 (dd, J=10, 5.6 Hz, 1H), 3.38 (s, 3H), 3.17 (dd, J=14, 4.8 Hz, 1H), 3.04 (dd, J=14.4, 9.6 Hz, 1H), 3.01 (s, 3H), 2.75 (q, J=7.6 Hz, 2H), 2.73-2.55 (m, 2H), 2.53 (d, J=5.0 Hz, 1H), 2.40-1.35 (m, 16H), 1.27 (t, J=7.6 Hz, 3H), 1.20-1.15 (m, 6H), 1.07 (d, J=7.6 Hz, 3H), 0.88 (s, 9H), 0.87 (s, 9H), 0.07 (s, 6H), 0.05 (s, 3H), 0.04 (s, 3H), 0.00 (s, 6H).

Example 16: Preparation of the Compound of Formula Vg

To a reaction flask were added the compound of formula VIIg (0.87 g, 1.6 mmol), the compound of formula VIa (1.5 g), ligand 1 (2.3 g), CrCl$_2$ (1.2 g) and NiCl$_2$ (0.16 g). The mixture was dissolved by addition of methyl t-butyl ether (10 mL) and Et$_3$N (0.36 g). The reaction solution was stirred at 40° C. for 15 h. After completion of the reaction was indicated by TLC, the reaction was quenched by saturated NaHCO$_3$ aqueous solution. The resultant was extracted with ethyl acetate. The organic phase was separated and concentrated, and then purified by column chromatography to obtain the compound of formula Vg (1.1 g).

MS (ESI) m/z: 1075 (M+H$^+$).

$^1$H NMR (400 MHz, Chloroform-d) δ 7.81 (d, J=8.4 Hz, 2H), 7.42 (d, J=8.4 Hz, 2H), 5.21 (s, 1H), 4.99-4.86 (m, 1H), 4.89-4.84 (m, 3H), 4.78-4.75 (m, 1H), 4.57 (t, J=5.2 Hz, 1H), 4.45-4.40 (m, 1H), 4.20-4.15 (m, 1H), 4.05-3.65 (m, 7H), 3.57 (dd, J=10.4, 5.2 Hz, 1H), 3.46 (dd, J=10, 5.6 Hz, 1H), 3.38 (s, 3H), 3.17 (dd, J=14, 4.8 Hz, 1H), 3.05 (dd, J=14.4, 9.6 Hz, 1H), 3.01 (s, 3H), 2.74 (q, J=7.6 Hz, 2H), 2.74-2.66 (m, 1H), 2.60-2.55 (m, 1H), 2.52 (d, J=5.0 Hz, 1H), 2.40-1.35 (m, 16H), 1.27 (t, J=7.6 Hz, 3H), 1.26-1.09 (m, 12H), 1.07 (d, J=7.6 Hz, 3H), 0.88 (s, 9H), 0.87 (s, 9H), 0.08 (s, 6H), 0.05 (s, 3H), 0.03 (s, 3H), 0.00 (s, 6H).

Example 17: Preparation of the Compound of Formula Vh

To a reaction flask were added the compound of formula VIIa (0.87 g, 1.6 mmol), the compound of formula VIb (1.3 g), ligand 1 (2.3 g), CrCl$_2$ (1.1 g) and NiCl$_2$ (0.15 g). The mixture was dissolved by addition of THF (20 mL) and Et$_3$N (0.32 g). The reaction solution was stirred at 30° C. for 12 h. After completion of the reaction was indicated by TLC, the reaction was quenched by saturated NaHCO$_3$ aqueous solution. The mixture was extracted with ethyl acetate. The organic phase was separated and concentrated, and then purified by column chromatography to obtain the compound of formula Vh (1.2 g).

MS (ESI) m/z: 989 (M+H$^+$).

$^1$H NMR (400 MHz, Chloroform-d) δ 7.99-7.92 (m, 2H), 7.75-7.66 (m, 1H), 7.65-7.59 (m, 2H), 5.20 (s, 1H), 4.99-4.88 (m, 1H), 4.89-4.85 (m, 3H), 4.80-4.76 (m, 1H), 4.36-4.35 (m, 1H), 4.19-4.15 (m, 1H), 4.05-3.68 (m, 10H), 3.57 (dd, J=10.4, 5.2 Hz, 1H), 3.47 (dd, J=10, 5.6 Hz, 1H), 3.37 (s, 3H), 3.17 (dd, J=14, 4.8 Hz, 1H), 3.04 (dd, J=14.4, 9.6 Hz, 1H), 3.01 (s, 3H), 2.70-2.63 (m, 1H), 2.59-2.55 (m, 1H), 2.33-1.38 (m, 16H), 1.08 (d, J=7.6 Hz, 3H), 0.88 (s, 9H), 0.88 (s, 9H), 0.07 (s, 6H), 0.05 (s, 3H), 0.04 (s, 3H), 0.00 (s, 6H).

Example 18: Preparation of the Compound of Formula Vi

To a reaction flask were added the compound of formula VIIa (0.87 g, 1.6 mmol), the compound of formula VIc (1.4 g), ligand 2 (2.1 g), CrCl$_2$ (1.6 g) and NiCl$_2$ (0.23 g). The mixture was dissolved by addition of 2-methyltetrahydrofuran (20 mL) and proton sponge (0.36 g). The reaction solution was stirred at 30° C. for 24 h. After completion of the reaction was indicated by TLC, the reaction was quenched by saturated NaHCO$_3$ aqueous solution. The mixture was extracted with ethyl acetate. The organic phase was separated and concentrated, and then purified by column chromatography to obtain the compound of formula Vi (1.1 g).

MS (ESI) m/z: 1003 (M+H$^+$).

$^1$H NMR (400 MHz, Chloroform-d) δ 7.81 (d, J=8.0 Hz, 2H), 7.39 (d, J=8.0 Hz, 2H), 5.20 (s, 1H), 5.00-4.88 (m, 1H), 4.86-4.82 (m, 3H), 4.80-4.76 (m, 1H), 4.39-4.35 (m, 1H), 4.19-4.15 (m, 1H), 4.05-3.66 (m, 10H), 3.57 (dd, J=10.2, 5.2 Hz, 1H), 3.46 (dd, J=10, 5.6 Hz, 1H), 3.37 (s, 3H), 3.17 (dd, J=14, 4.8 Hz, 1H), 3.04 (dd, J=14.4, 9.6 Hz, 1H), 3.01 (s, 3H), 2.70-2.65 (m, 1H), 2.59-2.55 (m, 1H), 2.46 (s, 3H), 2.33-1.38 (m, 16H), 1.08 (d, J=7.6 Hz, 3H), 0.88 (s, 9H), 0.88 (s, 9H), 0.07 (s, 6H), 0.05 (s, 3H), 0.04 (s, 3H), 0.00 (s, 6H).

Examples 19-22 disclosed the synthesis of the compound of formula VA

Example 19: Preparation of the Compound of Formula VAa

To a reaction flask were added the compound of formula VIIAa (1.2 g, 2.6 mmol), the compound of formula VIa (2.1 g), ligand 1 (3.8 g), CrCl$_2$ (1.9 g) and NiCl$_2$ (0.29 g). The mixture was dissolved by addition of tetrahydrofuran (30 mL) and Et$_3$N (0.62 g). The reaction solution was stirred at 20° C. for 12 h. After completion of the reaction was indicated by TLC, the reaction was quenched by saturated NaHCO$_3$ aqueous solution. The mixture was extracted with ethyl acetate. The organic phase was separated and concentrated, and then purified by column chromatography to obtain the compound of formula VAa (1.7 g).

MS (ESI) m/z: 957 (M+H$^+$).

$^1$H NMR (400 MHz, Chloroform-d) δ 7.83 (d, J=8.4 Hz, 2H), 7.42 (d, J=8.4 Hz, 2H), 5.21 (s, 1H), 5.00-4.86 (m, 1H), 4.89-4.82 (m, 3H), 4.39-4.35 (m, 1H), 4.20-4.15 (m, 1H), 4.05-3.70 (m, 11H), 3.55 (dd, J=10.4, 5.2 Hz, 1H), 3.48 (dd, J=10, 5.6 Hz, 1H), 3.38 (s, 3H), 3.15 (dd, J=14, 4.8 Hz, 1H), 3.05 (dd, J=14.4, 9.6 Hz, 1H), 2.75 (q, J=7.6 Hz, 2H), 2.69-2.63 (m, 1H), 2.59-2.55 (m, 1H), 2.33-1.38 (m, 16H), 1.27 (t, J=7.6 Hz, 3H), 1.07 (d, J=7.6 Hz, 3H), 0.88 (s, 9H), 0.87 (s, 9H), 0.07 (s, 6H), 0.05 (s, 3H), 0.04 (s, 3H), 0.00 (s, 6H).

Example 20: Preparation of the Compound of Formula VAb

To a reaction flask were added the compound of formula VIIAb (1.2 g, 2.56 mmol), the compound of formula VIa (2.1 g), ligand 2 (3.8 g), CrCl$_2$ (1.9 g) and NiCl$_2$ (0.29 g). The mixture was dissolved by addition of tetrahydrofuran (30 mL) and Et$_3$N (0.62 g). The reaction solution was stirred at 60° C. for 4 h. After completion of the reaction was indicated by TLC, the reaction was quenched by saturated NaHCO$_3$ aqueous solution. The mixture was extracted with ethyl acetate. The organic phase was separated and concentrated, and then purified by column chromatography to obtain the compound of formula VAb (1.5 g).

MS (ESI) m/z: 971 (M+H$^+$).

$^1$H NMR (400 MHz, Chloroform-d) δ 7.82 (d, J=8.4 Hz, 2H), 7.43 (d, J=8.4 Hz, 2H), 5.21 (s, 1H), 5.00-4.85 (m, 1H), 4.90-4.85 (m, 3H), 4.82-4.75 (m, 1H), 4.45-4.40 (m, 1H), 4.15-3.65 (m, 10H), 3.58 (dd, J=10.4, 5.2 Hz, 1H), 3.46 (dd, J=10, 5.6 Hz, 1H), 3.38 (s, 3H), 3.16 (dd, J=14, 4.8 Hz, 1H), 3.05 (dd, J=14.4, 9.6 Hz, 1H), 2.73 (q, J=7.6 Hz, 2H), 2.69-2.65 (m, 1H), 2.60-2.57 (m, 1H), 2.30-1.35 (m, 18H), 1.27 (t, J=7.6 Hz, 3H), 1.07 (d, J=7.6 Hz, 3H), 0.88 (s, 9H), 0.87 (s, 9H), 0.07 (s, 6H), 0.05 (s, 3H), 0.04 (s, 3H), 0.00 (s, 6H).

Example 21: Preparation of the Compound of Formula VAc

To a reaction flask were added the compound of formula VIIAa (1.2 g, 2.6 mmol), the compound of formula VIb (2.1 g), ligand 1 (3.8 g), CrCl$_2$ (1.9 g) and NiCl$_2$ (0.29 g). The mixture was dissolved by addition of 2-methyltetrahydrofuran (30 mL) and iPr$_2$NEt (0.85 g). The reaction solution was stirred at 0° C. for 48 h. After completion of the reaction was indicated by TLC, the reaction was quenched by saturated NaHCO$_3$ aqueous solution. The mixture was extracted with ethyl acetate. The organic phase was separated and concentrated, and then purified by column chromatography to obtain the compound of formula VAc (1.3 g).

MS (ESI) m/z: 929 (M+H$^+$).

$^1$H NMR (400 MHz, Chloroform-d) δ 7.97-7.88 (m, 2H), 7.70-7.63 (m, 3H), 5.22 (s, 1H), 5.00-4.85 (m, 1H), 4.90-4.80 (m, 3H), 4.37-4.35 (m, 1H), 4.18-4.13 (m, 1H), 4.03-3.70 (m, 11H), 3.54 (dd, J=10.4, 5.2 Hz, 1H), 3.48 (dd, J=10, 5.6 Hz, 1H), 3.38 (s, 3H), 3.14 (dd, J=14, 4.8 Hz, 1H), 3.03 (dd, J=14.4, 9.6 Hz, 1H), 2.70-2.65 (m, 1H), 2.60-2.52 (m, 1H), 2.30-1.35 (m, 16H), 1.05 (d, J=7.6 Hz, 3H), 0.89 (s, 9H), 0.87 (s, 9H), 0.08 (s, 6H), 0.05 (s, 3H), 0.04 (s, 3H), 0.01 (s, 6H).

Example 22: Preparation of the Compound of Formula VAd

To a reaction flask were added the compound of formula VIIAa (1.2 g, 2.6 mmol), the compound of formula VIc (2.1 g), ligand 2 (3.8 g), CrCl$_2$ (1.9 g) and NiCl$_2$ (0.29 g). The mixture was dissolved by addition of 2-methyltetrahydrofuran (30 mL) and proton sponge (1.2 g). The reaction solution was stirred at 30° C. for 24 h. After completion of the reaction was indicated by TLC, the reaction was quenched by saturated NaHCO$_3$ aqueous solution. The mixture was extracted with ethyl acetate. The organic phase was separated and concentrated, and then purified by column chromatography to obtain the compound of formula VAd (1.6 g).

MS (ESI) m/z: 943 (M+H$^+$).

$^1$H NMR (400 MHz, Chloroform-d) δ 7.80 (d, J=8.0 Hz, 2H), 7.41 (d, J=8.0 Hz, 2H), 5.23 (s, 1H), 5.02-4.86 (m, 1H), 4.88-4.81 (m, 3H), 4.36-4.35 (m, 1H), 4.18-4.10 (m, 1H), 4.03-3.72 (m, 11H), 3.53 (dd, J=10.4, 5.2 Hz, 1H), 3.46 (dd, J=10, 5.6 Hz, 1H), 3.39 (s, 3H), 3.15 (dd, J=14, 4.8 Hz, 1H), 3.02 (dd, J=14.4, 9.6 Hz, 1H), 2.70-2.65 (m, 1H), 2.60-2.50 (m, 1H), 2.46 (s, 3H), 2.30-1.35 (m, 16H), 1.05 (d, J=7.6 Hz, 3H), 0.89 (s, 9H), 0.87 (s, 9H), 0.08 (s, 6H), 0.05 (s, 3H), 0.04 (s, 3H), 0.01 (s, 6H).

Examples 23-35 disclosed the synthesis of the compound of formula III

Example 23: Preparation of the Compound of Formula IIIa

KHMDS (0.5 M, 6.0 mL) was added dropwise to a solution of the compound of formula Va (2.0 g, 1.99 mmol) in THF (75 mL) at room temperature. The reaction solution was stirred at the same temperature for 30 min. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIa (1.06 g).

MS (ESI) m/z: 944 (M+Na$^+$).

$^1$H NMR (400 MHz, Chloroform-d) δ 7.81 (d, J=8.0 Hz, 2H), 7.39 (d, J=8.0 Hz, 2H), 4.95-4.87 (m, 2H), 4.84 (s, 1H), 4.76 (d, J=1.8 Hz, 1H), 4.64 (d, J=1.8 Hz, 1H), 4.25 (brs, 1H), 4.04-3.71 (m, 8H), 3.70-3.45 (m, 4H), 3.43 (s, 3H), 3.39-3.32 (m, 1H), 3.08-2.93 (m, 2H), 2.74 (q, J=7.6 Hz, 2H), 2.67-2.44 (m, 2H), 2.26-1.32 (m, 16H), 1.25 (t, J=7.6 Hz, 3H), 1.05 (d, J=6.4 Hz, 3H), 0.88 (s, 18H), 0.09 (s, 3H), 0.08 (s, 3H), 0.04 (s, 3H), 0.03 (s, 3H).

Example 24: Preparation of the Compound of Formula IIIa 2,6-Di-t-butyl-4-methylpyridine (2.3 g) and AgBF$_4$ (2.6 g) were added to a solution of the compound of formula VAa (1 g, 0.99 mmol) in t-butyl acetate (20 mL) at 0° C. The reaction solution was stirred at the same temperature for 48 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIa (0.8 g).

MS (ESI) m/z: 944 (M+Na$^+$).

$^1$H NMR (400 MHz, Chloroform-d) δ 7.81 (d, J=8.0 Hz, 2H), 7.39 (d, J=8.0 Hz, 2H), 4.95-4.87 (m, 2H), 4.84 (s, 1H), 4.76 (d, J=1.8 Hz, 1H), 4.64 (d, J=1.8 Hz, 1H), 4.25 (brs, 1H), 4.04-3.71 (m, 8H), 3.70-3.45 (m, 4H), 3.43 (s, 3H), 3.39-3.32 (m, 1H), 3.08-2.93 (m, 2H), 2.74 (q, J=7.6 Hz, 2H), 2.67-2.44 (m, 2H), 2.26-1.32 (m, 16H), 1.25 (t, J=7.6 Hz, 3H), 1.05 (d, J=6.4 Hz, 3H), 0.88 (s, 18H), 0.09 (s, 3H), 0.08 (s, 3H), 0.04 (s, 3H), 0.03 (s, 3H).

Example 25: Preparation of the Compound of Formula IIIb

LiHMDS (1 M, 3 mL) was added to a solution of the compound of formula Vb (1.0 g, 0.97 mmol) in THF (20 mL) at −30° C. The reaction solution was stirred at the same temperature for 6 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIb (0.62 g).

MS (ESI) m/z: 957 (M+Na$^+$).

$^1$H NMR (400 MHz, Chloroform-d) δ 7.89-7.78 (m, 2H), 7.46-7.36 (m, 2H), 4.88 (d, J=2.2 Hz, 1H), 4.83 (s, 1H), 4.76 (d, J=1.9 Hz, 1H), 4.63 (d, J=2.2 Hz, 1H), 4.55 (t, J=4.8 Hz, 1H), 4.25 (brs, 1H), 4.11-4.06 (m, 2H), 3.99-3.46 (m, 10H), 3.44 (s, 3H), 3.38-3.32 (m, 1H), 3.04-2.94 (m, 2H), 2.75 (q, J=7.6 Hz, 2H), 2.62-2.50 (m, 2H), 2.27-1.30 (m, 18H), 1.27 (t, J=7.6 Hz, 3H), 1.05 (d, J=6.4 Hz, 3H), 0.89 (s, 18H), 0.09 (s, 3H), 0.08 (s, 3H), 0.05 (s, 3H), 0.04 (s, 3H).

Example 26: Preparation of the Compound of Formula IIb 2,4,6-Trimethylpyridine (2.6 g) and AgPF$_6$ (3.2 g) were added to a solution of the compound of formula VAb (1 g, 0.97 mmol) in isopropyl acetate (20 mL) at 30° C. The reaction solution was stirred at the same temperature for 12 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIb (0.7 g).

MS (ESI) m/z: 944 (M+Na$^+$).

$^1$H NMR (400 MHz, Chloroform-d) δ 7.81 (d, J=8.0 Hz, 2H), 7.39 (d, J=8.0 Hz, 2H), 4.95-4.87 (m, 2H), 4.84 (s, 1H), 4.76 (d, J=1.8 Hz, 1H), 4.64 (d, J=1.8 Hz, 1H), 4.25 (brs, 1H), 4.04-3.71 (m, 8H), 3.70-3.45 (m, 4H), 3.43 (s, 3H), 3.39-3.32 (m, 1H), 3.08-2.93 (m, 2H), 2.74 (q, J=7.6 Hz, 2H), 2.67-2.44 (m, 2H), 2.26-1.32 (m, 16H), 1.25 (t, J=7.6 Hz, 3H), 1.05 (d, J=6.4 Hz, 3H), 0.88 (s, 18H), 0.09 (s, 3H), 0.08 (s, 3H), 0.04 (s, 3H), 0.03 (s, 3H).

Example 27: Preparation of the Compound of Formula IIIc

LDA (1 M, 2 mL) was added dropwise to a solution of the compound of formula Vc (1.0 g, 0.95 mmol) was dissolved in 2-methyltetrahydrofuran (20 mL) at −20° C. The reaction solution was stirred at the same temperature for 3 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula Mc (0.66 g).

MS (ESI) m/z: 985 (M+Na$^+$).

$^1$H NMR (400 MHz, Chloroform-d) δ 7.89-7.79 (m, 2H), 7.42 (d, J=8.3 Hz, 2H), 4.88 (d, J=2.2 Hz, 1H), 4.84 (s, 1H), 4.77 (d, J=1.9 Hz, 1H), 4.63 (d, J=2.2 Hz, 1H), 4.44 (dd, J=4.5 Hz, 1H), 4.25 (brs, 1H), 4.01-3.47 (m, 10H), 3.44 (s, 3H), 3.43-3.31 (m, 3H), 3.06-2.93 (m, 2H), 2.75 (q, J=7.6 Hz, 2H), 2.65-2.47 (m, 2H), 2.26-1.32 (m, 16H), 1.26 (t, J=7.6 Hz, 3H), 1.18 (s, 3H), 1.06 (d, J=6.4 Hz, 3H), 0.89 (s, 18H), 0.71 (s, 3H), 0.09 (s, 3H), 0.08 (s, 3H), 0.05 (s, 3H), 0.04 (s, 3H).

Example 28: Preparation of the Compound of Formula IIId

BuLi (2.5 M, 1 mL) was added dropwise to a solution of the compound of formula Vd (1.0 g, 0.95 mmol) in methyl t-butyl ether (20 mL) at −10° C. The reaction solution was stirred at the same temperature for 2 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIId (0.58 g).

MS (ESI) m/z: 989 (M+Na$^+$).

$^1$H NMR (400 MHz, Chloroform-d) δ 7.89-7.79 (m, 2H), 7.46-7.37 (m, 2H), 4.89 (d, J=2.2 Hz, 1H), 4.84 (s, 1H), 4.76 (d, J=1.8 Hz, 1H), 4.65 (d, J=2.2 Hz, 1H), 4.26-4.20 (m, 1H), 4.05 (t, 17.2 Hz, 1H), 4.00-3.47 (m, 8H), 3.43 (s, 3H), 3.40-3.32 (m, 1H), 3.06-2.94 (m, 2H), 2.94-2.79 (m, 4H), 2.75 (q, J=7.6 Hz, 2H), 2.66-2.46 (m, 2H), 2.25-1.32 (m, 18H), 1.27 (t, J=7.6 Hz, 3H), 1.06 (d, J=6.2 Hz, 3H), 0.89 (s, 18H), 0.09 (s, 3H), 0.08 (s, 3H), 0.05 (s, 3H), 0.04 (s, 3H).

Example 29: Preparation of the Compound of Formula IIIe

NaHDMS (1.0 M, 1.5 mL) was added to a solution of the compound of formula Ve (1.0 g, 0.98 mmol) in toluene (20 mL) at 0° C. The reaction solution was stirred at the same temperature for 30 min. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIe (0.60 g).

MS (ESI) m/z: 945 (M+Na$^+$).

$^1$H NMR (400 MHz, Chloroform-d) δ 7.87-7.78 (m, 2H), 7.47-7.36 (m, 2H), 4.89 (d, J=2.1 Hz, 1H), 4.84 (s, 1H), 4.76 (d, J=1.8 Hz, 1H), 4.64 (d, J=2.2 Hz, 1H), 4.36 (t, J=5.6 Hz, 1H), 4.00-3.47 (m, 8H), 3.43 (s, 3H), 3.38-3.33 (m, 1H), 3.31 (s, 3H), 3.30 (s, 3H), 3.06-2.95 (m, 2H), 2.75 (q, J=7.6 Hz, 2H), 2.67-2.44 (m, 2H), 2.27-1.33 (m, 16H), 1.27 (J=7.6 Hz, 3H), 1.06 (d, J=6.4 Hz, 3H), 0.89 (s, 18H), 0.09 (s, 3H), 0.08 (s, 3H), 0.05 (s, 3H), 0.04 (s, 3H).

Example 30: Preparation of the Compound of Formula IIIf t-BuOK (206 mg) was added to a solution of the compound of formula Vf (1.0 g, 0.96 mmol) n-heptane (20 mL) at 10° C. The reaction solution was stirred at the same temperature for 1 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIf (0.68 g).

MS (ESI) m/z: 973 (M+Na$^+$).

$^1$H NMR (400 MHz, Chloroform-d) δ 7.88-7.78 (m, 2H), 7.41 (d, J=8.2 Hz, 2H), 4.88 (d, J=2.1 Hz, 1H), 4.83 (s, 1H), 4.76 (d, J=1.8 Hz, 1H), 4.64 (d, J=2.2 Hz, 1H), 4.48 (t, J=5.6 Hz, 1H), 4.25 (brs, 1H), 3.97-3.92 (m, 1H), 3.87-3.46 (m, 10H), 3.43 (s, 3H), 3.38-3.32 (m, 1H), 3.06-2.93 (m, 2H), 2.74 (q, J=7.6 Hz, 2H), 2.65-2.46 (m, 2H), 2.27-1.33 (m, 16H), 1.26 (t, J=7.6 Hz, 3H), 1.19 (t, J=7.0 Hz, 6H), 1.05 (d, J=6.4 Hz, 3H), 0.88 (s, 18H), 0.09 (s, 3H), 0.08 (s, 3H), 0.05 (s, 3H), 0.04 (s, 3H).

Example 31: Preparation of the Compound of Formula IIIg

KHMDS (1.0 M, 1.5 mL) was added dropwise to a solution of the compound of formula Vg (1.0 g, 0.95 mmol) in n-hexane (20 mL) at 20° C. The reaction solution was stirred at the same temperature for 30 min. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIg (0.70 g).

MS (ESI) m/z: 1001 (M+Na$^+$).

$^1$H NMR (400 MHz, Chloroform-d) δ 7.90-7.79 (m, 2H), 7.46-7.36 (m, 2H), 4.88 (d, J=2.1 Hz, 1H), 4.83 (s, 1H), 4.76 (d, J=1.9 Hz, 1H), 4.63 (d, J=2.2 Hz, 1H), 4.55 (t, J=5.1 Hz, 1H), 4.25 (brs, 1H), 4.00-3.46 (m, 10H), 3.43 (s, 3H), 3.38-3.32 (m, 1H), 3.09-2.91 (m, 2H), 2.74 (q, J=7.6 Hz, 2H), 2.64-2.46 (m, 2H), 2.28-1.33 (m, 16H), 1.27 (t, J=7.6 Hz, 3H), 1.18 (d, J=6.0 Hz, 6H), 1.13 (d, J=6.0 Hz, 6H), 1.05 (d, J=6.4 Hz, 3H), 0.88 (s, 18H), 0.09 (s, 3H), 0.08 (s, 3H), 0.05 (s, 3H), 0.04 (s, 3H).

Example 32: Preparation of the Compound of Formula IIIh

NaH (102 mg) was added to a solution of the compound of formula Vh (1.0 g, 1.01 mmol) in THF (20 mL) at −20° C. The reaction solution was stirred at the same temperature for 30 min. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIh (0.59 g).

MS (ESI) m/z: 915 (M+Na$^+$).

$^1$H NMR (400 MHz, Chloroform-d) δ 7.98-7.93 (m, 2H), 7.73-7.66 (m, 1H), 7.65-7.58 (m, 2H), 4.96-4.88 (m, 2H), 4.84 (s, 1H), 4.76 (d, J=1.8 Hz, 1H), 4.64 (d, J=1.8 Hz, 1H), 4.25 (brs, 1H), 4.05-3.70 (m, 8H), 3.73-3.44 (m, 4H), 3.42 (s, 3H), 3.39-3.32 (m, 1H), 3.06-2.92 (m, 2H), 2.66-2.42 (m, 2H), 2.28-1.30 (m, 16H), 1.05 (d, J=6.4 Hz, 3H), 0.88 (s, 18H), 0.09 (s, 3H), 0.08 (s, 3H), 0.05 (s, 3H), 0.04 (s, 3H).

Example 33: Preparation of the Compound of Formula IIIh 2,6-Lutidine (3.6 g) and Ag$_2$O (4.5 g) were added to a solution of the compound of formula VAc (1 g, 1.08 mmol) in toluene (20 mL) at 60° C. The reaction solution was stirred at the same temperature for 6 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIh (0.6 g).

MS (ESI) m/z: 915 (M+Na$^+$).

$^1$H NMR (400 MHz, Chloroform-d) δ7.98-7.93 (m, 2H), 7.73-7.66 (m, 1H), 7.65-7.58 (m, 2H), 4.96-4.88 (m, 2H), 4.84 (s, 1H), 4.76 (d, J=1.8 Hz, 1H), 4.64 (d, J=1.8 Hz, 1H), 4.25 (brs, 1H), 4.05-3.70 (m, 8H), 3.73-3.44 (m, 4H), 3.42 (s, 3H), 3.39-3.32 (m, 1H), 3.06-2.92 (m, 2H), 2.66-2.42 (m, 2H), 2.28-1.30 (m, 16H), 1.05 (d, J=6.4 Hz, 3H), 0.88 (s, 18H), 0.09 (s, 3H), 0.08 (s, 3H), 0.05 (s, 3H), 0.04 (s, 3H).

Example 34: Preparation of the Compound of Formula IIIi t-BuONa (189 mg) was added to a solution of the compound of formula Vi (1.0 g, 1.0 mmol) THF (20 mL) at 30° C. The reaction solution was stirred at the same temperature for 10 min. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIi (0.72 g).

MS (ESI) m/z: 929 (M+Na$^+$).

$^1$H NMR (400 MHz, CDCl$_3$): δ 7.81 (d, J=8.0 Hz, 2H), 7.39 (d, J=8.0 Hz, 2H), 4.89-4.64 (m, 5H), 4.25 (br, 1H), 3.99-3.93 (m, 3H), 3.88-3.78 (m, 5H), 3.69-3.64 (m, 1H), 3.60-3.54 (m, 2H), 3.50-3.35 (m, 5H), 3.00-2.98 (m, 2H), 2.63-2.51 (m, 2H), 2.46 (s, 3H), 2.24-2.15 (m, 3H), 2.04-1.98 (m, 1H), 1.90-1.50 (m, 12H), 1.07 (d, J=6.4 Hz, 3H), 0.89 (s, 18H), 0.10 (s, 3H), 0.09 (s, 3H), 0.05 (s, 3H), 0.04 (s, 3H).

Example 35: Preparation of the Compound of Formula IIIi 2, 6-Di-t-butyl-4-methylpyridine (3.8 g) and AgOTf (6.2 g) were added to a solution of the compound of formula VAd (1 g, 1.08 mmol) in THF (20 mL) at 20° C. The reaction solution was stirred at the same temperature for 36 h. After completion of the reaction was indicated by TLC, the reaction was quenched by saturated NH$_4$Cl aqueous solution. The mixture was extracted with ethyl acetate. The organic phase was separated and concentrated, and then purified by column chromatography to obtain the compound of formula IIIi (0.7 g).

MS (ESI) m/z: 929 (M+Na$^+$).

$^1$H NMR (400 MHz, CDCl$_3$): δ 7.81 (d, J=8.0 Hz, 2H), 7.39 (d, J=8.0 Hz, 2H), 4.89-4.64 (m, 5H), 4.25 (br, 1H), 3.99-3.93 (m, 3H), 3.88-3.78 (m, 5H), 3.69-3.64 (m, 1H), 3.60-3.54 (m, 2H), 3.50-3.35 (m, 5H), 3.00-2.98 (m, 2H), 2.63-2.51 (m, 2H), 2.46 (s, 3H), 2.24-2.15 (m, 3H), 2.04-1.98 (m, 1H), 1.90-1.50 (m, 12H), 1.07 (d, J=6.4 Hz, 3H), 0.89 (s, 18H), 0.10 (s, 3H), 0.09 (s, 3H), 0.05 (s, 3H), 0.04 (s, 3H).

Examples 36-39 disclosed the synthesis of the compound of formula X

Example 36: Preparation of the Compound of Formula Xa n-BuLi (2.5 M in hexane, 0.36 mL) was added to a solution of the compound of formula IIIa (0.5 g, 0.55 mmol) in THF (10 mL) at −50° C. The reaction solution was stirred at the same temperature for 30 min. Then a solution of the compound of formula XIa (0.490 g) in THF (4 mL) was added to the reaction mixture. Then the reaction mixture was stirred for another 1 h. After completion of the reaction was indicated by TLC, the reaction was quenched by saturated NH$_4$Cl aqueous solution. The mixture was extracted with methyl t-butyl ether. The organic phase was separated and concentrated. The residual solvent was removed by evaporation with DCM, and the crude product of the compound of formula Xa was used directly for the next step without purification.

MS (ESI) m/z: 1662 (M+H$^+$).

$^1$H NMR (400 MHz, CDCl$_3$): δ 7.80 (d, J=8 Hz, 1H), 7.68 (d, J=8 Hz, 1H), 7.39 (d, J=8 Hz, 2H), 6.88-6.78 (m, 1H), 6.29-6.23 (m, 1H), 4.99-4.63 (m, 6H), 4.38-4.19 (m, 2H), 4.09-3.35 (m, 21H), 2.88-1.20 (m, 24H), 1.20-0.84 (m, 49H), 0.15-(−0.04) (m, 30H).

Example 37: Preparation of the Compound of Formula Xb

LDA (1.0 M in hexane, 0.6 mL) was added to a solution of the compound of formula Mb (0.5 g, 0.54 mmol) in 2-methyltetrahydrofuran (10 mL). at −78° C. The reaction solution was stirred at the same temperature for 1 h. Then a solution of the compound of formula XIa (0.49 g) in THF (4 mL) was added to the reaction mixture. The reaction mixture was stirred for another 4 h. After completion of the reaction was indicated by TLC, the reaction was quenched by saturated NH$_4$Cl aqueous solution. The mixture was extracted with methyl t-butyl ether. The organic phase was separated and concentrated. The residual solvent was removed by evaporation with DCM, and the crude product of the compound of formula Xb was used directly for the next step without purification.

MS (ESI) m/z: 1676 (M+H$^+$).

$^1$H NMR (400 MHz, CDCl$_3$): δ 7.80 (d, J=8 Hz, 1H), 7.68 (d, J=8 Hz, 1H), 7.39 (d, J=8 Hz, 2H), 6.88-6.78 (m, 1H), 6.29-6.23 (m, 1H), 5.02-4.60 (m, 7H), 4.40-4.16 (m, 2H), 4.11-3.30 (m, 20H), 2.90-1.20 (m, 26H), 1.20-0.84 (m, 49H), 0.15-(−0.04) (m, 30H).

Example 38: Preparation of the Compound of Formula Xc

LiHMDS (1.0 M in hexane, 0.6 mL) was added to a solution of the compound of formula IIIh (0.5 g, 0.56 mmol)

in n-heptane (10 mL) at 0° C. The reaction solution was stirred at the same temperature for 15 min. Then a solution of the compound of formula XIa (0.49 g) in THF (4 mL) was added to the reaction mixture. The reaction mixture was stirred for another 30 min. After completion of the reaction was indicated by TLC, the reaction was quenched by saturated NH$_4$Cl aqueous solution. The mixture was extracted with methyl t-butyl ether. The organic phase was separated and concentrated. The residual solvent was removed by evaporation with DCM, and the crude compound of formula Xc was used directly for the next step without purification.

MS (ESI) m/z: 1634 (M+H$^+$).

$^1$H NMR (400 MHz, CDCl$_3$): δ 7.97-7.90 (m, 2H), 7.70-7.58 (m, 1H), 7.60-7.50 (m, 2H), 6.88-6.78 (m, 1H), 6.29-6.23 (m, 1H), 4.99-4.63 (m, 6H), 4.38-4.19 (m, 2H), 4.09-3.35 (m, 21H), 2.88-1.20 (m, 19H), 1.15-0.84 (m, 49H), 0.15-(-0.04) (m, 30H).

Example 39: Preparation of the Compound of Formula Xd

KHMDS (1.0 M in hexane, 0.6 mL) was added dropwise to a solution of the compound of formula IIIi (0.5 g, 0.56 mmol) in n-heptane (10 mL) at -10° C. The reaction solution was stirred at the same temperature for 15 min. Then a solution of compound of formula XIa (0.49 g) in THF (4 mL) was added to the reaction mixture. The reaction mixture was stirred for 2 h. After completion of the reaction was indicated by TLC, the reaction was quenched by saturated NH$_4$Cl aqueous solution. The mixture was extracted with methyl t-butyl ether. The organic phase was separated and concentrated. The residual solvent was removed by evaporation with DCM, and the crude product of the compound of formula Xd was used directly for the next step without purification.

MS (ESI) m/z: 1648 (M+H$^+$).

$^1$H NMR (400 MHz, CDCl$_3$): δ 7.80-7.75 (m, 1H), 7.68-7.65 (m, 1H), 7.40-7.35 (m, 2H), 6.88-6.78 (m, 1H), 6.29-6.23 (m, 1H), 4.99-4.63 (m, 6H), 4.40-4.20 (m, 2H), 4.09-3.35 (m, 21H), 2.90-1.20 (m, 22H), 1.15-0.85 (m, 49H), 0.15-(-0.04) (m, 30H).

Examples 40-43 disclosed the synthesis of the compound of formula IX

Example 40: Preparation of the Compound of Formula IXa

NaHCO$_3$ (0.23 g) and DMP oxidant (0.51 g) were added to the solution of the above prepared crude product of the compound of formula Xa in DCM (5 mL) at -20° C. The reaction solution was stirred at room temperature for 2 h. After completion of the reaction was indicated by TLC, the reaction was quenched by an aqueous solution of Na$_2$S$_2$O$_3$ and NaHCO$_3$. The mixture was extracted with ethyl acetate. The organic phase was separated and concentrated, and then purified by column chromatography to obtain the compound of formula IXa (0.78 g), which was a pair of diastereomers as shown by NMR.

MS (ESI) m/z: 1660 (M+H$^+$).

$^1$H NMR (400 MHz, CDCl$_3$): δ 7.79-7.77 (m, 1H), 7.68-7.65 (m, 1H), 7.38-7.36 (m, 2H), 6.86-6.82 (m, 1H), 6.29-6.25 (m, 1H), 5.00-4.81 (m, 5H), 4.66 (d, J=20.4 Hz, 1H), 4.40-3.37 (m, 23H), 2.89-2.48 (m, 6H), 2.45-1.00 (m, 27H), 0.88-0.80 (m, 45H), 0.11-0.01 (m, 30H).

Example 41: Preparation of the Compound of Formula IXb

TEMPO (0.02 g) and PhI(OAc)$_2$ (0.43 g) were added to a solution of the above prepared crude product of the compound of formula Xb in DCM (5 mL) at 40° C. The reaction solution was stirred at room temperature for 6 h. After completion of the reaction was indicated by TLC, the reaction was quenched by an aqueous solution of Na$_2$S$_2$O$_3$ and NaHCO$_3$. The mixture was extracted with ethyl acetate. The organic phase was separated and concentrated, and then purified by column chromatography to obtain the compound of formula IXb (0.72 g).

MS (ESI) m/z: 1674 (M+H$^+$).

$^1$H NMR (400 MHz, CDCl$_3$): δ 7.79-7.77 (m, 1H), 7.68-7.65 (m, 1H), 7.38-7.36 (m, 2H), 6.86-6.82 (m, 1H), 6.29-6.25 (m, 1H), 5.00-4.81 (m, 5H), 4.65 (d, J=20.4 Hz, 1H), 4.60-3.35 (m, 23H), 2.90-2.48 (m, 6H), 2.45-1.00 (m, 29H), 0.88-0.80 (m, 45H), 0.11-0.00 (m, 30H).

Example 42: Preparation of the Compound of Formula IXc

TEMPO (0.02 g), NaClO (5 mL) and saturated NaHCO$_3$ aqueous solution (5 mL) were added to a solution of the above prepared crude product of the compound of formula Xc in DCM (5 mL) at 20° C. The reaction solution was stirred at room temperature for 1 h. After completion of the reaction was indicated by TLC, the reaction was quenched by an aqueous solution of Na$_2$S$_2$O$_3$ and NaHCO$_3$. The mixture was extracted with ethyl acetate. The organic phase was separated and concentrated, and then purified by column chromatography to obtain the compound of formula IXc (0.66 g).

MS (ESI) m/z: 1632 (M+H$^+$).

$^1$H NMR (400 MHz, CDCl$_3$): δ 7.95-7.92 (m, 2H), 7.55-7.81 (m, 3H), 6.85-6.80 (m, 1H), 6.30-6.25 (m, 1H), 5.00-4.80 (m, 5H), 4.67 (d, J=20.4 Hz, 1H), 4.40-3.37 (m, 23H), 2.89-2.48 (m, 6H), 2.45-1.00 (m, 27H), 0.88-0.80 (m, 45H), 0.11-0.01 (m, 30H).

Example 43: Preparation of the Compound of Formula IXd

IBX oxidant (1.2 g) was added to a solution of the above prepared crude product of the compound of formula Xd in DMSO (5 mL) at 60° C. The reaction solution was stirred at 60° C. for 4 h. After completion of the reaction was indicated by TLC, the reaction was quenched by an aqueous solution of Na$_2$S$_2$O$_3$ and NaHCO$_3$. The mixture was extracted with ethyl acetate. The organic phase was separated and concentrated, and then purified by column chromatography to obtain the compound of formula IXd (0.59 g), which is a pair of diastereomers as shown by NMR.

MS (ESI) m/z: 1646 (M+H$^+$).

$^1$H NMR (400 MHz, CDCl$_3$): δ 7.78-7.76 (m, 1H), 7.68-7.64 (m, 1H), 7.38-7.36 (m, 2H), 6.86-6.82 (m, 1H), 6.28-6.25 (m, 1H), 5.01-4.80 (m, 5H), 4.66 (d, J=20.4 Hz, 1H), 4.42-3.34 (m, 23H), 2.89-2.81 (m, 2H), 2.65-2.48 (m, 2H), 2.45-1.00 (m, 27H), 0.88-0.80 (m, 45H), 0.10-0.00 (m, 30H).

Examples 44-47 disclosed the synthesis of the compound of formula XII

Example 44: Preparation of the Compound of Formula XIIa 2,6-Lutidine (0.62 g) and TMSOTf (1.3 g) were added sequentially to a solution of the compound of formula IXa (0.78 g, 0.47 mmol) in DCM (10 mL) under ice-water bath. The reaction solution was stirred at the same temperature for 1 h. After completion of the reaction was indicated by TLC, the reaction was quenched by 1 N HCl aqueous solution. The mixture was extracted with ethyl acetate. The organic phase was separated and concentrated, and then purified by column chromatography to obtain the compound of formula XIIa (0.625 g), which was a pair of diastereomers as shown by NMR.

MS (ESI) m/z: 1615 (M+H$^+$).

$^1$H NMR (400 MHz, CDCl$_3$): δ 9.78 (s, 1H), 7.78-7.68 (m, 1H), 7.67-7.65 (m, 1H), 7.39-7.35 (m, 2H), 6.86-6.82 (m, 1H), 6.29-6.25 (m, 1H), 5.01-4.81 (m, 5H), 4.34-3.43 (m, 18H), 2.88-2.86 (m, 2H), 2.85-1.02 (m, 31H), 0.90-0.78 (m, 45H), 0.13-0.01 (m, 30H).

Example 45: Preparation of the Compound of Formula XIIa

Pyridine (0.55 g) and TMSOTf (1.2 g) were added sequentially to a solution of the compound of formula IXb (0.7 g, 0.42 mmol) in DCM (10 mL) at −20° C. The reaction solution was stirred at the same temperature for 4 h. After completion of the reaction was indicated by TLC, the reaction was quenched by 1 N HCl aqueous solution. The mixture was extracted with ethyl acetate. The organic phase was separated and concentrated, and then purified by column chromatography to obtain the compound of formula XIIa (0.58 g).

MS (ESI) m/z: 1615 (M+H$^+$).

$^1$H NMR (400 MHz, CDCl$_3$): δ 9.78 (s, 1H), 7.78-7.68 (m, 1H), 7.67-7.65 (m, 1H), 7.39-7.35 (m, 2H), 6.86-6.82 (m, 1H), 6.29-6.25 (m, 1H), 5.01-4.81 (m, 5H), 4.34-3.43 (m, 18H), 2.88-2.86 (m, 2H), 2.85-1.02 (m, 31H), 0.90-0.78 (m, 45H), 0.13-0.01 (m, 30H).

Example 46: Preparation of the Compound of Formula XIIc

Pyridinium p-toluenesulfonate (1.8 g) was added to a solution of the compound of formula IXc (0.6 g, 0.37 mmol) in toluene (10 mL) at 30° C. The reaction solution was stirred at the same temperature for 12 h. After completion of the reaction was indicated by TLC, the reaction was quenched by 1 N HCl aqueous solution. The mixture was extracted with ethyl acetate. The organic phase was separated and concentrated, and then purified by column chromatography to obtain the compound of formula XIIc (0.47 g).

MS (ESI) m/z: 1588 (M+H$^+$).

$^1$H NMR (400 MHz, CDCl$_3$): δ 9.78 (s, 1H), 7.93 (d, J=8.0 Hz, 2H), 7.80-7.55 (m, 3H), 6.87-6.81 (m, 1H), 6.28-6.24 (m, 1H), 5.05-4.81 (m, 5H), 4.35-3.42 (m, 18H), 2.88-2.85 (m, 2H), 2.85-1.03 (m, 26H), 0.90-0.75 (m, 45H), 0.13-0.00 (m, 30H).

Example 47: Preparation of the Compound of Formula XIId

Cerium ammonium nitrate (1.2 g) was added to a solution of the compound of formula IXd (0.6 g, 0.37 mmol) in acetonitrile (10 mL) at 40° C. The reaction solution was stirred at the same temperature for 6 h. After completion of the reaction was indicated by TLC, the reaction was quenched by 1 N HCl aqueous solution. The mixture was extracted with ethyl acetate. The organic phase was separated and concentrated, and then purified by column chromatography to obtain the compound of formula XIId (0.51 g).

MS (ESI) m/z: 1602 (M+H$^+$).

$^1$H NMR (400 MHz, CDCl$_3$): δ 9.78 (s, 1H), 7.77-7.68 (m, 1H), 7.68-7.65 (m, 1H), 7.39-7.35 (m, 2H), 6.87-6.80 (m, 1H), 6.29-6.25 (m, 1H), 5.05-4.80 (m, 5H), 4.35-3.40 (m, 18H), 2.88-2.85 (m, 2H), 2.85-1.00 (m, 29H), 0.90-0.75 (m, 45H), 0.13-0.00 (m, 30H).

Examples 48-51 disclosed the synthesis of the compound of formula II

Example 48: Preparation of the Compound of Formula IIa

A solution of SmI$_2$ in THF (0.1 M in THF, 2 mL) was added to a solution of the compound of formula IXa (100 mg, 0.06 mmol) in THF (3 mL) at −78° C. The reaction solution was stirred at the same temperature for 10 min. After completion of the reaction was indicated by TLC, the reaction was quenched by K$_2$CO$_3$ aqueous solution. The mixture was extracted with ethyl acetate. The organic phase was separated and concentrated, and then purified by column chromatography to obtain the compound of formula IIa (82 mg).

MS (ESI) m/z: 1492 (M+H$^+$).

$^1$H NMR (400 MHz, CDCl$_3$): δ 9.79 (s, 1H), 6.85 (dd, J=14.4, 3.6 Hz, 1H), 6.28 (dd, J=14.4, 1H), 4.99 (d, J=2 Hz, 1H), 4.89-4.85 (m, 3H), 4.79 (s, 1H), 4.34-4.33 (m, 1H), 4.06-4.02 (m, 2H), 3.89-3.43 (m, 11H), 3.33 (s, 3H), 3.23 (d, J=3.6 Hz, 1H), 2.93 (d, J=9.6 Hz, 2 Hz, 1H), 2.75-2.22 (m, 10H), 2.09-1.26 (m, 16H), 1.07 (3H, d, J=6.0 Hz), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Example 49: Preparation of the Compound of Formula IIa

CrCl$_2$ (205 mg) and Mn powder (300 mg) were added to a solution of the compound of formula IXc (100 mg, 0.06 mmol) in THF (3 mL) at 0° C. The reaction solution was stirred at the same temperature for 12 h. After completion of the reaction was indicated by TLC, the reaction was quenched by K$_2$CO$_3$ aqueous solution. The mixture was extracted with ethyl acetate. The organic phase was separated and concentrated, and then purified by column chromatography to obtain the compound of formula IIa (78 mg).

MS (ESI) m/z: 1492 (M+H$^+$).

$^1$H NMR (400 MHz, CDCl$_3$): δ 9.79 (s, 1H), 6.85 (dd, J=14.4, 3.6 Hz, 1H), 6.28 (dd, J=14.4, 1H), 4.99 (d, J=2 Hz, 1H), 4.89-4.85 (m, 3H), 4.79 (s, 1H), 4.34-4.33 (m, 1H), 4.06-4.02 (m, 2H), 3.89-3.43 (m, 11H), 3.33 (s, 3H), 3.23 (d, J=3.6 Hz, 1H), 2.93 (d, J=9.6 Hz, 2 Hz, 1H), 2.75-2.22 (m, 10H), 2.09-1.26 (m, 16H), 1.07 (3H, d, J=6.0 Hz), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Example 50: Preparation of the Compound of Formula IIa

Zn powder (600 mg) and acetic acid (600 mg) were added to a solution of the compound of formula IXd (100 mg, 0.06 mmol) in THF (3 mL) at 30° C. The reaction solution was stirred at the same temperature for 6 h. After completion of the reaction was indicated by TLC, the reaction was quenched by $K_2CO_3$ aqueous solution. The mixture was extracted with ethyl acetate. The organic phase was separated and concentrated, and then purified by column chromatography to obtain the compound of formula IIa (63 mg).

MS (ESI) m/z: 1492 (M+H$^+$).

$^1$H NMR (400 MHz, CDCl$_3$): δ 9.79 (s, 1H), 6.85 (dd, J=14.4, 3.6 Hz, 1H), 6.28 (dd, J=14.4, 1H), 4.99 (d, J=2 Hz, 1H), 4.89-4.85 (m, 3H), 4.79 (s, 1H), 4.34-4.33 (m, 1H), 4.06-4.02 (m, 2H), 3.89-3.43 (m, 11H), 3.33 (s, 3H), 3.23 (d, J=3.6 Hz, 1H), 2.93 (d, J=9.6 Hz, 2 Hz, 1H), 2.75-2.22 (m, 10H), 2.09-1.26 (m, 16H), 1.07 (3H, d, J=6.0 Hz), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Example 51: Preparation of the Compound of Formula IIb

A solution of SmI$_2$ in THF (0.1 M, 3 mL) was added to a solution of the compound of formula IXb (100 mg, 0.06 mmol) in THF (3 mL) at −30° C. The reaction solution was stirred at the same temperature for 2 h. After completion of the reaction was indicated by TLC, the reaction was quenched by $K_2CO_3$ aqueous solution. The mixture was extracted with ethyl acetate. The organic phase was separated and concentrated, and then purified by column chromatography to obtain the compound of formula IIb (77 mg).

MS (ESI) m/z: 1506 (M+H$^+$).

$^1$H NMR (400 MHz, CDCl$_3$): δ 9.78 (s, 1H), 6.83 (dd, J=14.4, 3.6 Hz, 1H), 6.26 (dd, J=14.4, 1H), 5.00 (d, J=2 Hz, 1H), 4.90-4.85 (m, 3H), 4.78 (s, 1H), 4.62-4.51 (m, 1H), 4.42-4.38 (m, 1H), 4.16-4.00 (m, 3H), 3.90-3.42 (m, 9H), 3.34 (s, 3H), 3.21 (d, J=3.6 Hz, 1H), 2.90 (d, J=9.6 Hz, 2 Hz, 1H), 2.75-2.20 (m, 10H), 2.10-1.20 (m, 18H), 1.08 (3H, d, J=6.0 Hz), 0.95 (s, 9H), 0.92 (s, 9H), 0.90 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Examples 52-56 disclosed the synthesis of the compound of formula IVa

Example 52: Preparation of the Compound of Formula IVa

A solution of SmI$_2$ in THF (0.1 M in THF, 1 mL) was added to a solution of the compound of formula XIIa (86 mg, 0.05 mmol) in THF (2 mL) at −30° C. The reaction solution was stirred at the same temperature for 30 min. After completion of the reaction was indicated by TLC, the reaction was quenched by $K_2CO_3$ aqueous solution. The mixture was extracted with ethyl acetate. The organic phase was separated and concentrated, and then purified by column chromatography to obtain the compound of formula IVa (80 mg).

MS (ESI) m/z: 1448 (M+H$^+$).

$^1$H NMR (400 MHz, CDCl$_3$): δ 9.78 (s, 1H), 6.86 (dd, J=15.0, 8.0 Hz, 1H), 6.28 (d, J=15.0 Hz, 1H), 4.99-4.97 (m, 1H), 4.89 (dd, J=8.0, 3.0 Hz, 1H), 4.88-3.64 (m, 13H), 3.57 (dd, J=10.0, 6.0 Hz, 1H), 3.53-3.41 (m, 3H), 3.33 (s, 3H), 3.25 (d, J=2.8 Hz, 1H), 2.95 (dd, J=10.0, 2.0 Hz, 1H), 2.77-1.06 (m, 26H), 1.07 (d, J=6.0 Hz, 3H), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Example 53: Preparation of the Compound of Formula IVa

CrCl$_2$ (100 mg) and Mn powder (100 mg) were added to a solution of the compound of formula XIIc (50 mg, 0.03 mmol) in THF (2 mL) at −50° C. The reaction solution was stirred at the same temperature for 4 h. After completion of the reaction was indicated by TLC, the reaction was quenched by $K_2CO_3$ aqueous solution. The mixture was extracted with ethyl acetate. The organic phase was separated and concentrated, and then purified by column chromatography to obtain the compound of formula IVa (39 mg).

MS (ESI) m/z: 1448 (M+H$^+$).

$^1$H NMR (400 MHz, CDCl$_3$): δ 9.78 (s, 1H), 6.86 (dd, J=15.0, 8.0 Hz, 1H), 6.28 (d, J=15.0 Hz, 1H), 4.99-4.97 (m, 1H), 4.89 (dd, J=8.0, 3.0 Hz, 1H), 4.88-3.64 (m, 13H), 3.57 (dd, J=10.0, 6.0 Hz, 1H), 3.53-3.41 (m, 3H), 3.33 (s, 3H), 3.25 (d, J=2.8 Hz, 1H), 2.95 (dd, J=10.0, 2.0 Hz, 1H), 2.77-1.06 (m, 26H), 1.07 (d, J=6.0 Hz, 3H), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Example 54: Preparation of the Compound of Formula IVa

Zn powder (200 mg) and acetic acid (200 mg) were added to a solution of the compound of formula XIId (50 mg, 0.03 mmol) in THF (2 mL) at 30° C. The reaction solution was stirred at the same temperature for 2 h. After completion of the reaction was indicated by TLC, the reaction was quenched by $K_2CO_3$ aqueous solution. The mixture was extracted with ethyl acetate. The organic phase was separated and concentrated, and then purified by column chromatography to obtain the compound of formula IVa (35 mg).

MS (ESI) m/z: 1448 (M+H$^+$).

$^1$H NMR (400 MHz, CDCl$_3$): δ 9.78 (s, 1H), 6.86 (dd, J=15.0, 8.0 Hz, 1H), 6.28 (d, J=15.0 Hz, 1H), 4.99-4.97 (m, 1H), 4.89 (dd, J=8.0, 3.0 Hz, 1H), 4.88-3.64 (m, 13H), 3.57 (dd, J=10.0, 6.0 Hz, 1H), 3.53-3.41 (m, 3H), 3.33 (s, 3H), 3.25 (d, J=2.8 Hz, 1H), 2.95 (dd, J=10.0, 2.0 Hz, 1H), 2.77-1.06 (m, 26H), 1.07 (d, J=6.0 Hz, 3H), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Example 55: Preparation of the Compound of Formula IVa 2,6-lutidine (0.12 g) and TMSOTf (0.26 g) were added sequentially to a solution of the compound of formula IIa (80 mg, 0.05 mmol) in DCM (2 mL) at −30° C. under ice-water bath. The reaction solution was stirred at the same temperature for 24 h. After completion of the reaction was indicated by TLC, the reaction was quenched by 1 N HCl aqueous solution. The mixture was extracted with ethyl acetate. The organic phase was separated and concentrated, and then purified by column chromatography to obtain the compound of formula IVa (56 mg).

MS (ESI) m/z: 1448 (M+H$^+$).

$^1$H NMR (400 MHz, CDCl$_3$): δ 9.78 (s, 1H), 6.86 (dd, J=15.0, 8.0 Hz, 1H), 6.28 (d, J=15.0 Hz, 1H), 4.99-4.97 (m, 1H), 4.89 (dd, J=8.0, 3.0 Hz, 1H), 4.88-3.64 (m, 13H), 3.57 (dd, J=10.0, 6.0 Hz, 1H), 3.53-3.41 (m, 3H), 3.33 (s, 3H), 3.25 (d, J=2.8 Hz, 1H), 2.95 (dd, J=10.0, 2.0 Hz, 1H), 2.77-1.06 (m, 26H), 1.07 (d, J=6.0 Hz, 3H), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

Example 56: Preparation of the Compound of Formula IVa

Pyridine (0.15 g) and TMSOTf (0.22 g) were added sequentially to a solution of the compound of formula IIb (50 mg, 0.03 mmol) in DCM (2 mL) at 40° C. The reaction solution was stirred at the same temperature for 1 h. After completion of the reaction was indicated by TLC, the reaction was quenched by 1 N HCl aqueous solution. The mixture was extracted with ethyl acetate. The organic phase was separated and concentrated, and then purified by column chromatography to obtain the compound of formula IVa (33 mg).

MS (ESI) m/z: 1448 (M+H$^+$).

$^1$H NMR (400 MHz, CDCl$_3$): δ 9.78 (s, 1H), 6.86 (dd, J=15.0, 8.0 Hz, 1H), 6.28 (d, J=15.0 Hz, 1H), 4.99-4.97 (m, 1H), 4.89 (dd, J=8.0, 3.0 Hz, 1H), 4.88-3.64 (m, 13H), 3.57 (dd, J=10.0, 6.0 Hz, 1H), 3.53-3.41 (m, 3H), 3.33 (s, 3H), 3.25 (d, J=2.8 Hz, 1H), 2.95 (dd, J=10.0, 2.0 Hz, 1H), 2.77-1.06 (m, 26H), 1.07 (d, J=6.0 Hz, 3H), 0.95 (s, 9H), 0.92 (s, 9H), 0.89 (s, 9H), 0.88 (s, 9H), 0.86 (s, 9H), 0.12 (s, 3H), 0.11 (s, 3H), 0.10 (s, 3H), 0.09 (s, 3H), 0.08 (s, 3H), 0.07 (s, 3H), 0.06 (s, 3H), 0.04 (s, 3H), 0.03 (s, 3H), 0.02 (s, 3H).

While the present disclosure has been described with reference to the specific examples, some modifications and equivalent variations will be apparent to those skilled in the art and are also within the scope of the present disclosure.

The invention claimed is:
1. A compound of formula V, VA, VII, VIIA, II, IX or X;

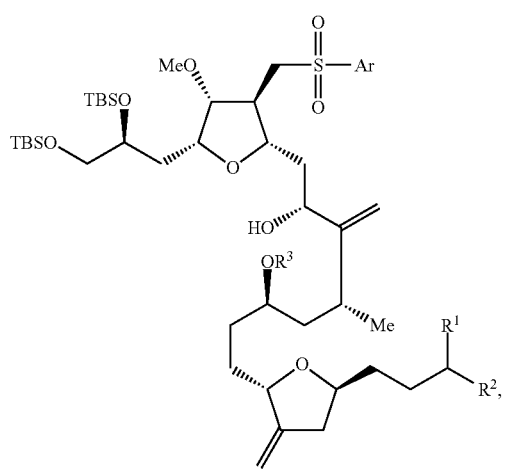

V

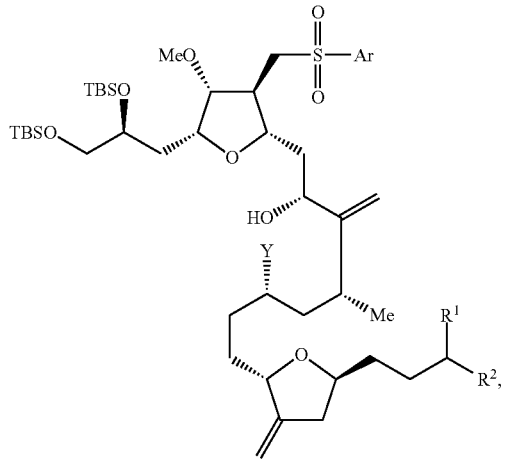

VA

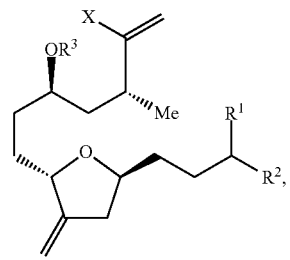

VII

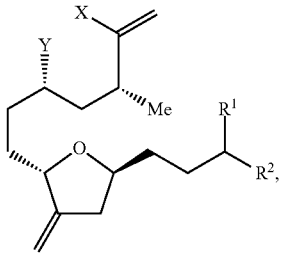

VIIA

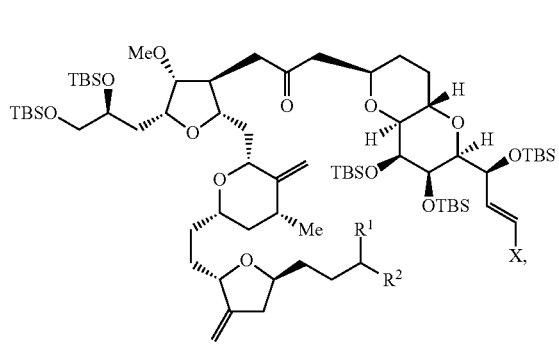

II

IX

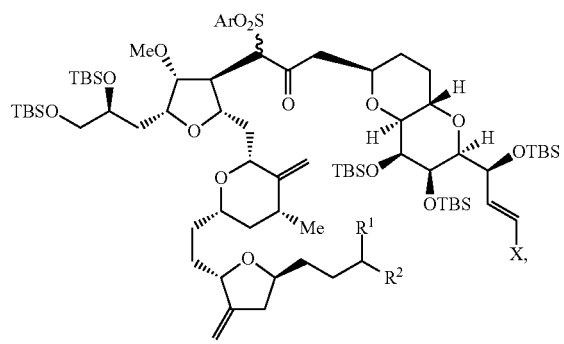

X

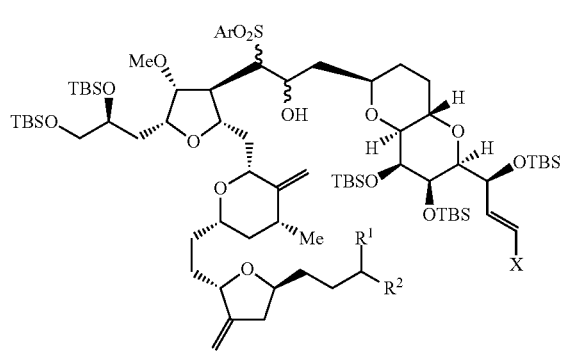

wherein Ar is an aryl substituted by $C_{1-10}$ alkyl or alkoxy, or an unsubstituted aryl;

$R^1$ and $R^2$ are acetal or thioacetal protecting group, and $R^1$ and $R^2$ are each independently $C_{1-10}$ alkoxy or $C_{1-10}$ alkylthio, or $R^1$ and $R^2$ together with the carbon atom to which they are attached form cyclic acetal or cyclic thioacetal;

$R^3$ is methanesulfonyl, p-toluenesulfonyl or trifluoromethanesulfonyl;

Y is chloride, bromide or iodide; and

X is chloride, bromide, iodide or trifluoromethanesulfonyloxy.

2. A preparation method of the compound of formula V according to claim 1, comprising conducting a NHK reaction of the compound of formula VI and the compound of formula VII to give the compound of formula V;

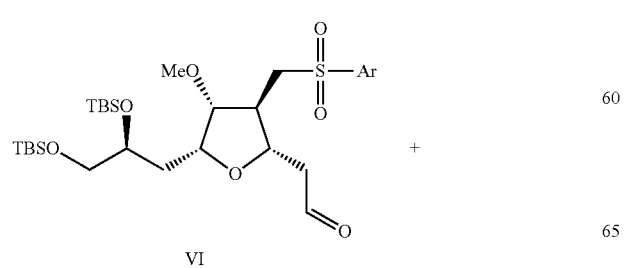

VII

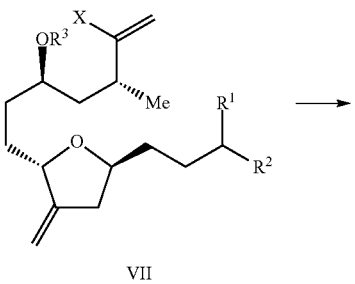

V

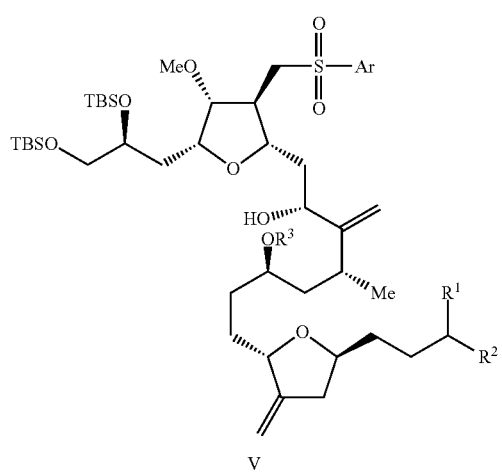

wherein Ar, $R^1$, $R^2$ and $R^3$ are as defined in claim 1;

X is chloride, bromide, iodide or trifluoromethanesulfonyloxy.

3. A preparation method of the compound of formula VA according to claim 1, comprising conducting a NHK reaction of the compound of formula VI and the compound of formula VIIA to give the compound of formula VA;

VI

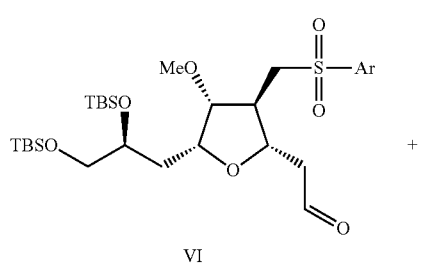

+

VIIA

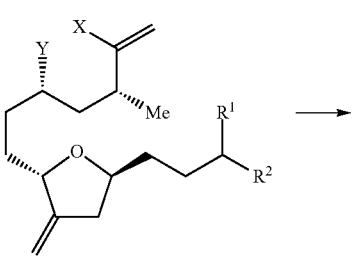

-continued

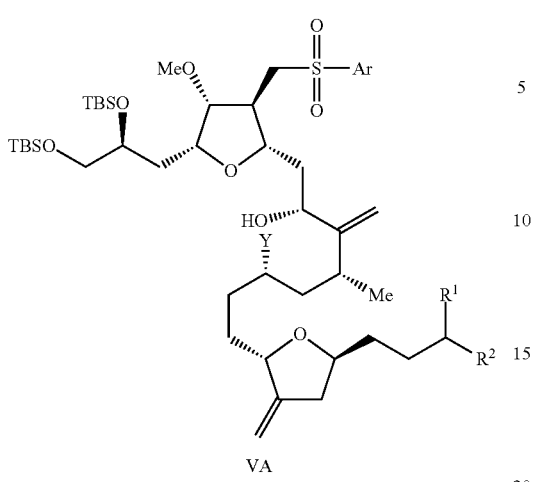

VA wherein Ar, $R^1$, $R^2$ and Y are as defined in claim 1;

X is chloride, bromide, iodide or trifluoromethanesulfonyloxy.

4. A preparation method of the compound of formula VII according to claim 1, comprising conducting a hydroxyl protecting reaction of the compound of formula VIII to give the compound of formula VII;

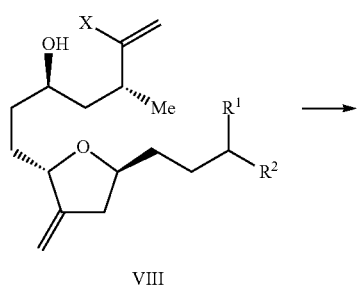

VIII

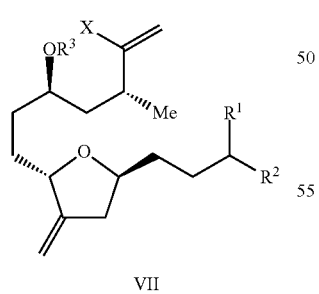

VII wherein $R^1$, $R^2$, $R^3$ and X are as defined in claim 1.

5. A preparation method of the compound of formula VIIA according to claim 1, comprising conducting a substitution reaction of the compound of formula VII to give the compound of formula VIIA;

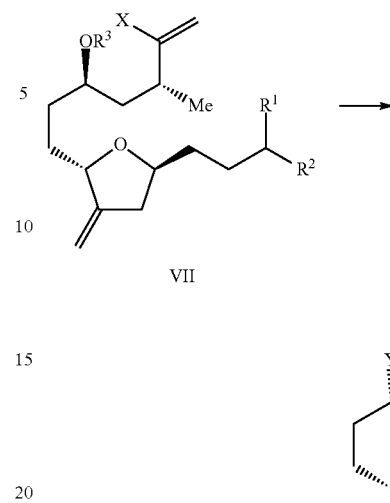

VII

VIIA wherein $R^1$, $R^2$, X and Y are as defined in claim 1;

$R^3$ is methanesulfonyl, p-toluenesulfonyl or trifluoromethanesulfonyl.

6. A preparation method of the compound of formula II according to claim 1, comprising conducting a reductive elimination reaction of the compound of formula IX to give the compound of formula II;

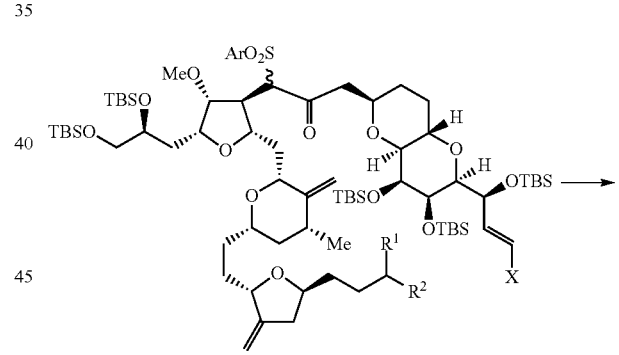

IX

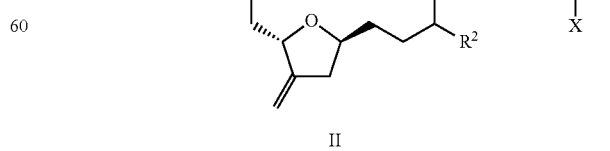

II wherein Ar, X, $R^1$ and $R^2$ are as defined in claim 1.

7. A preparation method of the compound of formula IV, comprising conducting a hydrolysis reaction of the compound of formula II to give the compound of formula IV;

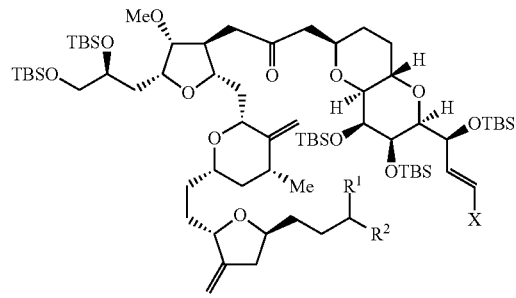

II

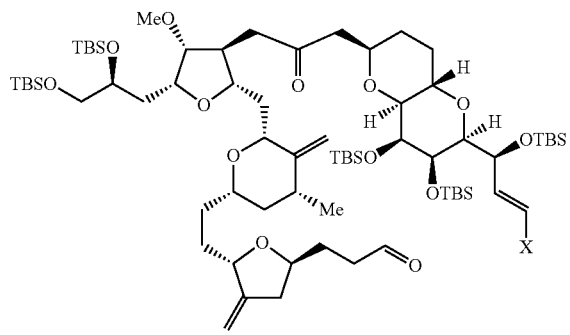

IV wherein X, R¹ and R² are as defined in claim 1.

8. A preparation method of the compound of formula IX according to claim 1, comprising conducting an oxidation reaction of the compound of formula X to give the compound of formula IX;

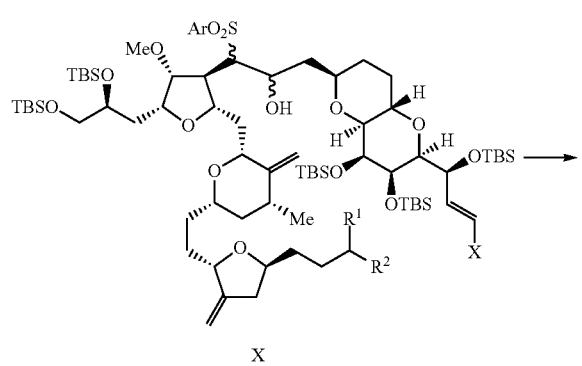

X

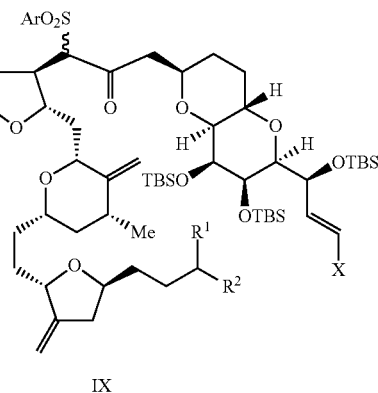

IX wherein Ar, X, R¹ and R² are as defined in claim 1.

9. A preparation method of the compound of formula XII, comprising conducting a hydrolysis reaction of the compound of formula IX to give the compound of formula XII;

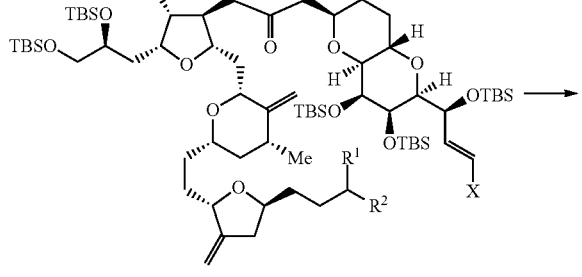

IX

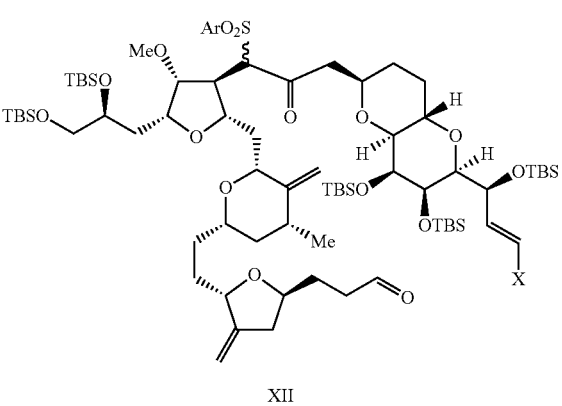

XII wherein Ar, X, R¹ and R² are as defined in claim 1.

10. A preparation method of the compound of formula X according to claim 1, comprising conducting a condensation reaction of the compound of formula III and the compound of formula XI under a basic condition;

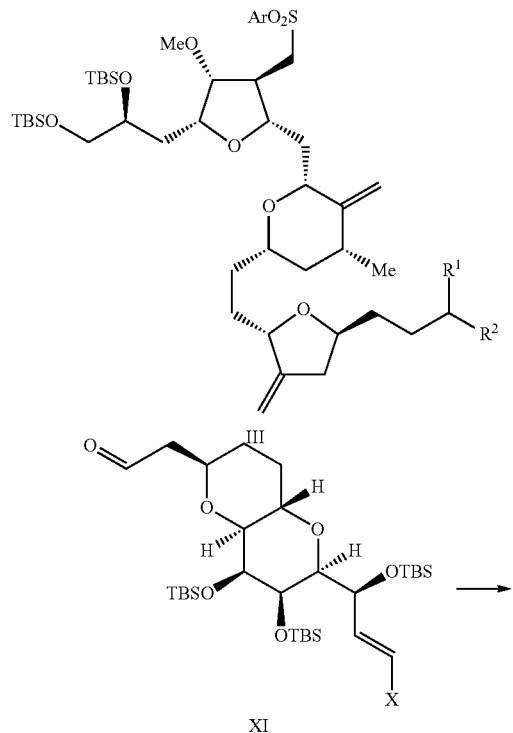

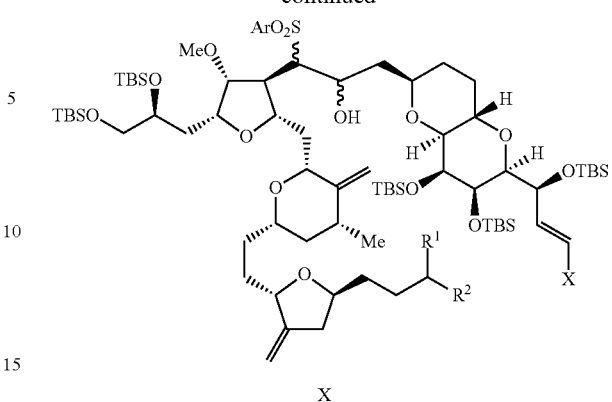

wherein Ar, X, $R^1$ and $R^2$ are as defined in claim 1.

11. A preparation method of the compound of formula IV, comprising the following steps:
   i) conducting a condensation reaction of the compound of formula III and the compound of formula XI to prepare the compound of formula X;
   ii) conducting an oxidation reaction of the compound of formula X to prepare the compound of formula IX;
   iii) conducting a reductive elimination reaction of the compound of formula IX to prepare the compound of formula II;
   iv) conducting a hydrolysis reaction of the compound of formula II to give the compound of formula IV;

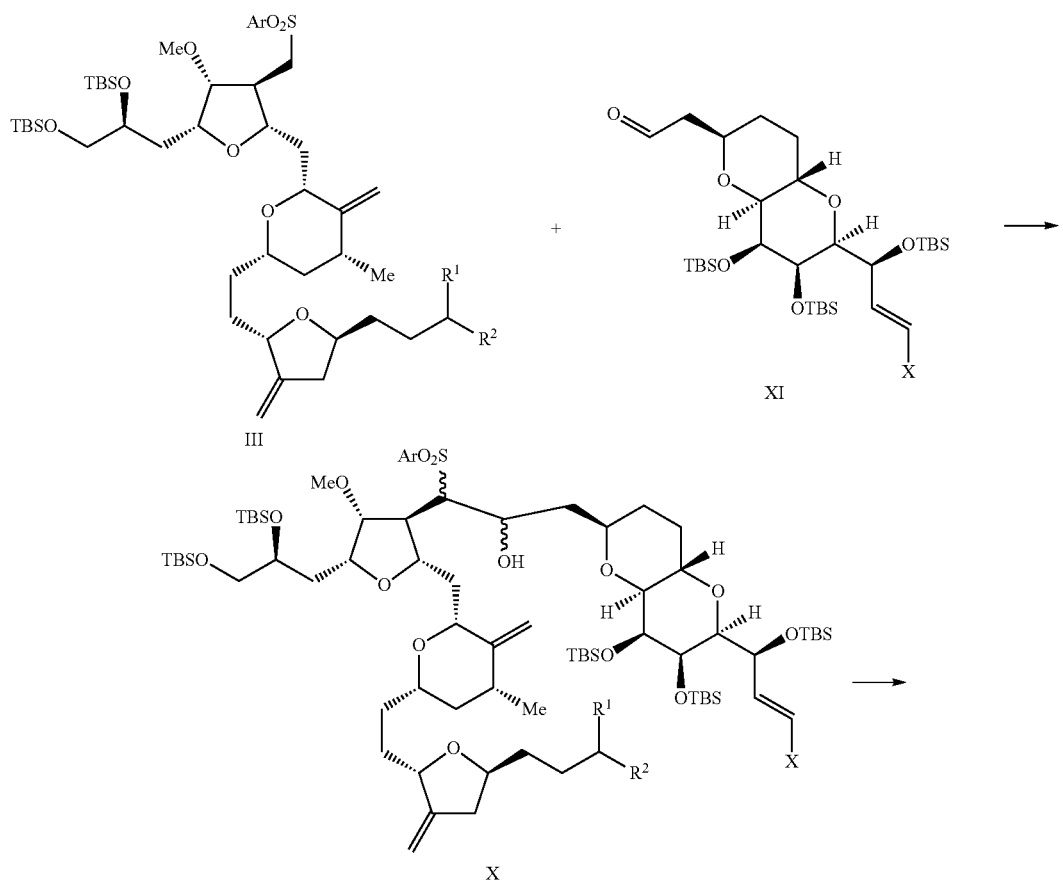

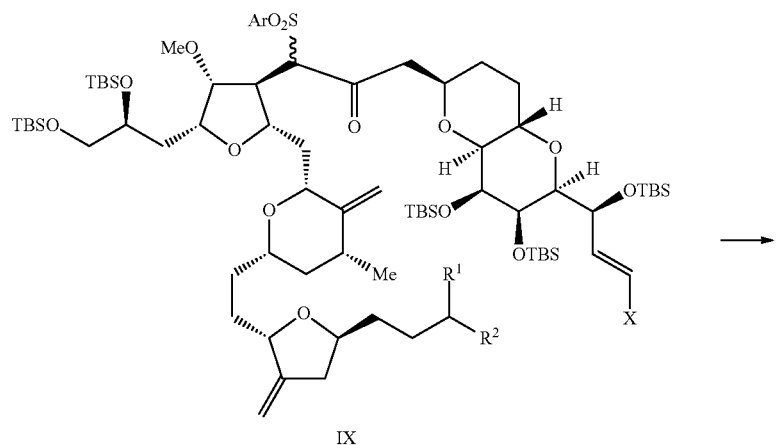

IX

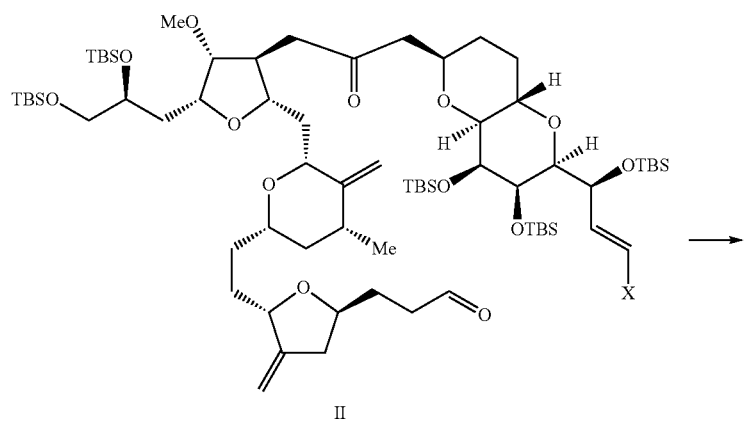

II

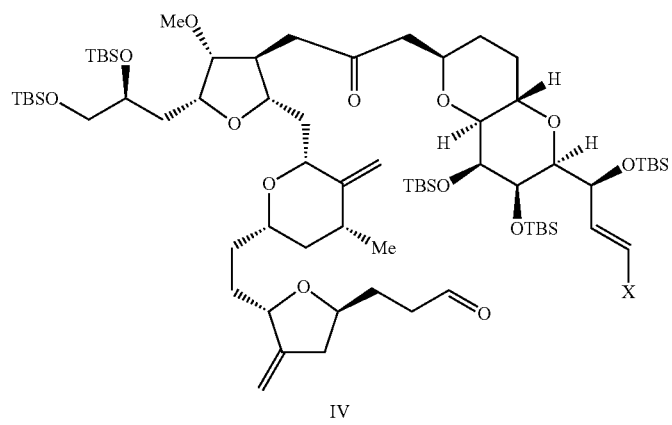

IV wherein Ar, X, R¹ and R² are as defined in claim 1.

12. A preparation method of the compound of formula IV, comprising the following steps:

i) conducting a condensation reaction of the compound of formula III and the compound of formula XI to prepare the compound of formula X;

ii) conducting an oxidation reaction of the compound of formula X to prepare the compound of formula IX;

iii) conducting a hydrolysis reaction of the compound of formula IX to prepare the compound of formula XII;

iv) conducting a reductive elimination reaction of the compound of formula XII to give the compound of formula IV;

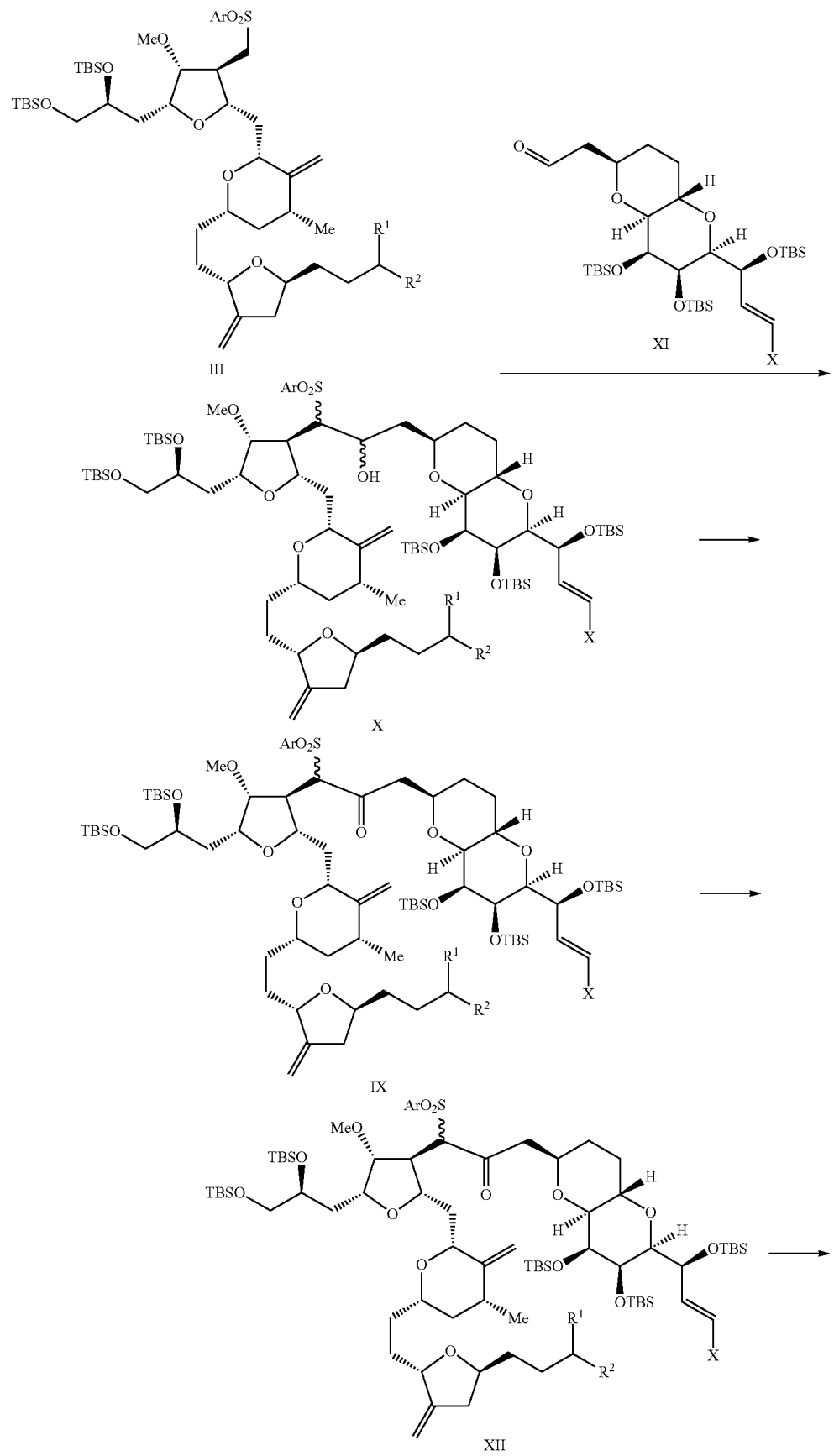

-continued

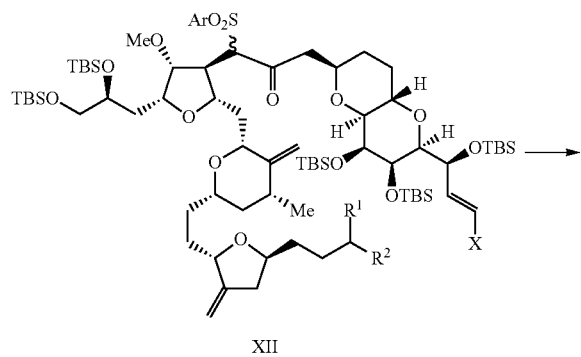

XII

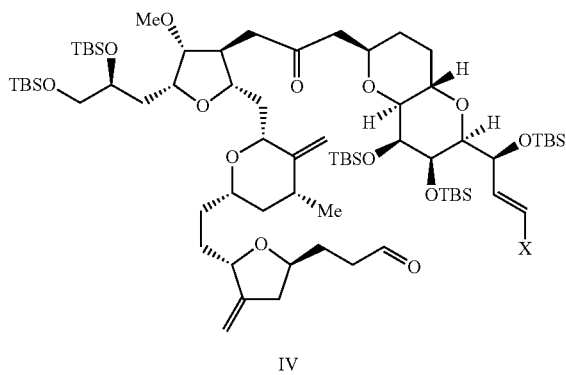

IV wherein Ar, X, $R^1$ and $R^2$ are as defined in claim 1.

13. A preparation method of the compound of formula IV, comprising the following steps:
   i) conducting a hydroxyl protecting reaction of the compound of formula VIII to prepare the compound of formula VII;
   ii) conducting a NHK reaction of the compound of formula VII and the compound of formula VI to prepare the compound of formula V;
   iii) conducting an intramolecular cyclization reaction of the compound of formula V to prepare the compound of formula III;
   iv) conducting a condensation reaction of the compound of formula III and the compound of formula XI to prepare the compound of formula X;
   v) conducting an oxidation reaction of the compound of formula X to prepare the compound of formula IX;
   vi) conducting a reductive elimination reaction of the compound of formula IX to prepare the compound of formula II;
   vii) conducting a hydrolysis reaction of the compound of formula II to give the compound of formula IV;

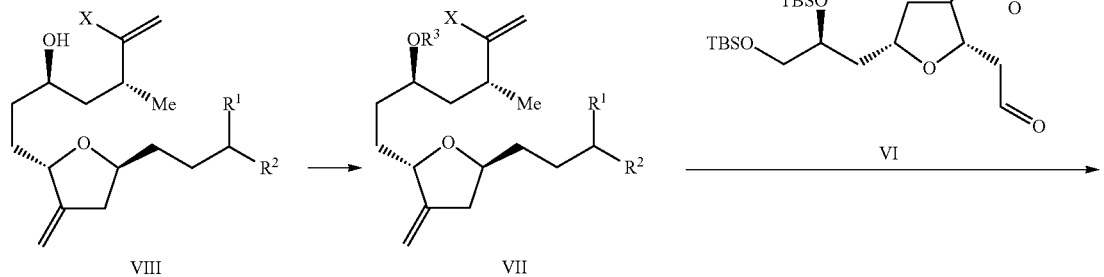

-continued
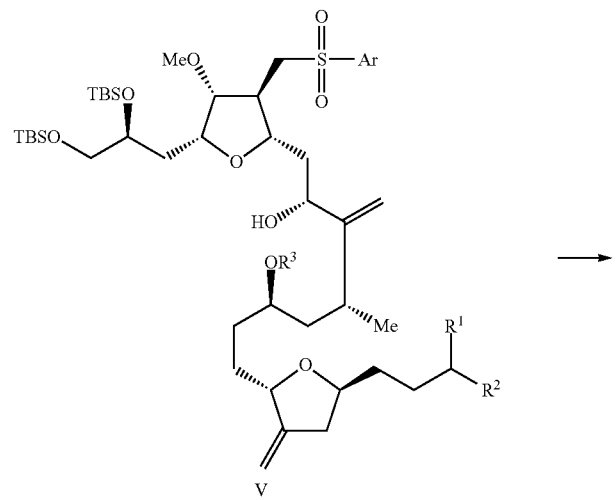
V
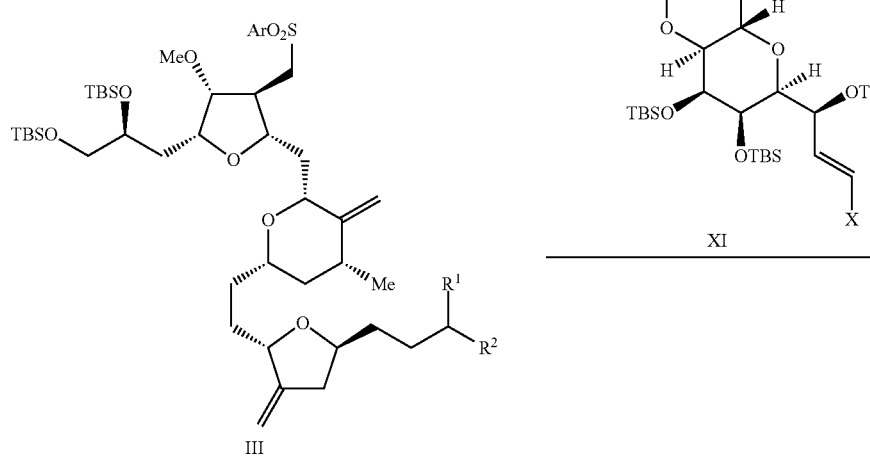
III
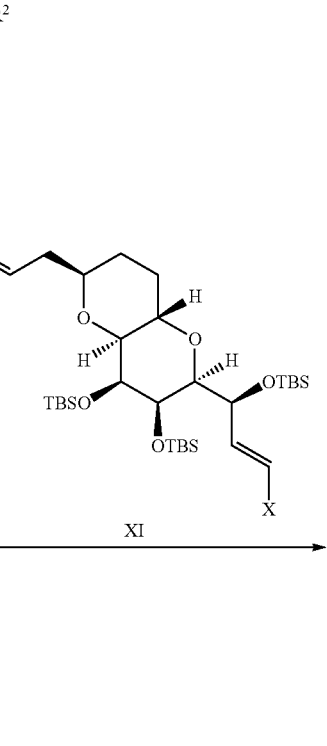
XI
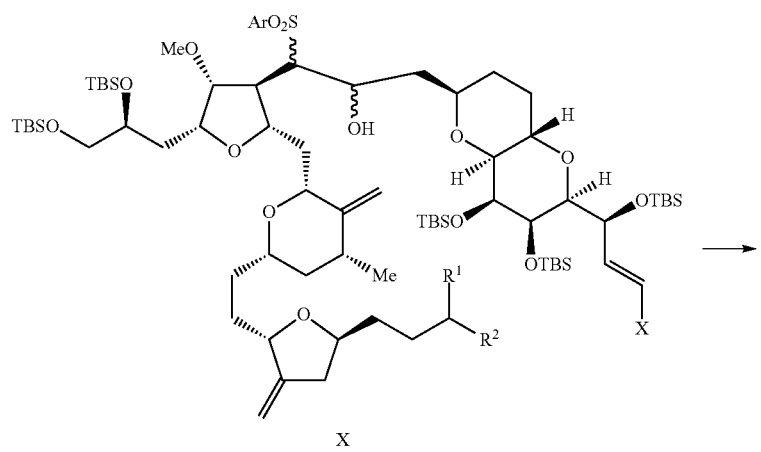
X

-continued

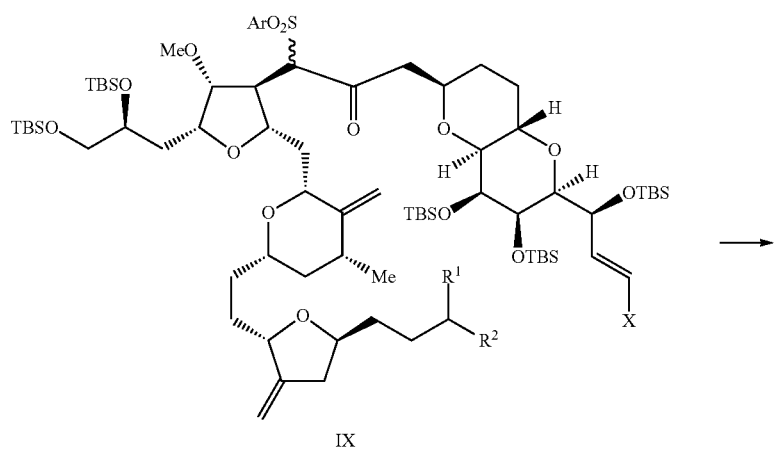

IX

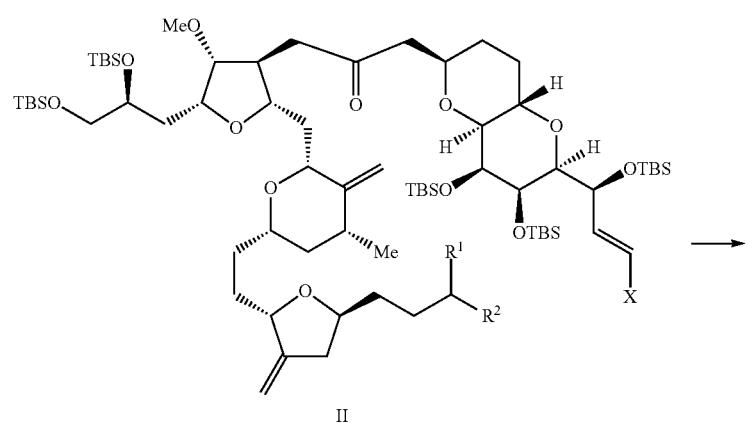

II

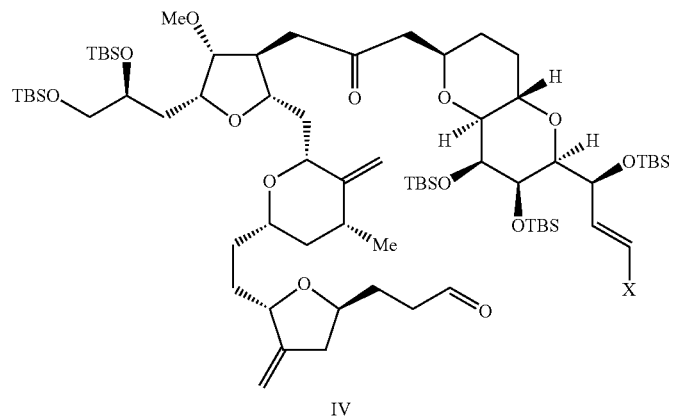

IV wherein Ar, X, R¹, R², and R³ are as defined in claim 1.

14. A preparation method of the compound of formula IV, comprising the following steps:
i) conducting a hydroxyl protecting reaction of the compound of formula VIII to prepare the compound of formula VII;
ii) conducting a NHK reaction of the compound of formula VII and the compound of formula VI to prepare the compound of formula V;
iii) conducting an intramolecular cyclization reaction of the compound of formula V to prepare the compound of formula III;
iv) conducting a condensation reaction of the compound of formula III and the compound of formula XI to prepare the compound of formula X;
v) conducting an oxidation reaction of the compound of formula X to prepare the compound of formula IX;
vi) conducting a hydrolysis reaction of the compound of formula IX to prepare the compound of formula XII;
vii) conducting a reductive elimination reaction of the compound of formula XII to give the compound of formula IV;

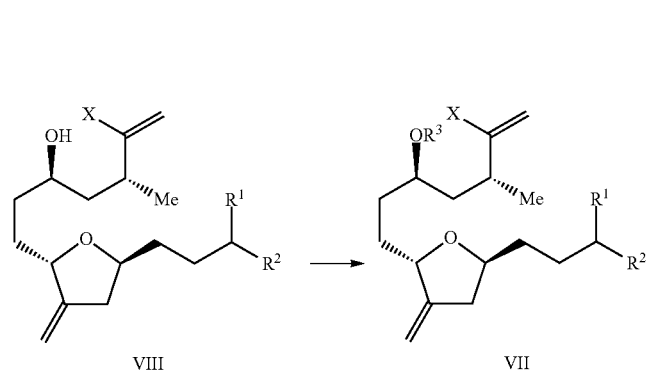
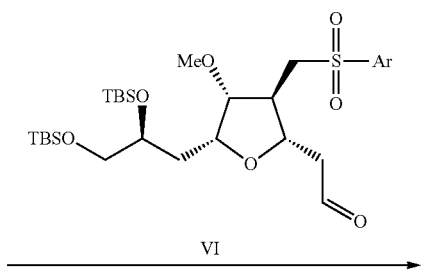
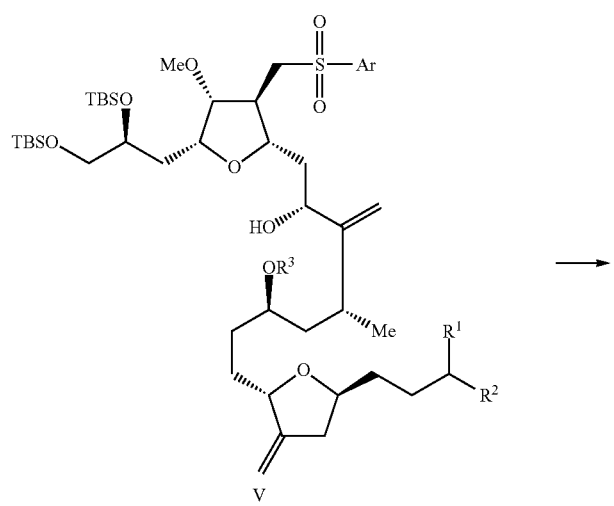
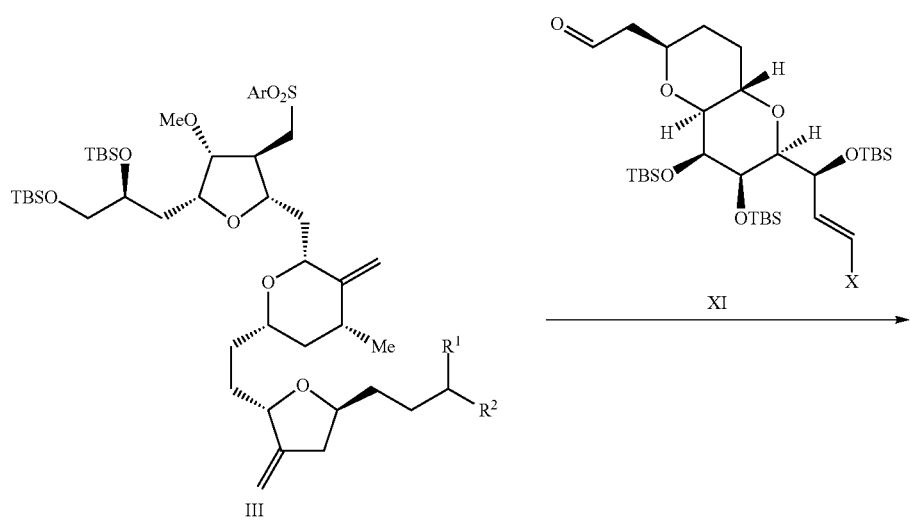

-continued
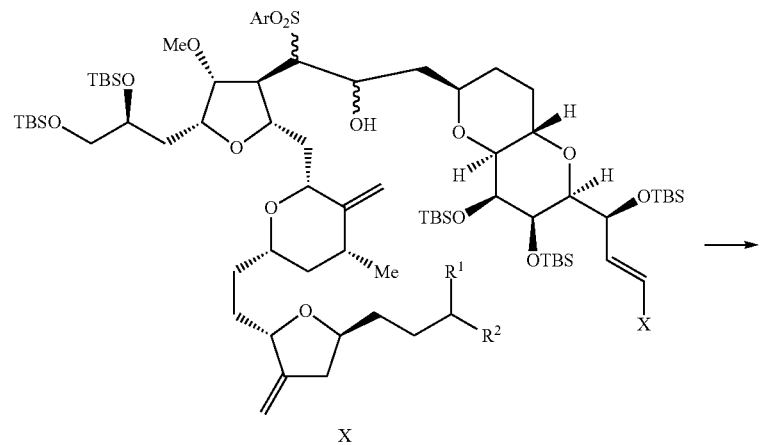
X
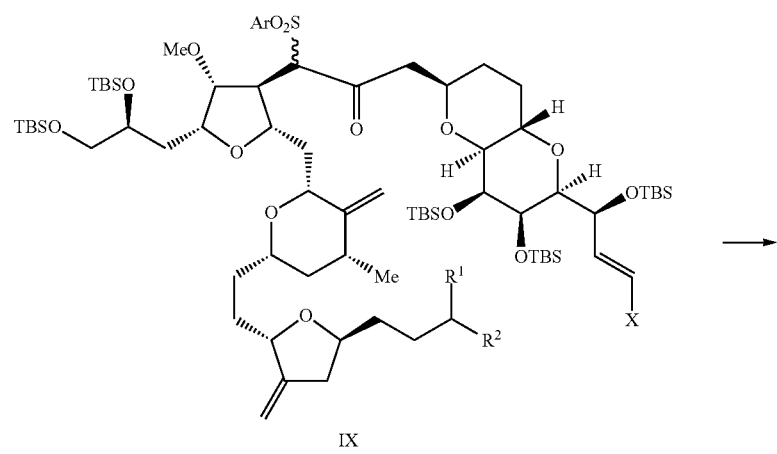
IX
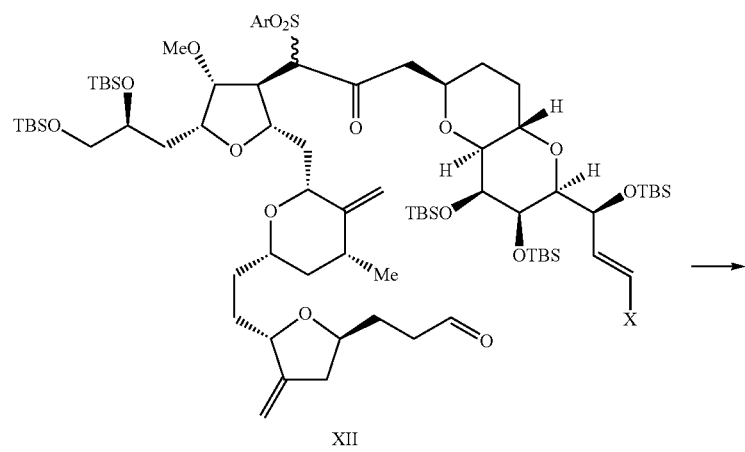
XII

-continued

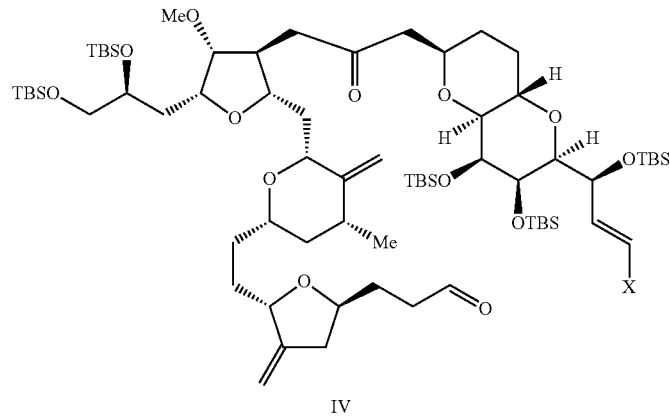

IV wherein Ar, X, R¹, R² and R³ are as defined in claim 1.

15. A preparation method of the compound of formula IV, comprising the following steps:
   i) conducting a hydroxyl protecting reaction of the compound of formula VIII to prepare the compound of formula VII;
   ii) conducting a substitution reaction of the compound of formula VII to prepare the compound of formula VIIA;
   iii) conducting a NHK reaction of the compound of formula VIIA and the compound of formula VI to prepare the compound of formula VA;
   iv) conducting an intramolecular cyclization reaction of the compound of formula VA to prepare the compound of formula III;
   v) conducting a condensation reaction of the compound of formula III and the compound of formula XI to prepare the compound of formula X;
   vi) conducting an oxidation reaction of the compound of formula X to prepare the compound of formula IX;
   vii) conducting a reductive elimination reaction of the compound of formula IX to prepare the compound of formula II;
   viii) conducting a hydrolysis reaction of the compound of formula II to give the compound of formula IV;

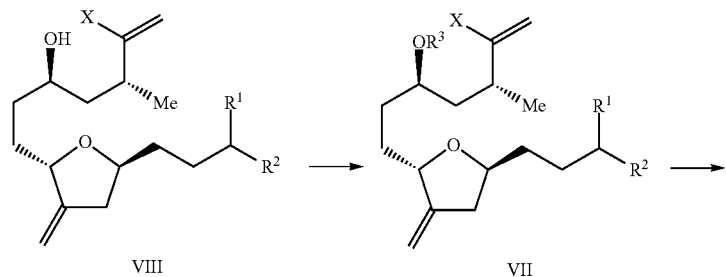

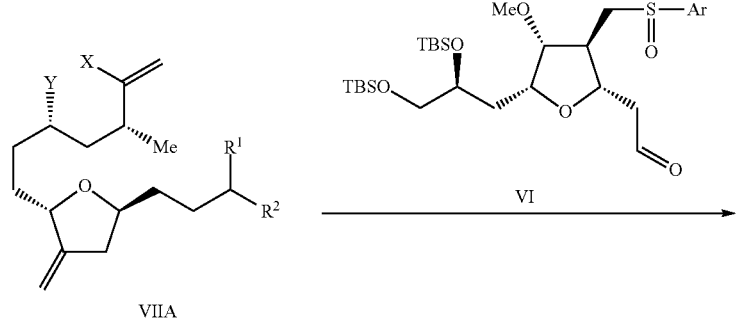

-continued
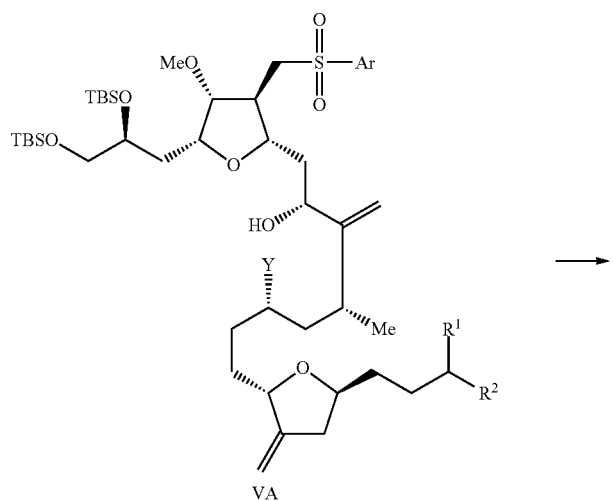
VA
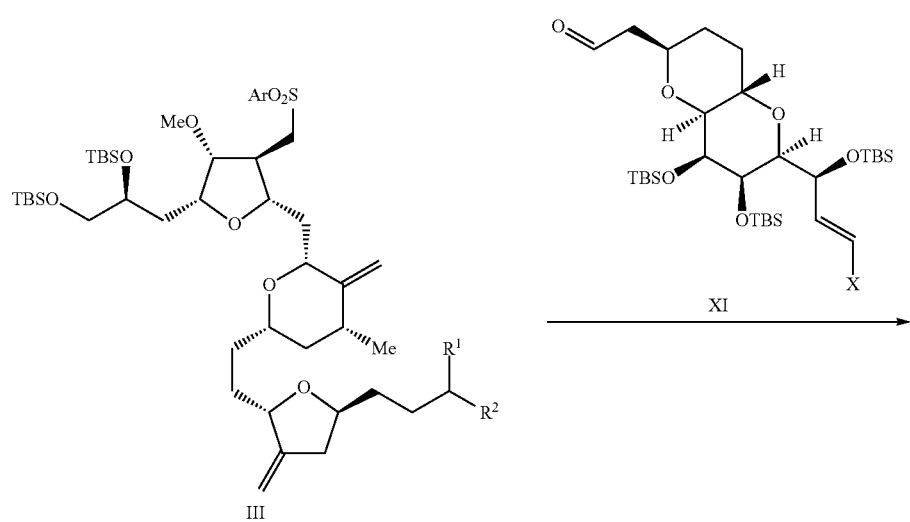
III                    XI
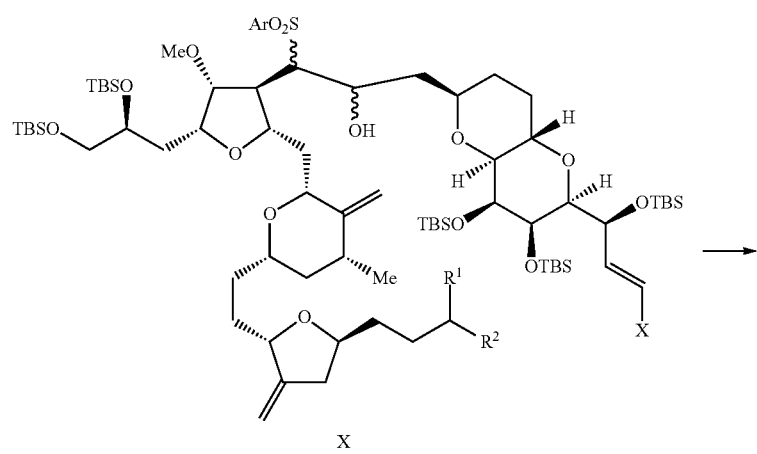
X

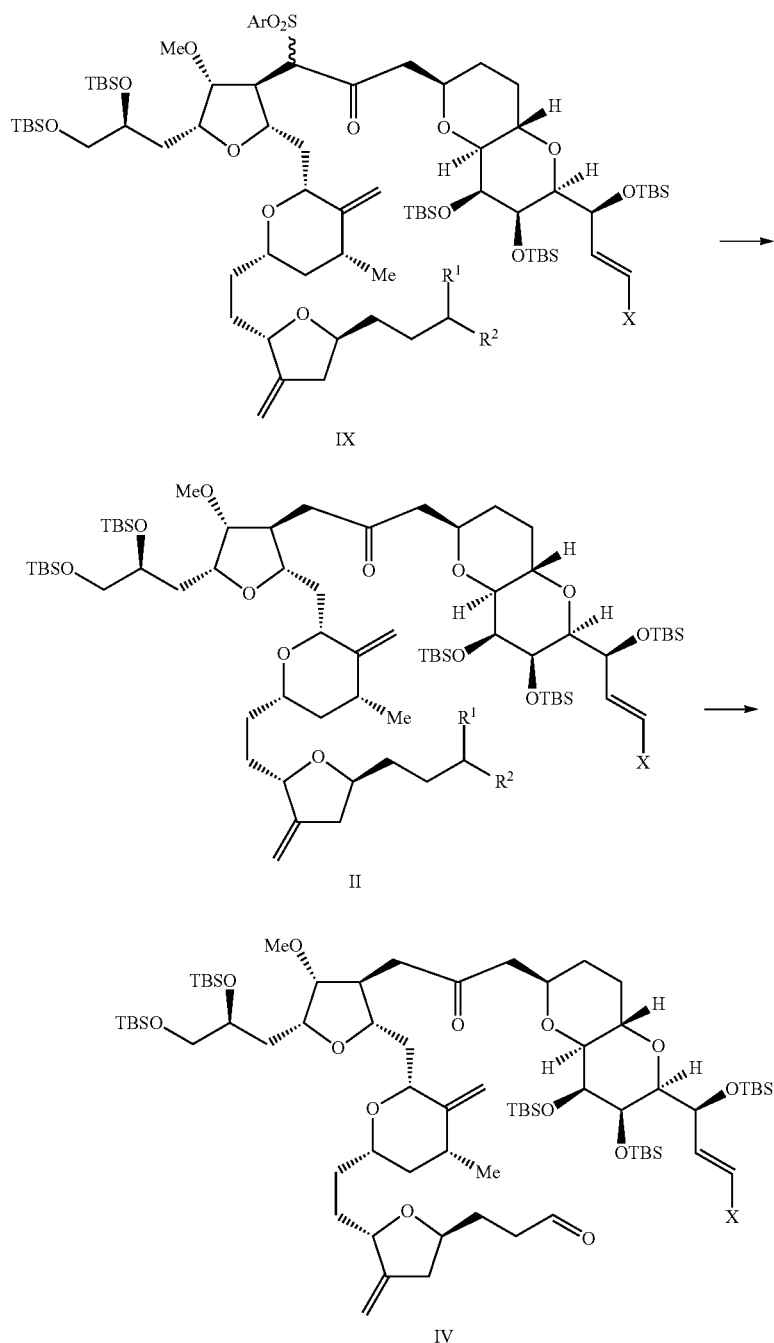

wherein Ar, X, $R^1$, $R^2$ and $R^3$ are as defined in claim 1; Y is chloride, bromide or iodide.

16. A preparation method of the compound of formula IV, comprising the following steps:
  i) conducting a hydroxyl protecting reaction of the compound of formula VIII to prepare the compound of formula VII;
  ii) conducting a substitution reaction of the compound of formula VII to prepare the compound of formula VIIA;
  iii) conducting a NHK reaction of the compound of formula VIIA and the compound of formula VI to prepare the compound of formula VA;
  iv) conducting an intramolecular cyclization reaction of the compound of formula VA to prepare the compound of formula III;
  v) conducting a condensation reaction of the compound of formula III and the compound of formula XI to prepare the compound of formula X;
  vi) conducting an oxidation reaction of the compound of formula X to prepare the compound of formula IX;
  vii) conducting a hydrolysis reaction of the compound of formula IX to prepare the compound of formula XII;
  viii) conducting a reductive elimination reaction of the compound of formula XII to give the compound of formula IV;

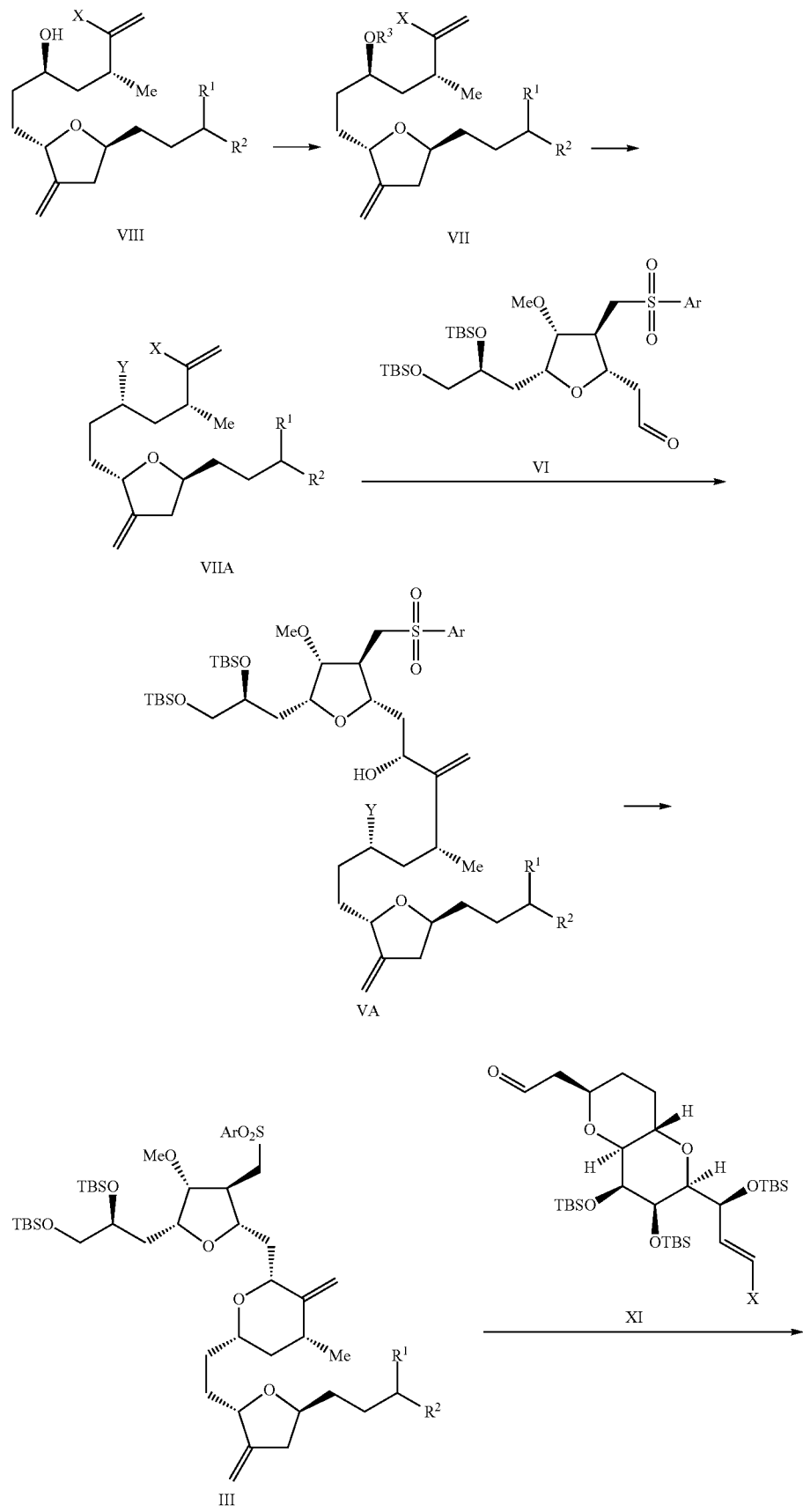

-continued
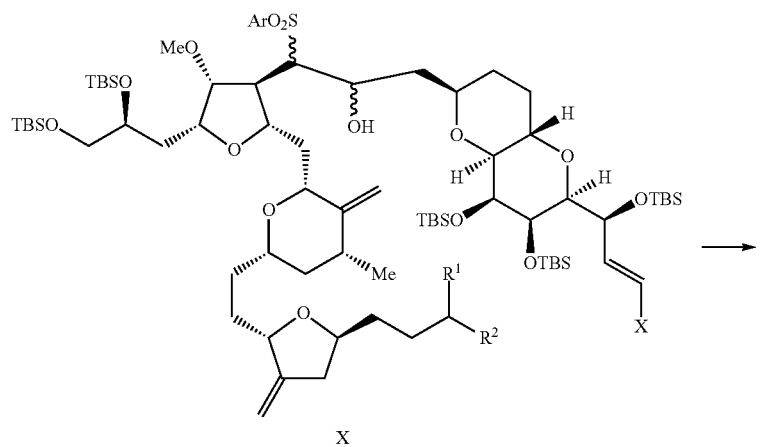
X
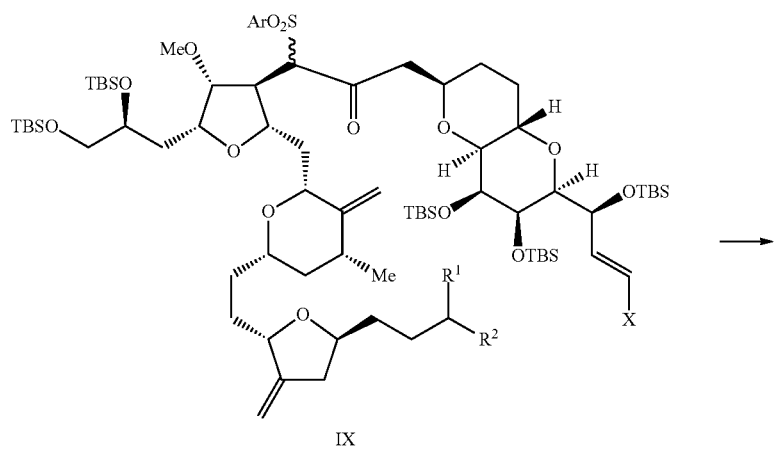
IX
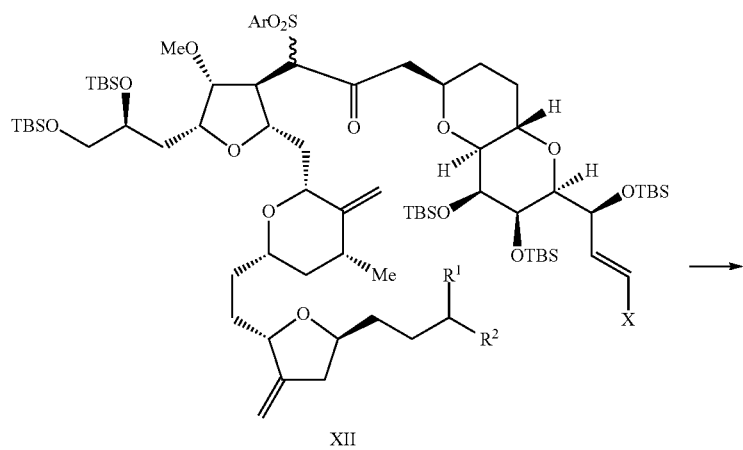
XII

-continued

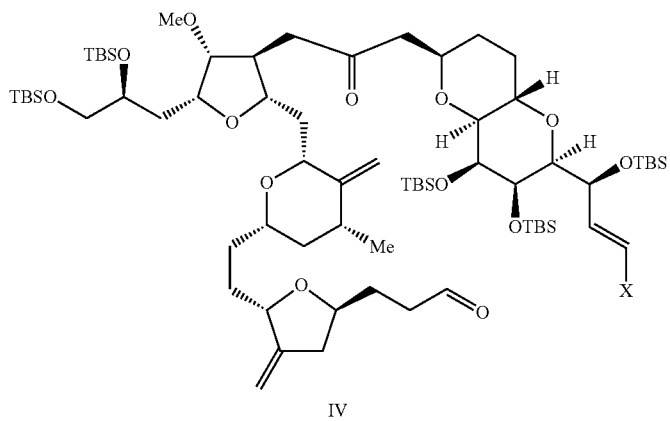

IV wherein Ar, X, $R^1$, $R^2$ and $R^3$ are as defined in claim 1; Y is chloride, bromide or iodide.

17. The compound of formula V, VA, VII, VIIA, II, IX or X according to claim 1, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form cyclic acetal or cyclic thioacetal.

18. The compound of formula V, VA, VII, VIIA, II, IX or X according to claim 17, wherein $R^1$ and $R^2$ together with the carbon atom to which they are attached form substituted or unsubstituted ethylene glycol acetal, or substituted or unsubstituted propanediol acetal.

19. The preparation method of the compound of formula V according to claim 2, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form substituted or unsubstituted ethylene glycol acetal, or substituted or unsubstituted propanediol acetal.

20. The preparation method of the compound of formula VA according to claim 3, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form substituted or unsubstituted ethylene glycol acetal, or substituted or unsubstituted propanediol acetal.

21. The preparation method of the compound of formula IX according to claim 8, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form substituted or unsubstituted ethylene glycol acetal, or substituted or unsubstituted propanediol acetal.

22. The preparation method of the compound of formula IV according to claim 12, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form substituted or unsubstituted ethylene glycol acetal, or substituted or unsubstituted propanediol acetal.

23. The preparation method of the compound of formula IV according to claim 13, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form substituted or unsubstituted ethylene glycol acetal, or substituted or unsubstituted propanediol acetal.

24. The preparation method of the compound of formula IV according to claim 14, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form substituted or unsubstituted ethylene glycol acetal, or substituted or unsubstituted propanediol acetal.

25. The preparation method of the compound of formula IV according to claim 16, wherein Ar is an aryl substituted by $C_{1-10}$ alkyl or alkoxy, or an unsubstituted aryl, or a phenyl substituted by $C_{1-10}$ alkyl at para-position, or an unsubstituted phenyl;
or $R^1$ and $R^2$ together with the carbon atom to which they are attached form substituted or unsubstituted ethylene glycol acetal, or substituted or unsubstituted propanediol acetal.

* * * * *